(12) United States Patent
Peters et al.

(10) Patent No.: US 9,073,870 B2
(45) Date of Patent: Jul. 7, 2015

(54) ALICYCLIC CARBOXYLIC ACID DERIVATIVES OF BENZOMORPHANS AND RELATED SCAFFOLDS, MEDICAMENTS CONTAINING SUCH COMPOUNDS AND THEIR USE

(71) Applicants: Stefan Peters, Biberach an der Riss (DE); Matthias Eckhardt, Biberach an der Riss (DE); Bradford S. Hamilton, Biberach an der Riss (DE); Frank Himmelsbach, Mittelbiberach (DE); Joerg Kley, Mittelbiberach (DE)

(72) Inventors: Stefan Peters, Biberach an der Riss (DE); Matthias Eckhardt, Biberach an der Riss (DE); Bradford S. Hamilton, Biberach an der Riss (DE); Frank Himmelsbach, Mittelbiberach (DE); Joerg Kley, Mittelbiberach (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 14/191,951

(22) Filed: Feb. 27, 2014

(65) Prior Publication Data
US 2014/0179669 A1    Jun. 26, 2014

Related U.S. Application Data

(63) Continuation of application No. 12/991,722, filed as application No. PCT/EP2009/005687 on May 12, 2009, now Pat. No. 8,765,780.

(30) Foreign Application Priority Data

May 13, 2008 (EP) .................... 08156122

(51) Int. Cl.
| | | |
|---|---|---|
| *A61K 31/439* | (2006.01) | |
| *C07D 221/22* | (2006.01) | |
| *C07D 221/26* | (2006.01) | |
| *C07D 471/18* | (2006.01) | |
| *C07D 491/18* | (2006.01) | |
| *C07D 401/06* | (2006.01) | |
| *C07D 401/08* | (2006.01) | |
| *C07D 401/12* | (2006.01) | |
| *C07D 405/06* | (2006.01) | |
| *C07D 405/12* | (2006.01) | |
| *C07D 491/08* | (2006.01) | |

(52) U.S. Cl.
CPC ............ *C07D 221/26* (2013.01); *C07D 221/22* (2013.01); *C07D 471/18* (2013.01); *C07D 491/18* (2013.01); *C07D 401/06* (2013.01); *C07D 401/08* (2013.01); *C07D 401/12* (2013.01); *C07D 405/06* (2013.01); *C07D 405/12* (2013.01); *C07D 491/08* (2013.01)

(58) Field of Classification Search
USPC ............................................ 514/295; 546/97
See application file for complete search history.

(56) References Cited

U.S. PATENT DOCUMENTS

| | | | |
|---|---|---|---|
| 3,341,538 | A | 9/1967 | Block et al. |
| 3,378,587 | A | 4/1968 | Reinhardt |
| 3,474,106 | A | 10/1969 | Ziering et al. |
| 3,539,637 | A | 11/1970 | Clarke, Jr. et al. |
| 3,703,529 | A | 11/1972 | Cavalla et al. |
| 3,823,150 | A | 7/1974 | Merz et al. |
| 3,856,795 | A | 12/1974 | Yardley |
| 3,919,047 | A | 11/1975 | Vidic et al. |
| 3,931,194 | A | 1/1976 | Merz et al. |
| 3,981,874 | A | 9/1976 | Merz et al. |
| 4,009,171 | A | 2/1977 | Albertson |
| 4,043,927 | A | 8/1977 | Duling et al. |
| 4,108,857 | A | 8/1978 | Albertson |
| 4,166,174 | A | 8/1979 | Tanaka et al. |
| 4,268,673 | A | 5/1981 | Akkerman et al. |
| 5,354,758 | A | 10/1994 | Lawson et al. |
| 5,607,941 | A | 3/1997 | Merz et al. |
| 6,145,103 | A | 11/2000 | Typaldos et al. |
| 6,368,816 | B2 | 4/2002 | Walker et al. |
| 6,838,253 | B2 | 1/2005 | Walker et al. |
| 6,946,487 | B2 | 9/2005 | Walker et al. |

(Continued)

FOREIGN PATENT DOCUMENTS

| | | |
|---|---|---|
| CA | 1049008 A1 | 2/1979 |
| CA | 1049511 A1 | 2/1979 |

(Continued)

OTHER PUBLICATIONS

Vidic, H.J. et al.: Microbiological transformations of nonsteroidal structures, VIII. Chemische Berichte, vol. 109, pp. 2657-2669, 1976.*

(Continued)

*Primary Examiner* — Charanjit Aulakh
(74) *Attorney, Agent, or Firm* — Michael P. Morris; David L. Kershner

(57) ABSTRACT

The present invention relates to compounds defined by formula I

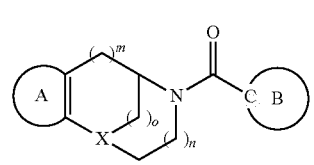

wherein the groups A, B, X, m, n and o are defined as in claim 1, possessing valuable pharmacological activity. Particularly the compounds are inhibitors of 11β-hydroxysteroid dehydrogenase (HSD) 1 and thus are suitable for treatment and prevention of diseases which can be influenced by inhibition of this enzyme, such as metabolic diseases, in particular diabetes type 2, obesity and dyslipidemia.

7 Claims, No Drawings

(56) References Cited

U.S. PATENT DOCUMENTS

| | | |
|---|---|---|
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,897,773 B2 | 3/2011 | Aletru et al. |
| 8,048,825 B2 | 11/2011 | Hino et al. |
| 8,497,281 B2 | 7/2013 | Eckhardt et al. |
| 8,735,585 B2 | 5/2014 | Qu et al. |
| 2006/0089349 A1 | 4/2006 | Gundertofte et al. |
| 2006/0194780 A1 | 8/2006 | Nargund et al. |
| 2009/0170894 A1 | 7/2009 | Aletru et al. |
| 2010/0256363 A1 | 10/2010 | Xu |
| 2011/0015157 A1 | 1/2011 | Claremon et al. |
| 2011/0028445 A1 | 2/2011 | Eckhardt et al. |
| 2011/0112062 A1 | 5/2011 | Claremon et al. |
| 2011/0136800 A1 | 6/2011 | Eckhardt et al. |
| 2011/0190262 A1 | 8/2011 | Himmelsbach et al. |
| 2011/0263583 A1 | 10/2011 | Claremon et al. |
| 2011/0269736 A1 | 11/2011 | Eckhardt et al. |
| 2011/0269791 A1 | 11/2011 | Peters et al. |
| 2011/0275595 A1 | 11/2011 | Eckhardt et al. |
| 2012/0108579 A1 | 5/2012 | Renz et al. |
| 2012/0115853 A1 | 5/2012 | Eckhardt et al. |
| 2012/0172357 A1 | 7/2012 | Himmelsbach |

FOREIGN PATENT DOCUMENTS

| | | |
|---|---|---|
| CA | 1056377 A1 | 6/1979 |
| CA | 1107280 A1 | 8/1981 |
| DE | 2105743 A1 | 8/1972 |
| DE | 2108954 A1 | 9/1972 |
| DE | 2229695 A1 | 1/1974 |
| DE | 2338369 A1 | 2/1975 |
| DE | 2354002 A1 | 5/1975 |
| DE | 2411382 A1 | 9/1975 |
| DE | 2437610 A1 | 2/1976 |
| DE | 2828039 A1 | 1/1980 |
| DE | 10034623 A1 | 1/2002 |
| EP | 0847275 A1 | 6/1998 |
| EP | 1864971 A1 | 12/2007 |
| EP | 1935420 A1 | 6/2008 |
| FR | 2796940 A1 | 2/2001 |
| GB | 1077711 A | 8/1967 |
| JP | 2003057815 A | 2/2003 |
| JP | 2006342093 A | 12/2006 |
| JP | 2007015930 A | 1/2007 |
| JP | 2007016223 A | 1/2007 |
| JP | 2007140188 A | 6/2007 |
| JP | 2007254409 A | 10/2007 |
| JP | 2007269721 A | 10/2007 |
| JP | 2011519374 A | 7/2011 |
| WO | 9413641 A1 | 6/1994 |
| WO | 9637494 A1 | 11/1996 |
| WO | 9707789 A1 | 3/1997 |
| WO | 9822462 A1 | 5/1998 |
| WO | 9852940 A1 | 11/1998 |
| WO | 0155063 A1 | 8/2001 |
| WO | 03097608 A2 | 11/2003 |
| WO | 2004089896 A1 | 10/2004 |
| WO | 2005108360 A1 | 11/2005 |
| WO | 2005108361 A1 | 11/2005 |
| WO | 2006024628 A1 | 3/2006 |
| WO | 2006040329 A1 | 4/2006 |
| WO | 2006044174 A2 | 4/2006 |
| WO | 2007051810 A2 | 5/2007 |
| WO | 2007076055 A2 | 7/2007 |
| WO | 2007081570 A2 | 7/2007 |
| WO | 2007124337 A1 | 11/2007 |
| WO | 2007127693 A1 | 11/2007 |
| WO | 2007127763 A2 | 11/2007 |
| WO | 2008000951 A2 | 1/2008 |
| WO | 2008059948 A1 | 5/2008 |
| WO | 2008106128 A2 | 9/2008 |
| WO | 2009017664 A1 | 2/2009 |
| WO | 2009017671 A1 | 2/2009 |
| WO | 2009061498 A1 | 5/2009 |
| WO | 2009063061 A2 | 5/2009 |
| WO | 2009100872 A1 | 8/2009 |
| WO | 2009102428 A2 | 8/2009 |
| WO | 2009102460 A2 | 8/2009 |
| WO | 2009117109 A1 | 9/2009 |
| WO | 2009134400 A1 | 11/2009 |
| WO | 2009138386 A2 | 11/2009 |
| WO | 2010010157 A2 | 1/2010 |
| WO | 2010010174 A1 | 1/2010 |
| WO | 2010011314 A1 | 1/2010 |
| WO | 2010023161 A1 | 3/2010 |
| WO | 2010046445 A2 | 4/2010 |
| WO | 2010139673 A1 | 12/2010 |
| WO | 2011057054 A1 | 5/2011 |
| WO | 2012061708 A1 | 5/2012 |

OTHER PUBLICATIONS

Abstract in English for German DE10034623, publication date Jan. 31, 2002.

Abstract in English for German DE2105743, publication date Aug. 31, 1972.

Abstract in English for German DE2108954, publication date Sep. 7, 1972.

Abstract in English for JP2003057815, publication date Feb. 28, 2003.

Abstract in English for JP2006342093, publication date Dec. 21, 2006.

Abstract in English for JP2007016223, publication date Jan. 25, 2007.

Abstract in English for JP2007140188 publication date 2007.

Abstract in English for JP2007269721, publication date Oct. 18, 2007.

Bosch, J. et al., "Benzomorphan Related Compounds. A Versatile Method for the Synthesis of Heteromorphans." Heterocycles, 1980, vol. 14, No. 12, pp. 1983-1988.

Caplus—133:4656—Anantanarayan, A. et. al., "Preparation of heteroarylpyrazoles as P38 kinase inhibitors". 2000.

Caplus—147:134403, Hembrough, T.A., et al., Composition and methods comprising proteinase activated receptor 2 antagonists for treatment of angiogenesis and inflammatory disorders and cancer. 2007.

Caplus—77:5360, Helsley, G. C. "Antispasmodic 8-carbamoyl-3-phenylnortropanes". 1972.

ChemAbstract—Accession No. 958599-31-0, Chemical Abstracts Service, Columbus, Ohio, Source: Emory MLSC database, Dec. 2007.

ChemAbstract—Accession No. 958625-83-7, Chemical Abstracts Service, Columbus, Ohio, Source: Emory MLSC database, Dec. 2007.

ChemAbstract—Accession No. 958629-14-6, Chemical Abstracts Service, Columbus, Ohio, Source: Emory MLSC database, Dec. 2007.

ChemAbstract—Accession No. 958629-22-6, Chemical Abstracts Service, Columbus, Ohio, Source: Emory MLSC database, Dec. 2007.

ChemAbstract—Accession No. 958629-39-5, Chemical Abstracts Service, Columbus, Ohio, Source: Emory MLSC database, Dec. 2007.

ChemAbstract—Accession No. 958696-32-7, Chemical Abstracts Service, Columbus, Ohio, Source: Emory MLSC database, Dec. 2007.

ChemAbstract—Accession No. 958696-39-4, Chemical Abstracts Service, Columbus, Ohio, Source: Emory MLSC database, Dec. 2007.

ChemAbstract—Accession No. 958700-63-5, Chemical Abstracts Service, Columbus, Ohio, Source: Emory MLSC database, Dec. 2007.

De Luis et al., Control of Metabolic Syndrome with Metformin in Obese Type 2 Diabetes Mellitus Patients, Diabetes Research and Clinical Practice, 2000, vol. 50, Suppl. 1, pp. S51-S52.

(56) References Cited

OTHER PUBLICATIONS

Demarinis, R. M. et al., "a-Adrenergic Agents, 1. Direct-Acting a1 Agonists Related to Methoxamine." Journal of Medicinal Chemistry, 1981, vol. 24, No. 12, pp. 1432-1437.

Eberle, M. K. et al., "Carbocyclic Phenylhydrazines in The Fischer Indole Synthesis—II" Tetrahedron, 1973, vol. 29, No. 24, pp. 4049-4052.

Gutkowska, et al, Acta Poloniae Pharmaceutica, 1982, 39, p. 61-64.

Harno, E. et al., "Will treating diabetes with 11b-HSD1 inhibitors affect the HPA axis?" Trends in Endocrinology and Metabolism, 2010, vol. 21, No. 10, pp. 619-627.

Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.

International Search Report and Written Opinon for PCT/EP2009/055687 mailed Dec. 22, 2009.

Kametani, T. et al., "Azabenzomorphane and Related Compounds." Chem. Pharma. Bull., 1965, vol. 13, No. 3, pp. 295-299.

Ma, Z. et al., "A Concise Formal Synthesis of Unnatural (+)-Aphanorphine from (2S,4R)-4-Hydroxyproline." Synlett, 2007, No. 1, pp. 161-163.

Ma, Z. et al., "Formal Syntheses of (−)- and (+)-aphanorphine from (2S,4R)-4-hydroxyproline." Tetrahedron, 2007, 63, pp. 7523-7531.

Masamune, T. et al., "The Synthesis and the Exhaustive Methylation of the cis and trans Isomers of 1,2,3,4,4a,5,6,10b-Octahydrophenanthridine and 1,2,3,4,4a,5,6,10b-Octahydrobenzo[f]quinoline." Journal of Organic Chemistry, 1964, vol. 29, No. 6, pp. 1419-1424.

Mehta, P. et al., "Synthesis of cis & trans-1-substituted 1,2,3,4,4a,5,11,11a-octahydro-6H-pyrido[3,2-b]carbazoles, 4-substituted 1,2,3,4,4a,5,6,11c-octa-hydro-7H-pyrido[2,3,-c]carbazoles, cis-4-methyl-1,2,3,4,4a,5,6,12b-octa-hydro-7H-pyrido[2,3-c]acridine & cis-1-methyl-1,2,3,4,4a,5,12,12a-octa-hydro-6H-pyrido[3,2-b]-acridine—A new class of potential antiparkinsonian agents." Indian Journal of Chemistry, 1991, vol. 30B, No. 2, pp. 213-221.

Nyenwe, E. at al., "Management of type 2 diabetes: evolving strategies for the treatment of patients with type 2 diabetes." Metabolism Clinical and Experimental, 2011, vol. 62, pp. 1-23.

Olesen, Preben H.; the Use of Bioisosteric Groups in Lead Optimization; Current Opinion in Drug Discovery & Development (2001) vol. 4, No. 4 pp. 471-478.

Patani, George A. et al., "Bioisosterism: A Rational Approach in Drug Design" Chem. Rev. (1996) vol. 96, pp. 3147-3176.

Rammamjireddy, T. et al., "Importance of Metformin with Repaglinide in the Treatment of Type II Diabetes Mellitus: A Decadel Review." Asian Journal of Pharmaceutical and Clinical Research, 2012, vol. 5, pp. 1-4.

Rosenstock, J. "The 11-b-Hydroxysteroid Dehydrogenase Type 1 Inhibitor INCB13739 Improves Hyperglycemia in Patients With Type 2 Diabetes Inadequately Contolled by Metformin Monotherapy." Diabetes Care, 2010, vol. 33, No. 7, pp. 1516-1522.

Serajuddin, Abu T.M., "Salt formation to improve drug solubility." Advanced Drug Delivery Reviews 59, 2007, pp. 603-616.

Stewart, P. et al., "11b-Hydroxysteroid Dehydrogenase." Advances in Research and Applications, 1999, vol. 57, pp. 249-324.

Tadayyon, M. et al., "Insulin sensitisation in the treatment of Type 2 diabetes." Expert Opinion on Investigational Drugs, 2003, vol. 12, No. 3, pp. 307-324.

Thornber, C.W.; Isosterism and Molecular Modification in Drug Design; Chem. Soc, Rev (1979) vol. 8 pp. 563-580.

WO09017664 Published Feb. 5, 2009. Applicant: Vitae Pharmaceuticals, Inc. Inventor: D. A. Claremon et al. This foreign patent is over 25KB and will not upload using EFS. Also published as US Publication US2011015157 and US201025636.

Yokoyama, N. et al., "Syntheses, Analgetic Activity, and Physical Dependence Capacity of 5-Phenyl-6,7-benzomorphan Derivatives." Journal of Medicinal Chemistry, 1979, vol. 22, No. 5, pp. 537-553.

Brittain et al., "Effects Due to Compression." Brittain's Publication, 1999, pp. 348-361.

* cited by examiner

ALICYCLIC CARBOXYLIC ACID DERIVATIVES OF BENZOMORPHANS AND RELATED SCAFFOLDS, MEDICAMENTS CONTAINING SUCH COMPOUNDS AND THEIR USE

The present invention relates to compounds derived from the following chemical scaffold which is structurally defined by the formula I

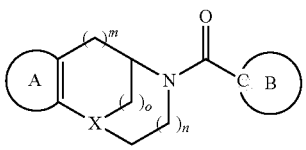

wherein the groups A, B, X, m, n, and o are as defined hereinafter, including the tautomers, the stereoisomers, the mixtures thereof and the salts thereof. The invention further relates to pharmaceutical compositions containing a compound of formula I according to the invention as well as the use of a compound according to the invention for preparing a pharmaceutical composition for the treatment of metabolic disorders. In addition, the invention relates to processes for preparing a pharmaceutical composition as well as a compound according to the invention.

In the literature, compounds which have an inhibitory effect on the enzyme 11β-hydroxysteroid dehydrogenase (HSD) 1 are proposed for the treatment of the metabolic syndrome, in particular diabetes type 2, obesity, and dyslipidemia.

In the scientific publications *Acta Poloniae Pharmaceutica* 1982, 39, p. 61-64 and *Acta Poloniae Pharmaceutica* 1987, 39, p. 411-414 the syntheses of the following benzomorphans that may have various pharmacological activities, particularly analgetic acitivity, are described:

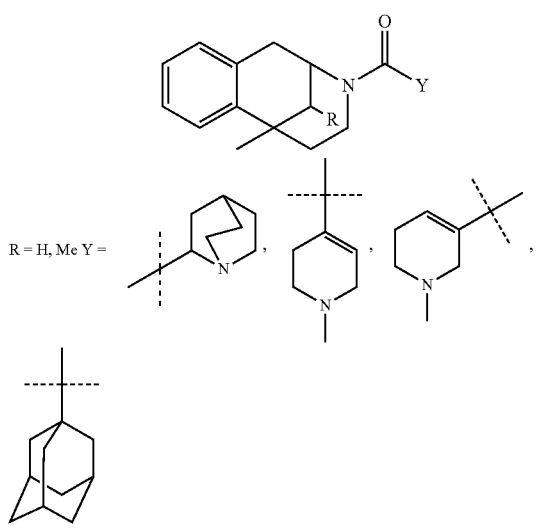

The scientific publication *J. Med. Chem.* 1979, 22, p. 537-553 describes the synthesis and analgetic activity of a large number of benzomorphans among which two stereoisomers of the benzomorphan of the formula

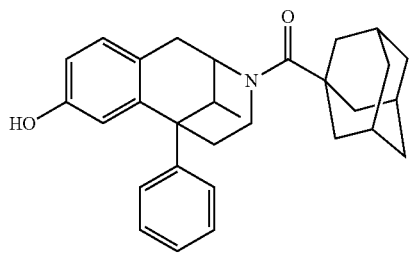 [SMILES: CC1C2Cc3ccc(O)cc3C1(c1ccccc1)CCN2C(=O)C12CC3CC(CC(C3)C1)C2]

are mentioned.

The scientific publication *Chem. Ber.* 1976, 109, p. 2657-2669 reports the microbiological and chemical transformation of the benzomorphan of the formula T1 into products of general formula

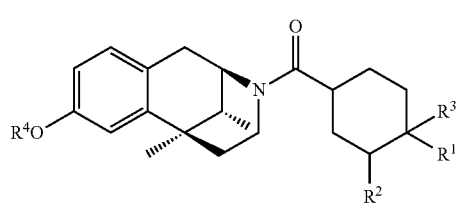

$R^1, R^2, R^3, R^4 = H\ R^1, R^3, R^4 = H\ R^2 = OH\ (S)\ R^1 = OH, R^2, R^3, R^4 = H\ R^1, R^3, R^4 = H$
$R^2 = OAc\ (S)\ R^1 = OAc, R^2, R^3, R^4 = H\ R^1, R^3 = H\ R^2 = OH, R^4 = Me\ (S)\ R^1 = OH, R^2,$
$R^3 = H, R^4 = Me\ R^1\ and\ R^3 = (= O), R^2 = H, R^4 = Me.$ In the WO 03/097608 opioid and opioid-like compounds of the general formula R-A-X wherein R, A, and X are as defined therein, are described for the treatment and prevention of septic shock and other disorders. Inter alia A denotes a benzomorphan partial structure of the formula

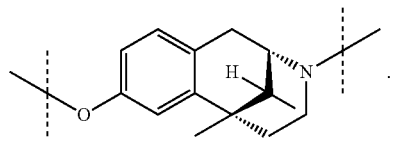

In the U.S. Pat. No. 4,103,857 derivatives of benzomorphans of the general formula

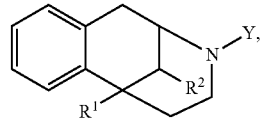

wherein $R^1$, $R^2$, and Y are as defined therein, are described as compounds having anticonvulsant, central nervous system depressant, and diuretic activity. Besides alternative synthetic routes, the invention describes a principal access to the compounds of the invention via a route employing N-acylated (Y is acyl) compounds of the general formula depicted above. The following N-acylated compounds are explicitly mentioned as intermediates therein:

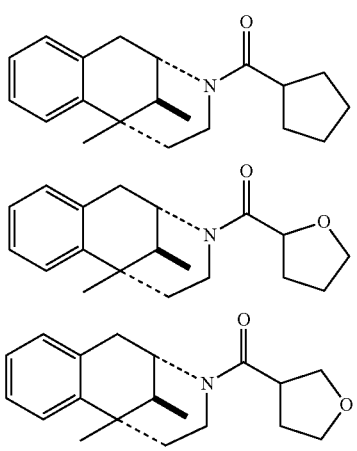

In the U.S. Pat. No. 4,009,171 derivatives of benzomorphans of the general formula

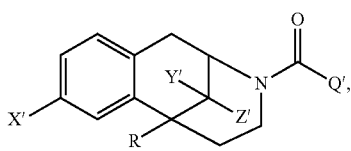

wherein R, Q', X', Y', and Z' are as defined therein, are described as intermediates for the preparation of benzomorphans that may be useful as narcotic antagonists. Inter alia Q' has the meaning cycloalkyl or cycloalkenyl having 3 to 7 ring carbon atoms and having 3 to 9 total carbon atoms.

In the DE 28 28g 039 derivatives of benzomorphans of the general formula

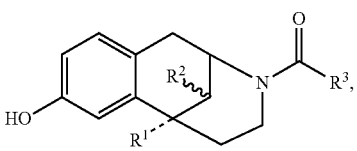

wherein $R^1$, $R^2$, and $R^3$ are as defined therein, are described as intermediates for the preparation of benzomorphans that may have analgetic activity. Inter alia the following meanings of $R^3$ are defined:

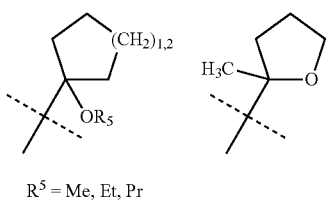

$R^5$ = Me, Et, Pr

In the DE 24 11 382 derivatives of benzomorphans of the general formula

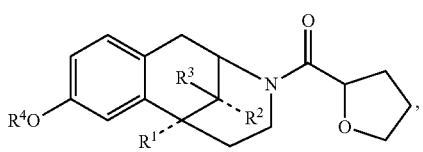

wherein $R^1$, $R^2$, $R^3$, and $R^4$ are as defined therein, are described as intermediates for the preparation of benzomorphans that have analgetic activity.

In the DE 24 37 610 derivatives of benzomorphans of the general formula

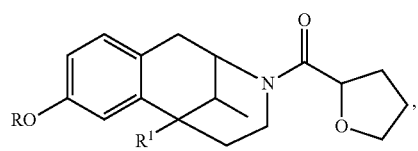

wherein R is hydrogen, methyl, or acetyl and $R^1$ is methyl or phenyl, are described as intermediates for the preparation of the corresponding N-tetrahydrofuran-2-ylmethyl benzomorphans.

The inventors are not aware that alicyclic carboxylic acid derivatives of benzomorphans have been described as inhibitors of 11β-hydroxysteroid dehydrogenase (HSD) 1.

AIM OF THE INVENTION

The aim of the present invention is to find new benzomorphans or related compounds, particularly those which are active with regard to the enzyme 11β-hydroxysteroid dehydrogenase (HSD) 1. A further aim of the present invention is to discover benzomorphans or related compounds which have an inhibitory effect on the enzyme 11β-hydroxysteroid dehydrogenase (HSD) 1 in vitro and/or in vivo and possess suitable pharmacological and pharmacokinetic properties to use them as medicaments.

A further aim of the present invention is to provide new pharmaceutical compositions which are suitable for the prevention and/or treatment of metabolic disorders, particularly diabetes and dyslipidemia.

Other aims of the present invention will become apparent to the skilled man directly from the foregoing and following remarks.

OBJECT OF THE INVENTION

In a first aspect the present invention relates to compounds derived from the following chemical scaffold which is structurally defined by the formula I

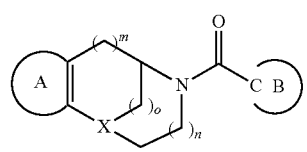

I wherein
X denotes CH or N,
m, n, o independently of each other denote 0, 1, or 2, wherein the bicyclic azacycloalkene core structure of general formula I annelated with ring A and attached to the carbonyl group is optionally substituted with 1, 2, or more substituents, preferably with 1 to 5, independently of each other selected from the group consisting of $R^{11}$ and $R^{12}$, A denotes a benzo ring, which is optionally substituted with one to four substituents independently of each other selected from $R^1$ or wherein 2 adjacent C-atoms are optionally substituted with $R^2$ and $R^3$ and one or two carbon atoms are optionally substituted independently with substituents selected from $R^1$; or a pyrido ring, which is optionally substituted with one to three substituents independently of each other selected from $R^1$ or wherein 2 adjacent C-atoms are optionally substituted with $R^2$ and $R^3$ and one carbon atom is optionally substituted with $R^1$; or a pyrrolo, furo, thieno, pyridazino, or pyrazino ring wherein each of said rings is optionally substituted with one or two substituents, independently of each other selected from $R^1$ or wherein 2 adjacent C-atoms of each of said rings are optionally substituted with $R^2$ and $R^3$; or a pyrimido ring, which is optionally substituted with one or two substituents, independently of each other selected from $R^1$; or a pyrazolo, imidazo, oxazolo, thiazolo, isoxazolo, or isothiazolo ring wherein each of said rings is optionally substituted with $R^1$; or a 1,2,3-triazolo ring substituted with $R^N$; and B denotes a 5- to 8-membered monocyclic, 7- to 12-membered spirocyclic, 6- to 12-membered bicyclic, or 9- to 15-membered tricyclic cycloalkyl group, each of which is optionally saturated or partially unsaturated, and wherein 1 or 2 —$CH_2$— groups optionally are replaced by —$NR^N$—, and wherein 1 to 4 —$CH_2$— groups, which are not directly linked together, optionally are replaced independently of each other by O, S, carbonyl, or sulfonyl, and wherein 1 or 2 CH groups optionally are replaced by N, and wherein each cycloalkyl group mentioned above optionally is substituted with one or more substituents independently of each other selected from $L^1$, and wherein each said cycloalkyl group optionally is substituted with 1 or 2 substituents independently of each other selected from $L^2$, and wherein 2 adjacent C-atoms of each said cycloalkyl group optionally are substituted with $L^3$ and $L^4$, and wherein 2 adjacent C-atoms of each said cycloalkyl group optionally are substituted with $L^5$ and $L^6$, with the proviso that two of $L^3$ to $L^6$ are not attached to the same carbon atom;

$R^N$ independently of each other denotes hydrogen, $C_{1-6}$-alkyl, $C_{3-6}$-alkenyl, $C_{3-6}$-alkynyl, $C_{3-6}$-cycloalkyl, (het)aryl, $C_{1-4}$-alkylcarbonyl, $C_{1-4}$-alkyloxycarbonyl, $C_{1-4}$-alkylaminocarbonyl, di-($C_{1-3}$-alkyl)aminocarbonyl, $C_{1-4}$-alkylsulfonyl, (het)arylcarbonyl, (het)arylaminocarbonyl, or (het)arylsulfonyl, wherein each alkyl, alkenyl, and alkynyl group optionally is mono- or polysubstituted with fluorine, and optionally is monosubstitued with hydroxy, $C_{1-4}$-alkoxy, $C_{1-4}$-alkylsulfanyl, $C_{1-4}$-alkylsulfinyl, $C_{1-4}$-alkylsulfonyl, amino, $C_{1-4}$-alkylamino, di-($C_{1-4}$-alkyl)amino, $C_{1-4}$-alkylcarbonylamino, cyano, carboxy, $C_{1-4}$-alkoxycarbonyl, aminocarbonyl, $C_{1-4}$-alkylaminocarbonyl, di-($C_{1-4}$-alkyl)aminocarbonyl, or (het)aryl, $R^1$ denotes fluorine, chlorine, bromine, iodine, cyano, nitro, $C_{1-4}$-alkyl, hydroxy, $C_{1-4}$-alkyloxy, $C_{3-6}$-alkenyloxy, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, tetrahydrofuran-3-yloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, $C_{1-3}$-alkyl-carbonyl, (het)aryl-carbonyl, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)aryl-carbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, $C_{1-3}$-alkyl-sulfonylamino, aminosulfonylamino, $C_{1-3}$-alkylamino-sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, piperazin-1-yl-sulfonylamino, 4-($C_{1-3}$-alkyl)-piperazin-1-yl-sulfonylamino, ($C_{1-3}$-alkyloxy-carbonylamino)carbonylamino, (het)arylsulfonylamino, (het)aryl-$C_{1-3}$-alkyl-sulfonylamino, N—($C_{1-3}$-alkyl)-$C_{1-3}$-alkyl-carbonylamino, N—($C_{1-3}$-alkyl)-(het)arylcarbonylamino, N—($C_{1-3}$-alkyl)-(het)aryl-$C_{1-3}$-alkyl-carbonylamino, N—($C_{1-3}$-alkyl)-$C_{1-3}$-alkyloxy-carbonylamino, N-(aminocarbonyl)-$C_{1-3}$-alkylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino, N—($C_{1-3}$-alkyl)-$C_{1-3}$-alkyl-sulfonylamino, N—($C_{1-3}$-alkyl)-(het)arylsulfonylamino, N—($C_{1-3}$-alkyl)-(het)aryl-$C_{1-3}$-alkyl-sulfonylamino, oxo-imidazolidin-1-yl, 2,4-dioxo-imidazolidin-1-yl, 2,5-dioxo-imidazolidin-1-yl, 2-oxo-hexahydropyrimidin-1-yl, wherein the nitrogen atom in position 3 of the aforementioned groups is optionally substituted with methyl or ethyl, (hydroxyimino)aminomethyl, ($C_{1-3}$-alkyloxyimino)aminomethyl, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl)-piperazin-1-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di- ($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyloxy, piperazin-1-yl-carbonyl-$C_{1-3}$-alkyloxy, 4-($C_{1-3}$-alkyl)-piperazin-1-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, $C_{1-4}$-alkylcarbonyl-amino-$C_{1-3}$-alkyl, N—($C_{1-3}$-alkyl)-$C_{1-4}$-alkylcarbonyl-amino-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)-piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)-piperazin-1-yl-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)-piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkysulfonyl, $C_{1-3}$-alkylsulfonyl, $C_{1-3}$-alkylsulfonyloxy, (het)arylsulfonyl, (het)arylsulfonyloxy, trifluoromethylsulfanyl, trifluoromethylsulfinyl, trifluoromethylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, or 4-($C_{1-3}$-alkyl)-piperazin-1-yl-sulfonyl, wherein the above-mentioned saturated heterocycles and cycloalkyl-rings are optionally substituted with one or two groups selected independently from fluorine, $C_{1-3}$-alkyl, $C_{1-3}$-alkoxy, $C_{1-3}$-alkoxy-$C_{1-3}$-alkyl, and hydroxy, $R^2$, $R^3$ are linked to each other to form a methylenedioxy, ethylenedioxy or $C_{3-5}$-alkylene bridging group, which optionally is mono- or disubstituted with methyl, and which optionally and independently is mono- or polyfluorinated; or $R^2$ and $R^3$ together, and combined with the carbon atoms to which they are attached, form a benzo, pyrido, pyrazino, pyridazino, pyrimido, pyrrolo, furano, thieno, pyrazolo, imidazo, triazolo, oxazolo, thiazolo, isoxazolo, or isothiazolo ring, wherein each of said rings optionally is substituted with one or more substituents, preferably one to three substituents, independently of each other selected from halogen, $C_{1-3}$-alkyl, trifluoromethyl, amino, $C_{1-3}$-alkylamino, di-($C_{1-3}$-alkyl)amino, $C_{1-3}$-alkylcarbonylamino, $C_{1-3}$-alkylsulfonylamino, hydroxy, cyano, carboxy, $C_{1-3}$-alkyloxycarbonyl and $C_{1-3}$-alkyloxy, $R^{10}$ denotes halogen, $C_{1-3}$-alkyl, difluoromethyl, trifluoromethyl, cyano, nitro, amino, $C_{1-3}$-alkylamino, di-($C_{1-3}$-alkyl)amino, acetylamino, $C_{1-3}$-alkylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, hydroxy, $C_{1-3}$-alkyloxy, difluoromethoxy, trifluoromethoxy, or phenyl optionally substituted with 1 or 2 substituents independently of each other selected from fluorine, methyl, methoxy, cyano, and hydroxy, $R^{11}$ denotes fluorine, $C_{1-4}$-alkyl, (het)aryl, hydroxy, $C_{1-4}$-alkyloxy, cyano, carboxy, $C_{1-4}$-alkyloxycarbonyl, aminocarbonyl, $C_{1-4}$-alkylamino-carbonyl, di-($C_{1-4}$-alkyl)-aminocarbonyl, hydroxy-$C_{1-4}$-alkyl or $C_{1-3}$-alkyloxy-$C_{1-4}$-alkyl, $R^{12}$ denotes fluorine or $C_{1-4}$-alkyl, and $L^1$ denotes halogen, $C_{1-4}$-alkyl, trifluoromethyl, hydroxy, $C_{1-4}$-alkyloxy, or cyano;

$L^2$ denotes fluorine, chlorine, bromine, iodine, nitro, cyano, hydroxy, $C_{3-6}$-cycloalkyl, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl, (het)aryloxy, $C_{1-6}$-alkyl, $C_{2-6}$-alkenyl, $C_{2-6}$-alkynyl, $C_{1-6}$-alkyloxy, $C_{1-6}$-alkylamino, wherein in each group one $CH_2$ group optionally is replaced by carbonyl or sulfonyl, and wherein each group optionally is mono or polyfluorinated, and wherein each group optionally is additionally substituted with hydroxy, chlorine, $C_{1-3}$-alkyl, $C_{3-6}$-cycloalkyl, $C_{1-3}$-alkyloxy, amino, $C_{1-3}$-alkyl-amino, di-($C_{1-3}$-alkyl)-amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 2-oxo-4-($C_{1-3}$-alkyl)-piperazin-1-yl, 3-oxo-4-($C_{1-3}$-alkyl)-piperazin-1-yl, carboxy, $C_{1-3}$-alkyloxy-carbonyl, cyano, aminocarbonyl, $C_{1-3}$-alkylaminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, $C_{1-3}$-alkylcarbonylamino, arylcarbonylamino, $C_{1-3}$-alkylsulfanyl, $C_{1-3}$-alkylsulfinyl, $C_{1-3}$-alkylsulfonyl, $C_{3-6}$-cycloalkyl, (het)aryl, or (het)aryloxy;

or $L^2$ denotes amino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, (het)aryl-carbonylamino, $C_{1-4}$-alkyloxy-carbonylamino, aminocarbonylamino, $C_{1-4}$-alkyl-aminocarbonylamino, (het)aryl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, aminosulfonylamino, $C_{1-3}$-alkylamino-sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, piperazin-1-yl-sulfonylamino, 4-($C_{1-3}$-alkyl)-piperazin-1-yl-sulfonylamino, ($C_{1-3}$-alkyloxy-carbonylamino)carbonylamino, (het)arylsulfonylamino, N—($C_{1-3}$-alkyl)-$C_{1-3}$-alkyl-carbonylamino, N—($C_{1-3}$-alkyl)-(het)arylcarbonylamino, N—($C_{1-3}$-alkyl)-(het)aryl-$C_{1-3}$-alkyl-carbonylamino, N—($C_{1-3}$-alkyl)-$C_{1-3}$-alkyloxy-carbonylamino, N-(aminocarbonyl)-$C_{1-3}$- alkylamino, N—(C$_{1-3}$-alkyl-aminocarbonyl)-C$_{1-3}$-alkylamino, N-[di-(C$_{1-3}$-alkyl)aminocarbonyl]-C$_{1-3}$-alkylamino,
N—(C$_{1-3}$-alkyl)-C$_{1-3}$-alkyl-sulfonylamino, N—(C$_{1-3}$-alkyl)-(het)arylsulfonylamino, N—(C$_{1-3}$-alkyl)-(het)aryl-C$_{1-3}$-alkyl-sulfonylamino,
carboxy, C$_{1-3}$-alkyloxy-carbonyl, aminocarbonyl, C$_{1-3}$-alkyl-aminocarbonyl, di-(C$_{1-3}$-alkyl)-aminocarbonyl, azetidin-1-yl-carbonyl, pyrrolidin-1-yl-carbonyl, piperidin-1-yl-carbonyl, morpholin-4-yl-carbonyl, piperazin-1-yl-carbonyl, 4-(C$_{1-3}$-alkyl)-piperazin-1-yl-carbonyl, (het)arylaminocarbonyl, N—(C$_{1-3}$-alkyl)-(het)arylaminocarbonyl, (het)aryl-C$_{1-3}$-alkylaminocarbonyl, N—(C$_{1-3}$-alkyl)-(het)aryl-C$_{1-3}$-alkylaminocarbonyl,
C$_{1-3}$-alkylsulfanyl, C$_{1-3}$-alkylsulfinyl, (het)arylsulfonyl, trifluoromethylsulfanyl, trifluoromethylsulfinyl,
aminosulfonyl, C$_{1-3}$-alkyl-aminosulfonyl, di-(C$_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-(C$_{1-3}$-alkyl)-piperazin-1-yl-sulfonyl,
wherein the saturated heterocycles and cycloalkyl-rings mentioned in the definition of L$^2$ as a single unit or a sub-moiety within another group are optionally substituted with one or two groups selected from fluorine, C$_{1-3}$-alkyl, C$_{1-3}$-alkoxy, C$_{1-3}$-alkoxy-C$_{1-3}$-alkyl, and hydroxy, and
L$^3$ and L$^4$ are linked to each other and
L$^5$ and L$^6$ are linked to each other, such that independently of each other and in each case together with the 2 adjacent C-atoms to which either L$^3$ and L$^4$ or L$^5$ and L$^6$ are attached an aryl- or heteroaryl-group is formed which is fused to the cyclic group B and which is optionally substituted with 1, 2, or 3 identical or different groups selected from R$^{10}$,
while by aryl is meant phenyl or naphthyl and
by heteroaryl is meant pyrrolyl, furanyl, thienyl, pyridyl, indolyl, benzofuranyl, benzothiophenyl, quinolinyl, isoquinolinyl, or
pyrrolyl, furanyl, thienyl, and pyridyl wherein in each 1 or 2 CH groups are replaced by N, or indolyl, benzofuranyl, benzothiophenyl, quinolinyl, and isoquinolinyl wherein in each 1 to 3 CH groups are replaced by N, and
where in each >N—H containing heteroaryl all the >N—H groups present are optionally replaced by other groups independently selected from >N—R$^N$,
while the (het)aryl mentioned hereinbefore as a single unit or a sub-moiety within another group is an aryl group as defined hereinbefore, or a heteroaryl group as defined hereinbefore, or a ring selected from the group consisting of 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl and 3,4-dihydro-3-oxo-2H-benzo-[1,4]oxazinyl, wherein each of said rings is optionally substituted with 1, 2, or 3 substituents independently of each other selected from R$^{10}$, and
where in each >N—H containing (het)aryl all the >N—H groups present are optionally replaced by other groups independently selected from >N—R$^N$,
whilst each of the above-mentioned alkyl or alkylene moieties may be branched or unbranched,
the tautomers, the stereoisomers thereof, the mixtures thereof, and the salts thereof,
while the compounds comprised by the general formula II

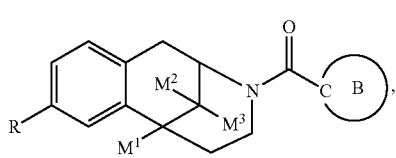

wherein
R is hydrogen or R'O, while R' is any substituent,
M$^1$ is methyl, ethyl, propyl, or phenyl,
M$^2$ and M$^3$ independently of each other are hydrogen, methyl, ethyl, or hydroxy, and ring B is
C$_{5-8}$-cycloalkyl or C$_{5-8}$-cycloalkenyl each of which is optionally substituted with one or more C$_{1-5}$-alkyl groups resulting in B having ≤10 carbon atoms in total, or cyclopentyl which is substituted with one methyl group and wherein one or more carbon atoms are replaced by O, S, N, or
1-(C$_{1-3}$-alkoxy)-cyclopent-1-yl, 1-(C$_{1-3}$-alkoxy)-cyclohex-1-yl, 3-hydroxycyclohexyl, 4-hydroxycyclohexyl, 3-acetoxy-cyclohexyl, 4-acetoxy-cyclohexyl, cyclohexanon-4-yl, tetrahydrofuryl, 1-methyl-1,2,3,6-tetrahydro-pyridin-4-yl, 1-methyl-1,2,5,6-tetrahydro-pyridin-3-yl, 1,2,3,4-tetrahydro-naphthalen-1-yl, 1,2,3,4-tetrahydro-naphthalen-2-yl, bicyclo[2.2.1]heptyl, bicyclo[2.2.1]heptenyl, bicyclo[2.2.1]hepta-2,5-dien-7-yl, 1-aza-bicyclo[2.2.1]heptyl, 1-aza-bicyclo[2.2.2]octyl, or adamant-1-yl,
are excluded.

The compounds of general formula I according to the invention and the physiologically acceptable salts thereof have valuable pharmacological properties, particularly an inhibitory effect on the enzyme 11β-hydroxysteroid dehydrogenase (HSD) 1.

A further aspect of the invention also relates to the physiologically acceptable salts of the compounds of general formula I according to this invention with inorganic or organic acids.

In a further aspect this invention relates to pharmaceutical compositions, containing at least one compound of general formula I or a physiologically acceptable salt according to the invention, optionally together with one or more inert carriers and/or diluents.

In a further aspect this invention relates to the compounds according to general formula I, including the compounds of general formula II, or the physiologically acceptable salts thereof, for treatment or prevention of diseases or conditions which can be influenced by inhibiting the enzyme 11β-hydroxysteroid dehydrogenase (HSD) 1, such as metabolic disorders.

In a further aspect this invention relates to the use of at least one compound according to general formula I, including the compounds of general formula II, or one of the physiologically acceptable salts thereof for preparing a pharmaceutical composition which is suitable for the treatment or prevention of diseases or conditions which can be influenced by inhibiting the enzyme 11β-hydroxysteroid dehydrogenase (HSD) 1, such as metabolic disorders.

In a further aspect the present invention relates to a process for preparing the compounds of general formula I, characterized in that
in order to prepare compounds of general formula I which are defined as hereinbefore and hereinafter,
an amine of the general formula III

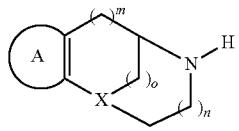

III wherein
the groups A, X, m, n, and o are defined as hereinbefore and hereinafter,
is reacted with a compound of the general formula IV

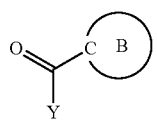

IV wherein B is defined as hereinbefore and hereinafter and wherein Y is a leaving group and in particular denotes
fluorine, chlorine, bromine, cyano, $C_{1-4}$-alkoxy, $C_{2-4}$-alkenyloxy, $C_{2-4}$-alkynyloxy, partially or fully fluorinated $C_{2-10}$-alkoxy, $C_{1-4}$-alkylsulfanyl, oxyarylotriazol, oxyheteroarylotriazol, heteroaryl, succinyl-N-oxy, $C_{1-4}$-alkylcarbonyloxy, di-($C_{1-4}$-alkyl)-aminocarbonyloxy, pyrrolylcarbonyloxy, piperidinylcarbonyloxy, morpholinyl-carbonyloxy, tri-($C_{1-4}$-alkyl)-carbamimidoyloxy, N,N,N',N'-tetra-($C_{1-4}$-alkyl)uronyl, N,N'-dicyclohexyluronyl, di-($C_{1-4}$-alkyloxy)-phosphoryloxy, di-(di-$C_{1-4}$-alkylamino)-phosphoryloxy, dipyrrolidinophosphoryloxy, aryloxy, arylsulfanyl, heterosulfanyl, or heteroaryloxy,
while the alkyl, alkenyl, and alkynyl groups mentioned in the definition of the above groups, either alone or as part of another group, optionally are mono- or polysubstituted with fluorine, chlorine, $C_{1-3}$-alkyl, and/or $C_{1-3}$-alkoxy,
while the aryl groups mentioned in the definition of the above groups, either alone or as part of another group, denote phenyl or naphthyl groups and the heteroaryl groups mentioned in the definition of the above groups, either alone or as part of another group, denote pyridinyl, pyrimidinyl, triazinyl, imidazolyl, pyrazolyl, triazolyl, tetrazolyl, whilst both the aryl and heteroaryl groups optionally are independently mono- or polysubstituted with fluorine, chlorine, bromine, $C_{1-3}$-alkyl, $C_{1-3}$-alkyloxy, nitro, cyano, and/or di-($C_{1-3}$-alkyl)amino groups,
optionally in the presence of a base such as an amine, e.g. ethyldiisopropylamine, triethylamine, imidazole, or pyridine, or an inorganic base, e.g. potassium carbonate or calcium oxide, and/or an additive such as 4-dimethylaminopyridine or 1-hydroxybenzotriazol; while the reations are preferably conducted between 0 and 120° C. in solvents or mixture of solvents that are preferably selected from tetrahydrofuran, 1,2-dimethoxyethane, ether, 1,4-dioxane, N,N-dimethylformamide, N,N-dimethylacetamide, N-methylpyrrolidinone, acetonitrile, dichloromethane, 1,2-dichloroethane, toluene, benzene, hexanes, and ethyl acetate, but also aqueous and alcoholic solutions may be usable for some of the combinations listed above;
and, if necessary any protective group used in the reactions described above is cleaved concurrently or subsequently;
if desired a compound of general formula I thus obtained is resolved into its stereoisomers;
if desired a compound of general formula I thus obtained is converted into the salts thereof, particularly for pharmaceutical use into the physiologically acceptable salts thereof.

DETAILED DESCRIPTION OF THE INVENTION

Unless otherwise stated, the groups, residues, and substituents, particularly A, B, $R^N$, $R^1$, $R^2$, $R^3$, $R^{10}$, $R^{11}$, $R^{12}$, $L^1$, $L^2$, $L^3$, $L^4$, $L^5$, $L^6$, X, m, n, and o are defined as above and hereinafter. If residues, substituents, or groups occur several times in a compound they may have the same or different meanings. Some preferred meanings of individual scaffolds, groups, and substituents of the compounds according to the invention will be given hereinafter.

The indexes m, n, and o each denote independently of each other 0, 1, or 2. Preferably m, n, and o are chosen such that the sum of m+n+o is 2, 3, or 4.

Preferred embodiments of this invention are described by each of the formulae I.1 to I.9

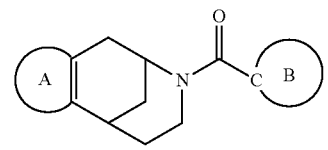

I.1

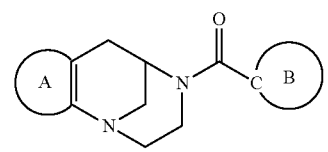

I.2

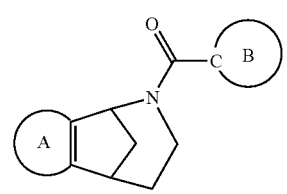

I.3

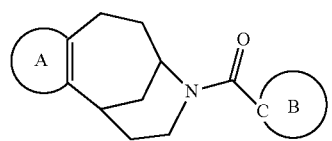

I.4

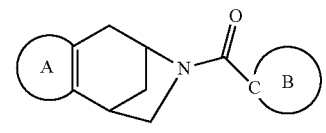

I.5

-continued

I.6

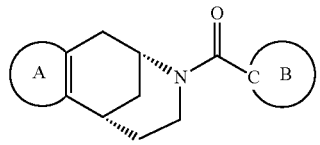

I.1-SS

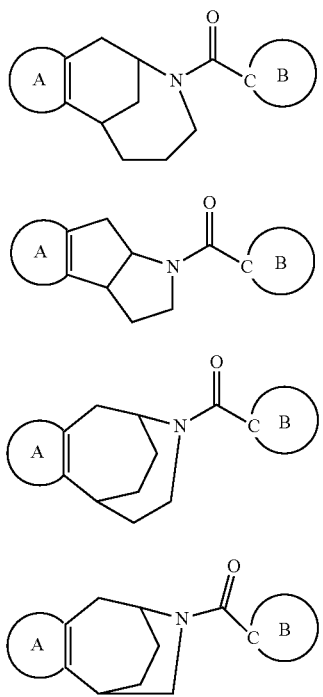

wherein the bicyclic azacycloalkene core structure of general formulae I.1 to I.9 condensed with ring A and attached to the carbonyl group is optionally substituted with 1, 2, or more substituents, preferably with 1 to 5, most preferred 1, 2, or 3 substituents, independently of each other selected from the group consisting of $R^{11}$ and $R^{12}$, and wherein the rings A and B are defined as hereinbefore and hereinafter, their tautomers, their stereoisomers, mixtures thereof, and the salts thereof, while the compounds of general formula II as defined above are excluded.

According to a preferred embodiment of the general formula I.1 compounds of the invention are described by the formula I.1-RR

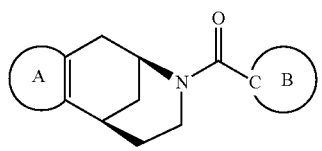

I.1-RR wherein the 2,6-methano-azocin core structure with the stereochemical configuration as depicted is optionally substituted with 1, 2, or more substituents independently of each other selected from the group consisting of $R^{11}$ and $R^{12}$, and wherein the rings A, B and $R^{11}$, $R^{12}$ are defined as hereinbefore and hereinafter, their tautomers, their stereoisomers, mixtures thereof, and the salts thereof.

According to another preferred embodiment of the general formula I.1a compounds of the invention are described by the formula I.1-SS wherein the 2,6-methano-azocin core structure with the stereochemical configuration as depicted is optionally substituted with 1, 2, or more substituents, preferably 1, 2, 3, 4, or 5 substituents, independently of each other selected from the group consisting of $R^{11}$ and $R^{12}$, and wherein the rings A, B and $R^{11}$, $R^{12}$ are defined as hereinbefore and hereinafter, their tautomers, their stereoisomers, mixtures thereof, and the salts thereof.

Even more preferred compounds are described by the formulae I.1 to I.9 and I.1-RR and I.1-SS wherein the bicyclic azacycloalkene core structure of general formulae I.1 to I.9 condensed with ring A and attached to the carbonyl group is optionally mono-substituted with $R^{11}$ and optionally substituted with 1, 2, or 3 substituents independently of each other selected from $R^{12}$.

Further preferred embodiments of the invention are characterized by the following definitions:

a) Definitions ($a^i$) for A in the order of preference, ascending from preferably ($a^1$) to more preferably ($a^2$) up to most preferably ($a^3$):

($a^1$): Preferably, the ring A denotes a benzo ring, which is optionally substituted with one to three substituents independently of each other selected from $R^1$ or wherein 2 adjacent C-atoms are optionally substituted with $R^2$ and $R^3$ and one carbon atom is optionally substituted with $R^1$;

or a pyrido, pyrrolo, furo, thieno, pyridazino, or pyrazino ring, wherein each of said rings 2 adjacent C-atoms are optionally substituted with $R^2$ and $R^3$ and/or any hydrogen atom bound to a carbon atom of said rings optionally is substituted by a group independently selected from $R^1$; or a pyrimido ring which is optionally substituted with one or two substituents independently of each other selected from $R^1$; or a pyrazolo, oxazolo, thiazolo, or imidazo ring each of which is optionally substituted with $R^1$.

($a^2$): More preferably, the ring A denotes a benzo, pyrrolo, or pyrido ring, wherein each of said rings is optionally substituted with one or two substituents, independently of each other selected from $R^1$, and wherein 2 adjacent C-atoms of each of said rings are optionally substituted with $R^2$ and $R^3$.

($a^3$): Most preferably, the ring A denotes a benzo ring, which is optionally substituted with one or two substituents, independently of each other selected from $R^1$, and wherein 2 adjacent C-atoms are optionally substituted with $R^2$ and $R^3$.

b) Definitions ($b^i$) for B in the order of preference, ascending from preferably ($b^1$) to more preferably ($b^2$) up to most preferably ($b^3$):

($b^1$): Ring B preferably denotes cyclopentyl, cyclohexyl, cycloheptyl, or cyclooctyl, each of which optionally is partially unsaturated, and wherein one or two —$CH_2$— groups independently of each other optionally are replaced by O, S, carbonyl, or sulfonyl, and wherein one or two —$CH_2$— group(s) optionally are replaced by —$NR^N$—, bicyclohexyl, bicycloheptyl, bicyclooctyl, bicyclononyl, bicyclodecyl, or bicycloundecyl, each of which optionally is partially unsaturated, and in each of which one or two —$CH_2$— groups optionally are replaced independently of each other by O, S, —NR$^N$—, carbonyl, or sulfonyl, and in each of which one CH group optionally is replaced by N, spiro[2.4]heptyl, spiro[3.4]octyl, spiro[4.4]nonyl, spiro[4.5]decyl, or spiro[5.5]undecyl, each of which optionally is partially unsaturated, and in each of which one or two —CH$_2$— groups optionally are replaced independently of each other by O, S, —NR$^N$—, carbonyl, or sulfonyl, tricyclononyl, tricyclodecyl, tricycloundecyl, tricyclododecyl, tricyclotridecyl, or tricyclotetradecyl, in each of which one or two —CH$_2$— groups optionally are replaced independently of each other by O, S, NR$^N$, carbonyl, or sulfonyl, and in each of which one CH group optionally is replaced by N, wherein each of the rings B above optionally is substituted with one or more substituents, preferably 1, 2, 3, or 4 substituents, independently of each other selected from L$^1$, and/or wherein each of the rings B above optionally is substituted with 1 or 2 substituents independently of each other selected from L$^2$, and/or wherein 2 adjacent C-atoms of each of the rings B above optionally are substituted with L$^3$ and L$^4$, and/or wherein 2 adjacent C-atoms of each of the rings B above optionally are substituted with L$^5$ and L$^6$, with the proviso that two of L$^3$ to L$^6$ cannot be attached to the same carbon atom.

(b$^2$): More preferably, the ring B denotes cyclopentyl, cyclohexyl, or cycloheptyl, each of which optionally is partially unsaturated, and wherein one or two —CH$_2$— groups independently of each other optionally are replaced by O, S, carbonyl, or sulfonyl, and wherein one or two —CH$_2$— group(s) optionally are replaced by —NR$^N$—, bicyclo[3.1.0]hexyl, bicyclo[2.1.1]hexyl, bicyclo[2.2.1]heptyl, bicyclo[4.1.0]heptyl, bicyclo-[2.2.2]octyl, bicyclo[3.2.1]octyl, bicyclo[3.3.1]nonyl, bicyclo[4.2.1]nonyl, bicyclo[3.2.2]nonyl, bicyclo[5.2.1]decyl, bicyclo[4.2.2]decyl, bicyclo[3.3.2]decyl, each of which is optionally partially unsaturated, and in each of which one or two —CH$_2$— groups are optionally replaced independently of each other by O, S, —NR$^N$—, carbonyl, or sulfonyl, and in each of which one CH group is optionally replaced by N, adamantyl, in which one —CH$_2$— group may be replaced by O, S, —NR$^N$—, carbonyl, or sulfonyl, and in which one CH group is optionally replaced by N, wherein each of the rings B above is optionally substituted with one or more, preferably 1, 2, 3, or 4 substituents, independently of each other selected from L$^1$, and/or wherein each of the above rings B optionally is substituted with 1 or 2 substituents independently of each other selected from L$^2$, and/or wherein 2 adjacent C-atoms of each of the above rings B optionally are substituted with L$^3$ and L$^4$.

(b$^3$): Most preferably, the ring B denotes cyclopentyl, cyclohexyl, cycloheptyl, 4-oxo-cyclohexyl, pyrrolidin-2-yl, pyrrolidin-3-yl, 2-oxo-pyrrolidin-3-yl, 5-oxo-pyrrolidin-2-yl, 5-oxo-pyrrolidin-3-yl, piperidin-2-yl, piperidin-2-yl, piperidin-3-yl, 6-oxo-piperidin-3-yl, 1,4-dioxanyl, 2-aza-bicyclo[3.1.0]hex-1-yl, 2-aza-bicyclo[2.1.1]hex-1-yl, bicyclo[2.2.1]hept-2-yl, bicyclo[2.2.1]hept-5-en-2-yl, 3-oxo-2-oxa-bicyclo[2.2.1]hept-1-yl, bicyclo[2.2.2]oct-1-yl, bicyclo[2.2.2]oct-2-yl, adamant-1-yl, or adamant-2-yl, wherein each of the above rings B optionally is substituted with one or more, preferably 1, 2, or 3 substituents, independently of each other selected from L$^1$, and/or wherein each of the rings B above optionally is substituted with 1 or 2 substituents independently of each other selected from L$^2$, and/or wherein 2 adjacent C-atoms of each of the above rings B optionally are substituted with L$^3$ and L$^4$ and wherein each >N—H group in the rings B above is replaced by >N—R$^N$.

c) Definitions (c$^i$) for R$^N$ in the order of preference, ascending from preferably (c$^1$) to more preferably (c$^2$) up to most preferably (c$^3$):

(c$^1$): Preferably, R$^N$ denotes hydrogen, C$_{1-6}$-alkyl, C$_{3-6}$-alkenyl, C$_{3-6}$-cycloalkyl, C$_{1-4}$-alkyl-carbonyl, phenylcarbonyl, C$_{1-4}$-alkyloxycarbonyl, C$_{1-3}$-alkylaminocarbonyl, phenylaminocarbonyl, phenyl, C$_{1-4}$-alkylsulfonyl, or phenylsulfonyl, wherein each alkyl group and alkyl sub-moiety optionally is mono- or polysubstituted with fluorine and optionally monosubstituted with hydroxy, C$_{1-4}$-alkoxy, C$_{1-4}$-alkylcarbonylamino, cyano, carboxy, C$_{1-4}$-alkoxycarbonyl, aminocarbonyl, C$_{1-4}$-alkylaminocarbonyl, di-(C$_{1-4}$-alkyl)aminocarbonyl, or phenyl, and wherein each phenyl group and phenyl sub-moiety again optionally is mono- or disubstituted with R$^{10}$.

(c$^2$): More preferably, R$^N$ denotes hydrogen, C$_{1-6}$-alkyl, C$_{5-6}$-cycloalkyl, C$_{1-4}$-alkylcarbonyl, phenylcarbonyl, C$_{1-4}$-alkyloxycarbonyl, C$_{1-3}$-alkylaminocarbonyl, phenylaminocarbonyl, phenyl, C$_{1-4}$-alkylsulfonyl, or phenylsulfonyl, wherein each alkyl group and alkyl sub-moiety optionally is mono- or polysubstituted with fluorine and optionally monosubstitued with hydroxy, C$_{1-4}$-alkoxy, cyano, or phenyl, and wherein each phenyl group and phenyl sub-moiety again optionally is mono- or disubstituted with R$^{10}$.

(c$^3$): Most preferably, R$^N$ denotes hydrogen, methyl, propyl, isopropyl, 3-methyl-but-1-yl, cyclopentyl, cyanoethyl, benzyl, acetyl, ethylcarbonyl, propylcarbonyl, benzylcarbonyl, phenylcarbonyl, teributoxycarbonyl, ethylaminocarbonyl, phenylaminocarbonyl, phenyl, methylsulfonyl, phenylsulfonyl, or 3-chloro-2-methylphenylsulfonyl.

d) definitions (d$^i$) for L$^1$ in the order of preference, ascending from preferably (d$^1$) to more preferably (d$^2$) up to most preferably (d$^3$):

(d$^1$): Preferably, substituents L$^1$ are selected from the group consisting of fluorine, chlorine, C$_{1-4}$-alkyl, trifluoromethyl, hydroxy, C$_{1-4}$-alkoxy, and cyano, (d$^2$): more preferably, fluorine, methyl, ethyl, trifluoromethyl, hydroxy, methoxy, ethoxy, and cyano, (d$^3$): most preferably, fluorine, methyl, hydroxy, and methoxy.

e) Definitions (e$^i$) for L$^2$ in the order of preference, ascending from preferably (e$^1$) to more preferably (e$^2$) up to most preferably (e$^3$):

(e$^1$): Preferably, substituents L$^2$, are selected from the group consisting of fluorine, chlorine, bromine, cyano, hydroxy, C$_{1-6}$-alkyl, C$_{2-6}$-alkenyl, C$_{2-6}$-alkynyl, C$_{1-4}$-alkyloxy, difluoromethyl, trifluoromethyl, difluoromethoxy, trifluoromethoxy, C$_{3-6}$-cycloalkyl, C$_{3-6}$-cycloalkyloxy, C$_{3-6}$-cycloalkyl-C$_{1-3}$-alkyl, C$_{3-6}$-cycloalkyl-C$_{1-3}$-alkyloxy, (het)aryl, (het)aryloxy, (het)aryl-C$_{1-3}$-alkyl, (het)aryl-C$_{1-3}$-alkyloxy, (het)aryloxy-C$_{1-3}$-alkyl, amino, C$_{1-3}$-alkylamino, (het)aryl-C$_{1-3}$-alkylamino, di-(C$_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-(C$_{1-3}$-alkyl)-piperazin-1-yl, 4-(C$_{1-4}$-alkylcarbonyl)-piperazin-1-yl, 4-(C$_{3-6}$-cycloalkylcarbonyl)-piperazin-1-yl, 4-(C$_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)aryl-carbonylamino, (het)aryl-$C_{1-3}$-alkyl-carbonylamino, $C_{1-4}$-alkyloxy-carbonylamino, aminocarbonylamino, $C_{1-4}$-alkyl-aminocarbonylamino, (het)aryl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, $C_{1-3}$-alkyl-sulfonylamino, $C_{3-6}$-cycloalkylsulfonylamino, aminosulfonylamino, $C_{1-3}$-alkylamino-sulfonylamino, di-($C_{1-3}$-alkyl)aminosulfonylamino, pyrrolidin-1-yl-sulfonylamino, piperidin-1-yl-sulfonylamino, morpholin-4-yl-sulfonylamino, piperazin-1-yl-sulfonylamino, 4-($C_{1-3}$-alkyl)-piperazin-1-yl-sulfonylamino, ($C_{1-3}$-alkyloxy-carbonylamino)carbonylamino, (het)arylsulfonylamino, (het)aryl-$C_{1-3}$-alkyl-sulfonylamino, N—($C_{1-3}$-alkyl)-$C_{1-3}$-alkyl-carbonylamino, N—($C_{1-3}$-alkyl)-(het)arylcarbonylamino, N—($C_{1-3}$-alkyl)-(het)aryl-$C_{1-3}$-alkyl-carbonylamino, N—($C_{1-3}$-alkyl)-$C_{1-3}$-alkyloxy-carbonylamino, N-(aminocarbonyl)-$C_{1-3}$-alkylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino, N—($C_{1-3}$-alkyl)-$C_{1-3}$-alkyl-sulfonylamino, N—($C_{1-3}$-alkyl)-(het)arylsulfonylamino, N—($C_{1-3}$-alkyl)-(het)aryl-$C_{1-3}$-alkyl-sulfonylamino, carboxy, $C_{1-3}$-alkyloxy-carbonyl, aminocarbonyl, $C_{1-3}$-alkyl-aminocarbonyl, di-($C_{1-3}$-alkyl)-aminocarbonyl, azetidin-1-ylcarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, (het)arylaminocarbonyl, N—($C_{1-3}$-alkyl)-(het)arylaminocarbonyl, (het)aryl-$C_{1-3}$-alkylamino-carbonyl, N—($C_{1-3}$-alkyl)-(het)aryl-$C_{1-3}$-alkylaminocarbonyl, $C_{1-3}$-alkyl-carbonyl, (het)aryl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl)-piperazin-1-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbo-nyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, piperazin-1-yl-carbonyl-$C_{1-3}$-alkyloxy, 4-($C_{1-3}$-alkyl)-piperazin-1-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)-piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)-piperazin-1-yl-$C_{1-3}$-alkyl, $C_{1-3}$-alkylcarbonylamino-$C_{1-3}$-alkyl, arylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkyl-amino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)-piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkylsulfinyl, $C_{1-3}$-alkylsulfonyl, (het)arylsulfonyl, trifluoromethylsulfanyl, trifluoromethylsulfinyl and trifluoromethylsulfonyl, wherein the saturated heterocycles and cycloalkyl-rings mentioned hereinbefore as a single unit or a sub-moiety within another group are optionally substituted with one or two groups independently of each other selected from $C_{1-3}$-alkyl, $C_{1-3}$-alkoxy, $C_{1-3}$-alkoxy-$C_{1-3}$-alkyl, and hydroxy, and wherein the (het)aryl mentioned hereinbefore as a single unit or a sub-moiety within another group is phenyl, naphthyl, pyrrolyl, furanyl, thienyl, pyridyl, indolyl, benzofuranyl, benzothiophenyl, quinolinyl, isoquinolinyl, or pyrrolyl, furanyl, thienyl, and pyridyl in each which 1 or 2 CH are replaced by N, or indolyl, benzofuranyl, benzothiophenyl, quinolinyl, and isoquinolinyl in each of which 1 to 3 CH are replaced by N, and wherein these above-mentioned (het)aryl groups are optionally substituted with one or two $R^{10}$ which may be identical or different.

($e^2$): More preferably, substituents $L^2$ are selected from the group consisting of fluorine, chlorine, bromine, cyano, $C_{1-6}$-alkyl, $C_{2-6}$-alkenyl, $C_{2-6}$-alkynyl, hydroxy, $C_{1-4}$-alkyloxy, trifluoromethyl, difluoromethoxy, trifluoromethoxy, $C_{3-6}$-cycloalkyl, $C_{3-6}$-cycloalkyloxy, phenyl, phenoxy, amino, $C_{1-3}$-alkylamino, di-($C_{1-3}$-alkyl)amino, phenylmethylamino, $C_{1-3}$-alkyl-carbonylamino, phenylmethylcarbonylamino, phenyl-carbonylamino, $C_{1-4}$-alkyloxycarbonylamino, $C_{1-4}$-alkyl-aminocarbonylamino, phenylaminocarbonylamino, $C_{1-3}$-alkyl-sulfonylamino, $C_{3-6}$-cycloalkylsulfonylamino, phenylmethylsulfonylamino, phenylsulfonylamino, N—($C_{1-3}$-alkyl)-$C_{1-3}$-alkyl-carbonylamino, N—($C_{1-3}$-alkyl)-phenylcarbonylamino, N—($C_{1-3}$-alkyl)-phenylmethylcarbonylamino, N—($C_{1-3}$-alkyl)-$C_{1-3}$-alkyl-sulfonylamino, carboxy, $C_{1-3}$-alkyloxy-carbonyl, aminocarbonyl, $C_{1-3}$-alkyl-aminocarbonyl, di-($C_{1-3}$-alkyl)-aminocarbonyl, phenylmethylaminocarbonyl, phenylaminocarbonyl, N—($C_{1-3}$-alkyl)-phenylaminocarbonyl, azetidin-1-ylcarbonyl, pyrrolidin-1-ylcarbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, amino-carbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-3}$-alkylcarbonylamino-$C_{1-3}$-alkyl, hydroxy-$C_{1-3}$-alkyloxy, $C_{1-3}$-alkyloxy-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, $C_{1-3}$-alkylsulfanyl, $C_{1-3}$-alkylsulfinyl, and $C_{1-3}$-alkylsulfonyl, wherein the phenyl groups mentioned hereinbefore as a single unit or a sub-moiety within another group are optionally substituted with one or two $R^{10}$ which may be identical or different.

($e^3$): Most preferably, substituents $L^2$ are selected from the group consisting of fluorine, $C_{1-3}$-alkyl, trifluoromethyl, hydroxy, $C_{1-3}$-alkyloxy, $C_{1-3}$-alkylamino, benzylamino, $C_{1-3}$-alkylcarbonylamino, phenylmethylcarbonylamino, phenylcarbonylamino, N-methyl-phenylmethylcarbonylamino, N-methyl-phenylcarbonylamino, $C_{1-4}$-alkyloxycarbonylamino, $C_{1-3}$-alkylsulfonylamino, $C_{3-6}$-cycloalkylsulfonylamino, phenylmethylsulfonylamino, phenylsulfonylamino, furan-2-ylsulfonylamino, thien-2-ylsulfonylamino, pyrazol-4-ylsulfonylamino, pyrid-3-ylsulfonylamino, $C_{1-4}$-alkylaminocarbonylamino, phenylaminocarbonylamino, carboxy, $C_{1-3}$-alkyloxycarbonyl, aminocarbonyl, $C_{1-3}$-alkylaminocarbonyl, di-($C_{1-3}$-alkyl)aminocarbonyl, phenylmethylaminocarbonyl, phenylaminocarbonyl, N-methyl-phenylmethylaminocarbonyl, N—$C_{1-3}$-alkyl-N-methylaminocarbonyl, azetidin-1-ylcarbonyl, pyrrolidin-1-ylcarbonyl, hydroxy-$C_{1-3}$-alkyl, or phenyl, while all above-mentioned phenyl groups are optionally mono- or disubstituted independently with fluorine, methyl, methoxy, hydroxy, and cyano; particularly $L^2$ is fluorine, methyl, n-propyl, isopropyl, trifluoromethyl, hydroxy, methoxy, isopropylamino, benzylamino, acetylamine, ethylcarbonylamino, propylcarbonylamino, isopropylcarbonylamino, benzylcarbonylamino, phenylcarbonylamino, tertbutoxycarbonylamino, methylsulfonylamino, ethylsulfonylamino, propylsulfonylamino, isopropylsulfonylamino, cyclopropylsulfonylamino, cyclohexylsulfonylamino, benzylsulfonylamino, phenylsulfonylamino, 2-methyl-phenylsulfonylamino, 3-methyl-phenylsulfonylamino, 4-methyl-phenylsulfonylamino, 2-methoxy-phenylsulfonylamino, 3-methoxyphenylsulfonylamino, 4-methoxy-phenylsulfonylamino, 2-fluoro-phenylsulfonylamino, 3-fluoro-phenylsulfonylamino, 2-fluoro-5-methyl-phenylsulfonylamino, 5-fluoro-2-methyl-phenylsulfonylamino, 2,5-dimethylphenylsulfonylamino, furan-2-ylsulfonylamino, 2,5-dimethylfuran-3-ylsulfonylamino, thien-2-ylsulfonylamino, 1-methyl-pyrazol-4-ylsulfonylamino, pyrid-3-ylsulfonylamino, tertbutylaminocarbonylamino, phenylaminocarbonylamino, N-methyl-benzylcarbonylamino, N-methyl-phenylcarbonylamino, carboxy, methoxycarbonyl, isopropoxycarbonyl, aminocarbonyl, methylaminocarbonyl, n-propylaminocarbonyl, benzylaminocarbonyl, phenylaminocarbonyl, dimethylaminocarbonyl, N-methyl-N-ethylaminocarbonyl, N-methyl-N-n-propylaminocarbonyl, N-methyl-N-isopropylaminocarbonyl, azetidin-1-ylcarbonyl, pyrrolidin-1-ylcarbonyl, hydroxymethyl, 2-hydroxy-prop-2-yl, and phenyl.

f) definitions (f$^i$) for $L^3$ and $L^4$ in the order of preference, ascending from preferably (f$^1$) to more preferably (f$^2$) up to most preferably (f$^4$):

(f$^1$): Preferably, $L^3$ and $L^4$, which are linked to each other, form with the adjacent carbon atoms to which they are attached an aryl- or heteroaryl-group which is fused to the cyclic group B, and which is optionally substituted with one to three identical or different $R^{10}$, while said aryl- or heteroaryl group is selected from the group consisting of phenyl, pyrrolyl, furanyl, thienyl, pyridyl, indolyl, benzofuranyl, benzothiophenyl, quinolinyl, isoquinolinyl, and pyrrolyl, furanyl, thienyl, and pyridyl wherein in each of them one —CH= group is replaced by —N=, and indolyl, quinolinyl, and isoquinolinyl wherein in each of them one or two —CH= groups are each replaced by —N=.

(f$^2$): More preferably, $L^3$ and $L^4$, which are linked to each other, form with the adjacent carbon atoms to which they are attached an aryl- or heteroaryl-group which is fused to the cyclic group B, wherein said fused aryl- or heteroaryl-group is selected from the group consisting of benzo, pyrido, pyrimido, pyrazino, pyridazino, pyrrolo, furano, thieno, imidazo, pyrazolo, oxazolo, isoxazolo, thiazolo, and isothiazolo, each of which is optionally substituted with one to three identical or different $R^{10}$.

(f$^3$): Even more preferably $L^3$ and $L^4$, which are linked to each other, form with the atoms to which they are linked an aryl- or heteroaryl-group which is fused to the cyclic group B, wherein said fused aryl- or heteroaryl-group is selected from the group consisting of benzo, pyrido, pyrimido, pyrazino, pyridazino, pyrrolo, furano, thieno, imidazo, pyrazolo, oxazolo, isoxazolo, thiazolo, and isothiazolo, each of which is optionally substituted with one to three identical or different $R^{10}$.

(f$^4$): Most preferably $L^3$ and $L^4$, which are linked to each other, form with the adjacent carbon atoms to which they are attached an aryl- or heteroaryl-group which is fused to the cyclic group B, wherein said fused aryl- or heteroaryl-group is selected from the group consisting of benzo, pyrido, pyrimido, pyrrolo, furano, thieno, imidazo and oxazolo group, each of which is optionally substituted with 1, 2, or 3 identical or different $R^{10}$, particularly benzo, which is optionally substituted with 1, 2, or 3 identical or different $R^{10}$.

g) definitions (g$^i$) for $L^5$ and $L^6$ in the order of preference, ascending from preferably (g$^1$) to more preferably (g$^2$) up to most preferably (g$^3$):

(g$^1$): Preferably, $L^5$ and $L^6$, which are linked to each other, form with the adjacent carbon atoms to which they are attached an aryl- or heteroaryl-group which is fused to the cyclic group B, wherein said fused aryl- or heteroaryl-group is selected from the group consisting of benzo, pyrido, pyrimido, pyrazino, pyridazino, pyrrolo, furano, thieno, imidazo, pyrazolo, oxazolo, isoxazolo, thiazolo, and isothiazolo, each of which is optionally substituted with one to three identical or different $R^{10}$, (g$^2$): more preferably selected from the group consisting of benzo, pyrido, pyrimido, pyrazino, and pyridazino, each of which is optionally substituted with one to three identical or different $R^{10}$, (g$^3$): most preferably benzo, which is optionally substituted with one to three identical or different $R^{10}$.

Regarding the definitions of $L^3$ and $L^4$ and of $L^5$ and $L^6$ in cases where an N-containing heteroaryl-group fused to the cyclic group B is formed, and where said N-containing hetero-aryl-group is substituted with hydroxy at the carbon atom adjacent to the nitrogen, a tautomeric amide substructure may be formed and both tautomers are part of the invention. Examples of substructures of the ring B wherein two adjacent C-atoms are substituted with $L^3$ and $L^4$, wherein a tautomeric amide is formed are depicted in the following table 1:

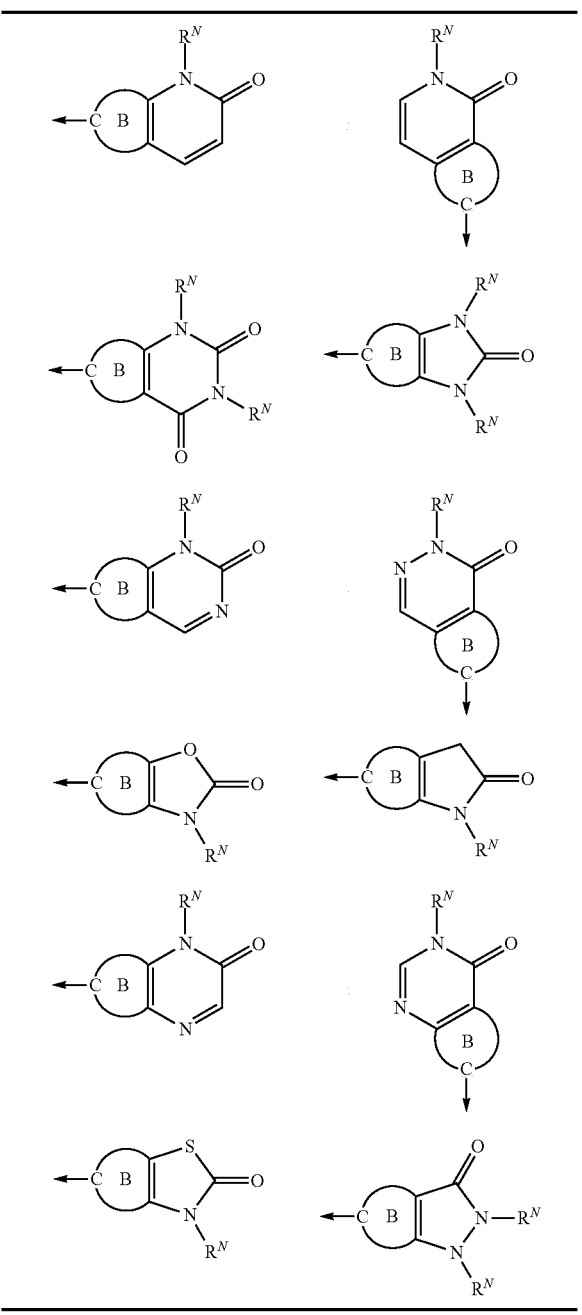

h) definitions (h$^i$) for R$^1$ in the order of preference, ascending from preferably (h$^1$) to more preferably (h$^2$) up to most preferably (h$^4$):

(h$^1$): Preferably, the substituent R$^1$ denotes fluorine, chlorine, cyano, C$_{1-4}$-alkyl, hydroxy, C$_{1-4}$-alkyloxy, C$_{3-5}$-alkenyloxy, difluoromethyl, trifluoromethyl, difluoromethoxy, trifluoromethoxy, C$_{3-6}$-cycloalkyl, C$_{3-6}$-cycloalkyloxy, C$_{3-6}$-cycloalkyl-C$_{1-3}$-alkyl, C$_{3-6}$-cycloalkyl-C$_{1-3}$-alkyloxy, tetrahydrofuran-3-yloxy, tetrahydropyran-3-yloxy, tetrahydropyran-4-yloxy, tetrahydrofuranyl-C$_{1-3}$-alkyloxy, tetrahydropyranyl-C$_{1-3}$-alkyloxy, (het)aryl, (het)aryloxy, (het)aryl-C$_{1-3}$-alkyl, (het)aryl-C$_{1-3}$-alkyloxy, (het)aryloxy-C$_{1-3}$-alkyl, C$_{1-3}$-alkyl-carbonyl, (het)aryl-carbonyl, amino, C$_{1-3}$-alkylamino, di-(C$_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, 3-oxo-piperazin-1-yl, 4-(C$_{1-4}$-alkylcarbonyl)-piperazin-1-yl, C$_{1-3}$-alkyl-carbonylamino, (het)aryl-carbonylamino, C$_{1-3}$-alkyloxy-carbonylamino, C$_{1-3}$-alkyl-aminocarbonylamino, di-(C$_{1-3}$-alkyl)aminocarbonylamino, pyrrolidin-1-yl-carbonylamino, piperidin-1-yl-carbonylamino, morpholin-4-yl-carbonylamino, C$_{1-3}$-alkyl-sulfonylamino, C$_{1-3}$-alkylamino-sulfonylamino, di-(C$_{1-3}$-alkyl)amino-sulfonylamino, pyrrolidin-1-yl-sulfonylamino, piperidin-1-yl-sulfonylamino, morpholin-4-yl-sulfonylamino, (het)arylsulfonylamino, N—(C$_{1-3}$-alkyl)-C$_{1-3}$-alkyl-carbonylamino, N—(C$_{1-3}$-alkyl)-(het)arylcarbonylamino, N—(C$_{1-3}$-alkyl)-C$_{1-3}$-alkyloxy-carbonylamino, N—(C$_{1-3}$-alkyl-aminocarbonyl)-C$_{1-3}$-alkylamino, N-[di-(C$_{1-3}$-alkyl)-aminocarbonyl]-C$_{1-3}$-alkylamino, N—(C$_{1-3}$-alkyl)-C$_{1-3}$-alkyl-sulfonylamino, N—(C$_{1-3}$-alkyl)-(het)arylsulfonylamino, (hydroxyimino)aminomethyl, (C$_{1-3}$-alkyloxyimino)aminomethyl, carboxy, C$_{1-3}$-alkyloxy-carbonyl, aminocarbonyl, C$_{1-3}$-alkyl-aminocarbonyl, di-(C$_{1-3}$-alkyl)-aminocarbonyl, pyrrolidin-1-yl-carbonyl, piperidin-1-yl-carbonyl, morpholin-4-yl-carbonyl, carboxy-C$_{1-3}$-alkyl, C$_{1-3}$-alkyloxy-carbonyl-C$_{1-3}$-alkyl, cyano-C$_{1-3}$-alkyl, aminocarbonyl-C$_{1-3}$-alkyl, C$_{1-3}$-alkyl-aminocarbonyl-C$_{1-3}$-alkyl, di-(C$_{1-3}$-alkyl)-aminocarbonyl-C$_{1-3}$-alkyl, pyrrolidin-1-yl-carbonyl-C$_{1-3}$-alkyl, piperidin-1-yl-carbonyl-C$_{1-3}$-alkyl, morpholin-4-yl-carbonyl-C$_{1-3}$-alkyl, carboxy-C$_{1-3}$-alkyloxy, C$_{1-3}$-alkyloxy-carbonyl-C$_{1-3}$-alkyloxy, cyano-C$_{1-3}$-alkyloxy, amino-carbonyl-C$_{1-3}$-alkyloxy, C$_{1-3}$-alkyl-aminocarbonyl-C$_{1-3}$-alkyloxy, di-(C$_{1-3}$-alkyl)-aminocarbonyl-C$_{1-3}$-alkyloxy, pyrrolidin-1-yl-carbonyl-C$_{1-3}$-alkyl-oxy, piperidin-1-yl-carbonyl-C$_{1-3}$-alkyloxy, morpholin-4-yl-carbonyl-C$_{1-3}$-alkyl-oxy, hydroxy-C$_{1-3}$-alkyl, C$_{1-3}$-alkyloxy-C$_{1-3}$-alkyl, amino-C$_{1-3}$-alkyl, C$_{1-3}$-alkylamino-C$_{1-3}$-alkyl, di-(C$_{1-3}$-alkyl)-amino-C$_{1-3}$-alkyl, pyrrolidin-1-yl-C$_{1-3}$-alkyl, 2-oxo-pyrrolidin-1-yl-C$_{1-3}$-alkyl, C$_{1-4}$-alkyl-carbonyl-amino-C$_{1-3}$-alkyl, N—(C$_{1-3}$-alkyl)-C$_{1-4}$-alkylcarbonyl-amino-C$_{1-3}$-alkyl, 2-oxo-piperidin-1-yl-C$_{1-3}$-alkyl, 3-oxo-morpholin-4-yl-C$_{1-3}$-alkyl, hydroxy-C$_{1-3}$-alkyloxy, C$_{1-3}$-alkyloxy-C$_{1-3}$-alkyloxy, C$_{1-3}$-alkylsulfinyl-C$_{1-3}$-alkyloxy, C$_{1-3}$-alkylsulfonyl-C$_{1-3}$-alkyloxy, di-(C$_{1-3}$-alkyl)-amino-C$_{1-3}$-alkyloxy, 2-oxo-pyrrolidin-1-yl-C$_{1-3}$-alkyloxy, 2-oxo-piperidin-1-yl-C$_{1-3}$-alkyloxy, morpholin-4-yl-C$_{1-3}$-alkyloxy, 3-oxo-morpholin-4-yl-C$_{1-3}$-alkyloxy, C$_{1-3}$-alkylsulfonyl, aminosulfonyl, C$_{1-3}$-alkyl-aminosulfonyl, di-(C$_{1-3}$-alkyl)-aminosulfonyl, pyrrolidin-1-yl-sulfonyl, piperidin-1-yl-sulfonyl, or morpholin-4-yl-sulfonyl, wherein the above-mentioned (het)aryl mentioned hereinbefore as a single unit or a sub-moiety within another group is defined as described hereinbefore and hereinafter.

(h$^2$): More preferably, R$^1$ denotes fluorine, chlorine, cyano, C$_{1-4}$-alkyl, hydroxy, C$_{1-4}$-alkyloxy, C$_{3-4}$-alkenyloxy, trifluoromethyl, difluoromethoxy, trifluoromethoxy, C$_{3-6}$-cycloalkyloxy, tetrahydrofuran-3-yloxy, tetrahydropyran-3-yloxy, tetrahydropyran-4-yloxy, tetrahydrofuranyl-C$_{1-3}$-alkyloxy, tetrahydropyranyl-C$_{1-3}$-alkyloxy, (het)aryl, (het)aryloxy, (het)aryl-C$_{1-3}$-alkyloxy, C$_{1-3}$-alkyl-carbonyl, amino, C$_{1-3}$-alkylamino, 2-oxo-pyrrolidin-1-yl, 2-oxo-piperidin-1-yl, morpholin-4-yl, 3-oxo-morpholin-4-yl, C$_{1-3}$-alkyl-carbonylamino, (het)aryl-carbonylamino, C$_{1-3}$-alkyl-sulfonylamino, N—(C$_{1-3}$-alkyl)-C$_{1-3}$-alkyl-carbonylamino, N—(C$_{1-3}$-alkyl)-(het)arylcarbonylamino, N—($C_{1-3}$-alkyl)-$C_{1-3}$-alkyl-sulfonylamino, N—($C_{1-3}$-alkyl)-(het)arylsulfonylamino, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, hydroxy-$C_{1-3}$-alkyl, $C_{1-3}$-alkyloxy-$C_{1-3}$-alkyl, $C_{1-4}$-alkylcarbonyl-amino-$C_{1-3}$-alkyl, N—($C_{1-3}$-alkyl)-$C_{1-4}$-alkylcarbonyl-amino-$C_{1-3}$-alkyl, 2-oxo-pyrrolidin-1-yl-$C_{1-3}$-alkyl, 2-oxo-piperidin-1-yl-$C_{1-3}$-alkyl, 3-oxo-morpholin-4-yl-$C_{1-3}$-alkyl, hydroxy-$C_{1-3}$-alkyloxy, $C_{1-3}$-alkyloxy-$C_{1-3}$-alkyloxy, $C_{1-3}$-alkylsulfonyl, aminosulfonyl, $C_{1-3}$-alkyl-aminosulfonyl, or di-($C_{1-3}$-alkyl)-aminosulfonyl, wherein the above-mentioned (het)aryl groups mentioned hereinbefore as a single unit or a sub-moiety within another group are selected from the group consisting of phenyl, furanyl, thienyl, oxazolyl, thiazolyl, isoxazolyl, imidazolyl, pyrazolyl, oxadiazolyl, triazolyl, tetrazolyl, pyridinyl, pyrimidinyl, pyrazinyl, pyridazinyl, and triazinyl, wherein each group is optionally mono- or disubstituted with identical or different $R^{10}$.

($h^3$): Even more preferably, $R^1$ denotes fluorine, chlorine, $C_{1-4}$-alkyl, hydroxy, $C_{1-3}$-alkyloxy, allyloxy, amino, $C_{1-3}$-alkyl-carbonylamino, $C_{1-3}$-alkyl-sulfonylamino, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, hydroxy-$C_{1-3}$-alkyl, $C_{1-3}$-alkyloxy-$C_{1-3}$-alkyl, $C_{1-3}$-alkyl-carbonyl-amino-$C_{1-3}$-alkyl, hydroxy-$C_{1-3}$-alkyloxy, $C_{1-3}$-alkyloxy-$C_{1-3}$-alkyloxy, trifluoromethyl, difluoromethoxy, trifluoromethoxy, $C_{1-3}$-alkylcarbonyl, methylsulfonyl, aminosulfonyl, $C_{1-3}$-alkyl-aminosulfonyl, di-($C_{1-3}$-alkyl)-aminosulfonyl, phenyl-$C_{1-3}$-alkyloxy, phenoxy or phenyl, wherein each phenyl mentioned hereinbefore as a single unit or a sub-moiety within another group is optionally monosubstituted with $R^{10}$.

($h^4$): Most preferably $R^1$ denotes fluorine, chlorine, methyl, hydroxy, methoxy, ethoxy, allyloxy, amino, cyano, ethoxycarbonyl, acetyl, methylsulfonyl, aminosulfonyl, methylaminosulfonyl, dimethylaminosulfonyl, 1-hydroxyethyl, benzyloxy, or phenyl.

j) Definitions ($j^i$) for $R^2$ and $R^3$ in the order of preference, ascending from preferably ($j^1$)/($j^4$) to more preferably ($j^2$)/($j^5$) up to most preferably ($j^3$)/($j^6$):

($j^1$): $R^2$ and $R^3$ are linked to each other to form a bridging group preferably selected from the group consisting of methylenedioxy, difluoromethylenedioxy, ethylenedioxy and a $C_{3-5}$-alkylene bridging group, ($j^2$): more preferably consisting of methylenedioxy, ethylenedioxy, propylene, and butylene, ($j^3$): most preferably methylenedioxy and ethylenedioxy.

($j^4$): Additionally, $R^2$ and $R^3$ optionally form, combined with the adjacent carbon atoms to which they are attached, a group preferably selected from the group consisting of a benzo, pyrazino, pyrazolo, imidazo, oxazolo, thiazolo, isoxazolo, and isothiazolo ring, wherein each of these rings is optionally substituted with one or more substituents. The six-membered aromatics, pyrazolo, and imidazo are optionally preferably substituted with one or two and the other five-membered aromatics with one substituent, independently of each other selected from fluorine, $C_{1-3}$-alkyl, trifluoromethyl, amino, $C_{1-3}$-alkylamino, di-($C_{1-3}$-alkyl)amino, hydroxyl, and $C_{1-3}$-alkyloxy, preferably independently of each other selected from fluorine, methyl, trifluoromethyl, methylamino, dimethylamino, hydroxyl, and methoxy.

($j^5$): As a more preferred option, $R^2$ and $R^3$ combined with the adjacent carbon atoms to which they are attached form a group selected from a benzo, pyrazino, imidazo, oxazolo, and thiazolo ring, wherein the six-membered rings and the imidazo ring are optionally substituted with one or two methyl groups and the other five-membered rings are optionally substituted with one methyl group.

($j^6$): Most preferably, $R^2$ and $R^3$ together denote methylenedioxy or, together with the adjacent carbon atoms to which they are attached, form a benzo, pyrazino, or imidazo ring. In cases where $R^2$ and $R^3$ together denote an N-containing heteroaryl-group fused to the cyclic group A and where said N-containing heteroaryl-group is substituted with hydroxy at the carbon atom adjacent to the nitrogen, a tautomeric amide substructure may be formed and both tautomers are part of the invention; examples of these substructures are analogous to those described above for the residue combinations $L^3/L^4$ and $L^5/L^6$.

k) definitions ($k^i$) for $R^{10}$ in the order of preference, ascending from preferably ($k^1$) to more preferably ($k^2$) up to most preferably ($k^3$):

($k^1$): Preferably, substituents $R^{10}$ are selected independently of each other from the group consisting of fluorine, chlorine, bromine, $C_{1-3}$-alkyl, difluoromethyl, trifluoromethyl, cyano, nitro, amino, acetylamine, methylsulfonylamino, carboxy, $C_{1-4}$-alkyloxycarbonyl, amino-carbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, phenyl, hydroxy, $C_{1-3}$-alkyloxy, difluoromethoxy, and trifluoromethoxy.

($k^2$): More preferably, substituents $R^{10}$ are selected independently from fluorine, chlorine, methyl, difluoromethyl, trifluoromethyl, cyano, hydroxy, methoxy, difluoromethoxy, and trifluoromethoxy.

($k^3$): Most preferably, substituents $R^{10}$ are selected independently from fluorine, chlorine, and methyl.

l) definitions ($l^i$) for $R^{11}$ in the order of preference, ascending from preferably ($l^1$) to more preferably ($l^2$) up to most preferably ($l^4$):

($l^1$): Preferably substituents $R^{11}$ are selected independently of each other from the group consisting of fluorine, $C_{1-3}$-alkyl, phenyl, hydroxy, $C_{1-3}$-alkyloxy, cyano, carboxy, $C_{1-4}$-alkyloxy-carbonyl, aminocarbonyl, $C_{1-4}$-alkylaminocarbonyl, di-($C_{1-4}$-alkyl)-aminocarbonyl, hydroxy-$C_{1-4}$-alkyl, and $C_{1-3}$-alkyloxy-$C_{1-4}$-alkyl.

($l^2$): More preferably, substituents $R^{11}$ are selected independently from fluorine, $C_{1-3}$-alkyl, hydroxy, and $C_{1-3}$-alkyloxy.

($l^3$): Most preferably, substituents $R^{11}$ are selected independently from methyl, ethyl, propyl, hydroxy, or methoxy, ($l^4$): particularly methyl and hydroxy.

m) Definitions ($m^i$) for m comprise the options $m^1$ for m=0, $m^2$ for m=1, and $m^3$ for m=2, n) definitions ($n^i$) for n comprise the options $n^1$ for n=0, $n^2$ for n=1, and $n^3$ for n=2, o) definitions ($o^i$) for o comprise the options $o^1$ for o=0, $o^2$ for o=1, and $o^3$ for o=2.

p) Definitions (p$^i$) for R$^{12}$ in the order of preference, ascending from preferably (p$^1$) to more preferably (p$^2$):
(p$^1$): Preferably, substituents R$^{12}$ are selected independently of each other from the group consisting of fluorine and C$_{1-3}$-alkyl,
(p$^2$): more preferably from methyl and ethyl.
x) Definitions (x$^i$) for X comprise the options x$^1$ for X=CH and x$^2$ for X=N.

Each a$^i$, b$^i$, c$^i$, d$^i$, . . . p$^i$, x$^i$ represents a characterised, individual embodiment for the corresponding substituent as described above. So given the above definitions, preferred individual embodiments of the first aspect of the invention are fully characterised by the term (a$^i$b$^i$c$^i$d$^i$e$^i$f$^i$g$^i$h$^i$j$^i$k$^i$l$^i$m$^i$n$^i$o$^i$p$^i$x$^i$) if for each letter i in this term an individual FIGURE is given. Indices i vary independently from each other. All individual embodiments described by the term in brackets with full permutation of indices i, referring to the above definitions, shall be comprised by the present invention.

The following table 2 shows, exemplarily and in the order of increasing preference from the first line to the last line, such embodiments E-1 to E-15 of the invention that are considered preferred. This means that embodiment E-15, represented by the entries in the last row of table 2 is the most preferred embodiment:

Particularly preferred embodiments of this invention are described by each of the formulae I.1a to I.9a

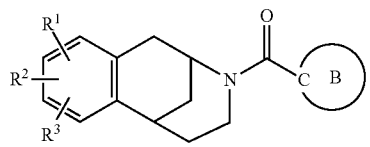

I.1a

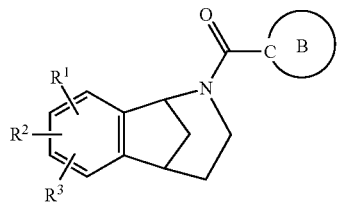

I.3a

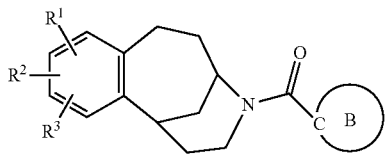

I.4a

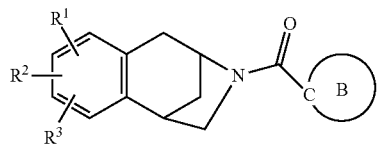

I.5a

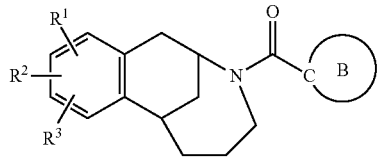

I.6a

TABLE 2

Preferred embodiments E-1 to E-15 of the invention

| | A | B | R$^N$ | L$^1$ | L$^2$ | L$^3$/L$^4$ | L$^5$/L$^6$ | R$^1$ | R$^2$/R$^3$ | R$^{10}$ | R$^{11}$ | m | n | o | R$^{12}$ | X |
|---|---|---|---|---|---|---|---|---|---|---|---|---|---|---|---|---|
| E-1 | a$^1$ | b$^1$ | c$^1$ | d$^1$ | e$^1$ | f$^1$ | g$^1$ | h$^1$ | j$^1$/j$^4$ | k$^1$ | l$^1$ | m$^1$,m$^2$,m$^3$ | n$^1$,n$^2$,n$^3$ | o$^1$,o$^2$,o$^3$ | p$^1$ | x$^1$,x$^2$ |
| E-2 | a$^1$ | b$^2$ | c$^1$ | d$^1$ | e$^2$ | f$^1$ | g$^1$ | h$^2$ | j$^1$/j$^4$ | k$^1$ | l$^1$ | m$^1$,m$^2$,m$^3$ | n$^1$,n$^2$,n$^3$ | o$^1$,o$^2$,o$^3$ | p$^2$ | x$^1$,x$^2$ |
| E-3 | a$^2$ | b$^2$ | c$^2$ | d$^2$ | e$^2$ | f$^2$ | g$^2$ | h$^2$ | j$^2$/j$^5$ | k$^2$ | l$^2$ | m$^1$,m$^2$,m$^3$ | n$^1$,n$^2$,n$^3$ | o$^1$,o$^2$,o$^3$ | p$^1$ | x$^1$,x$^2$ |
| E-4 | a$^2$ | b$^2$ | c$^2$ | d$^2$ | e$^2$ | f$^2$ | g$^2$ | h$^2$ | j$^2$/j$^5$ | k$^2$ | l$^2$ | m$^1$,m$^2$,m$^3$ | n$^1$,n$^2$,n$^3$ | o$^1$,o$^2$,o$^3$ | p$^2$ | x$^1$,x$^2$ |
| E-5 | a$^3$ | b$^3$ | c$^3$ | d$^3$ | e$^3$ | f$^3$ | g$^3$ | h$^3$ | j$^3$/j$^6$ | k$^3$ | l$^3$ | m$^1$,m$^2$ | n$^1$,n$^2$ | o$^1$,o$^2$ | p$^2$ | x$^1$,x$^2$ |
| E-6 | a$^3$ | b$^3$ | c$^3$ | d$^3$ | e$^3$ | f$^4$ | g$^3$ | h$^4$ | j$^3$/j$^6$ | k$^3$ | l$^4$ | m$^2$,m$^3$ | n$^2$,n$^3$ | o$^2$,o$^3$ | p$^2$ | x$^1$,x$^2$ |
| E-7 | a$^3$ | b$^3$ | c$^3$ | d$^3$ | e$^3$ | f$^3$ | g$^3$ | h$^3$ | j$^3$/j$^6$ | k$^3$ | l$^3$ | m$^3$ | n$^2$ | o$^2$ | p$^2$ | x$^1$,x$^2$ |
| E-9 | a$^3$ | b$^3$ | c$^3$ | d$^3$ | e$^3$ | f$^4$ | g$^3$ | h$^4$ | j$^3$/j$^6$ | k$^3$ | l$^4$ | m$^1$ | n$^2$ | o$^2$ | p$^2$ | x$^1$,x$^2$ |
| E-10 | a$^3$ | b$^3$ | c$^3$ | d$^3$ | e$^3$ | f$^4$ | g$^3$ | h$^4$ | j$^3$/j$^6$ | k$^3$ | l$^4$ | m$^2$ | n$^1$ | o$^2$ | p$^2$ | x$^1$,x$^2$ |
| E-11 | a$^3$ | b$^3$ | c$^3$ | d$^3$ | e$^3$ | f$^4$ | g$^3$ | h$^4$ | j$^3$/j$^6$ | k$^3$ | l$^4$ | m$^2$ | n$^1$ | o$^2$ | p$^2$ | x$^1$,x$^2$ |
| E-12 | a$^3$ | b$^3$ | c$^3$ | d$^3$ | e$^3$ | f$^4$ | g$^3$ | h$^4$ | j$^3$/j$^6$ | k$^3$ | l$^4$ | m$^2$ | n$^2$ | o$^1$ | p$^2$ | x$^1$,x$^2$ |
| E-13 | a$^3$ | b$^3$ | c$^3$ | d$^3$ | e$^3$ | f$^4$ | g$^3$ | h$^4$ | j$^3$/j$^6$ | k$^3$ | l$^4$ | m$^2$ | n$^2$ | o$^3$ | p$^2$ | x$^1$,x$^2$ |
| E-14 | a$^3$ | b$^3$ | c$^3$ | d$^3$ | e$^3$ | f$^4$ | g$^3$ | h$^4$ | j$^3$/j$^6$ | k$^3$ | l$^3$ | m$^2$ | n$^2$ | o$^2$ | p$^2$ | x$^2$ |
| E-15 | a$^3$ | b$^3$ | c$^3$ | d$^3$ | e$^3$ | f$^4$ | g$^3$ | h$^4$ | j$^3$/j$^6$ | k$^3$ | l$^3$ | m$^2$ | n$^2$ | o$^2$ | p$^2$ | x$^1$ |

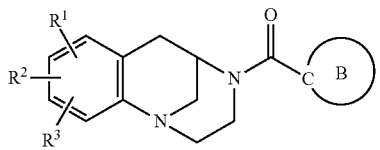

I.2a

-continued

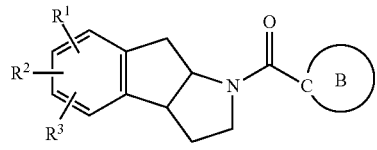

I.7a

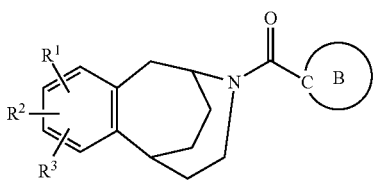
I.8a

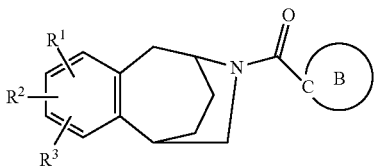
I.9a wherein the bicyclic azacycloalkene core structure of general formulae I.1 to I.9 condensed with ring A and attached to the carbonyl group is optionally substituted with 1, 2, or more substituents, preferably with 1 to 5, most preferred 1, 2, or 3 substituents, independently of each other selected from the group consisting of $R^{11}$ and $R^{12}$, and wherein the ring B and $R^1$, $R^2$, $R^3$, $R^{11}$, $R^{12}$ are defined as hereinbefore and hereinafter, their tautomers, their stereoisomers, mixtures thereof, and the salts thereof, while the compounds of general formula II as defined hereinbefore are excluded.

According to a preferred embodiment of the general formula I.1a compounds of the invention are described by the formula I.1a-RR

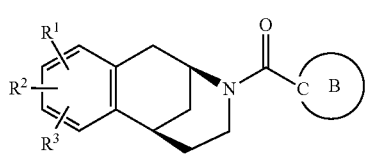
I.1a-RR wherein the 2,6-methano-azocin core structure with the stereochemical configuration as depicted is optionally substituted with 1, 2, or more substituents, preferably 1, 2, 3, 4, or 5 substituents, independently of each other selected from the group consisting of $R^{11}$ and $R^{12}$, and wherein the ring B and $R^1$, $R^2$, $R^3$, $R^{11}$, $R^{12}$ are defined as hereinbefore and hereinafter, their tautomers, their stereoisomers, mixtures thereof, and the salts thereof.

According to another preferred embodiment of the general formula I.1a compounds of the invention are described by the formula I.1a-SS

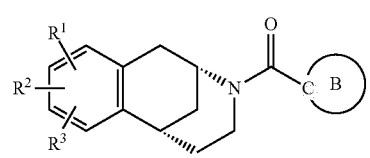
I.1a-SS wherein the 2,6-methano-azocin core structure with the stereochemical configuration as depicted is optionally substituted with 1, 2, or more substituents, preferably 1, 2, 3, 4, or 5 substituents, independently of each other selected from the group consisting of $R^{11}$ and $R^{12}$, and wherein the ring B and $R^1$, $R^2$, $R^3$, $R^{11}$, $R^{12}$ are defined as hereinbefore and hereinafter, their tautomers, their stereoisomers, mixtures thereof, and the salts thereof.

Even more preferred compounds are described by the formulae I.1a to I.9a and I.1a-RR and I.1a-SS wherein the bicyclic azacycloalkene core structure of general formulae I.1 to I.9 condensed with ring A and attached to the carbonyl group is optionally mono-substituted with $R^{11}$ and optionally substituted with 1, 2, or 3 substituents independently of each other selected from $R^{12}$, wherein the ring B and $R^1$, $R^2$, $R^3$, $R^{11}$, $R^{12}$ are defined as hereinbefore and hereinafter, their tautomers, their stereoisomers, mixtures thereof, and the salts thereof.

Terms and Definitions

Some terms used above and hereinafter to describe the compounds according to the invention will now be defined more closely.

The term "substituted" as used herein, means that any one or more hydrogens on the designated atom is replaced with a selection from the indicated group, provided that the designated atom's normal valence is not exceeded, and that the substitution results in a stable compound.

The term "partially unsaturated" as used herein, means that in the designated group or moiety 1, 2, or more, preferably 1 or 2, double bonds are present. Preferably as used herein, the term "partially unsaturated" does not cover fully unsaturated groups or moieties.

The term halogen denotes an atom selected from the group consisting of F, Cl, Br, and I.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkenyl, wherein n has a value of 3 to 6, denotes a branched or unbranched hydrocarbon group with 2 to n C atoms and a C=C double bond. Examples of such groups include ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl etc.

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc. Unless otherwise stated alkynyl groups are connected to the remainder of the molecule via the C atom in position 1. Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy, etc.

The term $C_{1-n}$-alkylcarbonyl denotes a $C_{1-n}$-alkyl-C(C=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc. Preferably the term $C_{3-7}$-cycloalkyl denotes saturated monocyclic groups.

The term $C_{5-n}$-cycloalkenyl denotes a $C_{5-n}$-cycloalkyl group which is as hereinbefore defined and additionally has at least one C=C double bond.

The term $C_{3-n}$-cycloalkylcarbonyl denotes a $C_{3-n}$-cycloalkyl-C(C=O) group wherein $C_{3-n}$-cycloalkyl is as hereinbefore defined.

The term tri-($C_{1-4}$-alkyl)silyl comprises silyl groups which have identical or two or three different alkyl groups.

The term di-($C_{1-3}$-alkyl)amino comprises amino groups which have identical or two different alkyl groups.

If groups or residues are optionally substituted, this applies to any form of the group or residue. For instance, if an alkyl group is optionally mono- or polyfluorinated this comprises also alkyl residues which are part of larger groups, e.g. alkyloxy, alkylcarbonyl, alkoxyalkyl, etc. or if a (het)aryl group is optionally mono- or polysubstituted with a certain substituent or a set of substituents this also includes (het)aryl groups which are part of larger groups, e.g. (het)aryl-$C_{1-n}$-alkyl, (het)aryloxy, (het)aryloxy-$C_{1-n}$-alkyl, (het)aryl-$C_{1-n}$-alkyloxy, etc. Accordingly, in cases where, for instance, $R^1$ or $L^2$ have e.g. the meaning (het)aryloxy, while (het)aryl residues are optionally mono- or polyfluorinated and (het)aryl denotes inter alia phenyl, the meanings mono-, di-, tri-, tetra-, and pentafluoro-phenoxy are also comprised. The same applies to groups or residues in which a $CH_2$ group may be replaced by O, S, NR, CO, or $SO_2$. For instance, a residue having inter alia the meaning hydroxy-$C_{1-3}$-alkyl, in which a $CH_2$ group may be replaced by CO, this comprises carboxy, carboxymethyl, hydroxymethylcarbonyl, carboxyethyl, hydroxymethylcarbonylmethyl, and hydroxyethyl-carbonyl.

The compounds according to the invention may be obtained using methods of synthesis known in principle. Preferably, the compounds are obtained by the following methods according to the invention which are described in more detail hereinafter.

A general strategy to access compounds of the invention is delineated in Scheme 1; A, X, m, n, and o have the meanings as defined hereinbefore and hereinafter. The key reaction to assemble the bicyclic framework is an intramolecular reaction of an amino functionality with a carboxy group that results in the formation of an amide linkage. The fusion of the carboxylic acid function and the amino group may be carried out with or without an additive at elevated temperatures, preferably between 20 and 200° C. Additives that remove the water forming during the reaction, such as molecular sieves or orthoesters, or other additives such as bases, e.g. hexamethyldisilazides, or boronic acids may facilitate the reaction. Though, more preferably the reaction is done with a more reactive entity of the carboxy function such as an acyl halide, ester, thioester, anhydride, mixed anhydride, or ketene which may be generated in a separate preceding reaction step or in situ. Preferred acyl halides or pseudohalides are acyl chloride, acyl fluoride, and acylcyanide. Preferred esters and thioesters are derived from e.g. methanol/methylthiol, ethanol/ethylthiol, 2,2,2-trifluoroethanol, phenol/thiophenol, substituted phenol/thiophenol such as 4-nitrophenol or pentafluorophenol, hydroxyheteroaryl such as hydroxybenzotriazol, hydroxypyridotriazol, or hydroxytriazines, or N-hydroxysuccinimide. Preferred mixed anhydrides are derived from alkylcarboxylic acids, e.g. pivalic acid, carbonates, e.g. methyl and ethyl carbonate, carbamates, e.g. N,N-dimethyl carbamate, phosphoric acids, e.g. dimethylphosphoric acid or $(Me_2N)_2P(O)OH$, or ureas, e.g. dicyclohexylurea, dimethylurea, or tetramethylurea. Additionally, N acylated derivatives derived from azaheteroaromatics such as imidazole, triazole, tetrazole, or pyridine such as e.g. 4-dimethylaminopyridine may be used as well. Some of the more popular reagents used for the activation of the carboxylic acid function are N,N'-carbonyldiimidazol, dicyclohexylcarbodiimide, (benzotriazol-1-yloxy)dipiperidinocarbenium hexafluorophosphate or tetrafluoroborate, (benzotriazol-1-yloxy) dipyrrolidinocarbenium hexafluorophosphate or tetrafluoroborate, 1-(3-dimethylaminopropyl)-3-ethylcarbodiimide methiodide, $POCl_3$, $SOCl_2$, $(COCl)_2$, $COCl_2$, arylboronic acid, $TiCl_4$, $(MeO)_2POCl$, cyanuric chloride, 1-hydroxybenzotriazol, 1-hydroxy-7-azabenzotriazol, benzoltriazol-1-yloxytris(dimethylamino)phosphonium hexafluorophosphate or tetrafluoroborate, benzoltriazol-1-yloxytripyrrolidinophosphonium hexafluorophosphate or tetrafluoroborate, (7-aza-benzoltriazol-1-yloxy)tripyrrolidino-phosphonium hexafluorophosphate or tetrafluoroborate, O-(benzotriazol-1-yl)-N,N,N',N'-tetramethyluronium hexafluorophosphate or tetrafluoroborate, O-(7-aza-1H-benzotriazol-1-yl)-1,1,3,3-tetramethyluronium hexafluorophosphate or tetrafluoroborate. This compilation of reagents represents only a few possibilities to activate an carboxylic acid function a host of additional reagents is known and may be used here as well. The reactive carboxylic acid derivatives may also serve as intermediates for other acylating reagents also sufficiently reactive for this transformation. The activation step and the ensuing amide forming step are often best carried out in the presence of additional additives such as bases, e.g. ethyldiisopropylamine, triethylamine, alkali metal carbonate, pyridine, 4-dimethylamino-pyridine, imidazole, dimethylaluminum amides, lithium amides, alkali metal cyanide, or alkali metal hexamethyldisilazide. The reactions are preferably conducted in organic solvents but may also be carried out in aqueous solvents. Among the organic solvents ordinarily used are N,N-dimethylformamide, N,N-dimethylacetamide, N-methylpyrrolidinone, dimethylsulfoxide, tetrahydrofuran, hexane, ether, 1,4-dioxane, 1,2-dimethoxyethane, dichloromethane, 1,2-dichloroethane, toluene, benzene, ethyl acetate, quinoline, pyridine, or mixtures thereof. The reactions may be carried out at −80° C. to 220° C., preferably between −10° C. and 120° C. Subsequently, the lactam group is reduced to give the secondary amine. This transformation is a well established reaction that may be carried out, for example, using $LiAlH_4$, hydrogen in the presence of a catalyst, $NaBH_4$ in the presence of e.g. iodine, $LiBH_4$, borane, sodium in propanol, $Cl_3SiH$, silanes, e.g. $Et_3SiH$, in the presence of a transition metal such as rhenium, 9-borabicyclo[3.3.1]nonane (9-BBN), $LiBH_3NMe_2$, or $Et_3SiH$ combined with $LiEt_3BH$. Solvents such as e.g. tetrahydrofuran, ether, 1,2-dimethoxyethane, 1,4-dioxane, hexane, benzene, toluene, dichloromethane, alcohols, water, or mixtures thereof may be employed at −78° C. to 200° C., preferably between −10° C. and 120° C.; though, in combination with some reducing reagents only a few of these solvents are usable. This strategy is well suited for the synthesis of the scaffolds I.1 to I.9.

Scheme 1. Strategy 1 to build the bicyclic skeleton

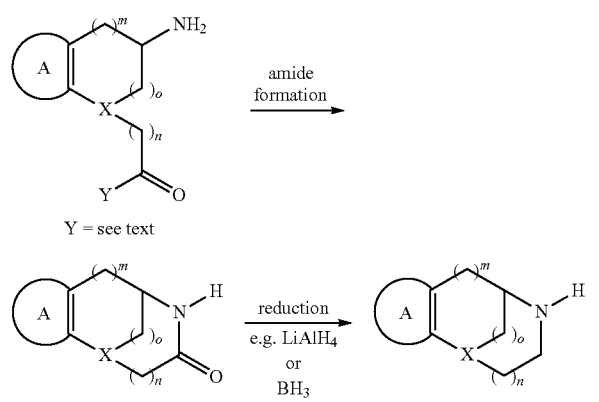

Y = see text

Another common synthetic route to acquire the compounds of the invention is summarized in Scheme 2; A, X, m, n, and o have the meanings as defined hereinbefore and hereinafter. The bicyclic framework is formed via an intramolecular reductive amination reaction of a primary amine with a ketone functionality. Reductive aminations have large precedence in organic chemistry and may be carried out e.g. using hydrogen in the presence of a transition metal catalyst such as one derived from Ni, Rh, Pd, or Pt, borohydride reagents, e.g. sodium borohydride, sodium cyanoborohydride, or sodium triacetoxyborohydride, zinc in combination with hydrochloric acid, $PhSiH_3$ with $Bu_2SnCl_2$, $B_{10}H_{14}$, or formic acid or salts thereof. Some of these reagents are preferably used in combination with an additive such as acid, e.g. acetic acid or mineral acid. The reactions are preferably conducted in organic solvents or aqueous mixtures, e.g. N,N-dimethylformamide, N,N-dimethylacetamide, N-methylpyrrolidinone, dimethylsulfoxide, tetrahydrofuran, hexane, ether, 1,4-dioxane, 1,2-dimethoxyethane, dichloromethane, 1,2-dichloroethane, toluene, benzene, alcohols, water, or mixtures thereof. The reactions may be carried out at −80° C. to 200° C., preferably between −10° C. and 100° C.

Scheme 2. Strategy 2 to build the bicyclic skeleton

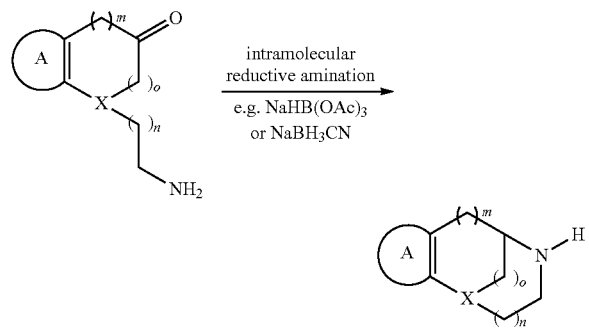

The strategy shown in Scheme 3, wherein A, X, m, n, and o have the meanings as defined hereinbefore and hereinafter, is another valid approach based on the reductive amination reaction already delineated in Scheme 2. Reaction conditions described there may be employed analogously here.

Scheme 3. Strategy 3 to build the bicyclic skeleton

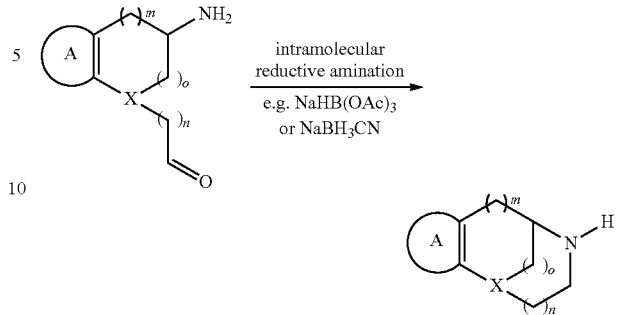

Scheme 4, wherein A, X, m, n, and o have the meanings as defined hereinbefore and hereinafter, shows another approach to assemble the bicyclic framework. This approach is based on an intramolecular alkylation of the nitrogen group with an appropriate electrophile of the side-chain. The nitrogen group may be an amino group, i.e. $R^a$ denotes e.g. hydrogen, methyl, allyl, benzyl, or dimethoxybenzyl, or an amide group, i.e. $R^a$ denotes e.g. methoxycarbonyl, benzyloxycarbonyl, allyloxycarbonyl, tert-butoxycarbonyl, trifluormethyl-carbonyl, acetyl, 2,2,2-trichloroethoxycarbonyl, tolylsulfonyl, phenylsulfonyl, methoxyphenyl-sulfonyl, nitrophenylsulfonyl, 2,2,2-trichloroethylsulfonyl, or 2-trimethylsilylethylsulfonyl. The nitrogen function is reacted with an electrophilic $C_{sp3}$-center in the side-chain, i.e. LG in Scheme 4 denotes e.g. chlorine, bromine, iodine, mesyloxy, tosyloxy, or trifluoromethlysulfonyloxy, in the presence of a base such as e.g. triethylamine, ethyldiisopropylamine, diazabicycloundecene, alkali metal carbonate, alkali metal tert-butoxide, alkali metal diisopropylamide, butyllithium, or sodium hydride. The stronger bases among them are preferably used in combination with the amides in e.g. N-methylpyrrolidinone, dimethylsulfoxide, tetrahydrofuran, hexane, ether, 1,4-dioxane, 1,2-dimethoxyethane, toluene, benzene, tert-butanol, isopropanol, or mixtures thereof at temperatures between −70 and 100° C., preferably between −30 and 60° C. The milder bases listed are preferably used in combination with the amines in dichloromethane, N,N-dimethylformamide, N-methylpyrrolidinone, dimethylsulfoxide, tetrahydrofuran, hexane, ether, 1,4-dioxane, 1,2-dimethoxyethane, toluene, benzene, methanol, ethanol, tert-butanol, isopropanol, water, or mixtures thereof at temperatures between 0 and 140° C., preferably between 20 and 120° C. For the amides the conditions originally reported by Mitsunobu may be used as well. Accordingly, the side-chain leaving group LG is generated in situ from the hydroxy group (LG=OH) using a phosphine, e.g. triphenylphosphine or tributylphosphine, in combination with an azodicarboxylate, e.g. diethyl azodicarboxylate, diisopropyl azodicarboxylate, or azodicarboxylic dipiperidide. Suited solvents may be selected from among N,N-dimethylformamide, N-methylpyrrolidinone, dichloromethane, tetrahydrofuran, hexane, ether, 1,4-dioxane, 1,2-dimethoxyethane, toluene, benzene, and mixtures thereof. The reaction is preferably conducted at temperatures between 0 and 100° C.

The opposite way around, i.e. LG denotes $NHR^a$ and $NHR^a$ denotes LG, may be applicable as well. Reaction conditions are equivalent to the original way around.

Scheme 4. Strategy 4 to build the bicyclic skeleton

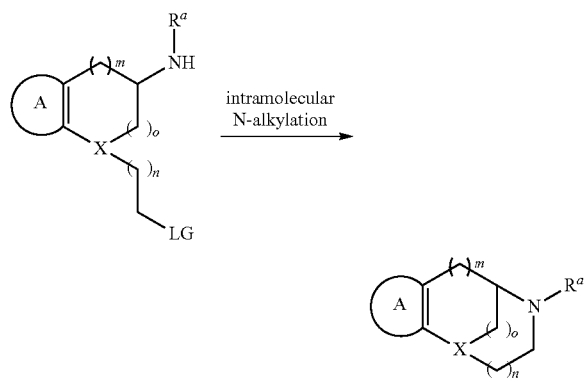

intramolecular
N-alkylation

Scheme 5. Strategy 5 to build the bicyclic skeleton

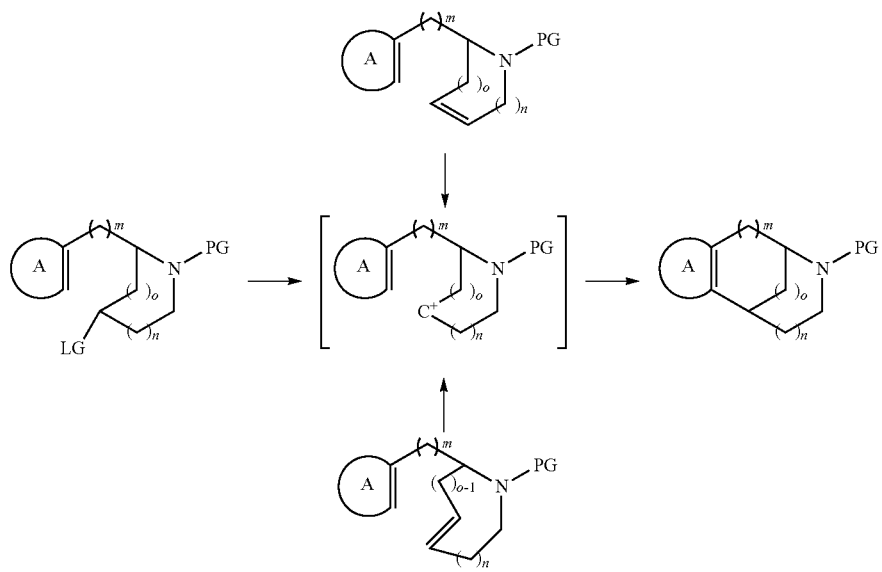

LG = e.g. OH, OSO$_2$Me, OSO$_2$Tol, OSO$_2$CF$_3$, Cl, Br, I, OC$_{1-3}$-alkyl, OCOC$_{1-4}$-alkyl, ...
PG = protective group e.g. Me, Bn, C = O-ring B BF$_3$, ZnCl$_2$, montmorillonites, POCl$_3$, and PCl$_5$. Depending on the inclination of the leaving group to be substituted and the electronic nature of the aromatic a more or less powerful acid catalyst has to be used. Besides the acid catalysts mentioned silver salts, e.g. AgOSO$_2$CF$_3$, may be useful in the reactions using halides as leaving group. Preferred solvents are hydrocarbons such as hexanes or cyclohexane, chlorinated hydrocarbons such as dichloromethane or 1,2-dichloroethane, perfluorinated hydrocarbons, nitrobenzene, chlorinated benzenes, heteroaromatics such as quinoline, dimethoxyethane, 1,4-dioxane, ether, ionic liquids, or mixtures thereof. The reactions may be carried out between −10° C. and 220° C., preferably between 20° C. and 180° C. The reactions may also be conducted under microwave irradiation.

This synthetic strategy is particularly suited for the scaffolds I.1 and I.3 to I.9 bearing an electron rich aromatic.

A further generally applicable approach is based on an electrophilic aromatic substitution reaction (Scheme 5); A, X, m, n, and o have the meanings as defined hereinbefore and hereinafter. Thereby the aromatic part of the molecule reacts with an activated carbon atom of the azacycle to form the bicyclic framework. The reactive intermediate bears a (partially) positively charged carbon atom in the azacycle that may be generated by the addition of a proton of an acid to an olefinic bond or by the activation of an appropriately positioned leaving group. A huge number of Brønstedt and Lewis acids have been described for this classical reaction that may also be used here. The following enumeration is supposed to give a few more widely used of them: hydrobromic acid, hydroiodic acid, hydrochloric acid, sulfuric acid, phosphoric acid, P$_4$O$_{10}$, trifluoroacetic acid, methanesulfonic acid, toluenesulfonic acid, trifluormethanesulfonic acid, Sc(OSO$_2$CF$_3$)$_3$, SnCl$_4$, FeCl$_3$, AlBr$_3$, AlCl$_3$, SbCl$_5$, BCl$_3$, The bicyclic scaffold may also be accessed via the route delineated in Scheme 6; m has the meaning as defined hereinbefore and hereinafter and PG and PG' are protective groups such as e.g. trialkylsilyl for PG and benzyl or methyl for PG'. The cyclization is realized by the addition of a radical intermediate, generated from the trichloromethyl group and a chlorine abstracting reagent, onto the double bond. Suited chlorine abstracting reagents are Bu$_3$Sn. and (Me$_3$SO$_3$Si. that are formed in situ by a radical initiator, such as azobisisobutyronitrile or dibenzoylperoxide, from Bu$_3$SnH and (Me$_3$Si)$_3$SiH, respectively. The reaction is preferably conducted in benzene, toluene, cyclohexane, or hexanes at elevated temperature. This approach is reported inter alia in *Tetrahedron: Asymmetry* 1999, 10, 2399-2410. Elaboration of the bicyclic scaffold to the desired compounds may be accomplished after reduction of the amide functionality to the amine and removal of the protecting group at the right-hand end of the molecule and transformation of the CH$_2$C=O sub-structure in the left-hand part of the molecule to one of the aromatics described hereinbefore. These transformations are described hereinbefore and hereinafter and are known for similar compounds from the organic chemistry literature (see e.g. Thomas L. Gilchrist, *Heterocyclenchemie*, VCH, Weinheim, 1995).

Scheme 6. Strategy 6 to build the bicyclic skeleton

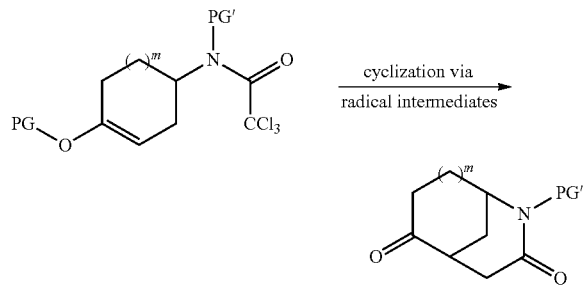

Besides the strategies presented a host of additional approaches to construct the bicyclic systems of the present invention can be envisaged and are also reported in the literature (see e.g. *J. Med. Chem.* 1970, 13, 630-634; *Chem. Rev.* 1977, 77, 1-36; *J. Med. Chem.* 1979, 22, 537-553; *J. Org. Chem.* 1984, 49, 4033-4044; *J. Med. Chem.* 1996, 39, 1956-1966; *Heterocycles* 1996, 43, 15-22; *J. Med. Chem.* 2002, 45, 3755-3764; *J. Org. Chem.* 2006, 71, 2046-2055; and references quoted therein). Therefore, the preceding strategies are in no way meant to restrict the possible synthetic pathways to access the compounds of the invention but are only supposed to show a few routes by way of example.

The synthetic routes presented may rely on the use of protecting groups. Suitable protecting groups for the respective functionalities and their removal have been described hereinbefore and may be employed analogously (see also: *Protecting Groups*, Philip J. Kocienski, 3$^{rd}$ edition, Georg Thieme Verlag, Stuttgart, 2004 and references quoted therein).

Compounds according to the invention obtained by the synthetic routes described may be subsequently converted into other compounds of the invention by routine processes applicable for conversion of functional groups. Examples for subsequent conversion processes are provided in the following paragraphs.

If in the process of manufacture according to the invention a compound of general formula I is obtained which contains an amino, alkylamino or imino group, this may be converted by acylation or sulfonylation into a corresponding acyl or sulfonyl compound of general formula I.

If a compound of general formula I is obtained which contains a hydroxy group, this may be converted by acylation or sulfonylation into a corresponding acyl or sulfonyl compound of general formula I.

If a compound of general formula I is obtained which contains a hydroxy group, this may be converted by alkylation into a corresponding ether of general formula I.

If a compound of general formula I is obtained which contains an amino, alkylamino or imino group, this may be converted by alkylation or reductive alkylation into a corresponding alkyl compound of general formula I.

If a compound of general formula I is obtained which contains an amino group, this may be converted by reaction with an isocyanate or carbamoyl chloride into a corresponding urea derivative of general formula I.

If a compound of general formula I is obtained which contains a nitro group, this may be converted by reduction into a corresponding amino compound.

If a compound of general formula I is obtained which contains an imino group, this may be converted by nitrosation and subsequent reduction into a corresponding N-amino-imino compound.

If a compound of general formula I is obtained which contains a $C_{1-3}$-alkyloxycarbonyl group, this may be converted by cleavage of the ester into the corresponding carboxy compound.

If a compound of general formula I is obtained which contains a carboxy group, this may be converted by esterification into a corresponding ester of general formula I.

If a compound of general formula I is obtained which contains a carboxy or ester group, this may be converted by reaction with an amine into a corresponding amide of general formula I.

If a compound of general formula I is obtained which contains an aromatic substructure, this may be derivatized with a chlorine, bromine, or iodine atom or a nitro, sulfonic acid, chlorosulfonyl, or acyl group to a corresponding compound of general formula I by an electrophilic substitution reaction.

If a compound of general formula I is obtained which contains an aromatic amino group, this may be transformed into a corresponding cyano, fluoro, chloro, bromo, iodo, hydroxy, mercapto, or azido compound of general formula I by diazotization and subsequent replacement of the diazo group with cyanide, fluoride, chloride, bromide, iodide, hydroxide, alkyl or hydrogen sulfide, or azide, respectively.

If a compound of general formula I is obtained which contains an aromatic amino group, this may be converted into a corresponding aryl derivatized aromatic compound of general formula I by diazotization and subsequent replacement of the diazo group with an appropriate aryl nucleophile mediated by a suited transition metal species.

If a compound of general formula I is obtained which contains an aromatic chloro, bromo, iodo, trifluoromethylsulfonyloxy, mesyloxy, or tosyloxy group, this may be converted into a corresponding aryl, alkenyl, alkynyl, or alkyl derivatized compound of general formula I by replacement of the respective group by aryl, alkenyl, alkynyl, or alkyl using a transition metal species mediated process.

If a compound of general formula I is obtained which contains an aromatic chloro, bromo, iodo, trifluoromethylsulfonyloxy, mesyloxy, or tosyloxy group, this may be replaced for hydrogen to give a corresponding aromatic compound of general formula I.

If a compound of general formula I is obtained which contains two adjacent heteroatoms that are amino and hydroxy, amino, or mercapto, these heteroatoms may be linked via a carboxy carbon atom to form a cyclic amidine, imino ester, or imino thioester substructure that may be part of an aromatic ring.

If a compound of general formula I is obtained which contains a cyano group, this may be converted into an amino alkyl derivatized compound of general formula I by reduction.

If a compound of general formula I is obtained which contains a cyano group, this may be converted into a N-hydroxycarbamimidoyl group by the treatment with hydroxylamine.

If a compound of general formula I is obtained which contains an N-hydroxycarbamimidoyl group, this may be converted to an oxadiazole derivatized compound of general formula I by the treatment with a carboxylic or related group.

If a compound of general formula I is obtained which contains an aminocarbonyl group, this may be converted by dehydration into a corresponding cyano compound of general formula I.

If a compound of general formula I is obtained which contains a keto or aldehydic group, this may be converted by reduction into a corresponding hydroxyl compound of general formula I.

If a compound of general formula I is obtained which contains a keto or aldehydic group, this may be converted by reaction with a carbon nucleophile into a corresponding hydroxy alkyl compound of general formula I.

If a compound of general formula I is obtained which contains a cyano group, this may be converted into a corresponding tetrazolyl compound of general formula I by reacting with an azide salt or derivative.

If a compound of general formula I is obtained which contains a keto or an aldehydic group, this may be converted by reaction with a carbon nucleophile into a corresponding hydroxy alkyl compound of general formula I.

If a compound of general formula I is obtained which contains a keto or aldehydic group, this may be converted by reduction into a corresponding hydroxyl compound of general formula I.

The subsequent esterification is optionally carried out in a solvent or mixture of solvents such as methylene chloride, dimethylformamide, benzene, toluene, chlorobenzene, tetrahydrofuran, benzene/tetrahydrofuran or 1,4-dioxane or particularly advantageously in the corresponding alcohol optionally in the presence of an acid such as hydrochloric acid or in the presence of a dehydrating agent. Isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclohexylcarbodiimide, N,N'-dicyclohexylcarbo-diimide/N-hydroxysuccinimide, N,N'-carbonyldiimidazole, triphenylphosphine/carbon tetrachloride, or combinations thereof optionally in the presence of 4-dimethylamino-pyridine and/or 1-hydroxy-benzotriazole are among the routinely used reagents to accomplish this transformation. The reactions are conducted between 0 and 150° C., preferably between 0 and 80° C.

The subsequent ester formation may also be carried out by reacting a compound which contains a carboxy group with a corresponding alkyl halide.

The subsequent acylation or sulfonylation is optionally carried out in a solvent or mixture of solvents such as methylene chloride, dimethylformamide, benzene, toluene, chlorobenzene, tetrahydrofuran, benzene/tetrahydrofuran, or 1,4-dioxane with a corresponding acyl or sulfonyl derivative optionally in the presence of a tertiary organic base or in the presence of an inorganic base or in the presence of a dehydrating agent. Routinely used agents are e.g. isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole, triphenylphosphine/carbon tetrachloride, or combinations thereof that may be employed in the presence of 4-dimethylamino-pyridine and/or 1-hydroxy-benzotriazole at temperatures between 0 and 150° C., preferably between 0 and 80° C.

The subsequent alkylation is optionally carried out in a solvent or mixture of solvents such as methylene chloride, dimethylformamide, benzene, toluene, chlorobenzene, tetrahydrofuran, benzene/tetrahydrofuran, or 1,4-dioxane with an alkylating agent such as a corresponding halide or sulfonic acid ester, e.g. methyl iodide, ethyl bromide, dimethylsulfate, or benzyl chloride, optionally in the presence of a tertiary organic base or in the presence of an inorganic base at temperatures between 0 and 150° C., preferably between 0 and 100° C.

The subsequent reductive alkylation is carried out with a corresponding carbonyl compound such as e.g. formaldehyde, acetaldehyde, propionaldehyde, acetone, or butyraldehyde in the presence of a complex metal hydride such as sodium borohydride, lithium borohydride, sodium triacetoxyborohydride, or sodium cyanoborohydride conveniently at a pH of 6-7 and at ambient temperature or using hydrogen in the presence of a transition metal catalyst, e.g. palladium/charcoal at a hydrogen pressure of 1 to 5 bar. Methylation may also be carried out in the presence of formic acid as reducing agent at elevated temperature, e.g. between 60 and 120° C.

The subsequent urea formation from an amine is optionally carried out in a solvent or mixture of solvents such as dimethylformamide, N-methylpyrrolidinone, toluene, acetonitrile, dichloromethane, 1,2-dichloroethane, ether, tetrahydrofuran, 1,2-dimethoxyethane, or 1,4-dioxane with an isocyanate or carbamoyl chloride optionally in the presence of a tertiary organic base, e.g. triethylamine or ethyldiisopropylamine, or in the presence of an inorganic base, e.g. potassium carbonate or calcium oxide, at temperatures between 0 and 180° C., preferably between 5 and 120° C. Additives such as pyridine or 4-dimethylaminopyridine may be beneficial.

The subsequent reduction of a nitro group is carried out, for example, with hydrogen and a catalyst such as palladium on carbon, platinum dioxide, or Raney nickel, or using other reducing agents such as iron or zinc in the presence of an acid such as acetic acid.

The subsequent nitrosation of an imino group followed by reduction to obtain the N-amino-imino compound is carried out, for example, with an alkyl nitrite such as isoamyl nitrite to form the N-nitroso-imino compound that is then reduced to the N-amino-imino compound using, for example, zinc in the presence of an acid such as acetic acid.

The subsequent cleaving of a $C_{1-3}$-alkyloxycarbonyl group to obtain the carboxy group is carried out, for example, by hydrolysis with an acid such as hydrochloric acid or sulfuric acid or an alkali metal hydroxide such as lithium hydroxide, sodium hydroxide, or potassium hydroxide.

The subsequent amide formation is carried out by reacting a corresponding reactive carboxylic acid derivative with a corresponding amine optionally in a solvent or mixture of solvents such as methylene chloride, dimethylformamide, benzene, toluene, chlorobenzene, tetrahydrofuran, benzene/tetrahydrofuran or 1,4-dioxane, while the amine used may also serve as solvent, optionally in the presence of a tertiary organic base or in the presence of an inorganic base or with a corresponding carboxylic acid in the presence of a dehydrating agent. Isobutyl chloroformate, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, 1-hydroxy-benzotriazole, N,N'-carbonyldiimidazole or triphenylphos-phine/carbon tetrachloride, or combinations thereof optionally in the presence of 4-dimethylamino-pyridine at temperatures between 0 and 150° C., preferably between 0 and 80° C., may be applied to achieve the coupling.

The subsequent introduction of a chlorine, bromine, or iodine atom onto an aromatic substructure may be carried out by reacting the aromatic compound with an appropriate electrophile of the halogen atom. Suited chlorine and bromine electrophiles may be e.g. N-halosuccinimide, HOCl, HOBr, tertBuOCl, tertBuOBr, chlorine, bromine, dibromoisocyanuric acid, pyridinium dichlorobromate, pyridinium tribromide, or sulfuryl chloride that may be used alone or in combination with an acid, e.g. hydrochloric acid, hydrobromic acid, tetrafluoroboric acid, triflic acid, sulfuric acid, or acetic acid, or a Lewis acid, e.g. iron(III) halide, borontrifluoride hydrate, borontrifluoride etherate, or aluminum halide. Further useful combinations may be LiBr and ceric ammonium nitrate, KCl or KBr with Oxone®, or KBr and sodium perborate. Suited iodine electrophiles may be generated from iodine combined with an oxidizing agent such as nitric acid, sulfur trioxide, manganese dioxide, $HIO_3$, hydrogen peroxide, sodium periodate, peroxydisulfates, and Oxone®. Further suited iodine electrophiles may be e.g. iodine chloride, dichloroiodates, and N-iodosuccinimide. These iodine electrophiles may be used without an additive or in the presence of an acid such as e.g. acetic acid, trifluoroacetic acid, or sulfuric acid, or a Lewis acid such as borontrifluoride hydrate, or copper salts. If a nitro group is to be introduced appropriate nitro electrophiles may be generated from, for example, nitric acid, acetyl nitrate, ceric ammonium nitrate, sodium nitrate, $N_2O_5$, alkyl nitrate, and nitronium tetrafluoroborate. Some of these reagents may be used without an additive, though, several of them are better used in combination with an acid, e.g. sulfuric acid or triflic acid, acetic anhydride, trifluoroacetic anhydride, Lewis acid, e.g. ytterbium triflate or iron acetate, $P_2O_5$, or a base. The $SO_3H$ group may be introduced by reacting the aromatic compound with, for example, concentrated sulfuric acid, $SO_3$, $ClSO_3H$, or $ClSO_2NMe_2$ combined with indium triflate. Reacting the aromatic compound with $ClSO_3H$ gives the corresponding chlorosulfonylated derivative that may be hydrolyzed to the sulfonic acid. Acylating the aromatic part is conducted using an acyl electrophile that may be generated from the respective acyl halide, e.g. chloride, or acyl anhydride and a Lewis acid such as e.g. aluminum halide, diethylaluminum halide, indium halide, iron(III) halide, tin(IV) halide, borontrifluoride, titanium(IV) halide, or a Brønsted acid, e.g. sulfuric acid or triflic acid. The formyl group is best introduced using the so-called Vilsmeier or Vilsmeier-Haack conditions: dialkylformamide combined with phosgene, thionyl chloride, $POCl_3$, or oxalyl chloride. Preferred solvents for the electrophilic substitutions described may differ depending on the electrophile employed; in the following some more generally applicable are mentioned: methylene chloride, 1,2-dichloroethane, chlorobenzene, dichlorobenzene, ether, fluorinated hydrocarbons, hexanes, quinoline, or acetonitrile. The temperatures preferably applied range from 0 to 180° C.

The subsequent replacement of an aromatic amino group is initiated by diazotization of the amino group using a nitrous acid or nitrosonium source or equivalent such as a nitrite salt combined with an acid, e.g. sodium nitrite and hydrochloric acid, nitrosonium tetrafluoroborate, or an alkylnitrite, e.g. tert-butylnitrite or iso-amylnitrite. The diazotization is optionally carried out in methylene chloride, 1,2-dichloroethane, N,N-dimethylformamide, N-methylpyrrolidinone, benzene, toluene, chlorobenzene, tetrahydrofuran, water, ethyl acetate, alcohol, ether, 1,2-dimethoxyethane, 1,4-dioxane, or mixtures thereof at temperatures between −10° C. and 100° C. (diazotization of amino groups is detailed in, for example, *Angew. Chem. Int. Ed.* 1976, 15, 251). The subsequent displacement of the diazo group for a cyano group, chlorine, or bromine using cuprous cyanide, chloride, or bromide, respectively, is known as the Sandmeyer reaction (see e.g. March's Advanced Organic Chemistry, Michael B. Smith and Jerry March, John Wiley & Sons Inc., 6. Ed., New Jersey, 2007 and references quoted therein); the reaction is optionally conducted between −10° C. and 120° C. in one of the solvents or mixtures mentioned above. The replacement of the diazo group for a fluorine atom may be achieved with a tetrafluoroborate salt or tetrafluoroboric acid and heating to 20 to 160° C.; the reaction is known as the Schiemann reaction. Iodine may be introduced by treatment of the diazo compound with an iodide salt, e.g. sodium iodide, preferably using water or an aqueous solvent mixture at temperatures between 0 and 120° C. The diazo group is replaced for hydroxy using water or an aqueous solvent mixture at temperatures between 0 and 180° C. The reaction usually works without further additives but the addition of cuprous oxide or strong acid may be advantageous. Mercapto or alkylmercapto may be introduced via their corresponding disulfide salts or dialkyldisulfides at temperatures between 0 and 120° C.; depending on the sulfur species used an inert solvent or aqueous solvent system may be preferred (see e.g. *Synth. Commun.* 2001, 31, 1857 and references quoted therein).

The subsequent replacement of an aromatic amino group by an aryl group may be carried out via the corresponding diazo compound obtainable as described above. The reaction with an aryl nucleophile, preferably an aryl boronic acid, boronic ester, trifluoroborate, zinc halide, or stannane, is conducted in the presence of a transition metal species derived from palladium, nickel, rhodium, copper, or iron, preferably palladium. The active catalyst may be a complex of the transition metal with ligands such as e.g. phosphines, phosphites, imdiazole carbenes, imidazolidine carbenes, dibenzylideneacetone, allyl, or nitriles, an elemental form of the transition metal such as palladium on carbon or nanoparticles, or salts such as chloride, bromide, acetate, or trifluoroacetate. In these reactions the diazo compound is preferably employed as its tetrafluoroborate salt optionally in methylene chloride, N,N-dimethylformamide, N-methylpyrrolidinone, benzene, toluene, tetrahydrofuran, water, ethyl acetate, alcohol, ether, 1,2-dimethoxyethane, 1,4-dioxane, or mixtures thereof at temperatures between 10° C. and 180° C., preferably between 20° C. and 140° C.

The subsequent replacement of an aromatic chloro, bromo, iodo atom or an aromatic trifluoromethylsulfonyloxy, mesyloxy, or tosyloxy group for an aryl, alkenyl, alkynyl, or alkyl residue is preferably mediated by a transition metal species derived from palladium, nickel, rhodium, copper, or iron. The active catalyst may be a complex of the transition metal with ligands such as e.g. phosphines (e.g. tritertbutylphosphine, tricyclohexylphosphine, substituted biphenyldicyclohexylphosphines, substituted biphenylditertbutylphosphines, triphenylphosphine, tritolylphosphine, trifurylphosphine, 1,1'-bis(diphenylphosphino)-ferrocene), phosphites, imdiazole carbenes, imidazolidine carbenes, dibenzylideneacetone, allyl, or nitriles, an elemental form of the transition metal such as palladium on carbon or nanoparticles of iron or palladium, or a salt such as fluoride, chloride, bromide, acetate, triflate, or trifluoroacetate. The replacement is preferably conducted with a trifluoroborate, boronic acid, or boronic ester (Suzuki or Suzuki-type reaction), zinc halide (Negishi or Negishi-type reaction), stannane (Stille reaction), silane (Hiyama or Hiyama-type reaction), magnesium halide (Kumada or Kumada-type reaction) of the aryl, alkenyl, or alkyl residue to be introduced. The terminal alkyne is preferably used as it is or as the zinc acetylide derivative. Depending on the electrophilic and nucleophilic reaction partners additives such as halide salts, e.g. lithium chloride, potassium fluoride, tetrabutylammonium fluoride, hydroxide sources such as potassium hydroxide or potassium carbonate, silver salts such as silver oxide or triflate, copper salts such as copper chloride or copper thiophenecarboxylate may be advantageous or even essential. Copper iodide is a preferred additive in the coupling with a terminal alkyne group (Sonogashira reaction). The coupling reactions are optionally conducted in methylene chloride, N,N-dimethylformamide, N-methylpyrrolidinone, benzene, toluene, tetrahydrofuran, water, ethyl acetate, alcohol, ether, dimethylsulfoxide, 1,2-dimethoxyethane, 1,4-dioxane, or mixtures thereof, though, depending on the nucleophile some of them are less or not suited at all. Preferred temperatures are in the range from −10° C. to 180° C.

The subsequent replacement of an aromatic chlorine, bromine, or iodine atom or an aromatic trifluoromethylsulfonyloxy, mesyloxy, or tosyloxy group for a hydrogen atom is preferably mediated by a transition metal species derived from palladium, nickel, platinum, or rhodium. The active catalyst may be a complex of the transition metal with ligands, an elemental form, or a salt of the transition metal as mentioned above. Raney nickel or palladium on carbon are among the preferred catalyst species. Suited hydrogen sources may be hydrogen, preferably at pressures of 1 to 5 bar, silanes, e.g. trialkoxysilane, boranes, hydrides, e.g. alkali metal borohydride, formic acid, or formates, e.g. ammonium formate. The reactions are preferably carried out in methylene chloride, N,N-dimethylformamide, N,N-dimethylacetamide, N-methylpyrrolidinone, benzene, toluene, tetrahydrofuran, water, ethyl acetate, alcohol, ether, 1,2-dimethoxyethane, 1,4-dioxane, or mixtures thereof at −10° C. to 180° C., more preferably at 20° C. to 140° C.

The subsequent cyclization of two adjacent heteroatoms is optionally conducted with a carboxy equivalent such as nitrile, carboxylic chloride or fluoride, carboxylic acid, ketene, carboxylic ester, or carboxylic thioester. The overall transformation consists of two reaction steps: attachment of the carboxy equivalent to one of the two heteroatoms followed by cyclization with the other heteroatom. The first step is an amide formation with the amino functionality that may be carried out as described hereinbefore. The ensuing reaction step, cyclization with the second heteroatom, may be accomplished by heating in the presence of an acid, e.g. acetic acid, trifluoroacetic acid, sulfuric acid, or hydrochloric acid, or a base, e.g. sodium hydroxide, sodium ethoxide, or sodium teributoxide. The use of dehydrating reagents such as anhydrides, e.g. acetic anhydride, orthoesters, e.g. trimethylorthoformate, thionylchloride, phosgene, diphosgene, triphosgene, phosphorous oxychloride, phosphorous pentachloride, dialkylcarbodiimides, combinations of phosphines, e.g. triphenylphosphine or trialkylphosphine with dialkyl azodicarboxylates, bromine, iodine, or 1,2-dihaloethanes, e.g. 1,2-dibromotetrafluoroethane, may be advantageous. The reactions are preferably carried out in inert solvents or mixtures such as methylene chloride, 1,2-dichloroethane, benzene, toluene, tetrahydrofuran, ether, or combinations thereof, though, cyclization in the presence of an acid or a base may also be conducted in water or an alcohol, e.g. methanol, ethanol, isopropanol, or teributanol, or combinations with these solvents. The reactions are carried out at temperatures between 0° C. and 200° C., preferably between 20° C. and 140° C.

The subsequent reduction of a cyano group to obtain an aminomethyl group is optionally conducted with hydrogen in the presence of a transition metal species or with a hydride. Suited transition metals may be derived from palladium, nickel, platinum, rhodium, or ruthenium such as, for example, palladium on charcoal, palladium hydroxide, platinum oxide, or Raney nickel that may be used in solvents such as ethyl acetate, alcohols, e.g. methanol or ethanol, dichloromethane, tetrahydrofuran, ether, benzene, toluene, N,N,-dimethylformamide, or N-methylpyrrolidinone at hydrogen pressures between 1 and 10 bar, preferably between 1 and 5 bar, and at temperatures between 0 and 180° C., preferably between 20 and 120° C. Additives such as acids, e.g. hydrochloric acid, methanesulfonic acid, sulfuric acid, or acetic acid, may be beneficial for the hydrogenation. Appropriate hydride sources may be selected from e.g. borohydrides, e.g. sodium borohydride, potassium trisecbutylborohydride, borane, or lithium triethylborohydride, or alanates, e.g. lithium aluminum hydride or diisobutylaluminum hydride. Some of these reagents are best used in combination with nickel chloride or cobalt chloride as sodium borohydride. These reagents may be used in e.g. tetrahydrofuran, ether, 1,4-dioxane, 1,2-dimethoxyethane, dichloromethane, 1,2-dichloroethane, benzene, or toluene; some are also compatible with alcoholic solutions. Preferred reaction temperatures range from −80° C. to 160° C., more preferred from −40° C. to 80° C.

The subsequent formation of a N-hydroxycarbamimidoyl group from a cyano group may be carried out by the treatment of the cyano compound with hydroxylamine. The reaction is preferably conducted in aqueous or alcoholic solvents at temperatures between 0° C. and 140° C.

The subsequent formation of an oxadiazole from an N-hydroxycarbamimidoyl is optionally conducted with a carboxy equivalent such as nitrile, carboxylic chloride or fluoride, carboxylic acid, ketene, carboxylic ester, or carboxylic thioester. The transformation is related to the formation of a ring starting from two adjacent heteroatoms described above and may be carried out analogously.

The subsequent formation of a cyano group from an amino carbonyl group is optionally conducted by using a dehydrating reagent such as e.g. anhydride, e.g. acetic anhydride, trifluoroacetic anhydride, or triflic anhydride, phosgene, thionyl chloride, oxalyl chloride, $POCl_3$, $PCl_5$, $P_4O_{10}$, triphenylphosphite, or triphenyl- or trialkylphosphine combined with tetrachloromethane, 1,2-dibromotetrafluoroethane, or bromine. The reactions are preferably carried out in dichloromethane, 1,2-dichloroethane, hexanes, ether, 1,4-dioxane, benzene, toluene, acetonitrile, mixtures thereof, or without a solvent at temperatures between 0° C. and 140° C. Additives such as amines, e.g. pyridine or triethylamine, or N,N-dimethylformamide may be beneficial.

The subsequent reduction of a keto or an aldehydic group to obtain a secondary or primary alcohol may be carried out with a complex metal hydride such as sodium borohydride, lithium borohydride, lithium triethylborohydride, diisobutylaluminum hydride, or lithium aluminum hydride. The reductions may be conducted in e.g. dichloromethane, 1,2-dichloroethane, hexanes, ether, 1,4-dioxane, tetrahydrofuran, N,N-dimethylformamide, N-methylpyrrolidinone, benzene, toluene, alcohols, e.g. methanol, water, or mixtures thereof, though, not all reducing agents are compatible with all of these solvents. Preferred temperatures are between −80° C. and 140° C. depending on the reducing power of the reagent. Alternatively, hydrogen in the presence of a transition metal catalyst may be used for the reduction.

The subsequent addition of a carbon nucleophile to a keto or an aldehydic group to obtain a tertiary or secondary alcohol may be carried out with an alkyl or aryl metal compound, preferably with a lithium or magnesium derivative. The reactions are preferably conducted in hexanes, ether, 1,4-dioxane, tetrahydrofuran, 1,2-dimethoxyethane, benzene, toluene, or mixtures thereof between −80° C. and 50° C.

The subsequent conversion of a cyano into a tetrazolyl group may be achieved by reacting the cyanide with sodium azide or trimethylsilyl azide in e.g. toluene, xylene, cyclohexane, N,N-dimethylformamide, N,N-dimethylacetamide, N-methylpyrrolidinone, tetrahydrofuran, 1,4-dioxane, 1,2-dimethoxyethane, alcohol, water, or mixtures thereof. Beneficial additives may be $ZnBr_2$, $Bu_3SnCl$, $NH_4Cl$, $Bu_2SnO$, AlCl$_3$, AlMe$_3$, HNEt$_3$Cl, and NEt$_3$. The reactions are preferably conducted between 20° C. and 160° C.

The subsequent addition of a carbon nucleophile to a keto or an aldehydic group to obtain a tertiary or secondary alcohol may be carried out with an alkyl or aryl metal compound, preferably with a lithium or magnesium derivative. The reactions are preferably conducted in hexanes, ether, 1,4-dioxane, tetrahydrofuran, 1,2-dimethoxyethane, benzene, toluene, or mixtures thereof between −80° C. and 50° C.

The subsequent reduction of a keto or an aldehydic group to obtain a secondary or primary alcohol may be carried out with a complex metal hydride such as sodium borohydride, lithium borohydride, lithium triethylborohydride, diisobutylaluminum hydride, or lithium aluminum hydride. The reductions may be conducted in e.g. dichloromethane, 1,2-dichloroethane, hexanes, ether, 1,4-dioxane, tetrahydrofuran, N,N-dimethylformamide, N-methylpyrrolidinone, benzene, toluene, alcohols, e.g. methanol, water, or mixtures thereof, though, not all reducing agents mentioned are compatible with all of these solvents. Preferred temperatures are between −80° C. and 140° C. depending on the reducing power of the reagent. Alternatively, hydrogen in the presence of a transition metal catalyst may be used for the reduction.

In the reactions described hereinbefore, any reactive group present such as hydroxy, carboxy, amino, alkylamino, or imino group may be protected during the reaction by conventional protecting groups which are cleaved again after the reaction.

For example, a protecting group for a hydroxy group may be a trimethylsilyl, tertbutyldimethylsilyl, triisopropylsilyl, acetyl, pivaloyl, benzoyl, methyl, tert-butyl, allyl, trityl, benzyl, 4-methoxybenzyl, tetrahydropyranyl, methoxymethyl, ethoxymethyl, or 2-trimethylsilylethoxymethyl group, protecting groups for a carboxy group may be trimethylsilyl, methyl, ethyl, tertbutyl, allyl, benzyl, or tetrahydropyranyl, protecting groups for a ketone or aldehyde may be a ketal or acetal, respectively, e.g. derived from methanol, glycol, or propane-1,3-diol, protecting groups for an amino, alkylamino, or imino group may be methyl, formyl, acetyl, trifluoroacetyl, ethoxycarbonyl, tert-butoxycarbonyl, benzyloxycarbonyl, benzyl, methoxy-benzyl, or 2,4-dimethoxybenzyl and for the amino group additionally phthalyl, and protecting groups for a terminal alkyne may be trimethylsilyl, trisopropylsilyl, teributyldimethylsilyl, or 2-hydroxy-isopropyl.

Any acyl protecting group may be cleaved, for example, hydrolytically in an aqueous solvent, e.g. in water, isopropanol/water, acetic acid/water, tetrahydrofuran/water, or 1,4-dioxane/water, in the presence of an acid such as trifluoroacetic acid, hydrochloric acid, or sulfuric acid or in the presence of an alkali metal base such as lithium hydroxide, sodium hydroxide, or potassium hydroxide or aprotically, e.g. in the presence of iodotrimethylsilane, at temperatures between 0 and 120° C., preferably between 10 and 100° C. A trifluoroacetyl group is preferably cleaved by treating with an acid such as hydrochloric acid, optionally in a solvent such as acetic acid, at temperatures between 50 and 120° C. or by treating with sodium hydroxide solution, optionally in an additional solvent such as tetrahydrofuran or methanol, at temperatures between 0 and 80° C.

Any acetal or ketal protecting group used may be cleaved, for example, hydrolytically in an aqueous solvent, e.g. in water, isopropanol/water, acetic acid/water, tetrahydrofuran/water, or 1,4-dioxane/water, in the presence of an acid such as trifluoroacetic acid, hydrochloric acid, or sulfuric acid or aprotically, e.g. in the presence of iodotrimethylsilane, at temperatures between 0 and 120° C., preferably between 10 and 100° C.

A trimethylsilyl group is cleaved, for example, in water, an aqueous solvent mixture or an alcohol, such as methanol or ethanol, in the presence of a base such as lithium hydroxide, sodium hydroxide, potassium carbonate, or sodium methoxide.

Acids such as e.g. hydrochloric acid, trifluoroacetic acid, or acetic acid may also be suitable. The cleavage usually takes place at comparatively low temperatures, e.g. between −60 and 60° C. Silyl groups other than trimethylsilyl are preferentially cleaved in the presence of an acid, e.g. trifluoroacetic acid, hydrochloric acid, or sulfuric acid, at temperatures between 0° C. and 100° C. A particularly suited cleaving method for silyl groups is based on the use of fluoride salts, e.g. tetrabutylammonium fluoride, hydrogen fluoride, or potassium fluoride, in organic solvents, such as for example diethyl ether, tetrahydrofuran, 1,4-dioxane, dimethoxyethane, toluene, benzene, dichloroethane, or dichloromethane at temperatures between −20 and 100° C.

A benzyl, methoxybenzyl, or benzyloxycarbonyl group is advantageously cleaved hydrogenolytically, e.g. with hydrogen in the presence of a catalyst such as palladium on carbon, palladium hydroxide, or platinum oxide in a solvent such as methanol, ethanol, ethyl acetate, or glacial acetic acid, optionally in the presence of an acid, such as hydrochloric acid, at temperatures between 0 and 100° C., preferably between 20 and 60° C., and at hydrogen pressures of 1 to 7 bar, preferably 3 to 5 bar. Trimethylsilyl iodide, boron trichloride, or boron trifluoride in the presence of a scavenger such as anisol, thioanisol, or pentamethylbenzene may also be used with benzylether derivatives. An electron-rich benzyl residue, such as methoxybenzyl, may also be cleaved oxidatively with e.g. 2,3-dichloro-5,6-dicyano-1,4-benzoquinone (DDQ) or ceric ammonium nitrate (CAN) preferably in an alcoholic or aqueous solvent at temperatures between 10 and 120° C. A 2,4-dimethoxybenzyl group is preferably cleaved in trifluoroacetic acid in the presence of a scavenger such as anisole.

A tertbutyl or tertbutyloxycarbonyl group is preferably cleaved by treating with an acid such as trifluoroacetic acid, sulfuric acid, or hydrochloric acid or by treating with iodotrimethylsilane optionally using a solvent such as methylene chloride, 1,4-dioxane, methanol, isopropanol, water, or diethylether.

A methyl group at an tertiary amine may be cleaved by the treatment with 1-chloroethyl chloroformate. Hydrobromic acid and borontribromide are particularly suited for the cleavage of methylethers.

The compounds of general formula I may be resolved into their enantiomers and/or diastereomers, as mentioned before. Thus, for example, cis/trans mixtures may be resolved into their cis and trans isomers, and racemic compounds may be separated into their enantiomers.

The cis/trans mixtures may be resolved, for example, by chromatography into the cis and trans isomers thereof. The compounds of general formula I which occur as racemates may be separated by methods known per se (cf. Allinger N. L. and Eliel E. L. in "Topics in Stereochemistry", Vol. 6, Wiley Interscience, 1971) into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallisation from an optically active solvent or by reacting with an optically active substance which forms salts or derivatives, such as e.g. esters or amides, with the racemic compound. Salts may be formed with enantiopure acids for basic compounds and with enantiopure bases for acidic compounds. Diastereomeric derivatives are formed with enantiopure auxiliary compounds such as e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, di-o-tolyltartaric acid, malic acid, mandelic acid, camphorsulfonic acid, glutamic acid, aspartic acid, or quinic acid. Optically active alcohols applicable as auxiliary may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the physiologically acceptable salts with inorganic or organic acids provided that compound I bears a basic residue. Acids which may be used for this purpose include for example hydrochloric acid, hydrobromic acid, sulfuric acid, methanesulfonic acid, phosphoric acid, fumaric acid, succinic acid, lactic acid, citric acid, tartaric acid, or maleic acid.

If the compounds of formula I contain an acidic residue like, for example, a carboxy group, they may be converted into the salts thereof with inorganic or organic bases, particularly for pharmaceutical use into the physiologically acceptable salts thereof. Suitable bases for this purpose include, for example, sodium hydroxide, potassium hydroxide, calcium hydroxide, calcium isopropoxide, magnesium hydroxide, magnesium ethoxide, ammonium hydroxide, cyclohexylamine, ethanolamine, diethanolamine, triethanolamine, N-methyl-D-glucamine, L-lysine, L-arginine, and piperazine.

The compounds according to the invention are advantageously also obtainable using the methods described in the examples that follow, which may also be combined for this purpose with methods known to the skilled man from the literature.

As already mentioned, the compounds of general formula I according to the invention and the physiologically acceptable salts thereof have valuable pharmacological properties, particularly an inhibitory effect on the enzyme 11β-hydroxysteroid dehydrogenase (HSD) 1.

The biological properties of the new compounds may be investigated as follows:

In vitro inhibition of 11β-HSD1 by test compounds was determined with HTRF (Homogeneous Time-Resolved Fluorescence) technology (cisbio international, France) detecting cortisol generated from cortisterone by human liver microsomes. Briefly, compounds were incubated for 1 hour at 37° C. in Tris buffer (20 mM tris, 5 mM EDTA, pH 6.0) containing NADPH (200 µM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction was typically 2 hours. The amount of cortisol is determined by reading the time-resolved fluorescence of the wells (Ex 320/75 nm; Em 615/8.5 nm and 665/7.5 nm). The ratio of the two emission signals is then calculated (Em665*10000/Em615). Each assay contained incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contained a calibration curve with cortisol to transform the fluorescent data into cortisol concentrations. Percent inhibition of each compound was determined relative to the carbenoxolone signal and $IC_{50}$ curves were generated.

The compounds of general formula I according to the invention may for example have $IC_{50}$ values below 10000 nM, particularly below 1000 nM, most preferably below 100 nM. In the Table 2 compounds of the invention (specified in Table 3) and their inhibitory activity determined as described above are compiled.

TABLE 2

| Ex. No. | 11β-HSD $IC_{50}$ (nM) | Ex. No. | 11β-HSD $IC_{50}$ (nM) | Ex. No. | 11β-HSD $IC_{50}$ (nM) | Ex. No. | 11β-HSD $IC_{50}$ (nM) |
|---|---|---|---|---|---|---|---|
| 1 | 964 | 44 | 175 | 93 | 1494 | 140 | 101 |
| 2 | 934 | 45 | 240 | 94 | 36 | 141 | 133 |
| 3 | 274 | 46 | 954 | 95 | 75 | 142 | 1938 |
| 4 | 156 | 47 | 106 | 98 | 1387 | 143 | 179 |
| 6 | 692 | 48 | 639 | 99 | 420 | 144 | 250 |
| 7 | 1192 | 49 | 186 | 101 | 59 | 145 | 254 |
| 8 | 847 | 50 | 1551 | 102 | 501 | 146 | 87 |
| 9 | 1509 | 51 | 101 | 100 | 1349 | 147 | 376 |
| 10 | 1767 | 52 | 1397 | 103 | 878 | 148 | 230 |
| 11 | 1347 | 53 | 863 | 104 | 762 | 149 | 91 |
| 5 | 4573 | 54 | 2656 | 106 | 1518 | 150 | 299 |
| 12 | 1510 | 56 | 2442 | 107 | 1633 | 151 | 242 |
| 13 | 4024 | 59 | 555 | 108 | 221 | 152 | 94 |
| 14 | 136 | 60 | 760 | 109 | 693 | 154 | 185 |
| 15 | 109 | 61 | 2104 | 110 | 2313 | 155 | 243 |
| 16 | 1070 | 62 | 666 | 112 | 1115 | 156 | 198 |
| 17 | 809 | 63 | 335 | 113 | 404 | 157 | 168 |
| 18 | 823 | 64 | 631 | 114 | 2118 | 158 | 135 |
| 19 | 421 | 66 | 2536 | 115 | 214 | 160 | 182 |
| 20 | 138 | 67 | 388 | 116 | 70 | 161 | 283 |
| 21 | 86 | 68 | 654 | 117 | 340 | 162 | 333 |
| 22 | 1434 | 69 | 6114 | 118 | 149 | 163 | 491 |
| 23 | 186 | 71 | 2375 | 119 | 2763 | 164 | 77 |
| 24 | 120 | 72 | 693 | 121 | 5930 | 165 | 1233 |
| 25 | 837 | 73 | 663 | 122 | 5564 | 166 | 2451 |
| 26 | 3509 | 75 | 6036 | 125 | 1572 | 167 | 1470 |
| 27 | 3484 | 76 | 667 | 126 | 2852 | 168 | 2371 |
| 29 | 1116 | 77 | 571 | 128 | 474 | 169 | 2061 |
| 30 | 1005 | 78 | 5870 | 129 | 2173 | 170 | 2132 |
| 31 | 1340 | 82 | 1485 | 130 | 1153 | 171 | 2236 |
| 34 | 859 | 84 | 1179 | 131 | 432 | 172 | 2583 |
| 35 | 1289 | 85 | 362 | 132 | 210 | 173 | 1487 |
| 37 | 197 | 86 | 67 | 133 | 363 | 174 | 178 |
| 38 | 106 | 87 | 555 | 134 | 1699 | 175 | 176 |
| 39 | 499 | 88 | 316 | 135 | 533 | 176 | 625 |
| 40 | 61 | 89 | 164 | 136 | 2076 | 177 | 76 |
| 41 | 373 | 90 | 255 | 137 | 3525 | 178 | 798 |
| 42 | 165 | 91 | 1545 | 138 | 1394 | 179 | 205 |
| 43 | 247 | 92 | 459 | 139 | 2972 | 181 | 3804 |
| 182 | 1510 | 183 | 338 | 184 | 202 | 185 | 294 |
| 188 | 695 | 189 | 1461 | 190 | 1256 | 191 | 398 |
| 192 | 789 | 193 | 1010 | 194 | 1692 | 195 | 275 |
| 196 | 252 | 197 | 796 | 198 | 2230 | 199 | 96 |
| 200 | 83 | 201 | 149 | 202 | 758 | 203 | 260 |
| 204 | 69 | 205 | 74 | 206 | 86 | 207 | 1437 |
| 208 | 40 | | | | | | |

In view of their ability to inhibit the enzyme 11β-hydroxysteroid dehydrogenase (HSD) 1, the compounds of general formula I according to the invention and the corresponding pharmaceutically acceptable salts thereof are theoretically suitable for the treatment and/or preventative treatment of all those conditions or diseases which may be affected by the inhibition of the 11β-hydroxysteroid dehydrogenase (HSD) 1 activity. Therefore, compounds according to the invention are particularly suitable for the prevention or treatment of diseases, particularly metabolic disorders, or conditions such as type 1 diabetes mellitus, type 2 diabetes mellitus, complications of diabetes (such as e.g. retinopathy, nephropathy or neuropathies, diabetic foot, ulcers, macroangiopathies, slow or poor wound healing), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. These substances are also suitable for preventing beta-cell degeneration such as e.g. apoptosis or necrosis of pancreatic beta cells. The substances are also suitable for improving or restoring the functionality of pancreatic cells, and also of increasing the number and size of pancreatic beta cells. The compounds according to the invention may also be used as diuretics or antihypertensives and are suitable for the prevention and treatment of acute renal failure.

Additionally, inhibition of 11β-hydroxysteroid dehydrogenase (HSD) 1 has been shown to lower intraocular pressure in subjects with ocular hypertension, therefore the compounds could be used to treat glaucoma.

In view of the role of 11β-hydroxysteroid dehydrogenase (HSD) 1 in modulating cortisol levels for interaction with the glucocorticoid receptor, and the known role of excess glucocorticoids in bone loss, the compounds may have beneficial effects in treatment or prevention of osteoporosis.

Stress and/or glucocorticoids have been shown to influence cognitive function, and excess cortisol has been associated with brain neuronal loss or dysfunction. Treatment with an 11β-hydroxysteroid dehydrogenase (HSD) 1 inhibitor may result in amelioration or prevention of cognitive impairment. Such compounds may also be useful in treating anxiety or depression.

The dynamic interaction between the immune system and the HPA (hypothalamopituitary-adrenal) axis is known, and glucocorticoids help balance between cell-mediated responses and humoral responses. The immune reaction is typically biased towards a humoral response in certain disease states, such as tuberculosis, leprosy, and psoriasis. More appropriate would be a cell-based response. An 11β-hydroxysteroid dehydrogenase (HSD) 1 inhibitor would bolster a temporal immune response in association with immunization to ensure that a cell based response would be obtained, and as such could be useful in immunomodulation.

In particular, the compounds according to the invention, including the physiologically acceptable salts thereof, are suitable for the prevention or treatment of diabetes, particularly type 1 diabetes mellitus, type 2 diabetes mellitus, and diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of an 11β-hydroxysteroid dehydrogenase (HSD) 1 inhibitor according to the invention with respect to one of the indications mentioned and/or which allow the dosage of an 11β-hydroxysteroid dehydrogenase (HSD) 1 inhibitor according to the invention to be reduced. Therapeutic agents which are suitable for such a combination include, for example, antidiabetic agents such as metformin, sulfonylureas (e.g. glibenclamide, tolbutamide, glimepiride), nateglinide, repaglinide, thiazolidinediones (e.g. rosiglitazone, pioglitazone), SGLT 2 inhibitors (e.g. dapagliflozin, remogliflozin etabonate), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. Sitagliptin, Vildagliptin, Saxagliptin, Alogliptin, Linagliptin), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase and glucokinase activators, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, SDRIs, axokine, leptin, leptin mimetics, antagonists of the cannabinoid) receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the enzyme 11β-hydroxysteroid dehydrogenase (HSD) 1. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

The Examples that follow are intended to illustrate the present invention without restricting it. The terms "ambient temperature" and "room temperature" are used interchangeably and designate a temperature of about 20° C.

Preparation of the Starting Compounds

EXAMPLE I

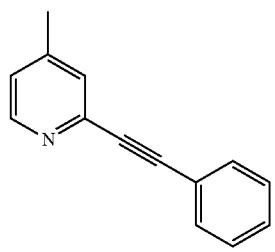

4-Methyl-2-phenylethynyl-pyridine

Phenylacetylene (15.4 mL) is added to a mixture of 2-bromo-4-methyl-pyridine (20.0 g), CuI (2.2 g), and Pd(PPh$_3$)$_2$Cl$_2$ (4.1 g) in triethylamine (600 mL) kept under argon atmosphere. The mixture is stirred at ambient temperature overnight. Then, water is added and the resulting mixture is extracted with diethyl ether. The combined organic extracts are washed with brine and dried (MgSO$_4$). The solvent is removed under reduced pressure and the residue is purified by chromatography on silica gel (cyclohexane/ethyl acetate 9:1->4:1) to give the product as an oil.

Yield: 18.6 g (83% of theory)
Mass spectrum (ESI$^+$): m/z=194 [M+H]$^+$

EXAMPLE II

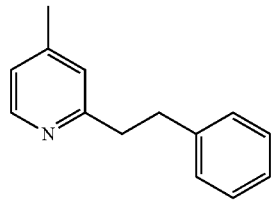

4-Methyl-2-phenethyl-pyridine

A mixture of 4-methyl-2-phenylethynyl-pyridine (18.2 g) and 10% palladium on carbon (2.0 g) in methanol (300 mL) is stirred under hydrogen atmosphere (50 psi) at ambient temperature until the triple bond is completely reduced (20 h). The mixture is filtrered and the solvent is removed under reduced pressure.

Yield: 17.6 g (95% of theory)
Mass spectrum (ESI$^+$): m/z=198 [M+H]$^+$

EXAMPLE III

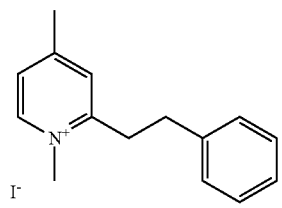 [SMILES: [I-] ; Cc1cc[n+](C)c(CCc2ccccc2)c1]

1,4-Dimethyl-2-phenethyl-pyridinium iodide

Iodomethane (8.3 mL) is added to a solution of 4-methyl-2-phenethyl-pyridine (17.5 g) in acetonitrile (70 mL). The resulting solution is stirred at room temperature overnight before another portion of iodomethane (2.8 mL) is added and the solution is further stirred at ca. 35° C. for another 14 h. After cooling to room temperature, the precipitate is separated by filtration, washed with acetonitrile, and dried at 50° C.

Yield: 20.9 g (69% of theory)
Mass spectrum (ESI$^+$): m/z=212 [1,4-dimethyl-2-phenethyl-pyridinium]$^+$

EXAMPLE IV

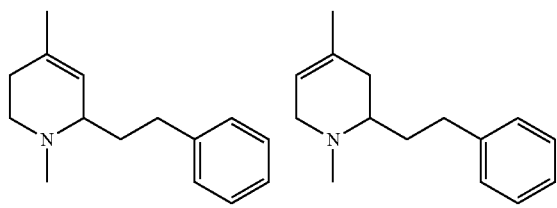

1,4-Dimethyl-6-phenethyl-1,2,3,6-tetrahydro-pyridine and 1,4-dimethyl-2-phenethyl-1,2,3,6-tetrahydro-pyridine Sodium borohydride (2.9 g) is added in one portion to a mixture of 1,4-dimethyl-2-phenethyl-pyridinium iodide (20.9 g) and sodium hydroxide (23.9 g) in water (60 mL) and methanol (75 mL). The mixture is stirred at 60° C. for 1 h and then cooled to room temperature. The reaction mixture is extracted with diethyl ether and the organic extracts are dried (MgSO$_4$). After removing the solvent, the residue is purified by chromatography on silica gel (dichloromethane/methanol 30:1->9:1) to give a mixture of the two title compounds (ca. 3:1).

Yield: 16.4 g (61% of theory)

Mass spectrum (ESI$^+$): m/z=216 [M+H]$^+$

EXAMPLE V

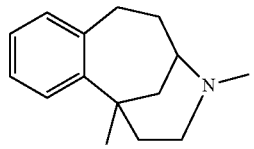 [SMILES: CN1CCC2(C)CC1CCc1ccccc12]

1,11-Dimethyl-11-aza-tricyclo[8.3.1.0*2,7*]tetradeca-2,4,6-triene

A mixture of 1,4-dimethyl-6-phenethyl-1,2,3,6-tetrahydro-pyridine and 1,4-dimethyl-2-phenethyl-1,2,3,6-tetrahydro-pyridine (ca. 3:1, 1.0 g) dissolved in polyphosphoric acid (5 mL) is stirred at 150° C. for 2 d. After cooling to ca. 80° C., water (30 mL) is added and the mixture is stirred vigorously for another 5 min. Then, the mixture is cooled in an ice bath, more water is added, and the mixture is basified using 40% NaOH in water. The resulting mixture is extracted with ethyl acetate, the combined organic extracts are washed with brine and dried (MgSO$_4$). The solvent is removed under reduced pressure to yield the title compound.

Yield: 0.76 g (76% of theory)

Mass spectrum (ESI$^+$): m/z=216 [M+H]$^+$

EXAMPLE VI

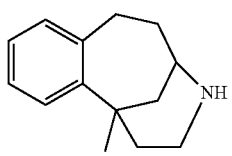

1-Methyl-11-aza-tricyclo[8.3.1.0*2,7*]tetradeca-2,4,6-triene

1-Chloroethyl chloroformate (3.8 mL) is added dropwise to a mixture of 1,11-dimethyl-11-aza-tricyclo[8.3.1.0*2,7*]tetradeca-2,4,6-triene (0.75 g) and NaHCO$_3$ (2.9 g) in 1,2-dichloroethane (3.5 mL) chilled in an ice bath. The reaction mixture is warmed to room temperature in the cooling bath and stirred overnight. Then, dichloromethane (20 mL) is added and the precipitate is removed by filtration. The filtrate is concentrated under reduced pressure and the residue is dissolved in methanol (20 mL). The resulting solution is stirred at reflux for 2 h. The solution is concentrated and the residue is purified by HPLC (water/MeCN/NH$_3$) to give the title compound.

Yield: 0.11 g (16% of theory)

The following compounds are obtained analogously to Example VI:

(1) 11,11-Dimethyl-2,3,4,5-tetrahydro-1H-2,6-methano-benzo[d]azocin-6-ol

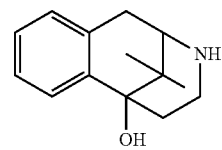 [SMILES: CC1(C)C2Cc3ccccc3C1(O)CCN2]

The starting material, 3,11,11-trimethyl-2,3,4,5-tetrahydro-1H-2,6-methano-benzo[d]azocin-6-ol, may be obtained in analogy to EP 28717 (1981) from 2-benzyl-1,3,3-trimethyl-piperidinone.

(2) 8-Hydroxy-2,3,4,5-tetrahydro-1H-2,6-methano-benzo[d]azocine-6-carboxylic acid methyl ester

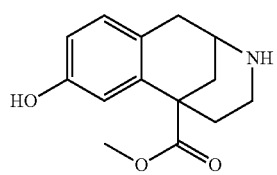 [SMILES: COC(=O)C12CCNC(Cc3ccc(O)cc31)C2]

The starting material, 8-hydroxy-3-methyl-2,3,4,5-tetrahydro-1H-2,6-methano-benzo[d]azocine-6-carboxylic acid methyl ester, may be obtained in analogy to J. Med. Chem. 1962, 5, 357-361 and U.S. Pat. No. 3,687,957 (1972) from 8-methoxy-3-methyl-1-oxo-2,3,4,5-tetrahydro-1H-2, 6-methano-benzo[d]azocine-6-carbonitrile. The methoxy group on the aromatic ring may be cleaved by using boron tribromide in dichloromethane or hydrobromic acid in acetic acid (see e.g. *J. Med. Chem.* 1992, 35, 4135-4142; *J. Med. Chem.* 2004, 47, 165-174).

Alternatively, the starting material may be obtained as described in Example XXII(1).

EXAMPLE VII

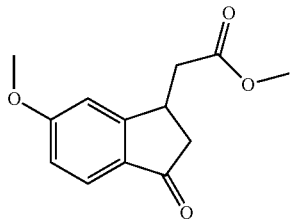 [SMILES: COC(=O)CC1CC(=O)c2ccc(OC)cc21]

(6-Methoxy-3-oxo-indan-1-yl)-acetic acid methyl ester

Concentrated sulfuric acid (3.0 mL) is added to 5-methoxy-1-indanone-3-acetic acid (13.0 g) dissolved in methanol (100 mL). The solution is stirred at reflux temperature for 4 h and then cooled to room temperature. About two thirds of the methanol is removed under reduced pressure and water (100 mL) and ethyl acetate (200 mL) are added to the remainder. The organic phase is separated and washed with water, 1 M NaOH solution, and brine. The organic phase is dried (MgSO$_4$) and the solvent is evaporated to give the product as a yellow oil.

Yield: 13.2 g (95% of theory)

Mass spectrum (ESI$^+$): m/z=235 [M+H]$^+$

EXAMPLE VIII

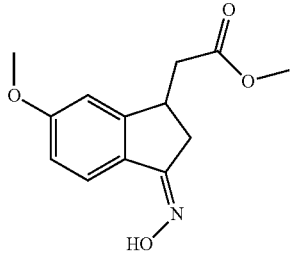 [SMILES: COC(=O)CC1C/C(=N/O)c2ccc(OC)cc21]

(3-Hydroxyimino-6-methoxy-indan-1-yl)-acetic acid methyl ester (6-Methoxy-3-oxo-indan-1-yl)-acetic acid methyl ester (12.0 g), hydroxylamine hydrochloride (4.6 g), and sodium acetate (5.5 g) dissolved in water (40 mL) and methanol (50 mL) are stirred at reflux temperature for 3 h. After cooling to room temperature, water (100 mL) is added and the solution is extracted with ethyl acetate. The combined organic extracts are washed with water and brine and dried (MgSO$_4$). The solvent is evaporated to give the product as a brown oil.

Yield: 12.5 g (98% of theory)

Mass spectrum (ESI$^+$): m/z=250 [M+H]$^+$

EXAMPLE IX

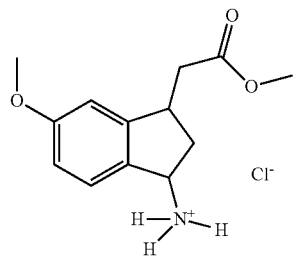 [SMILES: COC(=O)CC1CC([NH3+])c2ccc(OC)cc21 ; [Cl-]]

5-Methoxy-3-methoxycarbonylmethyl-indan-1-yl-ammonium chloride

A mixture of 10% palladium on carbon (3.0 g), (3-hydroxyimino-6-methoxy-indan-1-yl)-acetic acid methyl ester (12.5 g), and concentrated hydrochloric acid (4.7 mL) in methanol (150 mL) is stirred under hydrogen atmosphere at room temperature overnight. The mixture is filtered and the filtrate is concentrated under reduced pressure. The residue is azeotropically dried using toluene and washed with diisopropyl ether to give the product as a white solid after drying at 50° C.

Yield: 13.0 g (100% of theory)

Mass spectrum (ESI$^+$): m/z=236 [M+H]$^+$ ([M+H]$^+$ of (3-amino-6-methoxy-indan-1-yl)-acetic acid methyl ester)

EXAMPLE X

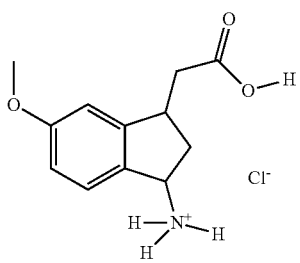 [SMILES: COc1ccc2c(c1)C(CC(=O)O)CC2[NH3+] ; [Cl-]]

3-Carboxymethyl-5-methoxy-indan-1-yl-ammonium chloride

5-Methoxy-3-methoxycarbonylmethyl-indan-1-yl-ammonium chloride (12.5 g) dissolved in 2 M hydrochloric acid (120 mL) is stirred at reflux temperature for 3 h. Then, the solvent is removed and the residue is azeotropically dried using toluene and further purified by washing with diisopropyl ether. The product is dried at 50° C.

Yield: 11.8 g (100% of theory)

Mass spectrum (ESI$^+$): m/z=222 [M+H]$^+$ ([M+H]$^+$ of (3-amino-6-methoxy-indan-1-yl)-acetic acid)

EXAMPLE XI

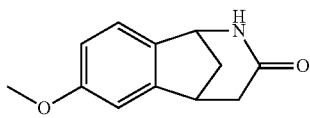

4-Methoxy-9-aza-tricyclo[6.3.1.0*2,7*]dodeca-2,4,6-trien-10-one

3-Carboxymethyl-5-methoxy-indan-1-yl-ammonium chloride (13.2 g) and 1-cyclohexyl-3-(2-morpholinoethyl) carbodiimide methyl-p-toluenesulfonate (21.7 g) dissolved in pyridine (500 mL) are stirred at room temperature for 7 d. Then, the pyridine is removed under reduced pressure and the residue is taken up in water (200 mL) and dichloromethane (200 mL). The organic phase is separated and the aqueous phase is extracted twice with dichloromethane. The combined organic phases are washed with 1 M hydrochloric acid, 1 M NaOH solution, and water. After drying (MgSO$_4$), the solvent is evaporated under reduced pressure to yield the product as a beige solid.

Yield: 3.0 g (29% of theory)

Mass spectrum (ESI$^+$): m/z=204 [M+H]$^+$

EXAMPLE XII

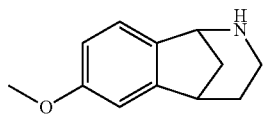

4-Methoxy-9-aza-tricyclo[6.3.1.0*2,7*]dodeca-2,4,6-triene

1 M Borane tetrahydrofuran complex (70 mL) is added dropwise to a solution of 4-methoxy-9-aza-tricyclo[6.3.1.0*2,7*]dodeca-2,4,6-trien-10-one (3.0 g) in tetrahydrofuran (20 mL) chilled in an ice bath. The resulting solution is stirred at reflux temperature for 5 h and then at room temperature overnight. The solution is cooled to ca. −10° C. and half-concentrated hydrochloric acid (50 mL) is added carefully. The mixture is stirred at room temperature for 1 h and an additional hour at reflux temperature. The solvent is removed and 2 M aqueous NaOH solution (50 mL) is added to the residue. The resulting mixture is extracted with dichloromethane and the combined organic extracts are dried (MgSO$_4$). After removal of the solvent, the residue is taken up in ethanol (20 mL) and the resulting solution is treated with oxalic acid (3 mL) to obtain the oxalate salt of the title compound.

Yield: 0.8 g (19% of theory)

Mass spectrum (ESI$^+$): m/z=190 [M+H]$^+$

EXAMPLE XIII

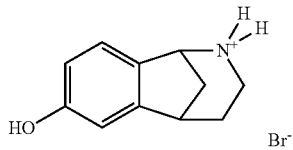 [SMILES: Oc1ccc2c(c1)C1CC[NH2+]C2C1 ; [Br-]]

4-Hydroxy-9-azonia-tricyclo[6.3.1.0*2,7*]dodeca-2,4,6-triene bromide

A solution of 4-methoxy-9-aza-tricyclo[6.3.1.0*2,7*]dodeca-2,4,6-triene (0.50 g of oxalate salt) in hydrobromic acid (48% in water, 10 mL) is stirred at reflux temperature for 3 h. Then, the solution is concentrated under reduced pressure and the residue is azetropically dried using toluene and ethanol. The residue is washed with acetone and dried to give the product as a solid.

Yield: 0.23 g (49% of theory)

Mass spectrum (ESI$^+$): m/z=176 [M+H]$^+$ (of free amine)

The following compound is obtained analogously to Example XIII:

(1) (2R,6S)-6,11,11-Trimethyl-1,2,3,4,5,6-hexahydro-2,6-methano-benzo[d]azocin-9-ol

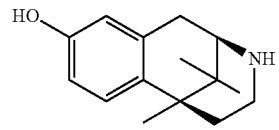 [SMILES: CC1(C)[C@H]2Cc3cc(O)ccc3[C@]1(C)CCN2]

Mass spectrum (ESI$^+$): m/z=232 [M+H]$^+$

The compound is prepared from (2R,6S)-9-methoxy-6,11,11-trimethyl-1,2,3,4,5,6-hexahydro-2,6-methano-benzo[d]azocine [tartaric acid salt, for preparation see WO 9959976 (1999)] and isolated as the hydrogen bromide salt.

EXAMPLE XIV

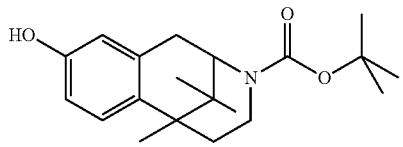 [SMILES: CC(C)(C)OC(=O)N1CCC2(C)c3ccc(O)cc3CC1C2(C)C]

9-Hydroxy-6,11,11-trimethyl-1,2,5,6-tetrahydro-4H-2,6-methano-benzo[d]azocine-3-carboxylic acid tert-butyl ester Di-tert-butyl dicarbonate (8.7 g) is added to a solution of 6,11,11-trimethyl-1,2,3,4,5,6-hexahydro-2,6-methano-benzo[d]azocin-9-ol (12.0 g) and triethylamine (8 ml) in 1,4-dioxane (100 mL) and water (100 mL). The solution is stirred at room temperature overnight. Then, ethyl acetate is added and the organic phase is separated. The aqueous phase is extracted with ethyl acetate and the organic extract and phase are combined. The organic phase is washed with 1 M hydrochloric acid, water, and brine, and then dried (MgSO$_4$). After removal of the solvent under reduced pressure, the residue is crystallized from diisopropyl ether to give the title compound.

Yield: 6.5 g (51% of theory)

Mass spectrum (ESI$^+$): m/z=332 [M+H]$^+$

The following compounds are be obtained analogously to Example XIV:

(1) (2R,6S)-10-Hydroxy-6,11,11-trimethyl-1,2,5,6-tetrahydro-4H-2,6-methano-benzo[d]azocine-3-carboxylic acid tert-butyl ester

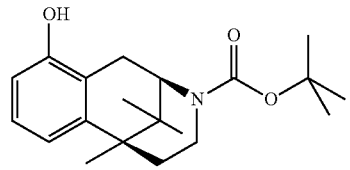 [SMILES: CC(C)(C)OC(=O)N1CC[C@@]2(C)c3cccc(O)c3C[C@@H]1C2(C)C]

Mass spectrum (ESI$^+$): m/z=332 [M+NH$_4$]$^+$ (2) (2R,6R,11S)-8-Hydroxy-6,11-dimethyl-1,2,5,6-tetrahydro-4H-2,6-methano-benzo[d]azocine-3-carboxylic acid tert-butyl ester

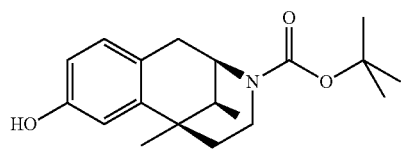 [SMILES: C[C@@H]1[C@H]2Cc3ccc(O)cc3[C@]1(C)CCN2C(=O)OC(C)(C)C]

(3) (2S,6R)-8-Hydroxy-6,9,11,11-tetramethyl-1,2,5,6-tetrahydro-4H-2,6-methano-benzo[d]azocine-3-carboxylic acid tert-butyl ester

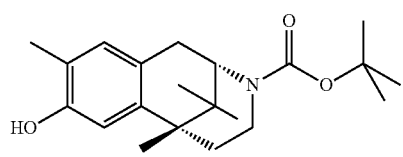 [SMILES: Cc1cc2c(cc1O)[C@@]1(C)CCN(C(=O)OC(C)(C)C)[C@@H](C2)C1(C)C]

The compound may be obtained by resolution of the racemic mixture by HPLC on chiral phase (4) (2R,6S)-8-Hydroxy-6,9,11,11-tetramethyl-1,2,5,6-tetrahydro-4H-2,6-methano-benzo[d]azocine-3-carboxylic acid tert-butyl ester

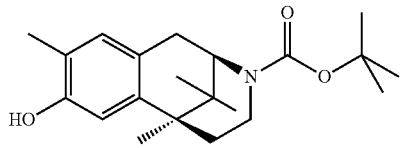 [SMILES: Cc1cc2c(cc1O)[C@]1(C)CCN(C(=O)OC(C)(C)C)[C@H](C2)C1(C)C]

The compound may be obtained by resolution of the racemic mixture by HPLC on chiral phase (5) (2S,6R)-9-Hydroxy-6,8,11,11-tetramethyl-1,2,5,6-tetrahydro-4H-2,6-methano-benzo[d]azocine-3-carboxylic acid tert-butyl ester

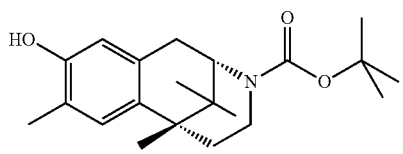 [SMILES: Cc1cc2c(cc1O)C[C@@H]1N(C(=O)OC(C)(C)C)CC[C@@]2(C)C1(C)C]

The compound may be obtained by resolution of the racemic mixture by HPLC on chiral phase (6) (2R,6S)-9-Hydroxy-6,8,11,11-tetramethyl-1,2,5,6-tetrahydro-4H-2,6-methano-benzo[d]azocine-3-carboxylic acid tert-butyl ester

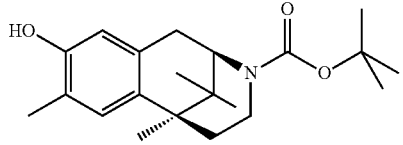 [SMILES: Cc1cc2c(cc1O)C[C@H]1N(C(=O)OC(C)(C)C)CC[C@]2(C)C1(C)C]

The compound may be obtained by resolution of the racemic mixture by HPLC on chiral phase (7) 8-Hydroxy-6,11,11-trimethyl-1,2,5,6-tetrahydro-4H-2,6-methano-benzo[d]azocine-3-carboxylic acid tert-butyl ester

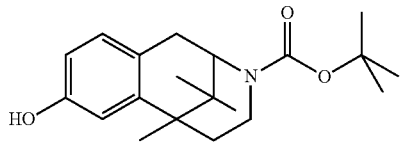 [SMILES: CC(C)(C)OC(=O)N1CCC2(C)c3cc(O)ccc3CC1C2(C)C]

8) (2R,6S)-9-Hydroxy-6,11,11-trimethyl-1,2,5,6-tetrahydro-4H-2,6-methano-benzo[d]azocine-3-carboxylic acid tert-butyl ester

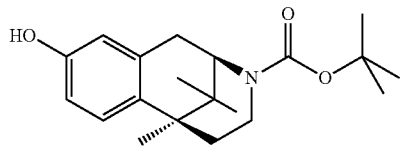 [SMILES: CC(C)(C)OC(=O)N1CC[C@@]2(C)c3ccc(O)cc3C[C@@H]1C2(C)C]

Mass spectrum (ESI⁺): m/z=332 [M+NH$_4$]$^+$

The compound may be obtained by resolution of the racemic mixture by HPLC on chiral phase or by using the enantiomerically pure starting material that in turn may be obtained as described in Example XIII(1) or by resolution of the racemic mixture by HPLC on chiral phase. The synthesis of the racemic starting material is described in EP 521422 (1993).

EXAMPLE XV

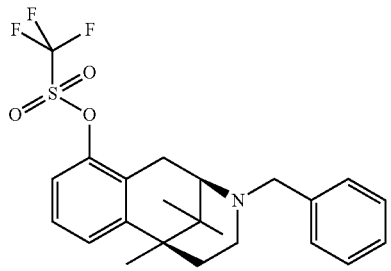 [SMILES: CC1(C)[C@H]2Cc3c(OS(=O)(=O)C(F)(F)F)cccc3[C@]1(C)CCN2Cc1ccccc1]

(2R,6S)-Trifluoro-methanesulfonic acid 3-benzyl-6,11,11-trimethyl-1,2,3,4,5,6-hexahydro-2,6-methano-benzo[d]azocin-10-yl ester Trifluoromethanesulfonic anhydride (9.7 mL) is added to a solution of 3-benzyl-6,11,11-trimethyl-1,2,3,4,5,6-hexahydro-2,6-methano-benzo[d]azocin-10-ol (13.7 g, the compound may be obtained by reductive amination of benzaldehyde with (2R,6S)-6,11,11-trimethyl-1,2,3,4,5,6-hexahydro-2,6-methano-benzo[d]azocin-10-ol and NaHB(OAc)$_3$ in 1,2-dichloroethane), triethylamine (43 mL), and 4-dimethylaminopyridine (50 mg) in dichloromethane (135 mL) chilled to −10° C. under argon atmosphere. The solution is stirred at ca. −5° C. for 30 min and then at room temperature overnight. The solution is added to ice-cold water and then aqueous ammonia solution is added. The resulting mixture is extracted with dichloromethane, the combined organic extracts are washed with water and dried (MgSO$_4$). The solvent is removed under reduced pressure to give the crude product that is used without further purification.

Yield: 18.0 g (93% of theory)

Mass spectrum (ESI⁺): m/z=454 [M+H]$^+$

The following compounds are obtained analogously to Example XV:

(1) 6,11,11-Trimethyl-9-trifluoromethanesulfonyloxy-1,2,5,6-tetrahydro-4H-2,6-methano-benzo[d]azocine-3-carboxylic acid tert-butyl ester

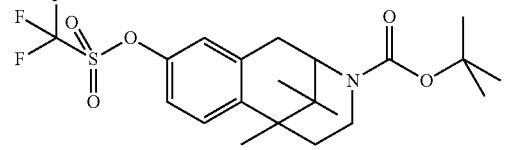

Mass spectrum (ESI⁺): m/z=464 [M+H]$^+$ (2) (2R,6S)-6,11,11-Trimethyl-10-trifluoromethanesulfonyloxy-1,2,5,6-tetrahydro-4H-2,6-methano-benzo[d]azocine-3-carboxylic acid tert-butyl ester

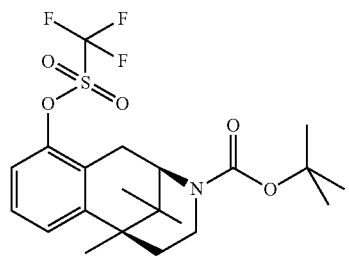 [SMILES: CC(C)(C)OC(=O)N1CC[C@@]2(C)c3cccc(OS(=O)(=O)C(F)(F)F)c3C[C@@H]1C2(C)C]

Mass spectrum (ESI⁺): m/z=481 [M+NH$_4$]$^+$ (3) (2R,6R)-6,11-Dimethyl-8-trifluoromethanesulfonyloxy-1,2,5,6-tetrahydro-4H-2,6-methano-benzo[d]azocine-3-carboxylic acid tert-butyl ester

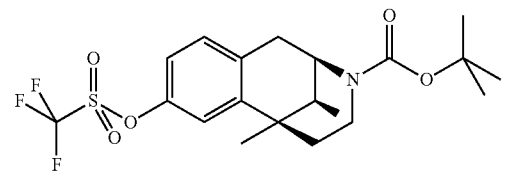 [SMILES: C[C@@H]1[C@H]2Cc3ccc(OS(=O)(=O)C(F)(F)F)cc3[C@]1(C)CCN2C(=O)OC(C)(C)C]

Mass spectrum (ESI⁺): m/z=450 [M+NH$_4$]$^+$ (4) 6,11,11-Trimethyl-8-trifluoromethanesulfonyloxy-1,2,5,6-tetrahydro-4H-2,6-methano-benzo[d]azocine-3-carboxylic acid tert-butyl ester

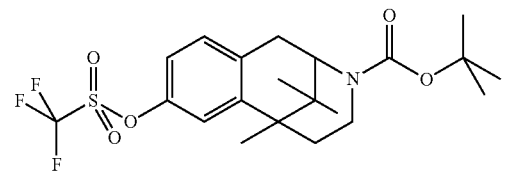 [SMILES: CC(C)(C)OC(=O)N1CCC2(C)c3cc(OS(=O)(=O)C(F)(F)F)ccc3CC1C2(C)C]

(5) (2R,6S)-6,11,11-Trimethyl-9-trifluoromethane-sulfonyloxy-1,2,5,6-tetrahydro-4H-2,6-methano-benzo[d]azocine-3-carboxylic acid tert-butyl ester

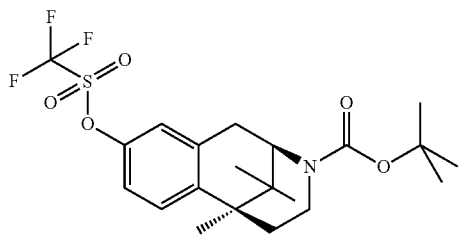 [SMILES: CC(C)(C)OC(=O)N1CC[C@@]2(C)c3ccc(OS(=O)(=O)C(F)(F)F)cc3C[C@@H]1C2(C)C]

Mass spectrum (ESI+): m/z=464 [M+NH$_4$]+

(6) (2R,6R,11R)-Trifluoro-methanesulfonic acid 3-((S)-2,3-dihydro-benzo[1,4]dioxine-2-carbonyl)-6,11-dimethyl-1,2,3,4,5,6-hexahydro-2,6-methano-benzo[d]azocin-8-yl ester

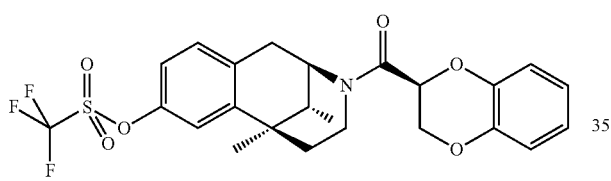

Mass spectrum (ESI+): m/z=512 [M+H]+

The synthesis of the starting material is described in Example 1 (Table 3).

(7) (2R,6R,11R)-Trifluoro-methanesulfonic acid 3-((R)-2,3-dihydro-benzo[1,4]dioxine-2-carbonyl)-6,11-dimethyl-1,2,3,4,5,6-hexahydro-2,6-methano-benzo[d]azocin-8-yl ester

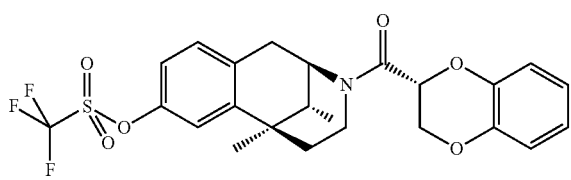 [SMILES: C[C@H]1[C@H]2Cc3ccc(OS(=O)(=O)C(F)(F)F)cc3[C@]1(C)CCN2C(=O)[C@H]1COc2ccccc2O1]

Mass spectrum (ESI+): m/z=512 [M+H]+

The synthesis of the starting material is described in Example 2 (Table 3).

(8) (2R,6R,11S)-Trifluoro-methanesulfonic acid 9-cyano-6,11-dimethyl-3-(2,2,2-trifluoro-acetyl)-1,2,3,4,5,6-hexahydro-2,6-methano-benzo[d]azocin-8-yl ester

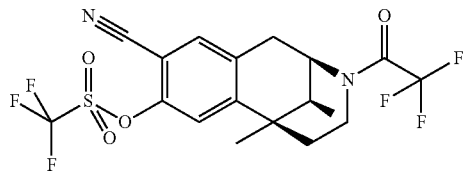 [SMILES: C[C@@H]1[C@H]2Cc3cc(C#N)c(OS(=O)(=O)C(F)(F)F)cc3[C@]1(C)CCN2C(=O)C(F)(F)F]

Mass spectrum (ESI+): m/z=488 [M+NH$_4$]+

(9) (2R,6R,11R)-Trifluoro-methanesulfonic acid 9-cyano-6,11-dimethyl-3-(2,2,2-trifluoro-acetyl)-1,2,3,4,5,6-hexahydro-2,6-methano-benzo[d]azocin-8-yl ester

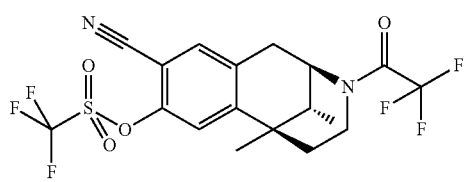 [SMILES: C[C@H]1[C@H]2Cc3cc(C#N)c(OS(=O)(=O)C(F)(F)F)cc3[C@]1(C)CCN2C(=O)C(F)(F)F]

Mass spectrum (ESI+): m/z=488 [M+NH$_4$]+

EXAMPLE XVI

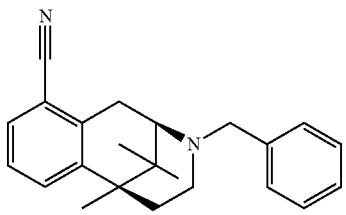 [SMILES: CC1(C)[C@H]2Cc3c(C#N)cccc3[C@]1(C)CCN2Cc1ccccc1]

(2R,6S)-3-Benzyl-6,11,11-trimethyl-1,2,3,4,5,6-hexahydro-2,6-methano-benzo[d]azocine-10-carbonitrile Tetrakis(triphenylphosphine)palladium(0) (2.79 g) is added to a mixture of (2R,6S)-trifluoro-methanesulfonic acid 3-benzyl-6,11,11-trimethyl-1,2,3,4,5,6-hexahydro-2,6-methano-benzo[d]azocin-10-yl ester (7.30 g) and zinc cyanide (2.85 g) in N,N-dimethylformamide (35 mL) kept in argon atmosphere. The resulting mixture is stirred at 100° C. for 6 h. After cooling to room temperature, water (300 mL), concentrated ammonia solution (10 mL), and ethyl acetate (150 mL) are added and the forming precipitate is separated by filtration. The organic layer of the filtrate is separated and the aqueous layer is extracted twice with ethyl acetate. The combined organic phases are washed with brine and dried (MgSO₄). The solvent is removed under reduced pressure and the residue is purified by chromatography on silica gel (cyclohexane/ethyl acetate 19:1) to give the product.

Yield: 4.43 g (62% of theory)

Mass spectrum (ESI⁺): m/z=331 [M+H]⁺

The following compounds are obtained analogously to Example XVI:

(1) (2R,6R,11S)-8-Cyano-6,11-dimethyl-1,2,5,6-tetrahydro-4H-2,6-methano-benzo[d]azocine-3-carboxylic acid tert-butyl ester

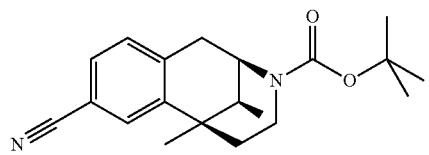 [SMILES: C[C@@H]1[C@H]2Cc3ccc(C#N)cc3[C@]1(C)CCN2C(=O)OC(C)(C)C]

Mass spectrum (ESI⁺): m/z=327 [M+NH₄]⁺

(2) 9-Cyano-6,11,11-trimethyl-1,2,5,6-tetrahydro-4H-2,6-methano-benzo[d]azocine-3-carboxylic acid tert-butyl ester

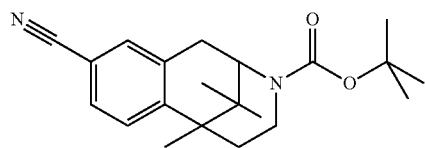 [SMILES: CC(C)(C)OC(=O)N1CCC2(C)c3ccc(C#N)cc3CC1C2(C)C]

Mass spectrum (ESI⁺): m/z=341 [M+H]⁺

(3) (2R,6S)-9-Cyano-6,11,11-trimethyl-1,2,5,6-tetrahydro-4H-2,6-methano-benzo[d]azocine-3-carboxylic acid tert-butyl ester

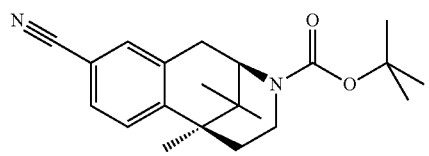 [SMILES: CC(C)(C)OC(=O)N1CC[C@@]2(C)c3ccc(C#N)cc3C[C@@H]1C2(C)C]

Mass spectrum (ESI⁺): m/z=341 [M+H]⁺

EXAMPLE XVII

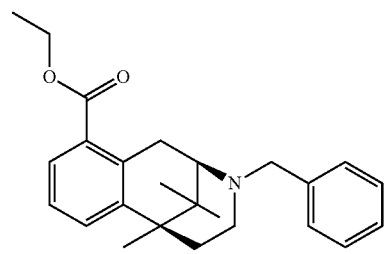 [SMILES: CCOC(=O)c1cccc2c1C[C@H]1N(Cc3ccccc3)CC[C@]2(C)C1(C)C]

(2R,6S)-3-Benzyl-6,11,11-trimethyl-1,2,3,4,5,6-hexahydro-2,6-methano-benzo[d]azocine-10-carboxylic acid ethyl ester A solution of (2R,6S)-3-benzyl-6,11,11-trimethyl-1,2,3,4,5,6-hexahydro-2,6-methano-benzo[d]azocine-10-carbonitrile (1.14 g) in 80% sulfuric acid (4 mL) is stirred at 150° C. for 1 h. After cooling to room temperature, ethanol (30 mL) is added and the solution is stirred at 100° C. for 2 d. Then, the cooled solution is added to water (100 mL) and the mixture is basified using 40% aqueous NaOH solution. The resulting mixture is extracted twice with ethyl acetate and dried (MgSO₄). The solvent is removed under reduced pressure to give the crude product.

Yield: 1.14 g (87% of theory)

Mass spectrum (ESI⁺): m/z=378 [M+H]⁺

The following compounds are obtained analogously to Example XVII:

(1) 6,11,11-Trimethyl-1,2,3,4,5,6-hexahydro-2,6-methano-benzo[d]azocine-9-carboxylic acid ethyl ester

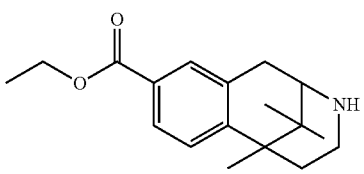 [SMILES: CCOC(=O)c1ccc2c(c1)CC1NCCC2(C)C1(C)C]

Mass spectrum (ESI⁺): m/z=288 [M+H]⁺

The compound is prepared from 6,11,11-trimethyl-1,2,3,4,5,6-hexahydro-2,6-methano-benzo[d]azocine-9-carbonitrile applying the procedure described above.

(2) (2R,6R,11S)-3-(3H-Benzoimidazole-5-carbo-nyl)-6,11-dimethyl-1,2,3,4,5,6-hexahydro-2,6-methano-benzo[d]azocine-8-carboxylic acid ethyl ester

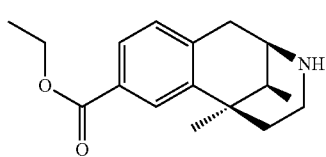 [SMILES: CCOC(=O)c1ccc2c(c1)[C@]1(C)CCN[C@H](C2)[C@H]1C]

Mass spectrum (ESI+): m/z=274 [M+H]+

The compound is prepared from (2R,6R,11S)-6,11-dimethyl-1,2,3,4,5,6-hexahydro-2,6-methano-benzo[d]azocine-8-carbonitrile applying the procedure described above.

EXAMPLE XVIII

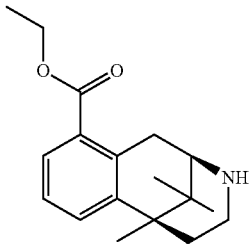 [SMILES: CCOC(=O)c1cccc2c1C[C@H]1NCC[C@]2(C)C1(C)C]

(2R,6S)-6,11,11-Trimethyl-1,2,3,4,5,6-hexahydro-2,6-methano-benzo[d]azocine-10-carboxylic acid ethyl ester Pd(OH)$_2$ (0.20 g) is added to a solution of (2R,6S)-3-benzyl-6,11,11-trimethyl-1,2,3,4,5,6-hexahydro-2,6-methano-benzo[d]azocine-10-carboxylic acid ethyl ester (1.13 g) in ethanol (20 mL). The resulting mixture is stirred under hydrogen atmosphere (50 psi) at room temperature overnight. Then, the catalyst is separated by filtration and the filtrate is concentrated under reduced pressure to give the product.

Yield: 0.61 g (71% of theory)

Mass spectrum (ESI+): m/z=288 [M+H]+

The following compound is obtained analogously to Example XVIII:

(1) (2R,6S)-6,11,11-Trimethyl-1,2,3,4,5,6-hexahydro-2,6-methano-benzo[d]azocine-10-carbonitrile

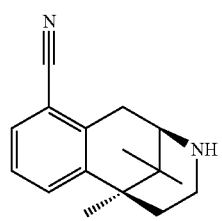 [SMILES: CC1(C)[C@H]2Cc3c(C#N)cccc3[C@]1(C)CCN2]

EXAMPLE XIX

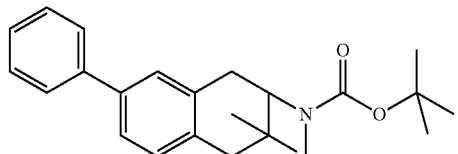

6,11,11-Trimethyl-9-phenyl-1,2,5,6-tetrahydro-4H-2,6-methano-benzo[d]azocine-3-carboxylic acid tert-butyl ester Aqueous 2 M Na$_2$CO$_3$ solution (5 mL) is added to a mixture of 6,11,11-trimethyl-9-trifluoromethanesulfonyloxy-1,2,5,6-tetrahydro-4H-2,6-methano-benzo[d]azocine-3-carboxylic acid tert-butyl ester (1.00 g) and phenylboronic acid (0.34 g) in N,N-dimethylformamide (5 mL) in argon atmosphere. The resulting mixture is flushed with argon and then 1,1'-bis(diphenylphosphino)ferrocene-palladium(II) dichloride dichloromethane complex (0.18 g) is added. The mixture is heated to 100° C. and stirred at this temperature for 4 h. After cooling to room temperature, water is added and the resulting mixture is extracted with ethyl acetate. The combined organic extracts are dried (MgSO$_4$) and the solvent is removed under reduced pressure. The residue is purified by chromatography on silica gel (cyclohexane/ethyl acetate 9:1->1:1) to give the product as a colorless oil.

Yield: 0.35 g (41% of theory)

Mass spectrum (ESI+): m/z=392 [M+H]+

EXAMPLE XX

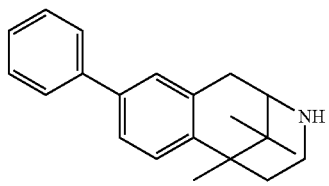 [SMILES: CC12CCNC(Cc3cc(-c4ccccc4)ccc31)C2(C)C]

6,11,11-Trimethyl-9-phenyl-1,2,3,4,5,6-hexahydro-2,6-methano-benzo[d]azocine

Trifluoroacetic acid (0.5 mL) is added to a solution of 6,11,11-trimethyl-9-phenyl-1,2,5,6-tetrahydro-4H-2,6-methano-benzo[d]azocine-3-carboxylic acid tert-butyl ester (0.30 g) in dichloromethane (2.5 mL). The solution is stirred at ambient temperature for 1 h and then concentrated under reduced pressure. The crude trifluoroacetic acid salt of the title compound is used without further purification.

Yield: 0.31 g (100% of theory)

The following compounds are obtained analogously to Example XX:

(Alternatively, in cases in which the purity of the product is insufficient after applying the procedure described above, the compounds are purified by HPLC on reversed phase (MeCN/water) to obtain the pure compounds.)

(1) (2R,6R,11S)-6,11-Dimethyl-1,2,3,4,5,6-hexahydro-2,6-methano-benzo[d]azocine-8-carbonitrile

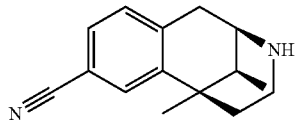 [SMILES: C[C@@H]1[C@H]2Cc3ccc(C#N)cc3[C@]1(C)CCN2]

Mass spectrum (ESI⁺): m/z=227 [M+NH₄]⁺

The compound is obtained as its trifluoroacetic acid salt.

(2) 6,11,11-Trimethyl-1,2,3,4,5,6-hexahydro-2,6-methano-benzo[d]azocine-9-carbonitrile

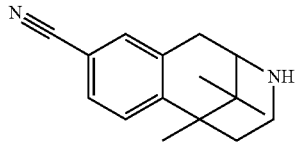 [SMILES: CC12CCNC(Cc3cc(C#N)ccc31)C2(C)C]

Mass spectrum (ESI⁺): m/z=241 [M+H]⁺

The compound is obtained as its trifluoroacetic acid salt.

(3) (2R,6S)-6,11,11-Trimethyl-1,2,3,4,5,6-hexahydro-2,6-methano-benzo[d]azocin-10-ylamine

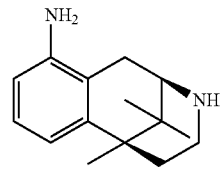 [SMILES: CC1(C)[C@H]2Cc3c(N)cccc3[C@]1(C)CCN2]

Mass spectrum (ESI⁺): m/z=231 [M+NH₄]⁺

The compound is obtained as its double trifluoroacetic acid salt.

(4) 6,11,11-Trimethyl-1,2,3,4,5,6-hexahydro-2,6-methano-benzo[d]azocin-9-ylamine

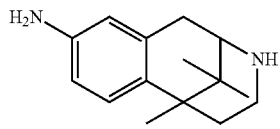

Mass spectrum (ESI⁺): m/z=231 [M+NH₄]⁺

The compound is obtained as its double trifluoroacetic acid salt.

(5) (2S,6R)-8-Methoxy-6,9,11,11-tetramethyl-1,2,3,4,5,6-hexahydro-2,6-methano-benzo[d]azocine

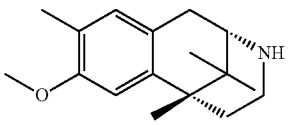 [SMILES: COc1cc2c(cc1C)C[C@@H]1NCC[C@@]2(C)C1(C)C]

The compound may be obtained by resolution of the racemic mixture by HPLC on chiral phase or by using the enantiomerically pure (2S,6R)-8-methoxy-6,9,11,11-tetramethyl-1,2,5,6-tetrahydro-4H-2,6-methano-benzo[d]azocine-3-carboxylic acid tert-butyl ester.

(6) (2R,6S)-8-Methoxy-6,9,11,11-tetramethyl-1,2,3,4,5,6-hexahydro-2,6-methano-benzo[d]azocine

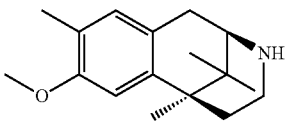 [SMILES: COc1cc2c(cc1C)C[C@H]1NCC[C@]2(C)C1(C)C]

The compound may be obtained by resolution of the racemic mixture by HPLC on chiral phase or by using the enantiomerically pure (2R,6S)-8-methoxy-6,9,11,11-tetramethyl-1,2,5,6-tetrahydro-4H-2,6-methano-benzo[d]azocine-3-carboxylic acid tert-butyl ester.

(7) (2S,6R)-9-Methoxy-6,8,11,11-tetramethyl-1,2,3,4,5,6-hexahydro-2,6-methano-benzo[d]azocine

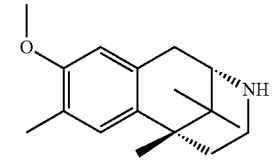 [SMILES: COc1cc2c(cc1C)[C@@]1(C)CCN[C@@H](C2)C1(C)C]

The compound may be obtained by resolution of the racemic mixture by HPLC on chiral phase or by using the enantiomerically pure (2S,6R)-9-methoxy-6,8,11,11-tetramethyl-1,2,5,6-tetrahydro-4H-2,6-methano-benzo[d]azocine-3-carboxylic acid tert-butyl ester.

(8) (2R,6S)-9-Methoxy-6,8,11,11-tetramethyl-1,2,3,4,5,6-hexahydro-2,6-methano-benzo[d]azocine

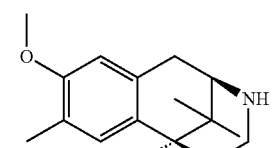

The compound may be obtained by resolution of the racemic mixture by HPLC on chiral phase or by using the enantiomerically pure (2R,6S)-9-methoxy-6,8,11,11-tetramethyl-1,2,5,6-tetrahydro-4H-2,6-methano-benzo[d]azocine-3-carboxylic acid tert-butyl ester.

(9) 8,9-Dimethoxy-6,11,11-trimethyl-1,2,3,4,5,6-hexahydro-2,6-methano-benzo[d]azocine

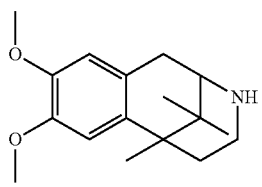 [SMILES: COc1cc2c(cc1OC)C1(C)CCNC(C2)C1(C)C]

(10) 8-Methoxy-6,11,11-trimethyl-1,2,3,4,5,6-hexahydro-2,6-methano-benzo[d]azocin-9-ol

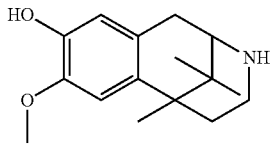

(11) 9-Methoxy-6,11,11-trimethyl-1,2,3,4,5,6-hexahydro-2,6-methano-benzo[d]azocin-8-ol

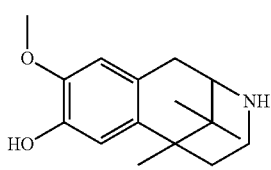 [SMILES: COc1cc2c(cc1O)C1(C)CCNC(C2)C1(C)C]

(12) (2R,6S)-6,11,11-Trimethyl-1,2,3,4,5,6-hexahydro-2,6-methano-benzo[d]azocine-9-carbonitrile

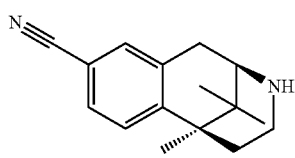 [SMILES: CC1(C)[C@H]2Cc3cc(C#N)ccc3[C@]1(C)CCN2]

Mass spectrum (ESI+): m/z=241 [M+H]+
The compound is obtained as its trifluoroacetic acid salt.

(13) (cis-4-Amino-cyclohexyl)-[(2R,6S)-10-hydroxy-6,11,11-trimethyl-1,2,5,6-tetrahydro-4H-2,6-methano-benzo[d]azocin-3-yl]-methanone

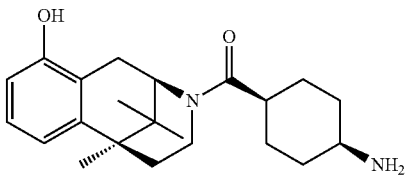 [SMILES: CC1(C)[C@H]2Cc3c(O)cccc3[C@]1(C)CCN2C(=O)[C@H]1CC[C@@H](N)CC1]

The starting material, {cis-4-[(2R,6S)-10-hydroxy-6,11,11-trimethyl-1,2,5,6-tetrahydro-4H-2,6-methano-benzo[d]azocine-3-carbonyl]-cyclohexyl}-carbamic acid tert-butyl ester, is obtained from (2R,6S)-6,11,11-trimethyl-1,2,3,4,5,6-hexahydro-2,6-methano-benzo[d]azocin-10-ol and cis-4-tert-butoxycarbonylamino-cyclohexanecarboxylic acid employing procedure B.

(14) [(1R,3R)-3-Amino-cyclopentyl]-[(2R,6S)-6,11,11-trimethyl-1,2,5,6-tetrahydro-4H-2,6-methano-benzo[d]azocin-3-yl]-methanone

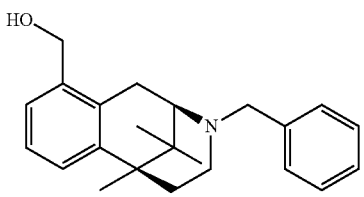 [SMILES: CC1(C)[C@H]2Cc3c(CO)cccc3[C@]1(C)CCN2Cc1ccccc1]

Isolated as the trifluoroacetic acid salt.
The starting material, {(1R,3R)-3-[(2R,6S)-6,11,11-trimethyl-1,2,5,6-tetrahydro-4H-2,6-methano-benzo[d]azocine-3-carbonyl]-cyclopentyl}-carbamic acid tert-butyl ester, is obtained from (2R,6S)-6,11,11-trimethyl-1,2,3,4,5,6-hexahydro-2,6-methano-benzo[d]azocine and (1R,3R)-3-tert-butoxycarbonylamino-cyclopentanecarboxylic acid employing procedure B.

EXAMPLE XXI

[(2R,6S)-3-Benzyl-6,11,11-trimethyl-1,2,3,4,5,6-hexahydro-2,6-methano-benzo[d]azocin-10-yl]-methanol A solution of (2R,6S)-3-benzyl-6,11,11-trimethyl-1,2,3,4,5,6-hexahydro-2,6-methano-benzo[d]azocine-10-carboxylic acid ethyl ester (0.96 g) in tetrahydrofuran (2 mL) is added dropwise to LiAlH₄ (1.6 mL, 2.4 mol/L in tetrahydrofuran) in tetrahydrofuran (1.5 mL). The reaction mixture is stirred at ambient temperature for 90 min. Then, water (4 mL) is added carefully and the resulting mixture is extracted with ethyl acetate. The combined organic extracts are washed with water and brine and dried (MgSO$_4$). The solvent is removed under reduced pressure to give the product.

Yield: 0.62 g (72% of theory)

Mass spectrum (ESI$^+$): m/z=336 [M+H]$^+$

EXAMPLE XXII

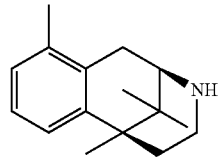 [SMILES: Cc1cccc2c1C[C@H]1NCC[C@]2(C)C1(C)C]

(2R,6S)-6,10,11,11-Tetramethyl-1,2,3,4,5,6-hexahydro-2,6-methano-benzo[d]azocine 10% Palladium on carbon (0.10 g) is added to a solution of (2R,6S)-(3-benzyl-6,11,11-trimethyl-1,2,3,4,5,6-hexahydro-2,6-methano-benzo[d]azocin-10-yl)-methanol (0.60 g) in methanol (10 mL). The mixture is stirred under hydrogen atmosphere (50 psi) at room temperature overnight. Then, another portion of 10% palladium on carbon (0.2 g) and 4 M hydrochloric acid (1 mL) are added and the mixture is further stirred in hydrogen atmosphere for 4 h. After the catalyst is separated by filtration, the filtrate is concentrated under reduced pressure to give the hydrochloric acid salt of the title product.

Yield: 0.50 g (100% of theory)

The following compound is obtained analogously to Example XXII:

(1) 8-Methoxy-3-methyl-2,3,4,5-tetrahydro-1H-2,6-methano-benzo[d]azocine-6-carboxylic acid methyl ester

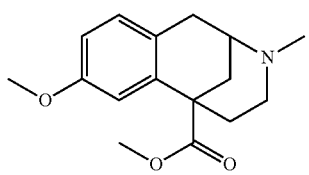

The compound may be obtained from 1-hydroxy-8-methoxy-3-methyl-2,3,4,5-tetrahydro-1H-2,6-methano-benzo[d]azocine-6-carboxylic acid methyl ester employing the procedure described above. Alternatively, the reduction may be conducted in analogy to J. Org. Chem. 1987, 52, 5233-5239.

EXAMPLE XXIII

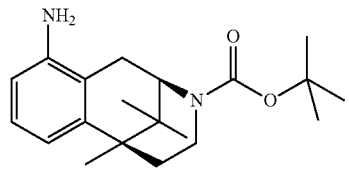 [SMILES: CC(C)(C)OC(=O)N1CC[C@@]2(C)c3cccc(N)c3C[C@@H]1C2(C)C]

(2R,6S)-10-Amino-6,11,11-trimethyl-1,2,5,6-tetrahydro-4H-2,6-methano-benzo[d]azocine-3-carboxylic acid tert-butyl ester A flask charged with a stir bar, (2R,6S)-6,11,11-trimethyl-10-trifluoromethanesulfonyloxy-1,2,5,6-tetrahydro-4H-2,6-methano-benzo[d]azocine-3-carboxylic acid tert-butyl ester (4.0 g), benzhydrylideneamine (3.2 mL), Cs$_2$CO$_3$ (5.6 g), and toluene (80 mL) is flushed with argon for 10 min. Then, 2,2'-bis-diphenylphosphanyl-[1,1']binaphthalenyl (0.35 g) and tris(dibenzylideneacetone)dipalladium (0.18 g) are added and the resulting mixture is stirred at reflux temperature overnight. After cooling to room temperature, the reaction mixture is washed with water and concentrated. The residue is taken up in tetrahydrofuran and 2 M hydrochloric acid is added. The mixture is stirred at ambient temperature for 4 h. The precipitate is separated by filtration and the filtrate is concentrated under reduced pressure. The residue is purified by chromatography on silica gel (cyclohexane/ethyl acetate 1:7) to give the product as a brown oil.

Yield: 0.83 g (29% of theory)

Mass spectrum (ESI$^+$): m/z=331 [M+H]$^+$

The following compounds are obtained analogously to Example XXIII:

(1) 9-Amino-6,11,11-trimethyl-1,2,5,6-tetrahydro-4H-2,6-methano-benzo[d]azocine-3-carboxylic acid tert-butyl ester

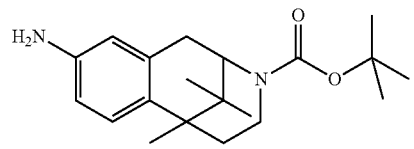 [SMILES: CC(C)(C)OC(=O)N1CCC2(C)c3ccc(N)cc3CC1C2(C)C]

Mass spectrum (ESI$^+$): m/z=331 [M+NH$_4$]$^+$ (2) 8-Amino-6,11,11-trimethyl-1,2,5,6-tetrahydro-4H-2,6-methano-benzo[d]azocine-3-carboxylic acid tert-butyl ester

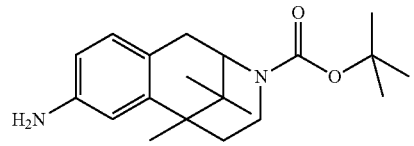 [SMILES: CC(C)(C)OC(=O)N1CCC2(C)c3cc(N)ccc3CC1C2(C)C]

Mass spectrum (ESI$^+$): m/z=331 [M+NH$_4$]$^+$

EXAMPLE XXIV

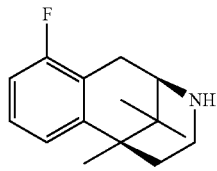 [SMILES: CC1(C)[C@H]2Cc3c(F)cccc3[C@]1(C)CCN2]

(2R,6S)-10-Fluoro-6,11,11-trimethyl-1,2,3,4,5,6-hexahydro-2,6-methano-benzo[d]azocine A solution of nitrosonium tetrafluoroborate (0.25 g) in 1,4-dioxane (2 mL) is added to a solution of (2R,6S)-10-amino-6,11,11-trimethyl-1,2,5,6-tetrahydro-4H-2,6-methano-benzo[d]azocine-3-carboxylic acid tert-butyl ester (0.10 g) in dioxane (2 mL). The solution is heated to 50° C. and stirred at this temperature overnight. The reaction solution is diluted with methanol and then concentrated under reduced pressure. The residue is purified by HPLC on reversed phase (MeCN/H$_2$O/F$_3$CCO$_2$H) to yield the title product.

Yield: 25 mg (36% of theory)

Mass spectrum (ESI$^+$): m/z=234 [M+H]$^+$

The following compounds are obtained analogously to Example XXIV:

(1) 8-Fluoro-6,11,11-trimethyl-1,2,3,4,5,6-hexahydro-2,6-methano-benzo[d]azocine

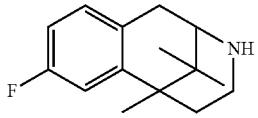

(2) 9-Fluoro-6,11,11-trimethyl-1,2,3,4,5,6-hexahydro-2,6-methano-benzo[d]azocine

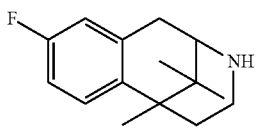

In cases in which the tert-butyloxycarbonyl group is not completely cleaved off after the reaction the crude product is treated with trifluoroacetic acid in dichloromethane.

EXAMPLE XXV

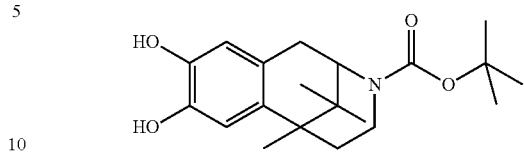

8,9-Dihydroxy-6,11,11-trimethyl-1,2,5,6-tetrahydro-4H-2,6-methano-benzo[d]azocine-3-carboxylic acid tert-butyl ester Di-tert-butyl dicarbonate (0.34 g) is added to a solution of 6,11,11-trimethyl-1,2,3,4,5,6-hexahydro-2,6-methano-benzo[d]azocine-8,9-diol (0.44 g) and triethylamine (0.43 mL) in dichloromethane (5 mL). The solution is stirred at room temperature for 2 h. Then, the solution is washed twice with water and once with brine. After drying (MgSO$_4$), the solvent is removed under reduced pressure to yield the product.

Yield: 0.43 g (80% of theory)

Mass spectrum (ESI$^-$): m/z=346 [M−H]$^-$

EXAMPLE XXVI

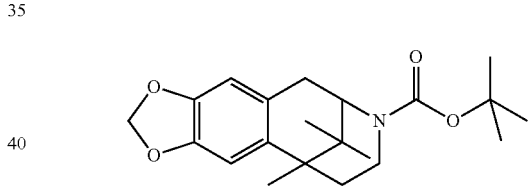

8,9-Methylenedioxy-6,11,11-trimethyl-1,2,5,6-tetrahydro-4H-2,6-methano-benzo[d]azocine-3-carboxylic acid tert-butyl ester A mixture of 8,9-dihydroxy-6,11,11-trimethyl-1,2,5,6-tetrahydro-4H-2,6-methano-benzo[d]azocine-3-carboxylic acid tert-butyl ester (0.21 g), K$_2$CO$_3$ (0.19 g), and diiodomethane (54 µL) in N,N-dimethylformamide (5 mL) is heated to 100° C. and stirred at this temperature for 2 h. Then, another portion of diiodomethane (54 µL) and K$_2$CO$_3$ (0.18 g) is added and the mixture is further stirred at 100° C. for 5 h. After cooling to room temperature, water is added and the resulting mixture is extracted with ethyl acetate. The combined organic extracts are washed with brine and dried (MgSO$_4$). After removal of the solvent, the residue is purified by chromatography on silica gel (cyclohexane/ethyl acetate 1:1).

Yield: 0.20 g (93% of theory)

Mass spectrum (ESI$^+$): m/z=360 [M+H]$^+$

EXAMPLE XXVII

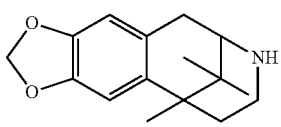 [SMILES: CC12CCNC(Cc3cc4c(cc31)OCO4)C2(C)C]

8,9-Methylenedioxy-6,11,11-trimethyl-1,2,3,4,5,6-hexahydro-2,6-methano-benzo[d]azocine Isopropanolic hydrochloric acid (5 mol/L, 0.55 mL) is added to 8,9-methylenedioxy-6,11,11-trimethyl-1,2,5,6-tetrahydro-4H-2,6-methano-benzo[d]azocine-3-carboxylic acid tert-butyl ester (0.19 g) dissolved in dichloromethane (2 mL). The resulting solution is stirred for 2 h at room temperature. Then, the solution is concentrated under reduced pressure to give the title product as its hydrochloric acid salt.

Yield: 0.15 g (97% of theory)

Mass spectrum (ESI⁺): m/z=260 [M+H]⁺

EXAMPLE XXVIII

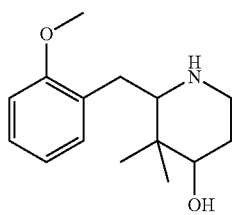 [SMILES: COc1ccccc1CC1NCCC(O)C1(C)C]

2-(2-Methoxy-benzyl)-3,3-dimethyl-piperidin-4-ol

Sodium borohydride (0.31 g) is added to 2-(2-methoxy-benzyl)-3,3-dimethyl-piperidin-4-one (2.00 g, prepared according to *J. Med. Chem.* 2002, 45, 3755-3765 from racemic starting material) dissolved in methanol (20 mL). The solution is stirred at room temperature for 3 h and then 1 M sodium hydroxide solution (40 mL) is added. After stirring for another 10 min, the mixture is extracted with dichloromethane. The combined organic extracts are washed with water and dried (MgSO₄). The solvent is evaporated to give the title product.

Yield: 2.00 g (99% of theory)

Mass spectrum (ESI⁺): m/z=250 [M+H]⁺

EXAMPLE XXIX

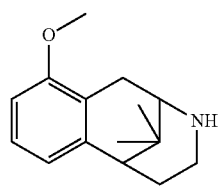 [SMILES: COc1cccc2c1CC1NCCC2C1(C)C]

10-Methoxy-11,11-dimethyl-1,2,3,4,5,6-hexahydro-2,6-methano-benzo[d]azocine

A solution of 2-(2-methoxy-benzyl)-3,3-dimethyl-piperidin-4-ol (0.80 g) in polyphosphoric acid (10 mL) is stirred at 120° C. overnight. After cooling the solution to ca. 80° C., water (300 mL) is added and the mixture is stirred vigorously for another 10 min. Then, the mixture is cooled in an ice bath, more water is added, and the mixture is basified using 10 M aqueous NaOH solution. The resulting mixture is extracted with ethyl acetate, the combined organic extracts are washed with brine and dried (MgSO₄). The solvent is removed under reduced pressure to yield the title product that is used without further purification.

Yield: 0.36 g (49% of theory)

The following compound is obtained analogously to Example XXIX:

(1) (2S,6R)-9-Methoxy-6,11,11-trimethyl-1,2,3,4,5,6-hexahydro-2,6-methano-benzo[d]azocine

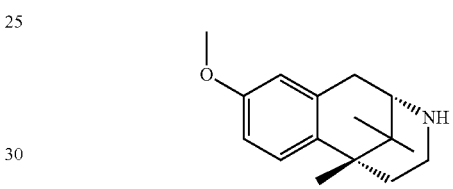

The racemic product mixture is resolved into its enantiomers by using HPLC on chiral phase. The compound may also be obtained in analogy to the procedure described in *J. Med. Chem.* 1997, 40, 2922-2930.

EXAMPLE XXX

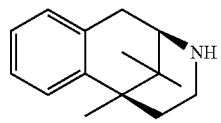 [SMILES: CC1(C)[C@H]2Cc3ccccc3[C@]1(C)CCN2]

(2R,6S)-6,11,11-Trimethyl-1,2,3,4,5,6-hexahydro-2,6-methano-benzo[d]azocine

10% Pd/C (0.20 g) is added to a solution of (2R,6S)-trifluoro-methanesulfonic acid 3-benzyl-6,11,11-trimethyl-1,2,3,4,5,6-hexahydro-2,6-methano-benzo[d]azocin-10-yl ester (0.50 g) in ethanol (10 mL). The resulting mixture is shaken under hydrogen atmosphere (50 psi) at room temperature overnight. Then, the catalyst is separated by filtration and Pd(OH)₂ (0.2 g) is added to the filtrate (the benzyl group was not completely removed after the treatment in the presence of Pd/C). The mixture is shaken in hydrogen atmosphere (50 psi) at room temperature for another 16 h. The catalyst is separated and the filtrate is concentrated under reduced pressure to give the crude product that is used without further purification.

Yield: 0.23 g (98% of theory)

The following compound is obtained analogously to Example XXX:

(1) 2,3,4,5,6,7-Hexahydro-2,6-methano-1H-azocino[5,4-b]indole (racemic mixture of the diastereomer shown)

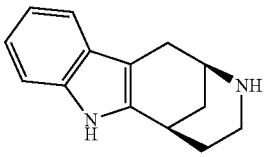 [SMILES: c1ccc2c3c([nH]c2c1)[C@@H]1CCN[C@H](C3)C1]

The debenzylation of the starting compound is carried out with Pd(OH)₂ as described above.

EXAMPLE XXXI

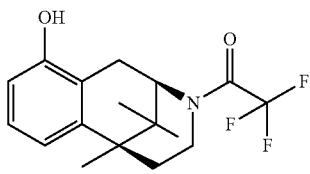 [SMILES: CC1(C)[C@H]2Cc3c(O)cccc3[C@]1(C)CCN2C(=O)C(F)(F)F]

2,2,2-Trifluoro-1-[(2R,6S)-10-hydroxy-6,11,11-trimethyl-1,2,5,6-tetrahydro-4H-2,6-methano-benzo[d]azocin-3-yl]-ethanone Trifluoroacetic anhydride (5.0 mL) is added to a solution of the hydrobromic acid salt of (2R,6S)-6,11,11-trimethyl-1,2,3,4,5,6-hexahydro-2,6-methano-benzo[d]azocin-10-ol (5.0 g) and triethylamine (5.5 mL) in dichloromethane (50 mL) chilled in an ice bath. The resulting solution is stirred at ambient temperature overnight. Then, water is added, the resulting mixture is stirred for an additional 15 min, and the organic phase is separated. The organic phase is washed with water and brine, dried (Na₂SO₄), and the solvent is evaporated. The residue is purified by chromatography on silica gel (ethyl acetate/cyclohexane 1:4) to give the product as a foam-like solid.
Yield: 3.34 g (64% of theory)
Mass spectrum (ESI⁺): m/z=328 [M+H]⁺
The following compounds are obtained analogously to Example XXXI:

(1) 2,2,2-Trifluoro-1-[(2R,6S)-6,11,11-trimethyl-1,2,5,6-tetrahydro-4H-2,6-methano-benzo[d]azocin-3-yl]-ethanone

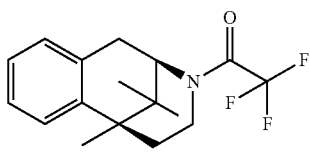 [SMILES: CC1(C)[C@H]2Cc3ccccc3[C@]1(C)CCN2C(=O)C(F)(F)F]

Mass spectrum (ESI⁺): m/z=312 [M+H]⁺

(2) 2,2,2-Trifluoro-1-[(2R,6R,11S)-8-hydroxy-6,11-dimethyl-1,2,5,6-tetrahydro-4H-2,6-methano-benzo[d]azocin-3-yl]-ethanone

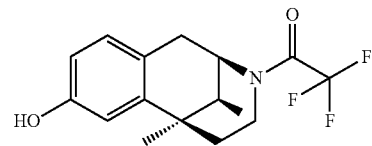 [SMILES: C[C@@H]1[C@H]2Cc3ccc(O)cc3[C@]1(C)CCN2C(=O)C(F)(F)F]

Mass spectrum (ESI⁺): m/z=314 [M+H]⁺

(3) 2,2,2-Trifluoro-1-[(2R,6R,11R)-8-hydroxy-6,11-dimethyl-1,2,5,6-tetrahydro-4H-2,6-methano-benzo[d]azocin-3-yl]-ethanone

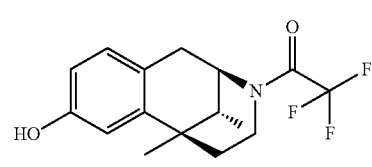 [SMILES: C[C@H]1[C@H]2Cc3ccc(O)cc3[C@]1(C)CCN2C(=O)C(F)(F)F]

Mass spectrum (ESI⁺): m/z=314 [M+H]⁺

EXAMPLE XXXII

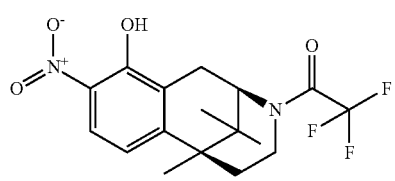 [SMILES: CC1(C)[C@H]2Cc3c(ccc([N+](=O)[O-])c3O)[C@]1(C)CCN2C(=O)C(F)(F)F]

2,2,2-Trifluoro-1-[(2R,6S)-10-hydroxy-6,11,11-trimethyl-9-nitro-1,2,5,6-tetrahydro-4H-2,6-methano-benzo[d]azocin-3-yl]-ethanone Nitric acid (0.4 mL) is slowly added to a solution of 2,2,2-trifluoro-1-[(2R,6S)-10-hydroxy-6,11,11-trimethyl-1,2,5,6-tetrahydro-4H-2,6-methano-benzo[d]azocin-3-yl]-ethanone (2.9 g) in acetic acid (5 mL) chilled in an ice bath. The ice bath is removed and the solution is stirred at ambient temperature overnight. The solution is poured into ice-cold water and the resulting mixture is extracted with ethyl acetate. The combined extracts are washed with brine and dried (Na₂SO₄). After removal of the solvent under reduced pressure, the residue is purified by chromatography on silica gel (ethyl acetate/cyclohexane 1:9->1:3).
Yield: 1.3 g (39% of theory)
Mass spectrum (ESI⁻): m/z=371 [M−H]⁻

The following compound is obtained analogously to Example XXXII:

(1) 2,2,2-Trifluoro-1-[(2R,6R,11S)-8-hydroxy-6,11-dimethyl-9-nitro-1,2,5,6-tetrahydro-4H-2,6-methano-benzo[d]azocin-3-yl]-ethanone

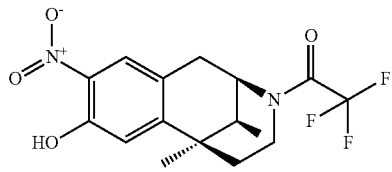 [SMILES: C[C@@H]1[C@H]2Cc3cc([N+](=O)[O-])c(O)cc3[C@]1(C)CCN2C(=O)C(F)(F)F]

Mass spectrum (ESI+): m/z=359 [M+H]+

EXAMPLE XXXIII

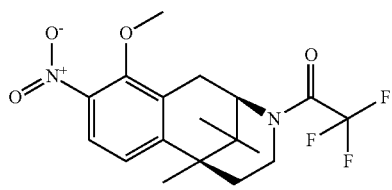 [SMILES: COc1c([N+](=O)[O-])ccc2c1C[C@H]1N(C(=O)C(F)(F)F)CC[C@]2(C)C1(C)C]

2,2,2-Trifluoro-1-[(2R,6S)-10-methoxy-6,11,11-trimethyl-9-nitro-1,2,5,6-tetrahydro-4H-2,6-methano-benzo[d]azocin-3-yl]-ethanone Methyl iodide (80 μL) is added to a mixture of 2,2,2-trifluoro-1-[(2R,6S)-10-hydroxy-6,11,11-trimethyl-9-nitro-1,2,5,6-tetrahydro-4H-2,6-methano-benzo[d]azocin-3-yl]-ethanone (0.40 g) and potassium carbonate (0.17 g) in N,N-dimethylformamide (5 mL). The mixture is stirred at room temperature overnight, before another portion of methyl iodide (80 μL) and potassium carbonate (0.16 g) are added. The mixture is stirred for another 6 h at room temperature. Then, water and ethyl acetate are added, the organic phase is separated, and the aqueous phase is extracted with ethyl acetate. The combined organic phases are washed with brine and dried (Na2SO4). The solvent is evaporated to give the crude product that is used without further purification.

Yield: 0.41 g (100% of theory)
Mass spectrum (ESI+): m/z=387 [M+H]+

The following compounds are obtained analogously to Example XXXIII:

(1) (2S,6R)-8-Methoxy-6,9,11,11-tetramethyl-1,2,5,6-tetrahydro-4H-2,6-methano-benzo[d]azocine-3-carboxylic acid tert-butyl ester

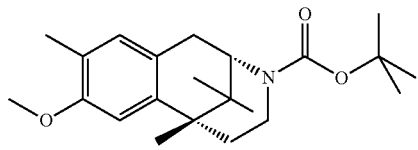 [SMILES: COc1cc2c(cc1C)C[C@@H]1N(C(=O)OC(C)(C)C)CC[C@@]2(C)C1(C)C]

The compound may be obtained by resolution of the racemic mixture by HPLC on chiral phase or by using the enantiomerically pure (2S,6R)-8-hydroxy-6,9,11,11-tetramethyl-1,2,5,6-tetrahydro-4H-2,6-methano-benzo[d]azocine-3-carboxylic acid tert-butyl ester.

(2) (2R,6S)-8-Methoxy-6,9,11,11-tetramethyl-1,2,5,6-tetrahydro-4H-2,6-methano-benzo[d]azocine-3-carboxylic acid tert-butyl ester

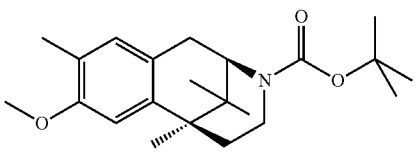 [SMILES: COc1cc2c(cc1C)C[C@H]1N(C(=O)OC(C)(C)C)CC[C@]2(C)C1(C)C]

The compound may be obtained by resolution of the racemic mixture by HPLC on chiral phase or by using the enantiomerically pure (2R,6S)-8-hydroxy-6,9,11,11-tetramethyl-1,2,5,6-tetrahydro-4H-2,6-methano-benzo[d]azocine-3-carboxylic acid tert-butyl ester.

(3) (2S,6R)-9-Methoxy-6,8,11,11-tetramethyl-1,2,5,6-tetrahydro-4H-2,6-methano-benzo[d]azocine-3-carboxylic acid tert-butyl ester

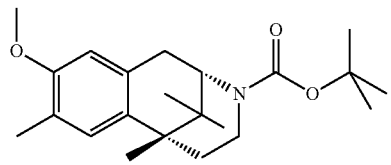 [SMILES: COc1cc2c(cc1C)[C@@]1(C)CCN(C(=O)OC(C)(C)C)[C@@H](C2)C1(C)C]

The compound may be obtained by resolution of the racemic mixture by HPLC on chiral phase or by using the enantiomerically pure (2S,6R)-9-hydroxy-6,8,11,11-tetramethyl-1,2,5,6-tetrahydro-4H-2,6-methano-benzo[d]azocine-3-carboxylic acid tert-butyl ester.

(4) (2R,6S)-9-Methoxy-6,8,11,11-tetramethyl-1,2,5,6-tetrahydro-4H-2,6-methano-benzo[d]azocine-3-carboxylic acid tert-butyl ester

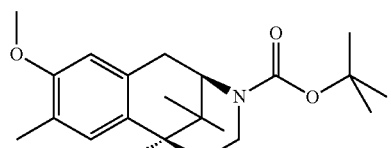

The compound may be obtained by resolution of the racemic mixture by HPLC on chiral phase or by using the enantiomerically pure (2R,6S)-9-hydroxy-6,8,11,11-tetramethyl-1,2,5,6-tetrahydro-4H-2,6-methano-benzo[d]azocine-3-carboxylic acid tert-butyl ester.

(5) 8,9-Dimethoxy-6,11,11-trimethyl-1,2,5,6-tetrahydro-4H-2,6-methano-benzo[d]azocine-3-carboxylic acid tert-butyl ester

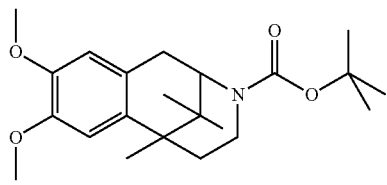 [SMILES: COc1cc2c(cc1OC)C1(C)CCN(C(=O)OC(C)(C)C)C(C2)C1(C)C]

Twice the amount of methyl iodide and potassium carbonate as described in the procedure above are employed to prepare the compound from 8,9-dihydroxy-6,11,11-trimethyl-1,2,5,6-tetrahydro-4H-2,6-methano-benzo[d]azocine-3-carboxylic acid tert-butyl ester.

(6) 9-Hydroxy-8-methoxy-6,11,11-trimethyl-1,2,5,6-tetrahydro-4H-2,6-methano-benzo[d]azocine-3-carboxylic acid tert-butyl ester

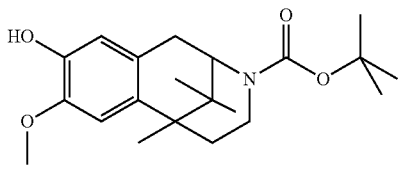 [SMILES: COc1cc2c(cc1O)CC1N(C(=O)OC(C)(C)C)CCC2(C)C1(C)C]

The compound is obtained in a mixture with 8-hydroxy-9-methoxy-6,11,11-trimethyl-1,2,5,6-tetrahydro-4H-2,6-methano-benzo[d]azocine-3-carboxylic acid tert-butyl ester and 8,9-dimethoxy-6,11,11-trimethyl-1,2,5,6-tetrahydro-4H-2,6-methano-benzo[d]azocine-3-carboxylic acid tert-butyl ester from 8,9-dihydroxy-6,11,11-trimethyl-1,2,5,6-tetrahydro-4H-2,6-methano-benzo[d]azocine-3-carboxylic acid tert-butyl ester that may be resolved by HPLC on reversed phase (MeCN/H$_2$O).

(7) 8-Hydroxy-9-methoxy-6,11,11-trimethyl-1,2,5,6-tetrahydro-4H-2,6-methano-benzo[d]azocine-3-carboxylic acid tert-butyl ester

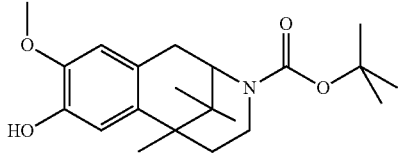 [SMILES: COc1cc2c(cc1O)C1(C)CCN(C(=O)OC(C)(C)C)C(C2)C1(C)C]

The compound is obtained in a mixture with 9-hydroxy-8-methoxy-6,11,11-trimethyl-1,2,5,6-tetrahydro-4H-2,6-methano-benzo[d]azocine-3-carboxylic acid tert-butyl ester and 8,9-dimethoxy-6,11,11-trimethyl-1,2,5,6-tetrahydro-4H-2,6-methano-benzo[d]azocine-3-carboxylic acid tert-butyl ester from 8,9-dihydroxy-6,11,11-trimethyl-1,2,5,6-tetrahydro-4H-2,6-methano-benzo[d]azocine-3-carboxylic acid tert-butyl ester that may be resolved by HPLC on reversed phase (MeCN/H$_2$O).

(8) 2,2,2-Trifluoro-1-[(2R,6R,11S)-8-methoxy-6,11-dimethyl-9-nitro-1,2,5,6-tetrahydro-4H-2,6-methano-benzo[d]azocin-3-yl]-ethanone

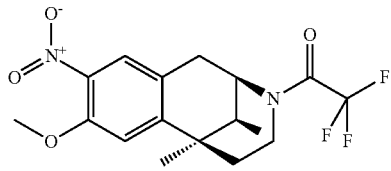 [SMILES: COc1cc2c(cc1[N+](=O)[O-])C[C@@H]1[C@@H](C)[C@@]2(C)CCN1C(=O)C(F)(F)F]

Mass spectrum (ESI$^+$): m/z=373 [M+H]$^+$

(9) 9-Methoxy-6,11,11-trimethyl-1,2,3,4,5,6-hexahydro-2,6-methano-benzo[d]azocine

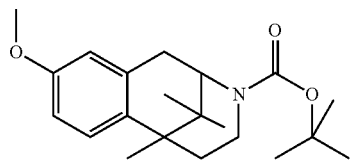 [SMILES: COc1ccc2c(c1)CC1N(C(=O)OC(C)(C)C)CCC2(C)C1(C)C]

(10) (2S,6R)-9-Methoxy-6,11,11-trimethyl-1,2,3,4,5,6-hexahydro-2,6-methano-benzo[d]azocine

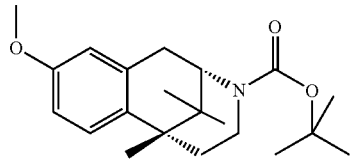 [SMILES: COc1ccc2c(c1)C[C@@H]1N(C(=O)OC(C)(C)C)CC[C@@]2(C)C1(C)C]

The compound may be obtained from the racemic mixture by HPLC on chiral phase.

EXAMPLE XXXIV

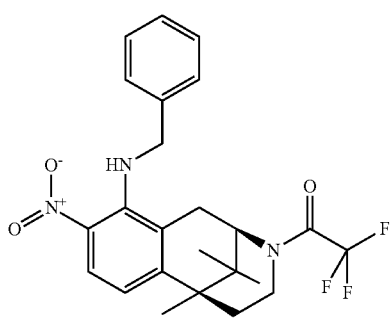 [SMILES: CC1(C)[C@H]2Cc3c(ccc([N+](=O)[O-])c3NCc3ccccc3)[C@]1(C)CCN2C(=O)C(F)(F)F]

1-[(2R,6S)-10-Benzylamino-6,11,11-trimethyl-9-nitro-1,2,5,6-tetrahydro-4H-2,6-methano-benzo[d]azocin-3-yl]-2,2,2-trifluoro-ethanone 2,2,2-Trifluoro-1-[(2R,6S)-10-methoxy-6,11,11-trimethyl-9-nitro-1,2,5,6-tetrahydro-4H-2,6-methano-benzo[d]azocin-3-yl]-ethanone (0.41 g) is combined with benzylamine (0.7 mL) and the resulting mixture is stirred at 70° C. overnight. After cooling to room temperature, the mixture is purified by HPLC on reversed phase (MeCN/H$_2$O/F$_3$CCO$_2$H) to give the product as an oil.

Yield: 0.19 g (38% of theory)

Mass spectrum (ESI$^+$): m/z=462 [M+H]$^+$

The following compound is obtained analogously to Example XXXIV:

(1) 1-[(2R,6R,11S)-8-Benzylamino-6,11-dimethyl-9-nitro-1,2,5,6-tetrahydro-4H-2,6-methano-benzo[d]azocin-3-yl]-2,2,2-trifluoro-ethanone

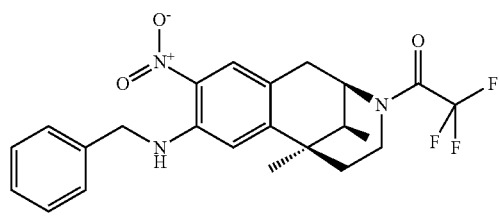 [SMILES: C[C@@H]1[C@H]2Cc3cc([N+](=O)[O-])c(NCc4ccccc4)cc3[C@]1(C)CCN2C(=O)C(F)(F)F]

EXAMPLE XXXV

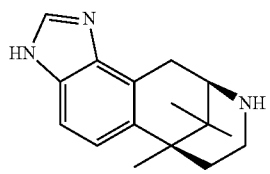 [SMILES: CC1(C)[C@H]2Cc3c(ccc4[nH]cnc34)[C@]1(C)CCN2]

(5R,9S)-4,5,6,7,8,9-hexahydro-9,12,12-trimethyl-5,9-methano-1H-imidazo[5,4-i][3]benzazocine A mixture of Raney-Ni (0.1 g), 1-[(2R,6S)-10-benzylamino-6,11,11-trimethyl-9-nitro-1,2,5,6-tetrahydro-4H-2,6-methano-benzo[d]azocin-3-yl]-2,2,2-trifluoro-ethanone (0.19 g), and formic acid (10 mL) is stirred in hydrogen atmosphere at 50° C. overnight. Then, the catalyst is separated by filtration and the filtrate is concentrated. The remainder is taken up in methanol (10 mL) and treated with 4 M aqueous NaOH solution (2 mL) at 50° C. overnight. After cooling to room temperature, the solution is neutralized with 2 M hydrochloric acid and the solvent is removed. The residue is purified by HPLC on reversed phase (MeCN/H$_2$O).

Yield: 35 mg (33% of theory)

The following compound is obtained analogously to Example XXXV:

(1) (6R,10R,12S)-5,6,7,8,9,10-Hexahydro-10,12-dimethyl-6,10-methano-1H-imidazo[5,4-i][3]benzazocine

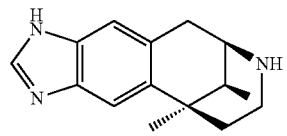 [SMILES: C[C@@H]1[C@H]2Cc3cc4[nH]cnc4cc3[C@]1(C)CCN2]

Mass spectrum (ESI$^+$): m/z=242 [M+H]$^+$

EXAMPLE XXXVI

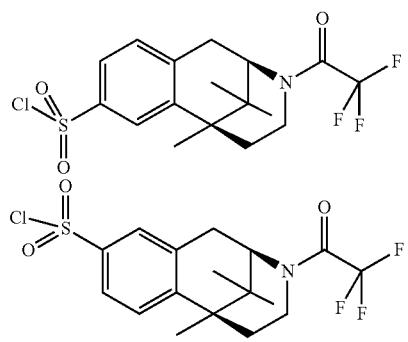

(2R,6S)-6,11,11-Trimethyl-3-(2,2,2-trifluoro-acetyl)-1,2,3,4,5,6-hexahydro-2,6-methano-benzo[d]azocine-8-sulfonyl chloride and (2R,6S)-6,11,11-trimethyl-3-(2,2,2-trifluoro-acetyl)-1,2,3,4,5,6-hexahydro-2,6-methano-benzo[d]azocine-9-sulfonyl chloride Chlorosulfonic acid (1.15 mL) is slowly added to a solution of 2,2,2-trifluoro-1-[(2R,6S)-6,11,11-trimethyl-1,2,5,6-tetrahydro-4H-2,6-methano-benzo[d]azocin-3-yl]-ethanone (0.90 g) in dichloromethane (10 mL) at room temperature. Then, the solution is stirred at ambient temperature overnight. The solution is poured into ice-cold water and the resulting mixture is extracted with ethyl acetate. The combined organic extracts are washed with brine and dried (MgSO$_4$). The solvent is removed under reduced pressure to give the crude title compounds as a mixture that is used without further purification.

Yield: 1.18 g

EXAMPLE XXXVII

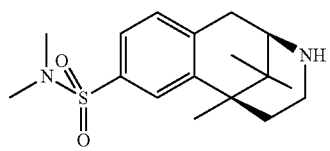

-continued

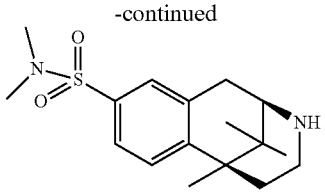

(2R,6S)-6,11,11-Trimethyl-1,2,3,4,5,6-hexahydro-2,
6-methano-benzo[d]azocine-8-sulfonic acid dimethylamide and (2R,6S)-6,11,11-trimethyl-1,2,3,4,5,
6-hexahydro-2,6-methano-benzo[d]azocine-9-sulfonic acid dimethylamide Dimethylamine (3.3 mL, 2 M in tetrahydrufuran) is added to a mixture of (2R,6S)-6,11,11-trimethyl-3-(2,2,2-trifluoro-acetyl)-1,2,3,4,5,6-hexahydro-2,6-methano-benzo[d]azocine-8-sulfonyl chloride and (2R,6S)-6,11,11-trimethyl-3-(2,2,2-trifluoro-acetyl)-1,2,3,4,5,6-hexahydro-2,6-methano-benzo[d]azocine-9-sulfonyl chloride (0.90 g, crude product from Example XXXVI) dissolved in ethanol (5 mL) and chilled in an ice bath. The cooling bath is removed and the solution is stirred at room temperature for 2 h. Then, 4 M aqueous NaOH solution (2.2 mL) is added to cleave off the trifluoroacetyl group. After stirring at room temperature for 1 h, the solution is diluted with water and the resulting mixture is extracted with ethyl acetate. The combined extracts are washed with brine and dried (MgSO$_4$). The solvent is removed and the residue is purified by HPLC on reversed phase (MeCN/H$_2$O/NF1$_3$) to give the two title compounds separated.

(2R,6S)-6,11,11-Trimethyl-1,2,3,4,5,6-hexahydro-2,
6-methano-benzo[d]azocine-8-sulfonic acid dimethylamide: Yield: 500 mg (71% of theory)

Mass spectrum (ESI$^+$): m/z=323 [M+H]$^+$ (2R,6S)-6,11,11-Trimethyl-1,2,3,4,5,6-hexahydro-2,
6-methano-benzo[d]azocine-9-sulfonic acid dimethylamide: Yield: 50 mg (7% of theory)

Mass spectrum (ESI$^+$): m/z=323 [M+H]$^+$

The following compounds are obtained analogously to Example XXXVII:

(1) (2R,6S)-6,11,11-Trimethyl-1,2,3,4,5,6-hexahydro-2,6-methano-benzo[d]azocine-8-sulfonic acid methylamide

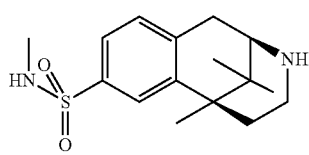 [SMILES: CNS(=O)(=O)c1ccc2c(c1)[C@]1(C)CCN[C@H](C2)C1(C)C]

Mass spectrum (ESI$^+$): m/z=309 [M+H]$^+$
Methylamine is used as coupling partner.

(2) (2R,6S)-6,11,11-Trimethyl-1,2,3,4,5,6-hexahydro-2,6-methano-benzo[d]azocine-8-sulfonic acid amide

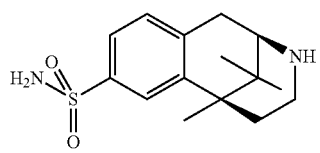 [SMILES: CC1(C)[C@H]2Cc3ccc(S(N)(=O)=O)cc3[C@]1(C)CCN2]

Mass spectrum (ESI$^+$): m/z=295 [M+H]$^+$
Ammonia is used as coupling partner.

EXAMPLE XXXVIII

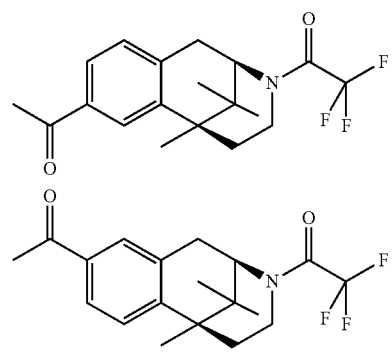

1-[(2R,6S)-8-Acetyl-6,11,11-trimethyl-1,2,5,6-tetrahydro-4H-2,6-methano-benzo[d]azocin-3-yl]-2,2,2-trifluoro-ethanone and 1-[(2R,6S)-9-acetyl-6,11,11-trimethyl-1,2,5,6-tetrahydro-4H-2,6-methano-benzo[d]azocin-3-yl]-2,2,2-trifluoro-ethanone Acetyl chloride (0.25 mL) is added to a suspension of AlCl$_3$ (1.3 g) in dichloromethane (5 mL) chilled in an ice bath. After stirring the mixture for 5 min, (2R,6S)-2,2,2-trifluoro-1-(6,11,11-trimethyl-1,2,5,6-tetrahydro-4H-2,6-methano-benzo[d]azocin-3-yl)-ethanone (1.0 g) dissolved in dichloromethane (5 mL) is added dropwise. The mixture is stirred at ambient temperature overnight and then poured into ice-cold half-concentrated hydrochloric acid (20 mL). The resulting mixture is extracted with dichloromethane and the combined organic extracts are washed with water, aqueous NaHCO$_3$ solution, and brine and dried (MgSO$_4$). The solvent is removed and the residue is purified by chromatography on silica gel (cyclohexane/ethyl acetate 3:1->1:1) to give the two regioisomeric title compounds in a ca. 3:1 mixture.

Yield: 0.83 g (73% of theory)

Mass spectrum (ESI$^+$): m/z=354 [M+H]$^+$

EXAMPLE XXXIX

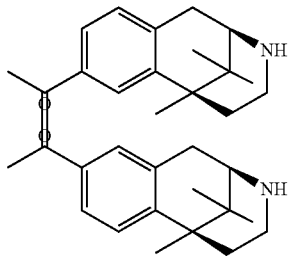

1-[(2R,6S)-6,11,11-Trimethyl-1,2,3,4,5,6-hexahydro-2,6-methano-benzo[d]azocin-8-yl]-ethanone and 1-[(2R,6S)-6,11,11-trimethyl-1,2,3,4,5,6-hexahydro-2,6-methano-benzo[d]azocin-9-yl]-ethanone 4 M NaOH solution (2.5 mL) is added to a ca. 3:1 mixture of 1-[(2R,6S)-8-acetyl-6,11,11-trimethyl-1,2,5,6-tetrahydro-4H-2,6-methano-benzo[d]azocin-3-yl]-2,2,2-trifluoro-ethanone and 1-[(2R,6S)-9-acetyl-6,11,11-trimethyl-1,2,5,6-tetrahydro-4H-2,6-methano-benzo[d]azocin-3-yl]-2,2,2-trifluoro-ethanone (0.83 g) in methanol (10 mL). The resulting solution is stirred at room temperature overnight. Then, the solution is neutralized with 1 M hydrochloric acid and concentrated. The residue is purified by HPLC on reversed phase (acetonitrile/water/NH$_3$) to give the two title compounds separated.

Yield: 0.35 g of 1-[(2R,6S)-6,11,11-trimethyl-1,2,3,4,5,6-hexahydro-2,6-methano-benzo[d]azocin-8-yl]-ethanone and 0.07 g of 1-[(2R,6S)-6,11,11-trimethyl-1,2,3,4,5,6-hexahydro-2,6-methano-benzo[d]azocin-9-yl]-ethanone (combined 71% of theory)

Mass spectrum (ESI$^+$): m/z=258 [M+H]$^+$

The following compounds are obtained analogously to Example XXXIX:

(1) (2R,6R,11S)-8-Hydroxy-6,11-dimethyl-1,2,3,4,5,6-hexahydro-2,6-methano-benzo[d]azocine-9-carbonitrile

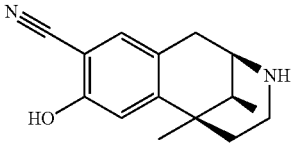 [SMILES: C[C@@H]1[C@H]2Cc3cc(C#N)c(O)cc3[C@]1(C)CCN2]

Mass spectrum (ESI$^+$): m/z=243 [M+H]$^+$ (2) (2R,6S)-8-Methanesulfonyl-6,11,11-trimethyl-1,2,3,4,5,6-hexahydro-2,6-methano-benzo[d]azocine

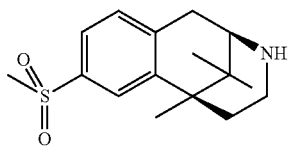 [SMILES: CC1(C)[C@H]2Cc3ccc(S(C)(=O)=O)cc3[C@]1(C)CCN2]

Mass spectrum (ESI$^+$): m/z=294 [M+H]$^+$ (3) (2R,6S)-10-Methanesulfonyl-6,11,11-trimethyl-1,2,3,4,5,6-hexahydro-2,6-methano-benzo[d]azocine

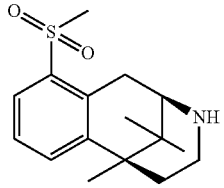 [SMILES: CC1(C)[C@H]2Cc3c(cccc3S(C)(=O)=O)[C@]1(C)CCN2]

Mass spectrum (ESI$^+$): m/z=294 [M+H]$^+$ (4) (6R,10S)-5,6,7,8,9,10-Hexahydro-2,10,12,12-tetramethyl-6,10-methano-1H-imidazo[5,4-i][3]benzazocine

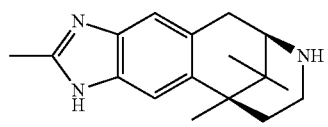 [SMILES: Cc1nc2cc3c(cc2[nH]1)[C@]1(C)CCN[C@H](C3)C1(C)C]

(5) (6R,10S)-5,6,7,8,9,10-Hexahydro-10,12,12-trimethyl-6,10-methano-1H-imidazo[5,4-i][3]benzazocine

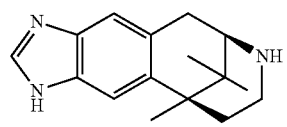 [SMILES: CC1(C)[C@H]2Cc3cc4nc[nH]c4cc3[C@]1(C)CCN2]

EXAMPLE XL

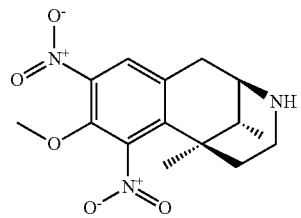 [SMILES: COc1c([N+](=O)[O-])cc2c(c1[N+](=O)[O-])[C@]1(C)CCN[C@H](C2)[C@@H]1C]

(2R,6R,11R)-8-Methoxy-6,11-dimethyl-7,9-dinitro-1,2,3,4,5,6-hexahydro-2,6-methano-benzo[d]azocine Ammonium nitrate (2.2 g) is added to a solution of (2R,6R,11R)-8-methoxy-6,11-dimethyl-1,2,3,4,5,6-hexahydro-2,6-methano-benzo[d]azocine (7.0 g) in concentrated sulfuric acid (25 mL) chilled to −5° C. Then, the cooling bath is removed and the solution is stirred at ambient temperature for 3 h. The reaction solution is diluted with water and basified using 1 M aqueous NaOH solution. The resulting mixture is extracted with dichloromethane, the combined extracts are dried (MgSO$_4$) and the solvent is evaporated. The residue is purified by HPLC on reversed phase (MeCN/H$_2$O/F$_3$CCO$_2$H) to give the product as the trifluoroacetic acid salt.

Yield: 1.27 g (11% of theory)

Mass spectrum (ESI$^+$): m/z=322 [M+H]$^+$

EXAMPLE XLI

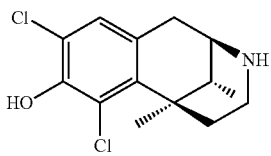

(2R,6R,11R)-7,9-Dichloro-6,11-dimethyl-1,2,3,4,5,6-hexahydro-2,6-methano-benzo[d]azocin-8-ol SO$_2$Cl$_2$ (1.6 mL) is added to a solution of (2R,6R,11R)-6,11-dimethyl-1,2,3,4,5,6-hexahydro-2,6-methano-benzo[d]azocin-8-ol (2.0 g) in acetic acid (100 mL). The solution is stirred at ambient temperature for 2 h, before another portion of SO$_2$Cl$_2$ (0.4 mL) is added. After stirring for another 1 h, the solution is concentrated under reduced pressure to give the crude acetic acid salt of the product that is dissolved in a solution of hydrogen chloride in ethylacetate (20 mL). The solution is concentrated and the residue is triturated with ether to give the hydrogen chloride salt of the title compound.

Yield: 2.40 g (81% of theory)
Mass spectrum (ESI$^+$): m/z=286/288/290 (2Cl) [m+H]$^+$ The following compound is obtained analogously to Example XLI:

(1) (2R,6S)-7,9-Dichloro-6-methyl-1,2,3,4,5,6-hexahydro-2,6-methano-benzo[d]azocin-8-ol

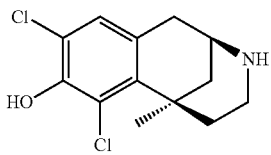 [SMILES: C[C@]12CCN[C@H](Cc3cc(Cl)c(O)c(Cl)c31)C2]

Mass spectrum (ESI$^+$): m/z=272/274/276 (2Cl) [M+H]$^+$

EXAMPLE XLII

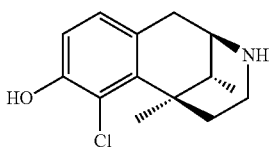 [SMILES: C[C@H]1[C@H]2Cc3ccc(O)c(Cl)c3[C@]1(C)CCN2]

(2R,6R,11R)-7-Chloro-6,11-dimethyl-1,2,3,4,5,6-hexahydro-2,6-methano-benzo[d]azocin-8-ol A mixture of 10% Pd/C (0.6 g) and the hydrogen chloride salt of (2R,6R,11R)-7,9-dichloro-6,11-dimethyl-1,2,3,4,5,6-hexahydro-2,6-methano-benzo[d]azocin-8-ol (1.0 g) in methanol (40 mL) is shaken in hydrogen atmosphere (3 bar) at room temperature for 24 h. Then, the catalyst is separated by filtration and the filtrate is concentrated. The residue is purified by HPLC on reversed phase (MeCN/H$_2$O/F$_3$CCO$_2$H) to give the trifluoroacetic acid salt of the title compound.

Yield: 0.59 g (52% of theory)
Mass spectrum (ESI$^+$): m/z=252/254 (Cl) [M+H]$^+$ The following compound is obtained analogously to Example XLII:

(1) (2R,6S)-7-Chloro-6-methyl-1,2,3,4,5,6-hexahydro-2,6-methano-benzo[d]azocin-8-ol

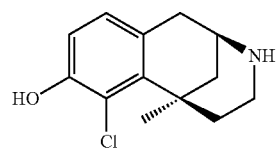 [SMILES: C[C@]12CCN[C@H](Cc3ccc(O)c(Cl)c31)C2]

Mass spectrum (ESI$^+$): m/z=238/240 (Cl) [M+H]$^+$

EXAMPLE XLIII

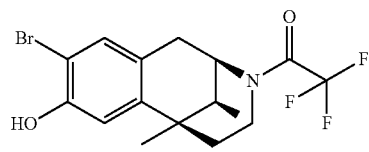 [SMILES: C[C@@H]1[C@H]2Cc3cc(Br)c(O)cc3[C@]1(C)CCN2C(=O)C(F)(F)F]

1-[(2R,6R,11S)-9-Bromo-8-hydroxy-6,11-dimethyl-1,2,5,6-tetrahydro-4H-2,6-methano-benzo[d]azocin-3-yl]-2,2,2-trifluoro-ethanone A solution of 2,2,2-trifluoro-1-[(2R,6R,11S)-8-hydroxy-6,11-dimethyl-1,2,5,6-tetrahydro-4H-2,6-methano-benzo[d]azocin-3-yl]-ethanone (3.0 g) and pyridinium tribromide (3.3 g) in acetic acid (2 mL) is stirred at 80° C. for 2 h. After cooling to room temperature, water is added and the resulting mixture is extracted with ethyl acetate. The combined organic extracts are washed with water, aqueous NaHCO$_3$ solution, and brine. After drying (Na$_2$SO$_4$), the solvent is removed and the residue is purified by chromatography on silica gel (cyclohexane/ethyl acetate 4:1->1:1).

Yield: 2.5 g (67% of theory)
Mass spectrum (ESI$^+$): m/z=392/394 (Br) [M+H]$^+$ The following compound is obtained analogously to Example XLIII:

(1) 1-[(2R,6R,11R)-9-Bromo-8-hydroxy-6,11-dimethyl-1,2,5,6-tetrahydro-4H-2,6-methano-benzo[d]azocin-3-yl]-2,2,2-trifluoro-ethanone

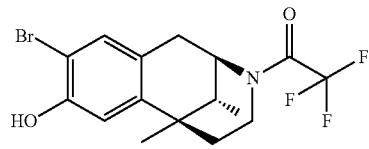 [SMILES: C[C@H]1[C@H]2Cc3cc(Br)c(O)cc3[C@]1(C)CCN2C(=O)C(F)(F)F]

Mass spectrum (ESI$^+$): m/z=392/394 (Br) [M+H]$^+$

EXAMPLE XLIV

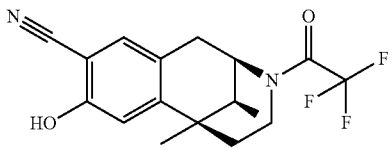 [SMILES: C[C@@H]1[C@H]2Cc3cc(C#N)c(O)cc3[C@]1(C)CCN2C(=O)C(F)(F)F]

(2R,6R,11S)-8-Hydroxy-6,11-dimethyl-3-(2,2,2-trifluoro-acetyl)-1,2,3,4,5,6-hexahydro-2,6-methano-benzo[d]azocine-9-carbonitrile A mixture of (2R,6R,11S)-1-(9-bromo-8-hydroxy-6,11-dimethyl-1,2,5,6-tetrahydro-4H-2,6-methano-benzo[d]azocin-3-yl)-2,2,2-trifluoro-ethanone (0.50 g) and copper cyanide (0.23 g) in N-methyl-pyrrolidone (2 mL) is stirred in a microwave oven with irradiation at 180° C. for 1 h. After cooling to room temperature, water is added and the resulting mixture is extracted with ethyl acetate. The combined organic extracts are washed with brine and dried ($Na_2SO_4$). After removing the solvent, the residue is purified by chromatography on silica gel (cyclohexane/ethyl acetate 2:1->1:2).

Yield: 0.20 g (46% of theory)
Mass spectrum ($ESI^+$): m/z=339 $[M+H]^+$

The following compound is obtained analogously to Example XLIV:

(1) (2R,6R,11R)-8-Hydroxy-6,11-dimethyl-3-(2,2,2-trifluoro-acetyl)-1,2,3,4,5,6-hexahydro-2,6-methano-benzo[d]azocine-9-carbonitrile

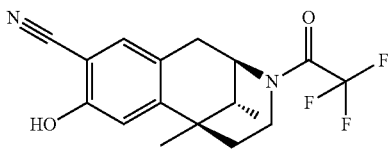 [SMILES: C[C@H]1[C@H]2Cc3cc(C#N)c(O)cc3[C@]1(C)CCN2C(=O)C(F)(F)F]

Mass spectrum ($ESI^+$): m/z=339 $[M+H]^+$

EXAMPLE XLV

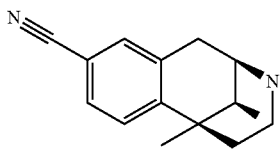 [SMILES: C[C@@H]1[C@H]2Cc3cc(C#N)ccc3[C@]1(C)CCN2]

(2R,6R,11S)-6,11-Dimethyl-1,2,3,4,5,6-hexahydro-2,6-methano-benzo[d]azocine-9-carbonitrile A solution of KF (76 mg) in water (1 mL) followed by polymethylhydrosiloxane (1.0 g) is added to a mixture of (2R,6R,11S)-trifluoro-methanesulfonic acid 9-cyano-6,11-dimethyl-3-(2,2,2-trifluoro-acetyl)-1,2,3,4,5,6-hexahydro-2,6-methano-benzo[d]azocin-8-yl ester (0.30 g) and $Pd(OAc)_2$ (7 mg) in tetrahydrofuran (3 mL). The resulting mixture is stirred at room temperature overnight, before 1 M aqueous NaOH solution (20 mL) is added. After stirring vigorously for 1 h, the organic phase is separated and the aqueous phase is extracted with ethyl acetate. The combined organic phases are washed with water and brine and dried ($MgSO_4$). The solvent is removed and the residue is taken up in 4 M aqueous NaOH solution (1 mL) and methanol (3 mL) and stirred at room temperature overnight. Then, the solution is neutralized with 1 M hydrochloric acid, filtered, and concentrated and the residue is purified by HPLC on reversed phase (MeCN/water).

Yield: 0.07 g (48% of theory)
Mass spectrum ($ESI^+$): m/z=227 $[M+H]^+$

The following compound is obtained analogously to Example XLV:

(1) (2R,6R,11R)-6,11-Dimethyl-1,2,3,4,5,6-hexahydro-2,6-methano-benzo[d]azocine-9-carbonitrile

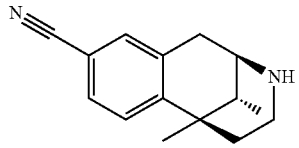 [SMILES: C[C@H]1[C@H]2Cc3cc(C#N)ccc3[C@]1(C)CCN2]

EXAMPLE XLVI

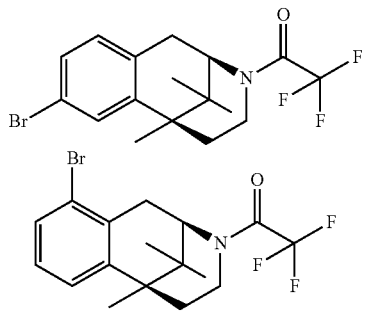

1-[(2R,6S)-8-Bromo-6,11,11-trimethyl-1,2,5,6-tetrahydro-4H-2,6-methano-benzo[d]azocin-3-yl]-2,2,2-trifluoro-ethanone and 1-[(2R,6S)-10-bromo-6,11,11-trimethyl-1,2,5,6-tetrahydro-4H-2,6-methano-benzo[d]azocin-3-yl]-2,2,2-trifluoro-ethanone $AlCl_3$ (147 mg) is added to a solution of 2,2,2-trifluoro-1-[(2R,6S)-6,11,11-trimethyl-1,2,5,6-tetrahydro-4H-2,6-methano-benzo[d]azocin-3-yl]-ethanone (275 mg) in 1,2-dichloroethane (10 mL). The resulting mixture is stirred at ambient temperature for 10 min before bromine (52 μL) is added. The mixture is heated to 50° C. After stirring at 50° C. for 1 h, the mixture is cooled to ambient temperature and diluted with dichloromethane (30 mL) and water (10 mL). The resulting mixture is stirred vigorously for 5 min and then 4 M hydrochloric acid (10 mL) is added. The organic phase is separated and washed with 4 M hydrochloric acid and water and dried ($MgSO_4$). The solvent is removed under reduced pressure to give the two title compounds in a mixture with a further regioisomerically brominated educt.

Yield: 328 mg (95% of theory)
Mass spectrum ($ESI^+$): m/z=390/392 (Br) $[M+H]^+$

EXAMPLE XLVII

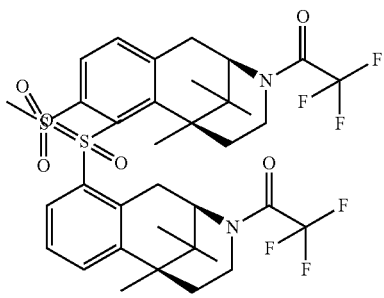

2,2,2-Trifluoro-1-[(2R,6S)-8-methanesulfonyl-6,11,11-trimethyl-1,2,5,6-tetrahydro-4H-2,6-methano-benzo[d]azocin-3-yl]-ethanone and 2,2,2-trifluoro-1-[(2R,6S)-10-methanesulfonyl-6,11,11-trimethyl-1,2,5,6-tetrahydro-4H-2,6-methano-benzo[d]azocin-3-yl]-ethanone MeSO$_2$Na (0.79 g) is added to a mixture of CuI (1.5 g) and 1-[(2R,6S)-8-bromo-6,11,11-trimethyl-1,2,5,6-tetrahydro-4H-2,6-methano-benzo[d]azocin-3-yl]-2,2,2-trifluoro-ethanone/1-[(2R,6S)-10-bromo-6,11,11-trimethyl-1,2,5,6-tetrahydro-4H-2,6-methano-benzo[d]azocin-3-yl]-2,2,2-trifluoro-ethanone (300 mg, crude product from Example XLVI) in dimethylsulfoxide (6 mL). The resulting mixture is heated to 120° C. and stirred at this temperature overnight. After cooling to ambient temperature, the mixture is poured into a solution of concentrated aqueous ammonia solution (20 mL) and water (80 mL). The resulting mixture is extracted with ethyl acetate and the combined organic extracts are washed with 2 M ammonia solution and brine. After drying (MgSO$_4$), the solvent is removed under reduced pressure and the residue is purified by HPLC on reversed phase (MeCN/water) to give the two title compounds separated.

2,2,2-Trifluoro-1-[(2R,6S)-8-methanesulfonyl-6,11,11-trimethyl-1,2,5,6-tetrahydro-4H-2,6-methano-benzo[d]azocin-3-yl]-ethanone: Yield: 150 mg (50% of theory)

Mass spectrum (ESI$^+$): m/z=390 [M+H]$^+$ 2,2,2-Trifluoro-1-[(2R,6S)-10-methanesulfonyl-6,11,11-trimethyl-1,2,5,6-tetrahydro-4H-2,6-methano-benzo[d]azocin-3-yl]-ethanone: Yield: 100 mg (33% of theory)

Mass spectrum (ESI$^+$): m/z=390 [M+H]$^+$

EXAMPLE XLVIII

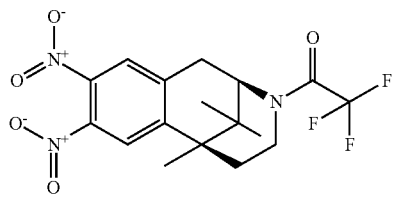 [SMILES: CC1(C)[C@H]2Cc3cc([N+](=O)[O-])c([N+](=O)[O-])cc3[C@]1(C)CCN2C(=O)C(F)(F)F]

2,2,2-Trifluoro-1-[(2R,6S)-6,11,11-trimethyl-8,9-dinitro-1,2,5,6-tetrahydro-4H-2,6-methano-benzo[d]azocin-3-yl]-ethanone Nitric acid (0.16 mL) is added to a solution of trifluoroacetic acid (0.65 mL) in dichloromethane (4 mL) chilled in an ice bath (ca. 0° C.). After stirring for 10 min, 2,2,2-trifluoro-1-[(2R,6S)-6,11,11-trimethyl-1,2,5,6-tetrahydro-4H-2,6-methano-benzo[d]azocin-3-yl]-ethanone (0.50 g) in dichloromethane (5 mL) is added. The resulting solution is stirred in the cooling bath for 2 h and then at ambient temperature overnight. The solution is poured into ice-cold water and the resulting mixture is extracted with dichloromethane. The combined organic extracts are washed with aqueous NaHCO$_3$ solution and dried (MgSO$_4$). The solvent is removed under reduced pressure and the residue is purified by chromatography on silica gel (cyclohexane/ethyl acetate 1:0->9:1).

Yield: 330 mg (51% of theory)
Mass spectrum (ESI$^+$): m/z=402 [M+H]$^+$

EXAMPLE IL

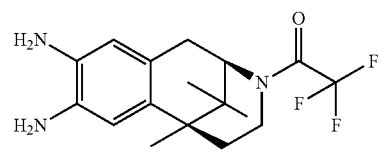 [SMILES: CC1(C)[C@H]2Cc3cc(N)c(N)cc3[C@]1(C)CCN2C(=O)C(F)(F)F]

1-[(2R,6S)-8,9-Diamino-6,11,11-trimethyl-1,2,5,6-tetrahydro-4H-2,6-methano-benzo[d]azocin-3-yl]-2,2,2-trifluoro-ethanone A mixture of 10% palladium on carbon (300 mg) and 2,2,2-trifluoro-1-[(2R,6S)-6,11,11-trimethyl-8,9-dinitro-1,2,5,6-tetrahydro-4H-2,6-methano-benzo[d]azocin-3-yl]-ethanone (330 mg) in methanol (5 mL) is shaken under hydrogen atmosphere at room temperature for 2 h. Then, the catalyst is separated by filtration and the solvent is removed under reduced pressure to give the crude title compound that is used without further purification.

Yield: 260 mg (93% of theory)
Mass spectrum (ESI$^+$): m/z=342 [M+H]$^+$

EXAMPLE L

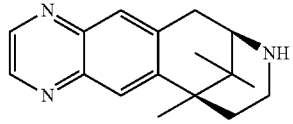 [SMILES: CC1(C)[C@H]2Cc3cc4nccnc4cc3[C@]1(C)CCN2]

(7R,11S)-6,7,8,9,10,11-Hexahydro-11,13,13-trimethyl-7,11-methano-pyrazino[2,3-i][3]benzazocine Glyoxal (40% in water, 95 µL) is added to 1-[(2R,6S)-8,9-diamino-6,11,11-trimethyl-1,2,5,6-tetrahydro-4H-2,6-methano-benzo[d]azocin-3-yl]-2,2,2-trifluoro-ethanone (260 mg) dissolved in ethanol (3 mL) and chilled in an ice bath. The cooling bath is removed and the solution is stirred at ambient temperature overnight. Then, the solution is concentrated and the residue is taken up in methanol (1 mL) and treated with 4 M aqueous NaOH solution (0.38 mL). After stirring at ambient temperature overnight, brine is added and the resulting mixture is extracted with ethyl acetate. The combined organic extracts are washed with brine, dried (MgSO$_4$), and the solvent is removed under reduced pressure to give the crude title compound that is used without further purification.

Yield: 204 mg

Mass spectrum (ESI$^+$): m/z=268 [M+H]$^+$

The following compound is obtained analogously to Example L:

(1) (7R,11S)-6,7,8,9,10,11-Hexahydro-2,3,11,13,13-pentamethyl-7,11-methano-pyrazino[2,3-i][3]benzazocine

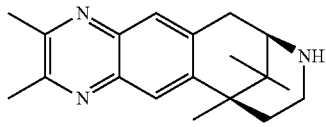 [SMILES: Cc1nc2cc3c(cc2nc1C)[C@]1(C)CCN[C@H](C3)C1(C)C]

Mass spectrum (ESI$^+$): m/z=296 [M+H]$^+$

The compound is obtained by using diacetyl according to the procedure described above.

EXAMPLE LI

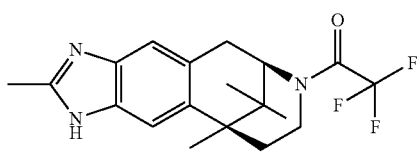 [SMILES: Cc1nc2cc3c(cc2[nH]1)[C@]1(C)CCN(C(=O)C(F)(F)F)[C@H](C3)C1(C)C]

2,2,2-Trifluoro-1-[(6R,10S)-5,6,7,8,9,10-hexahydro-2,10,12,12-tetramethyl-6,10-methano-1H-imidazo[5,4-i][3]benzazocin-7-yl]-ethanone 1-[(2R,6S)-8,9-Diamino-6,11,11-trimethyl-1,2,5,6-tetrahydro-4H-2,6-methano-benzo[d]azocin-3-yl]-2,2,2-trifluoro-ethanone (600 mg) dissolved in glacial acetic acid is stirred at 130° C. for 3 h. After cooling to ambient temperature, the solution is concentrated under reduced pressure and the residue is taken up in ethyl acetate. The organic solution is washed with aqueous K$_2$CO$_3$ solution and brine and dried (MgSO$_4$). The solvent is removed under reduced pressure to give the crude title compound as a foam-like solid.

Yield: 642 mg

Mass spectrum (ESI$^+$): m/z=366 [M+H]$^+$

The following compound is obtained analogously to Example LI:

(1) 2,2,2-Trifluoro-1-[(6R,10S)-5,6,7,8,9,10-hexahydro-10,12,12-trimethyl-6,10-methano-1H-imidazo[5,4-i][3]benzazocin-7-yl]-ethanone

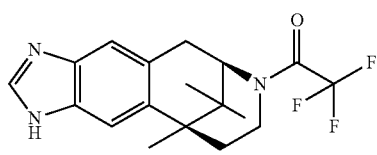 [SMILES: CC1(C)[C@H]2Cc3cc4nc[nH]c4cc3[C@]1(C)CCN2C(=O)C(F)(F)F]

Mass spectrum (ESI$^+$): m/z=352 [M+H]$^+$

The reaction is carried out with formic acid instead of acetic acid.

Example LII

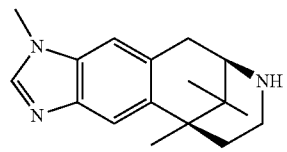

I

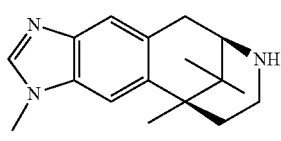

II (6R,10S)-5,6,7,8,9,10-Hexahydro-3,10,12,12-tetramethyl-6,10-methano-imidazo[4,5-i][3]benzazocine (I) and (6R,10S)-5,6,7,8,9,10-hexahydro-1,10,12,12-tetramethyl-6,10-methano-imidazo[5,4-i][3]benzazocine (II)

Methyl iodide (69 μL) is added to a mixture of (2R,6S)-1-(8,9-imidazo-6,11,11-trimethyl-1,2,5,6-tetrahydro-4H-2,6-methano-benzo[d]azocin-3-yl)-2,2,2-trifluoro-ethanone (300 mg) and K$_2$CO$_3$ (118 mg) in N,N-dimethylformamide (2 mL). The resulting mixture is stirred at room temperature overnight. Then, water is added and the mixture is extracted with ethyl acetate. The combined extracts are washed with brine and dried (MgSO$_4$). The solvent is removed and the residue is taken up in methanol (3 mL) and treated with 4 M aqueous NaOH solution (0.5 mL). The solution is stirred at room temperature overnight and then diluted with ethyl acetate. The resulting solution is washed with water and brine and dried (MgSO$_4$). The solvent is removed under reduced pressure to give the crude title compounds as a mixture.

Yield: 90 mg (39% of theory)

The following compounds are obtained analogously to Example LII:

(1) (6R,10S)-5,6,7,8,9,10-hexahydro-1,2,10,12,12-pentamethyl-6,10-methano-imidazo[5,4-i][3]benzazocine

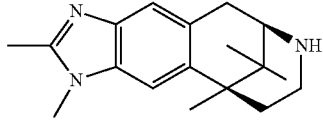 [SMILES: Cc1nc2cc3c(cc2n1C)[C@]1(C)CCN[C@H](C3)C1(C)C]

Mass spectrum (ESI$^+$): m/z=284 [M+H]$^+$ (2) (6R,10S)-5,6,7,8,9,10-hexahydro-2,3,10,12,12-pentamethyl-6,10-methano-imidazo[4,5-i][3]benzazocine

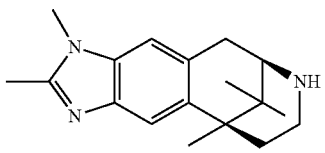 [SMILES: Cc1nc2cc3c(cc2n1C)C[C@H]1NCC[C@]3(C)C1(C)C]

Mass spectrum (ESI⁺): m/z=284 [M+H]⁺

The two isomeric compounds (1) and (2) were obtained from the same starting compound and separated by HPLC on reversed phase.

EXAMPLE LIII

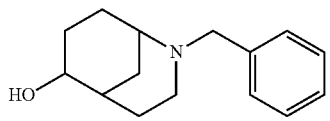 [SMILES: OC1CCC2CC1CCN2Cc1ccccc1]

2-Benzyl-2-aza-bicyclo[3.3.1]nonan-6-ol

Diisobutylaluminum hydride (1.5 mol/L in toluene, 21 mL) is added to a solution of acetic acid 2-benzyl-3-oxo-2-aza-bicyclo[3.3.1]non-6-yl ester (1.50 g, for synthesis see *J. Chem. Soc. Perkin Trans.* 1 1999, 1157-1162) in toluene (30 mL) cooled to −70° C. The cooling bath is removed and the solution is stirred at ambient temperature overnight. Then, another portion of diisobutylaluminum hydride (1.5 mol/L in toluene, 20 mL) is added and the solution is stirred for additional 4 h at room temperature. Then, the solution is poured into ice-cold water and the resulting mixture is extracted with ethyl acetate. The aqueous phase is acidified using 4 M hydrochloric acid and extracted one more time with ethyl acetate. The combined organic extracts are dried (Na₂SO₄) and the solvent is removed. The residue is purified by chromatography on silica gel (dichloromethane/methanol 1:0->2:1).

Yield: 440 mg (36% of theory)
Mass spectrum (ESI⁺): m/z=232 [M+H]⁺

EXAMPLE LIV

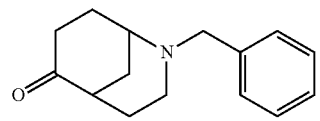 [SMILES: O=C1CCC2CC1CCN2Cc1ccccc1]

2-Benzyl-2-aza-bicyclo[3.3.1]nonan-6-one

Dess-Martin periodinane (1.30 g) is added to a solution of 2-benzyl-2-aza-bicyclo[3.3.1]nonan-6-ol (0.60 g) in dichloromethane (15 mL) chilled in an ice bath. The cooling bath is removed and the solution is stirred at ambient temperature for 1 h. Then, the solution is diluted with dichloromethane and washed with a mixture of aqueous Na₂S₂O₃ solution and aqueous NaHCO₃ solution. The solution is dried (Na₂SO₄) and the solvent is removed. The residue is purified by chromatography on silica gel (dichloromethane/methanol 1:0->2:1).

Yield: 250 mg (42% of theory)
Mass spectrum (ESI⁺): m/z=230 [M+H]⁺

EXAMPLE LV

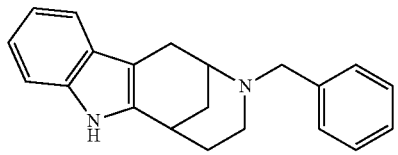 [SMILES: c1ccc(CN2CCC3CC2Cc2c3[nH]c3ccccc23)cc1]

3-Benzyl-2,3,4,5,6,7-hexahydro-2,6-methano-1H-azocino[5,4-b]indole

A solution of 2-benzyl-2-aza-bicyclo[3.3.1]nonan-6-one in acetic acid (0.24 g) is added to a solution of PhNHNH₂*HCl (173 mg) in acetic acid (4 mL) heated at reflux temperature. After stirring at this temperature for 2 h, the solution is cooled to room temperature and aqueous K₂CO₃ solution is added. The resulting mixture is extracted with ethyl acetate, the combined organic extracts are dried (Na₂SO₄), and the solvent is removed. The residue is purified by HPLC on reversed phase (MeCN/water).

Yield: 160 mg (49% of theory)

EXAMPLE LVI

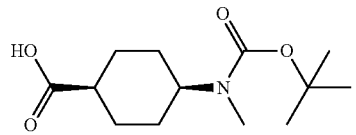 [SMILES: CN(C(=O)OC(C)(C)C)[C@H]1CC[C@@H](C(=O)O)CC1]

cis-4-(tert-Butoxycarbonyl-methyl-amino)-cyclohexanecarboxylic acid

Sodium hydride (0.22 g) is added to a solution of cis-4-tert-butoxycarbonylamino-cyclohexanecarboxylic acid (0.49 g) in N,N-dimethylacetamide (5 mL) chilled in an ice bath. The cooling bath is removed and the mixture is stirred at room temperature for 1.5 h. Then, the mixture is cooled in an ice bath and methyl iodide (0.63 mL) is added. The cooling bath is removed and the mixture is stirred at room temperature overnight. 1 M aqueous NaOH solution (6 mL) is added and the mixture is stirred at room temperature for another 12 h. Then diethyl ether is added and the aqueous phase is separated. The organic phase is extracted three times with water and the aqueous extracts and phase are combined and acidified using 2 M aqueous KHSO₄ solution. The acidic aqueous phase is extracted with diethyl ether and the combined organic extracts are dried (Na₂SO₄). The solvent is evaporated to afford the title compound as a solid.

Yield: 0.46 mg (89% of theory)
Mass spectrum (ESI⁺): m/z=258 [M+H]⁺

EXAMPLE LVII

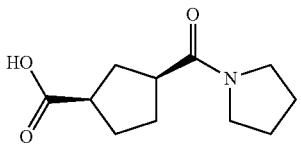 [SMILES: O=C(O)[C@@H]1CC[C@H](C(=O)N2CCCC2)C1]

cis-3-(Pyrrolidine-1-carbonyl)-cyclopentanecarboxylic acid

A mixture of cis-cyclopentane-1,3-dicarboxylic acid (1.00 g), acetic anhydride (1.20 mL), and toluene (5 mL) is stirred at 80° C. for 40 min. After cooling to room temperature, the solution is concentrated under reduced pressure. The residue is taken up in dichloromethane (20 mL) and the resulting solution is filtered to remove the non-dissolving part of the residue. Pyrrolidine (0.53 mL) is added to the filtrate and the solution is stirred at room temperature for 30 min. Then, the solution is concentrated under reduced pressure and the residue is dissolved in tetrahydrofuran and treated with Dowex H$^+$ resin. The mixture is filtered and the filrate is concentrated to afford the title compopund as an oil.

Yield: 1.34 g (quantitative)

The following compound is obtained analogously to Example LVII:

(1) cis-Cyclopentane-1,3-dicarboxylic acid monomethyl ester

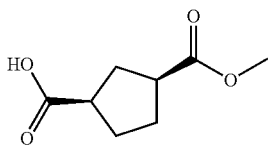

Methanol is used to open up the intermediate anhydride.
Preparation of the End Compounds:
Procedure A (Described for Example 1, Table 3)

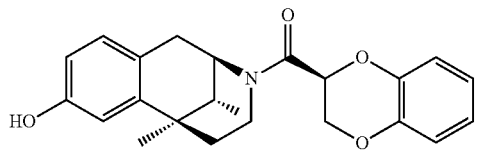 [SMILES: C[C@H]1[C@H]2Cc3ccc(O)cc3[C@]1(C)CCN2C(=O)[C@@H]1COc2ccccc2O1]

[(2S)-2,3-Dihydro-benzo[1,4]dioxin-2-yl]-[(2R,6R,11R)-8-hydroxy-6,11-dimethyl-1,2,5,6-tetrahydro-4H-2,6-methano-benzo[d]azocin-3-yl]-methanone Carbonyldiimidazole (0.47 g) is added to a solution of (S)-2,3-dihydro-benzo[1,4]dioxine-2-carboxylic acid (0.63 g) in dichloromethane (6 mL). The resulting solution is stirred at room temperature for 1 h before (2R,6R,11R)-6,11-dimethyl-1,2,3,4,5,6-hexahydro-2,6-methano-benzo[d]azocin-10-ol is added. The solution is further stirred at room temperature overnight. Then, dichloromethane (30 mL) is added and the resulting solution is washed with water. After drying (Na$_2$SO$_4$), the solvent is evaporated to give the product as a white foam-like solid.

Yield: 0.70 g (66% of theory)
Mass spectrum (ESI$^+$): m/z=380 [M+H]$^+$

The product is additionally purified by HPLC on reversed phase (H$_2$O/MeCN) in case the purity after the procedure described above is insufficient.
Procedure B (Described for Example 3, Table 3)

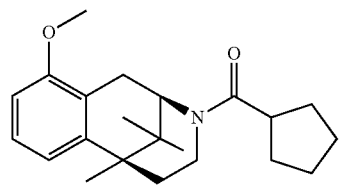 [SMILES: COc1cccc2c1C[C@H]1N(C(=O)C3CCCC3)CC[C@]2(C)C1(C)C]

Cyclopentyl-[(2R,6S)-10-methoxy-6,11,11-trimethyl-1,2,5,6-tetrahydro-4H-2,6-methano-benzo[d]azocin-3-yl]-methanone 2-(1H-Benzotriazol-1-yl)-1,1,3,3-tetramethyluronium tetrafluoroborate (0.27 g; alternatively N,N,N',N'-tetramethyl-O-(7-azabenzotriazol-1-yl)uronium hexafluorophosphate may be used) is added to a solution of cyclopentanecarboxylic acid (100 mg) and ethyldiisopropylamine (0.2 mL) in N,N-dimethylformamide (10 mL). The resulting solution is stirred at ambient temperature for 15 min before (2R,6S)-10-methoxy-6,11,11-trimethyl-1,2,3,4,5,6-hexahydro-2,6-methano-benzo[d]azocine (0.20 g) is added. After stirring the solution overnight, ethyl acetate is added and the resulting mixture is washed with aqueous Na$_2$CO$_3$ solution and dried (Na$_2$SO$_4$). After evaporation of the solvent under reduced pressure, the product is obtained as a yellow oil.

Yield: 0.27 g (99% of theory)
Mass spectrum (ESI$^+$): m/z=342 [M+H]$^+$

The product is additionally purified by HPLC on reversed phase (H$_2$O/MeCN) in case the purity after the procedure described above is insufficient.
Procedure C (Described for Example 4, Table 3)

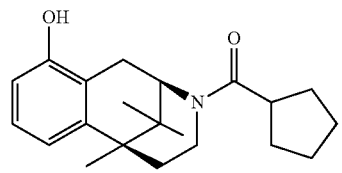 [SMILES: CC1(C)[C@H]2Cc3c(O)cccc3[C@]1(C)CCN2C(=O)C1CCCC1]

Cyclopentyl-[(2R,6S)-10-hydroxy-6,11,11-trimethyl-1,2,5,6-tetrahydro-4H-2,6-methano-benzo[d]azocin-3-yl]-methanone Boron tribromide (2.8 mL) is added to a solution of cyclopentyl-[(2R,6S)-10-methoxy-6,11,11-trimethyl-1,2,5,6-tetrahydro-4H-2,6-methano-benzo[d]azocin-3-yl]-methanone (280 g) in dichlormethane (10 mL). The resulting solution is stirred at ambient temperature for 2 h and then quenched by the addition of water. The organic phase is separated, washed with water and dried (Na$_2$SO$_4$). Evaporation of the solvent under reduced pressure affords the product.

Yield: 175 mg (65% of theory)
Mass spectrum (ESI⁺): m/z=328 [M+H]⁺

The product is additionally purified by HPLC on reversed phase (H₂O/MeCN) in case the purity is insufficient after the procedure described above.

Procedure D (Described for Example 5, Table 3)

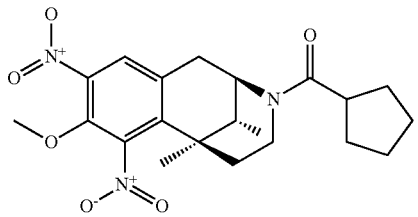

Cyclopentyl-[(2R,6R,11R)-8-methoxy-6,11-dimethyl-7,9-dinitro-1,2,5,6-tetrahydro-4H -2,6-methano-benzo[d]azocin-3-yl]-methanone Cyclopentanecarbonyl chloride (0.12 g) is added to the trifluoroacetic acid salt of (2R,6R,11R)-8-methoxy-6,11-dimethyl-7,9-dinitro-1,2,3,4,5,6-hexahydro-2,6-methano-benzo[d]azocine (0.43 g) and triethylamine (0.31 mL) dissolved in dichloromethane (10 mL). The resulting solution is stirred at room temperature overnight. Then, aqueous Na₂CO₃ solution is added and the resulting mixture is extracted with dichloromethane. The combined extracts are washed with water and dried (Na₂SO₄) and the solvent is evaporated. The residue is purified by HPLC on reversed phase (MeCN/H₂O) to give the product as a white solid.

Yield: 0.25 g (61% of theory)
Mass spectrum (ESI⁺): m/z=418 [M+H]⁺

Procedure E (Described for Example 7, Table 3)

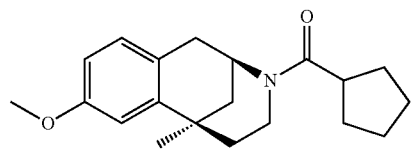 [SMILES: COc1ccc2c(c1)[C@]1(C)CCN(C(=O)C3CCCC3)[C@H](C2)C1]

Cyclopentyl-[(2R,6R)-8-methoxy-6-methyl-1,2,5,6-tetrahydro-4H-2,6-methano-benzo[d]azocin-3-yl]-methanone Sodium hydride (0.01 g) is added to a solution of cyclopentyl-[(2R,6R)-8-hydroxy-6-methyl-1,2,5,6-tetrahydro-4H-2,6-methano-benzo[d]azocin-3-yl]-methanone (0.10 g) in tetrahydrofuran (6 mL; alternatively N,N-dimethylformamide may be used). The mixture is stirred for 30 min at room temperature before methyl iodide (25 μL) is added. The resulting solution is stirred at room temperature overnight. Then, water is added and the resulting mixture is extracted with dichloromethane. The combined extracts are dried (Na₂SO₄) and the solvent is evaporated. The residue is purified by chromatography on silica gel (cyclohexane/ethyl acetate).

Yield: 0.10 g (97% of theory)
Mass spectrum (ESI⁺): m/z=314 [M+H]⁺

Procedure F (Described for Example 30, Table 3)

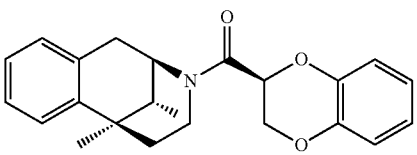 [SMILES: C[C@H]1[C@H]2Cc3ccccc3[C@]1(C)CCN2C(=O)[C@@H]1COc2ccccc2O1]

[(S)-2,3-Dihydro-benzo[1,4]dioxin-2-yl]-[(2R,6R,11R)-6,11-dimethyl-1,2,5,6-tetrahydro-4H -2,6-methano-benzo[d]azocin-3-yl]-methanone 10% Pd/C (0.10 g) is added to a solution of (2R,6R,11R)-trifluoro-methanesulfonic acid 3-[(S)-2,3-dihydro-benzo[1,4]dioxine-2-carbonyl]-6,11-dimethyl-1,2,3,4,5,6-hexahydro-2,6-methano-benzo[d]azocin-8-yl ester (0.50 g) in methanol (15 mL) and ethyl acetate (25 mL). The resulting mixture is shaken under hydrogen atmosphere (50 psi) at room temperature overnight. Then, the catalyst is separated by filtration and the filtrate is concentrated under reduced pressure. The residue is purified by HPLC on reversed phase (MeCN/H₂O) to give the product as a colorless gum-like solid.

Yield: 0.08 g (23% of theory)
Mass spectrum (ESI⁺): m/z=364 [M+H]⁺

Procedure G (Described for Example 52, Table 3)

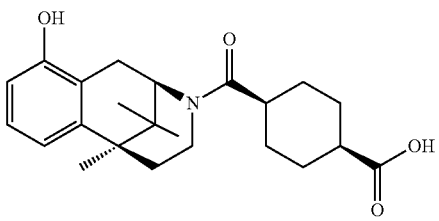 [SMILES: CC1(C)[C@H]2Cc3c(O)cccc3[C@]1(C)CCN2C(=O)[C@H]1CC[C@@H](C(=O)O)CC1]

cis-4-[(2R,6S)-10-Hydroxy-6,11,11-trimethyl-1,2,5,6-tetrahydro-4H-2,6-methano-benzo[d]azocine-3-carbonyl]-cyclohexane carboxylic acid 4 M aqueous NaOH solution (3.5 mL) is added to a solution of cis-4-[(2R,6S)-10-hydroxy-6,11,11-trimethyl-1,2,5,6-tetrahydro-4H-2,6-methano-benzo[d]azocine-3-carbonyl]-cyclohexane carboxylic acid methyl ester (1.2 g) in methanol (20 mL). The resulting solution is stirred at room temperature overnight. Then, 4 M hydrochloric acid is added, the resulting mixture is extratced with ethyl acetate, and the combined extratcs are dried (Na₂SO₄). After removal of the solvent, the residue is triturated with a mixture of acetonitrile and ether.

Yield: 0.83 g (71% of theory)
Mass spectrum (ESI⁺): m/z=386 [M+H]⁺

Procedure H (Described for Example 78, Table 3)

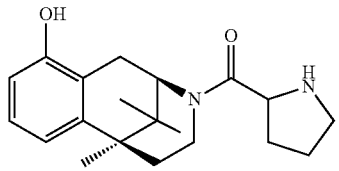 [SMILES: CC1(C)[C@H]2Cc3c(O)cccc3[C@]1(C)CCN2C(=O)C1CCCN1]

[(2R,6S)-10-Hydroxy-6,11,11-trimethyl-1,2,5,6-tetrahydro-4H-2,6-methano-benzo[d]azocin-3-yl]-pyrrolidin-2-yl-methanone A solution of 2-[(2R,6S)-10-hydroxy-6,11,11-trimethyl-1,2,5,6-tetrahydro-4H-2,6-methano-benzo[d]azocine-3-carbonyl]-pyrrolidine-1-carboxylic acid tert-butyl ester (10.9 mg) in trifluoroacetic acid (2 mL) is stirred at ambient temperature for 2 h. Then, the solution is concentrated under reduced pressure to give the trifluoroacetic acid salt of the title compound.

Yield: 8.7 mg (77% of theory)
Mass spectrum (ESI⁺): m/z=329 [M+H]⁺

Procedure I (described for Example 93, Table 3)

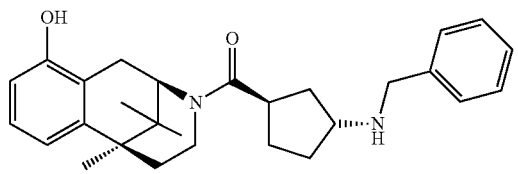

[(1R,3R)-3-Benzylamino-cyclopentyl]-[(2R,6S)-10-hydroxy-6,11,11-trimethyl-1,2,5,6-tetrahydro-4H-2,6-methano-benzo[d]azocin-3-yl]-methanone Benzyl bromide (16 µL) is added to a solution of [(1R,3R)-3-amino-cyclopentyl]-[(2R,6S)-10-hydroxy-6,11,11-trimethyl-1,2,5,6-tetrahydro-4H-2,6-methano-benzo[d]azocin-3-yl]-methanone (50 mg) and ethyldiisopropylamine (68 µL) in acetonitrile (1 mL). The resulting solution is stirred at 70° C. for 3 h. After cooling to room temperature, the solution is concentrated under reduced pressure and the residue is purified by HPLC on reversed phase (MeCN/H₂O/F₃CCO₂H) to give the trifluoroacetic acid salt of the title compound.

Yield: 28 mg (50% of theory)
Mass spectrum (ESI⁺): m/z=433 [M+H]⁺

Procedure J (Described for Example 101, Table 3)

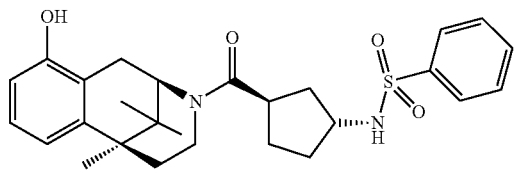

N-{(1R,3R)-3-[(2R,6S)-10-Hydroxy-6,11,11-trimethyl-1,2,5,6-tetrahydro-4H-2,6-methano-benzo[d]azocine-3-carbonyl]-cyclopentyl}-benzenesulfonamide Benzenesulfonyl chloride (41 mg) is added to a solution of [(1R,3R)-3-amino-cyclopentyl]-[(2R,6S)-10-hydroxy-6,11,11-trimethyl-1,2,5,6-tetrahydro-4H-2,6-methano-benzo[d]azocin-3-yl]-methanone (80 mg) and triethylamine (120 µL) in dichloromethane (1 mL). The resulting solution is stirred at room temperature overnight and then concentrated under reduced pressure. The residue is purified by HPLC on reversed phase (MeCN/H₂O/F₃CCO₂H) to give the title compound.

Yield: 36 mg (35% of theory)
Mass spectrum (ESI⁺): m/z=483 [M+H]⁺

Procedure K (Described for Example 104, Table 3)

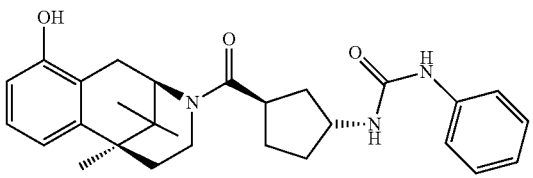

1-{(1R,3R)-3-[(2R,6S)-10-Hydroxy-6,11,11-trimethyl-1,2,5,6-tetrahydro-4H-2,6-methano-benzo[d]azocine-3-carbonyl]-cyclopentyl}-3-phenyl-urea Aniline (19 µL) and triethylamine (100 µL) dissolved in dichloromethane (0.5 mL) are added to a solution of triphosgene (19 mg) in dichloromethane (0.5 mL) chilled in an ice bath. After stirring the solution for 30 min, [(1R,3R)-3-amino-cyclopentyl]-[(2R,6S)-10-hydroxy-6,11,11-trimethyl-1,2,5,6-tetrahydro-4H-2,6-methano-benzo[d]azocin-3-yl]-methanone (80 mg) and triethylamine (30 µL) dissolved in dichloromethane (1 mL) are added. The resulting solution is stirred in the cooling bath for 15 min and then at room temperature for 2 h. The solution is concentrated under reduced pressure and the residue is purified by HPLC on reversed phase (MeCN/H₂O/F₃CCO₂H) to give the title compound.

Yield: 7 mg (5% of theory)
Mass spectrum (ESI⁺): m/z=462 [M+H]⁺

Procedure L (Described for Example 105, Table 3)

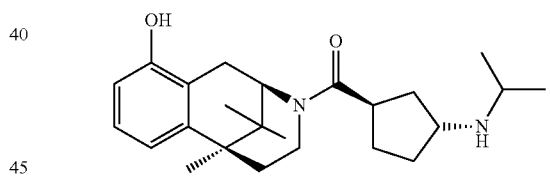

[(2R,6S)-10-Hydroxy-6,11,11-trimethyl-1,2,5,6-tetrahydro-4H-2,6-methano-benzo[d]azocin-3-yl]-[(1R,3R)-3-isopropylamino-cyclopentyl]-methanone Sodium triacetoxyborohydride (56 mg) is added to a solution of [(1R,3R)-3-amino-cyclopentyl]-[(2R,6S)-10-hydroxy-6,11,11-trimethyl-1,2,5,6-tetrahydro-4H-2,6-methano-benzo[d]azocin-3-yl]-methanone (50 mg), acetone (9 mg), trimethyl orthoformate (28 mg), and acetic acid (23 µL) in N,N-dimethylformamide (1 mL). The resulting mixture is stirred at room temperature for 3 h. The solution is concentrated under reduced pressure and the residue is purified by HPLC on reversed phase (MeCN/H₂O/F₃CCO₂H) to give the trifluoroacetic acid salt of the title compound.

Yield: 44 mg (66% of theory)
Mass spectrum (ESI⁺): m/z=385 [M+H]⁺

Procedure M (Described for Example 117, Table 3)

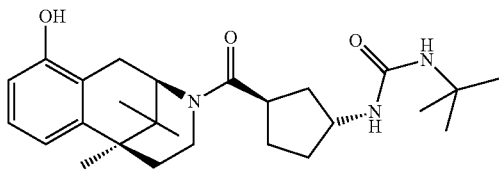

1-tert-Butyl-3-{(1R,3R)-3-[(2R,6S)-10-hydroxy-6,
11,11-trimethyl-1,2,5,6-tetrahydro-4H-2,6-methano-
benzo[d]azocine-3-carbonyl]-cyclopentyl}-urea tert-Butylisocyanate (30 mg) is added to a solution of [(1R,3R)-3-amino-cyclopentyl]-[(2R,6S)-10-hydroxy-6,11,11-trimethyl-1,2,5,6-tetrahydro-4H-2,6-methano-benzo[d]azocin-3-yl]-methanone (100 mg) and ethyldiisopropylamine (120 μL) in N,N-dimethylformamide (2 mL). The resulting solution is stirred at 40° C. overnight. Then, the solution is concentrated under reduced pressure and the residue is purified by HPLC on reversed phase (MeCN/H$_2$O/F$_3$CCO$_2$H) to give the title compound.

Yield: 7 mg (5% of theory)
Mass spectrum (ESI$^+$): m/z=462 [M+H]$^+$
Procedure N (Described for Example 128, Table 3)

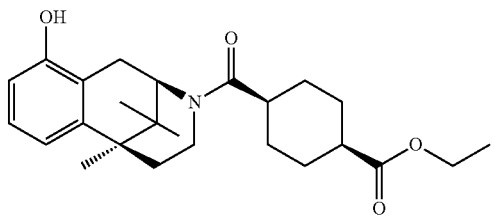 [SMILES: CCOC(=O)[C@H]1CC[C@@H](C(=O)N2CC[C@@]3(C)c4cccc(O)c4C[C@@H]2C3(C)C)CC1]

4-[(2R,6S)-10-Hydroxy-6,11,11-trimethyl-1,2,5,6-
tetrahydro-4H-2,6-methano-benzo[d]azocine-3-car-
bonyl)-cyclohexanecarboxylic acid ethyl ester SOCl$_2$ (5 mL) is added dropwise to a suspension of 4-[(2R,6S)-10-hydroxy-6,11,11-trimethyl-1,2,5,6-tetrahydro-4H-2,6-methano-benzo[d]azocine-3-carbonyl]-cyclohexanecarboxylic acid (100 mg) in ethanol (5 mL) cooled to −20° C. Then, the cooling bath is removed and the resulting mixture is stirred at ambient temperature overnight. The solution is concentrated under reduced pressure and the residue is triturated with acetone and dried.

Yield: 61 mg (58% of theory)
Mass spectrum (ESI$^+$): m/z=414 [M+H]$^+$
Procedure O (Described for Example 180, Table 3)

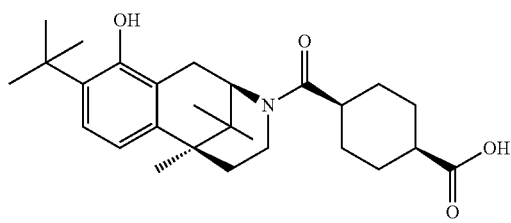 [SMILES: CC(C)(C)c1ccc2c(c1O)C[C@H]1N(C(=O)[C@H]3CC[C@@H](C(=O)O)CC3)CC[C@]2(C)C1(C)C]

cis-4-[(2R,6S)-9-tert-Butyl-10-hydroxy-6,11,11-
trimethyl-1,2,5,6-tetrahydro-4H-2,6-methano-benzo
[d]azocine-3-carbonyl]-cyclohexanecarboxylic acid SOCl$_2$ (1 mL) is added dropwise to a solution of cis-4-[(2R,6S)-10-hydroxy-6,11,11-trimethyl-1,2,5,6-tetrahydro-4H-2,6-methano-benzo[d]azocine-3-carbonyl]-cyclohexane carboxylic acid (100 mg) in tert-butanol (5 mL) cooled to −10° C. Then, the cooling bath is removed and the resulting solution is stirred at ambient temperature overnight before another portion of SOCl$_2$ (1 mL) is added. After stirring for additional 12 h more SOCl$_2$ (2 mL) is added and the solution is heated to 50° C. The solution is stirred at this temperature for 48 h before HCl in 1,4-dioxane (1 mL) is added. The resulting solution is stirred at reflux temperature overnight and then treated with concentrated H$_2$SO$_4$ (3 mL). After stirring at reflux temperature for additional 3 h, the solution is cooled to ambient temperature and concentrated under reduced pressure. The residue is treated with water and the precipitate is separated by filtration. The precipitate is taken up in ethyl acetate and washed with water and dried (MgSO$_4$). After removing the solvent, the residue is purified by HPLC (water/MeCN/F$_3$CCO$_2$H).

Yield: 12 mg (11% of theory)
Mass spectrum (ESI$^+$): m/z=442 [M+H]$^+$
Procedure P (Described for Example 195, Table 3)

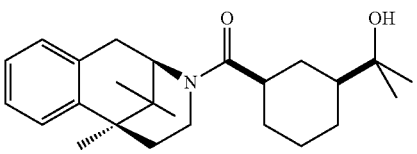

[cis-3-(1-Hydroxy-1-methyl-ethyl)-cyclohexyl]-
[(2R,6S)-6,11,11-trimethyl-1,2,5,6-tetrahydro-4H-2,
6-methano-benzo[d]azocin-3-yl]-methanone (diaste-
reomeric mixture derived from the two cis-
configured enantiomers of the cyclohexane moiety)

MeMgBr (1.4 M in tetrahydrofuran/toluene, 1.3 mL) is added dropwise to a solution of cis-3-[(2R,6S)-6,11,11-trimethyl-1,2,5,6-tetrahydro-4H-2,6-methano-benzo[d]azocine-3-carbonyl]-cyclohexanecarboxylic acid methyl ester (0.24 g, diastereomeric mixture derived from the two cis-configured enantiomers of the cyclohexane moiety) in tetrahydrofuran (2 mL) chilled in an ice bath. The solution is stirred with cooling for 2 h and then the reaction is quenched by the addition of aqueous NH$_4$Cl solution. The resulting mixture is extracted with tert-butyl methyl ether and the combined extracts are dried (MgSO$_4$). The solvent is evaporated to give the title compound as a foam-like solid.

Yield: 0.20 g (84% of theory)
Mass spectrum (ESI$^+$): m/z=384 [M+H]$^+$

Procedure Q (Described for Example 204, Table 3)

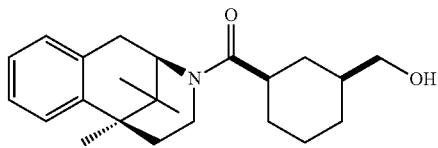

(cis-3-Hydroxymethyl-cyclohexyl)-[(2R,6S)-6,11,11-trimethyl-1,2,5,6-tetrahydro-4H-2,6-methano-benzo[d]azocin-3-yl]-methanone (diastereomeric mixture derived from the two cis-configured enantiomers of the cyclohexane moiety)

LiAlH$_4$ (1 M in tetrahydrofuran, 0.43 mL) is added dropwise to a solution of cis-3-[(2R,6S)-6,11,11-trimethyl-1,2,5,6-tetrahydro-4H-2,6-methano-benzo[d]azocine-3-carbonyl]-cyclohexanecarboxylic acid methyl ester (0.30 g, diastereomeric mixture derived from the two cis-configured enantiomers of the cyclohexane moiety) in tetrahydrofuran (3 mL) cooled to −10° C. The solution is stirred with cooling for 2 h and then the reaction is quenched by the addition of water. The resulting mixture is extracted with tert-butyl methyl ether and the combined extracts are are washed with brine and dried (MgSO$_4$). The solvent is evaporated to afford the title compound as a diastereomeric mixture.
Yield: 0.27 g (96% of theory)
Mass spectrum (ESI$^+$): m/z=356 [M+H]$^+$ Procedure R (Described for Example 203, Table 3)

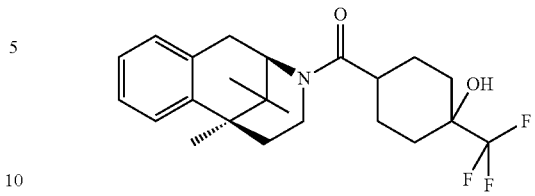

(4-Hydroxy-4-trifluoromethyl-cyclohexyl)-[(2R,6S)-6,11,11-trimethyl-1,2,5,6-tetrahydro-4H-2,6-methano-benzo[d]azocin-3-yl]-methanone (diastereomeric mixture derived from the two cyclohexane diastereomers)

(Trifluoromethyl)trimethylsilane (2 M in tetrahydrofuran, 0.42 mL) is added to a mixture of 4-[(2R,6S)-6,11,11-trimethyl-1,2,5,6-tetrahydro-4H-2,6-methano-benzo[d]azocine-3-carbonyl]-cyclohexanone (0.26 g) and CsF (12 mg) in tetrahydrofuran (5 mL) cooled to −5° C. The mixture is stirred at −5° C. for 1.5 h, before 1 M hydrochloric acid (5 mL) is added. The resulting mixture is stirred at room temperature overnight. The reaction mixture is concentrated and the residue is purified by HPLC on reversed phase (acetonitrile/water) to afford the title compound as a diastereomeric mixture.
Yield: 0.12 g (38% of theory)
Mass spectrum (ESI$^+$): m/z=410 [M+H]$^+$

TABLE 3

Compounds prepared in analogy to the examples described above

| Example No. | Chemical Name/Structure/Remarks | Prepared in analogy to Procedure | Characterization |
|---|---|---|---|
| 1 | [(2S)-2,3-Dihydro-benzo[1,4]dioxin-2-yl]-[(2R,6R,11R)-8-hydroxy-6,11-dimethyl-1,2,5,6-tetrahydro-4H-2,6-methano-benzo[d]azocin-3-yl]-methanone | A | Mass spectrum (ESI$^+$): m/z = 380 [M + H]$^+$ |
| 2 | [(2R)-2,3-Dihydro-benzo[1,4]dioxin-2-yl]-[(2R,6R,11R)-8-hydroxy-6,11-dimethyl-1,2,5,6-tetrahydro-4H-2,6-methano-benzo[d]azocin-3-yl]-methanone | A | Mass spectrum (ESI$^+$): m/z = 380 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 3 | Cyclopentyl-[(2R,6S)-10-methoxy-6,11,11-trimethyl-1,2,5,6-tetrahydro-4H-2,6-methano-benzo[d]azocin-3-yl]-methanone | B | Mass spectrum (ESI$^+$): m/z = 342 [M + H]$^+$ |
| 4 | Cyclopentyl-[(2R,6S)-10-hydroxy-6,11,11-trimethyl-1,2,5,6-tetrahydro-4H-2,6-methano-benzo[d]azocin-3-yl]-methanone | C | Mass spectrum (ESI$^+$): m/z = 328 [M + H]$^+$ |
| 5 | Cyclopentyl-[(2R,6R,11R)-8-methoxy-6,11-dimethyl-7,9-dinitro-1,2,5,6-tetrahydro-4H-2,6-methano-benzo[d]azocin-3-yl]-methanone | D | Mass spectrum (ESI$^+$): m/z = 418 [M + H]$^+$ |
| 6 | Cyclopentyl-[(2R,6R,11R)-8-hydroxy-6,11-dimethyl-7,9-dinitro-1,2,5,6-tetrahydro-4H-2,6-methano-benzo[d]azocin-3-yl]-methanone | C | Mass spectrum (ESI$^+$): m/z = 404 [M + H]$^+$ |
| 7 | Cyclopentyl-[(2R,6R,11R)-8-methoxy-6,11-dimethyl-1,2,5,6-tetrahydro-4H-2,6-methano-benzo[d]azocin-3-yl]-methanone | D | Mass spectrum (ESI$^+$): m/z = 328 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 8 | Cyclopentyl-[(2R,6R,11R)-8-hydroxy-6,11-dimethyl-1,2,5,6-tetrahydro-4H-2,6-methano-benzo[d]azocin-3-yl]-methanone | D | Mass spectrum (ESI$^+$): m/z = 314 [M + H]$^+$ |
| 9 | Cyclopentyl-[(2R,6R)-8-hydroxy-6-methyl-1,2,5,6-tetrahydro-4H-2,6-methano-benzo[d]azocin-3-yl]-methanone | D | Mass spectrum (ESI$^+$): m/z = 300 [M + H]$^+$ |
| 10 | Cyclopentyl-[(2R,6R)-8-methoxy-6-methyl-1,2,5,6-tetrahydro-4H-2,6-methano-benzo[d]azocin-3-yl]-methanone | E | Mass spectrum (ESI$^+$): m/z = 300 [M + H]$^+$ |
| 11 | Cyclopentyl-[(2R,6R,11R)-7,9-dichloro-8-hydroxy-6,11-dimethyl-1,2,5,6-tetrahydro-4H-2,6-methano-benzo[d]azocin-3-yl]-methanone | B | Mass spectrum (ESI$^+$): m/z = 382/384/386 (2Cl) [M + H]$^+$ |
| 12 | [(2R,6R,11R)-7-Chloro-8-hydroxy-6,11-dimethyl-1,2,5,6-tetrahydro-4H-2,6-methano-benzo[d]azocin-3-yl]-cyclopentyl-methanone | B | Mass spectrum (ESI$^+$): m/z = 348/350 (Cl) [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 13 | [(2R,6R)-7-Chloro-8-hydroxy-6-methyl-1,2,5,6-tetrahydro-4H-2,6-methano-benzo[d]azocin-3-yl]-cyclopentyl-methanone | B | Mass spectrum (ESI+): m/z = 334/336 (Cl) [M + H]+ |
| 14 | [(2R,6S)-10-Hydroxy-6,11,11-trimethyl-1,2,5,6-tetrahydro-4H-2,6-methano-benzo[d]azocin-3-yl]-(3-methoxy-cyclohexyl)-methanone | B | Mass spectrum (ESI+): m/z = 372 [M + H]+ |
| 15 | Bicyclo[2.2.1]hept-2-yl-[(2R,6S)-10-hydroxy-6,11,11-trimethyl-1,2,5,6-tetrahydro-4H-2,6-methano-benzo[d]azocin-3-yl]-methanone | B | Mass spectrum (ESI+): m/z = 354 [M + H]+ |
| 16 | cis-3-[(2R,6S)-10-Hydroxy-6,11,11-trimethyl-1,2,5,6-tetrahydro-4H-2,6-methano-benzo[d]azocine-3-carbonyl]-cyclopentanecarboxylic acid methyl ester | B | Mass spectrum (ESI+): m/z = 386 [M + H]+ |
| 17 | [(2R,6S)-10-Hydroxy-6,11,11-trimethyl-1,2,5,6-tetrahydro-4H-2,6-methano-benzo[d]azocin-3-yl]-[cis-3-(pyrrolidine-1-carbonyl)-cyclopentyl]-methanone | B | Mass spectrum (ESI+): m/z = 425 [M + H]+ |

TABLE 3-continued

Compounds prepared in analogy to the examples described above

| Example No. | Chemical Name/Structure/Remarks | Prepared in analogy to Procedure | Characterization |
|---|---|---|---|
| 18 | (1S,3R)-3-[(2R,6S)-10-Hydroxy-6,11,11-trimethyl-1,2,5,6-tetrahydro-4H-2,6-methano-benzo[d]azocine-3-carbonyl]-cyclohexane carboxylic acid methyl ester | B | Mass spectrum (ESI$^+$): m/z = 400 [M + H]$^+$ |
| 19 | (4,4-Difluoro-cyclohexyl)-[(2R,6S)-10-hydroxy-6,11,11-trimethyl-1,2,5,6-tetrahydro-4H-2,6-methano-benzo[d]azocin-3-yl]-methanone | B | Mass spectrum (ESI$^+$): m/z = 378 [M + H]$^+$ |
| 20 | {(1R,3R)-3-[(2R,6S)-10-Hydroxy-6,11,11-trimethyl-1,2,5,6-tetrahydro-4H-2,6-methano-benzo[d]azocine-3-carbonyl]-cyclopentyl}-carbamic acid tert-butyl ester | B | Mass spectrum (ESI$^+$): m/z = 387 [M − tertBu + 2H]$^+$ |
| 21 | [(2R,6S)-10-Hydroxy-6,11,11-trimethyl-1,2,5,6-tetrahydro-4H-2,6-methano-benzo[d]azocin-3-yl]-(4-methoxy-cyclohexyl)-methanone | B | Mass spectrum (ESI$^+$): m/z = 372 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 22 | [(2R,6S)-10-Hydroxy-6,11,11-trimethyl-1,2,5,6-tetrahydro-4H-2,6-methano-benzo[d]azocin-3-yl]-(1-phenyl-cyclopentyl)-methanone | B | Mass spectrum (ESI$^+$): m/z = 404 [M + H]$^+$ |
| 23 | Cycloheptyl-[(2R,6S)-10-hydroxy-6,11,11-trimethyl-1,2,5,6-tetrahydro-4H-2,6-methano-benzo[d]azocin-3-yl]-methanone | B | Mass spectrum (ESI$^+$): m/z = 356 [M + H]$^+$ |
| 24 | (2S)-Bicyclo[2.2.1]hept-5-en-2-yl-[(2R,6S)-10-hydroxy-6,11,11-trimethyl-1,2,5,6-tetrahydro-4H-2,6-methano-benzo[d]azocin-3-yl]-methanone | B | Mass spectrum (ESI$^+$): m/z = 352 [M + H]$^+$ |
| 25 | 4-[(2R,6S)-10-Hydroxy-6,11,11-trimethyl-1,2,5,6-tetrahydro-4H-2,6-methano-benzo[d]azocine-3-carbonyl]-cyclohexane carboxylic acid methyl ester | B | Mass spectrum (ESI$^+$): m/z = 400 [M + H]$^+$ |
| 26 | [(2R,6R,11R)-8-Hydroxy-6,11-dimethyl-1,2,5,6-tetrahydro-4H-2,6-methano-benzo[d]azocin-3-yl]-(1-phenyl-cyclohexyl)-methanone | A | Mass spectrum (ESI$^+$): m/z = 404 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 27 | ((S)-2,3-Dihydro-benzo[1,4]dioxin-2-yl)-[(2R,6R,11R)-8-ethoxy-6,11-dimethyl-1,2,5,6-tetrahydro-4H-2,6-methano-benzo[d]azocin-3-yl]-methanone | E | Mass spectrum (ESI$^+$): m/z = 408 [M + H]$^+$ |
| 28 | [(2R,6R,11R)-8-Benzyloxy-6,11-dimethyl-1,2,5,6-tetrahydro-4H-2,6-methano-benzo[d]azocin-3-yl]-((S)-2,3-dihydro-benzo[1,4]dioxin-2-yl)-methanone | E | Mass spectrum (ESI$^+$): m/z = 470 [M + H]$^+$ |
| 29 | [(2R,6R,11R)-8-Allyoxy-6,11-dimethyl-1,2,5,6-tetrahydro-4H-2,6-methano-benzo[d]azocin-3-yl]-((S)-2,3-dihydro-benzo[1,4]dioxin-2-yl)-methanone | E | Mass spectrum (ESI$^+$): m/z = 420 [M + H]$^+$ |
| 30 | ((S)-2,3-Dihydro-benzo[1,4]dioxin-2-yl)-[(2R,6R,11R)-6,11-dimethyl-1,2,5,6-tetrahydro-4H-2,6-methano-benzo[d]azocin-3-yl]-methanone | F | Mass spectrum (ESI$^+$): m/z = 364 [M + H]$^+$ |
| 31 | ((R)-2,3-Dihydro-benzo[1,4]dioxin-2-yl)-[(2R,6R,11R)-8-methoxy-6,11-dimethyl-1,2,5,6-tetrahydro-4H-2,6-methano-benzo[d]azocin-3-yl)-methanone | E | Mass spectrum (ESI$^+$): m/z = 394 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 32 | ((R)-2,3-Dihydro-benzo[1,4]dioxin-2-yl)-[(2R,6R,11R)-8-ethoxy-6,11-dimethyl-1,2,5,6-tetrahydro-4H-2,6-methano-benzo[d]azocin-3-yl]-methanone | E | Mass spectrum (ESI$^+$): m/z = 408 [M + H]$^+$ |
| 33 | [(2R,6R,11R)-8-Benzyloxy-6,11-dimethyl-1,2,5,6-tetrahydro-4H-2,6-methano-benzo[d]azocin-3-yl]-((R)-2,3-dihydro-benzo[1,4]dioxin-2-yl)-methanone | E | Mass spectrum (ESI$^+$): m/z = 470 [M + H]$^+$ |
| 34 | ((R)-2,3-Dihydro-benzo[1,4]dioxin-2-yl)-[(2R,6R,11R)-6,11-dimethyl-1,2,5,6-tetrahydro-4H-2,6-methano-benzo[d]azocin-3-yl]-methanone | F | Mass spectrum (ESI$^+$): m/z = 364 [M + H]$^+$ |
| 35 | (2,3-Dihydro-benzo[1,4]dioxin-2-yl)-[(2R,6R)-6-ethyl-8-hydroxy-1,2,5,6-tetrahydro-4H-2,6-methano-benzo[d]azocin-3-yl]-methanone<br><br>The starting material may be obtained by resolution of the racemate by HPLC on chiraL phase [for preparation see DE 2358248 (1974)] | A | Mass spectrum (ESI$^+$): m/z = 380 [M + H]$^+$ |
| 36 | (2,3-Dihydro-benzo[1,4]dioxin-2-yl)-[(2R,6R)-6-ethyl-8-methoxy-1,2,5,6-tetrahydro-4H-2,6-methano-benzo[d]azocin-3-yl]-methanone | E | Mass spectrum (ESI$^+$): m/z = 394 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 37 | [(2R,6S)-10-Hydroxy-6,11,11-trimethyl-1,2,5,6-tetrahydro-4H-2,6-methano-benzo[d]azocin-3-yl]-(4-methyl-cyclohexyl)-methanone | B | Mass spectrum (ESI$^+$): m/z = 356 [M + H]$^+$ |
| 38 | [(2R,6S)-10-Hydroxy-6,11,11-trimethyl-1,2,5,6-tetrahydro-4H-2,6-methano-benzo[d]azocin-3-yl]-(3-methyl-cyclohexyl)-methanone | B | Mass spectrum (ESI$^+$): m/z = 356 [M + H]$^+$ |
| 39 | (cis-4-Hydroxy-cyclohexyl)-[(2R,6S)-10-hydroxy-6,11,11-trimethyl-1,2,5,6-tetrahydro-4H-2,6-methano-benzo[d]azocin-3-yl]-methanone | B | Mass spectrum (ESI$^+$): m/z = 358 [M + H]$^+$ |
| 40 | Bicyclo[2.2.2]oct-2-yl-[(2R,6S)-10-hydroxy-6,11,11-trimethyl-1,2,5,6-tetrahydro-4H-2,6-methano-benzo[d]azocin-3-yl]-methanone | B | Mass spectrum (ESI$^+$): m/z = 368 [M + H]$^+$ |
| 41 | [(2R,6S)-10-Hydroxy-6,11,11-trimethyl-1,2,5,6-tetrahydro-4H-2,6-methano-benzo[d]azocin-3-yl]-(4-isopropyl-cyclohexyl)-methanone | B | Mass spectrum (ESI$^+$): m/z = 384 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 42 | (trans-4-Hydroxy-cyclohexyl)-[(2R,6S)-10-hydroxy-6,11,11-trimethyl-1,2,5,6-tetrahydro-4H-2,6-methano-benzo[d]azocin-3-yl]-methanone | B | Mass spectrum (ESI$^+$): m/z = 358 [M + H]$^+$ |
| 43 | cis-4-[(2R,6S)-10-Hydroxy-6,11,11-trimethyl-1,2,5,6-tetrahydro-4H-2,6-methano-benzo[d]azocine-3-carbonyl]-cyclohexane carboxylic acid methyl ester | B | Mass spectrum (ESI$^+$): m/z = 400 [M + H]$^+$ |
| 44 | (3-Hydroxy-adamantan-1-yl)-[(2R,6S)-10-hydroxy-6,11,11-trimethyl-1,2,5,6-tetrahydro-4H-2,6-methano-benzo[d]azocin-3-yl]-methanone | B | Mass spectrum (ESI$^+$): m/z = 410 [M + H]$^+$ |
| 45 | (4-Hydroxymethyl-cyclohexyl)-[(2R,6S)-10-hydroxy-6,11,11-trimethyl-1,2,5,6-tetrahydro-4H-2,6-methano-benzo[d]azocin-3-yl]-methanone | B | Mass spectrum (ESI$^+$): m/z = 372 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 46 | trans-4-[(2R,6S)-10-Hydroxy-6,11,11-trimethyl-1,2,5,6-tetrahydro-4H-2,6-methano-benzo[d]azocine-3-carbonyl]-cyclohexane carboxylic acid methyl ester | B | Mass spectrum (ESI$^+$): m/z = 400 [M + H]$^+$ |
| 47 | [(2R,6S)-10-Hydroxy-6,11,11-trimethyl-1,2,5,6-tetrahydro-4H-2,6-methano-benzo[d]azocin-3-yl]-(4-propyl-cyclohexyl)-methanone | B | Mass spectrum (ESI$^+$): m/z = 384 [M + H]$^+$ |
| 48 | 3-[(2R,6S)-10-Hydroxy-6,11,11-trimethyl-1,2,5,6-tetrahydro-4H-2,6-methano-benzo[d]azocine-3-carbonyl]-cyclohexane carboxylic acid methyl ester | B | Mass spectrum (ESI$^+$): m/z = 400 [M + H]$^+$ |
| 49 | Adamantan-1-yl-[(2R,6S)-10-hydroxy-6,11,11-trimethyl-1,2,5,6-tetrahydro-4H-2,6-methano-benzo[d]azocin-3-yl]-methanone | B | Mass spectrum (ESI$^+$): m/z = 394 [M + H]$^+$ |
| 50 | 3-[(2R,6S)-10-Hydroxy-6,11,11-trimethyl-1,2,5,6-tetrahydro-4H-2,6-methano-benzo[d]azocine-3-carbonyl]-cyclohexane carboxylic acid | G | Mass spectrum (ESI$^+$): m/z = 386 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 51 | (1S,2S,4R)-Bicyclo[2.2.1]hept-5-en-2-yl-[(2R,6S)-10-hydroxy-6,11,11-trimethyl-1,2,5,6-tetrahydro-4H-2,6-methano-benzo[d]azocin-3-yl]-methanone | B | Mass spectrum (ESI$^+$): m/z = 352 [M + H]$^+$ |
| 52 | cis-4-[(2R,6S)-10-Hydroxy-6,11,11-trimethyl-1,2,5,6-tetrahydro-4H-2,6-methano-benzo[d]azocine-3-carbonyl]-cyclohexane carboxylic acid | G | Mass spectrum (ESI$^+$): m/z = 386 [M + H]$^+$ |
| 53 | 1-Benzyl-4-[(2R,6S)-10-hydroxy-6,11,11-trimethyl-1,2,5,6-tetrahydro-4H-2,6-methano-benzo[d]azocine-3-carbonyl]-pyrrolidin-2-one | B | Mass spectrum (ESI$^+$): m/z = 433 [M + H]$^+$ |
| 54 | 2-[(2R,6S)-10-Hydroxy-6,11,11-trimethyl-1,2,5,6-tetrahydro-4H-2,6-methano-benzo[d]azocine-3-carbonyl)-pyrrolidine-1-carboxylic acid tert-butyl ester | B | Mass spectrum (ESI$^+$): m/z = 429 [M + H]$^+$ |
| 55 | 1-[2-((2R,6S)-10-Hydroxy-6,11,11-trimethyl-1,2,5,6-tetrahydro-4H-2,6-methano-benzo[d]azocine-3-carbonyl)-pyrrolidin-1-yl]-ethanone | B | Mass spectrum (ESI$^+$): m/z = 371 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 56 | 3-[2-((2R,6S)-10-Hydroxy-6,11,11-trimethyl-1,2,5,6-tetrahydro-4H-2,6-methano-benzo[d]azocine-3-carbonyl)-pyrrolidin-1-yl]-propionitrile | B | Mass spectrum (ESI$^+$): m/z = 382 [M + H]$^+$ |
| 57 | 3-{2-[(2R,6S)-10-Hydroxy-6,11,11-trimethyl-1,2,5,6-tetrahydro-4H-2,6-methano-benzo[d]azocine-3-carbonyl}-5-oxo-pyrrolidin-1-yl}-propionitrile | B | Mass spectrum (ESI$^+$): m/z = 396 [M + H]$^+$ |
| 58 | [(2R,6S)-10-Hydroxy-6,11,11-trimethyl-1,2,5,6-tetrahydro-4H-2,6-methano-benzo[d]azocin-3-yl]-(1-methyl-piperidin-3-yl)-methanone<br><br>the compound is isolated as trifluoroacetic acid salt | B | Mass spectrum (ESI$^+$): m/z = 357 [M + H]$^+$ |
| 59 | 1-{3-[(2R,6S)-10-Hydroxy-6,11,11-trimethyl-1,2,5,6-tetrahydro-4H-2,6-methano-benzo[d]azocine-3-carbonyl]-piperidin-1-yl}-2-phenyl-ethanone | B | Mass spectrum (ESI$^+$): m/z = 461 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 60 | (1-Benzyl-piperidin-3-yl)-[(2R,6S)-10-hydroxy-6,11,11-trimethyl-1,2,5,6-tetrahydro-4H-2,6-methano-benzo[d]azocin-3-yl]-methanone<br><br>the compound is isolated as trifluoroacetic acid salt | B | Mass spectrum (ESI$^+$):<br>m/z = 433 [M + H]$^+$ |
| 61 | 2-[(2R,6S)-10-Hydroxy-6,11,11-trimethyl-1,2,5,6-tetrahydro-4H-2,6-methano-benzo[d]azocine-3-carbonyl]-piperidine-1-carboxylic acid tert-butyl ester | B | Mass spectrum (ESI$^+$):<br>m/z = 433 [M + H]$^+$ |
| 62 | 3-[(2R,6S)-10-Hydroxy-6,11,11-trimethyl-1,2,5,6-tetrahydro-4H-2,6-methano-benzo[d]azocine-3-carbonyl]-piperidine-1-carboxylic acid benzyl ester | B | Mass spectrum (ESI$^+$):<br>m/z = 477 [M + H]$^+$ |
| 63 | 1-Cyclopentyl-4-[(2R,6S)-10-hydroxy-6,11,11-trimethyl-1,2,5,6-tetrahydro-4H-2,6-methano-benzo[d]azocine-3-carbonyl]-pyrrolidin-2-one | B | Mass spectrum (ESI$^+$):<br>m/z = 411 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 64 | 3-[(2R,6S)-10-Hydroxy-6,11,11-trimethyl-1,2,5,6-tetrahydro-4H-2,6-methano-benzo[d]azocine-3-carbonyl]-pyrrolidine-1-carboxylic acid tert-butyl ester | B | Mass spectrum (ESI$^+$): m/z = 429 [M + H]$^+$ |
| 65 | [(2R,6S)-10-Hydroxy-6,11,11-trimethyl-1,2,5,6-tetrahydro-4H-2,6-methano-benzo[d]azocin-3-yl]-(1-methyl-piperidin-2-yl)-methanone<br><br>the compound is isolated as trifluoroacetic acid salt | B | Mass spectrum (ESI$^+$): m/z = 357 [M + H]$^+$ |
| 66 | 4-[(2R,6S)-10-Hydroxy-6,11,11-trimethyl-1,2,5,6-tetrahydro-4H-2,6-methano-benzo[d]azocine-3-carbonyl]-1-methyl-pyrrolidin-2-one | B | Mass spectrum (ESI$^+$): m/z = 357 [M + H]$^+$ |
| 67 | (1-Benzyl-pyrrolidin-3-yl)-[(2R,6S)-10-hydroxy-6,11,11-trimethyl-1,2,5,6-tetrahydro-4H-2,6-methano-benzo[d]azocin-3-yl]-methanone<br><br>the compound is isolated as trifluoroacetic acid salt | B | Mass spectrum (ESI$^+$): m/z = 419 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 68 | [(2R,6S)-10-Hydroxy-6,11,11-trimethyl-1,2,5,6-tetrahydro-4H-2,6-methano-benzo[d]azocin-3-yl]-(1-isopropyl-piperidin-3-yl)-methanone<br><br>the compound is isolated as trifluoroacetic acid salt | B | Mass spectrum (ESI$^+$):<br>m/z = 385 [M + H]$^+$ |
| 69 | 5-[(2R,6S)-10-Hydroxy-6,11,11-trimethyl-1,2,5,6-tetrahydro-4H-2,6-methano-benzo[d]azocine-3-carbonyl]-piperidin-2-one | B | Mass spectrum (ESI$^+$):<br>m/z = 357 [M + H]$^+$ |
| 70 | 4-[(2R,6S)-10-Hydroxy-6,11,11-trimethyl-1,2,5,6-tetrahydro-4H-2,6-methano-benzo[d]azocine-3-carbonyl]-pyrrolidin-2-one | B | Mass spectrum (ESI$^+$):<br>m/z = 343 [M + H]$^+$ |
| 71 | 4-[(2R,6S)-10-Hydroxy-6,11,11-trimethyl-1,2,5,6-tetrahydro-4H-2,6-methano-benzo[d]azocine-3-carbonyl]-1-phenyl-pyrrolidin-2-one | B | Mass spectrum (ESI$^+$):<br>m/z = 419 [M + H]$^+$ |
| 72 | 3-[(2R,6S)-10-Hydroxy-6,11,11-trimethyl-1,2,5,6-tetrahydro-4H-2,6-methano-benzo[d]azocine-3-carbonyl]-piperidine-1-carboxylic acid tert-butyl ester | B | Mass spectrum (ESI$^+$):<br>m/z = 443 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 73 | (1-Benzoyl-piperidin-3-yl)-[(2R,6S)-10-hydroxy-6,11,11-trimethyl-1,2,5,6-tetrahydro-4H-2,6-methano-benzo[d]azocin-3-yl]-methanone | B | Mass spectrum (ESI+): m/z = 447 [M + H]+ |
| 74 | N-{(3S,5S)-5-[(2R,6S)-10-Hydroxy-6,11,11-trimethyl-1,2,5,6-tetrahydro-4H-2,6-methano-benzo[d]azocine-3-carbonyl]-2-oxo-pyrrolidin-3-yl}-methanesulfonamide<br><br>cis-4-Methanesulfonylamino-5-oxo-pyrrolidine-2-carboxylic acid is prepared in analogy to cis-4-benzenesulfonylamino-5-oxo-pyrrolidine-2-carboxylic acid (*J. Comb. Chem.* 2007, 9, 219-29) | B | Mass spectrum (ESI+): m/z = 436 [M + H]+ |
| 75 | [(2R,6S)-10-Hydroxy-6,11,11-trimethyl-1,2,5,6-tetrahydro-4H-2,6-methano-benzo[d]azocin-3-yl]-[(S)-1-methyl-pyrrolidin-2-yl]-methanone<br><br>the compound is isolated as trifluoroacetic acid salt | B | Mass spectrum (ESI+): m/z = 343 [M + H]+ |
| 76 | [(S)-1-Benzyl-pyrrolidin-2-yl]-[(2R,6S)-10-hydroxy-6,11,11-trimethyl-1,2,5,6-tetrahydro-4H-2,6-methano-benzo[d]azocin-3-yl]-methanone<br><br>the compound is isolated as trifluoroacetic acid salt | B | Mass spectrum (ESI+): m/z = 419 [M + H]+ |

TABLE 3-continued

Compounds prepared in analogy to the examples described above

| Example No. | Chemical Name/Structure/Remarks | Prepared in analogy to Procedure | Characterization |
|---|---|---|---|
| 77 | 3-[(2R,6S)-10-Hydroxy-6,11,11-trimethyl-1,2,5,6-tetrahydro-4H-2,6-methano-benzo[d]azocine-3-carbonyl]-1-phenyl-pyrrolidin-2-one | B | Mass spectrum (ESI$^+$): m/z = 419 [M + H]$^+$ |
| 78 | [(2R,6S)-10-Hydroxy-6,11,11-trimethyl-1,2,5,6-tetrahydro-4H-2,6-methano-benzo[d]azocin-3-yl]-pyrrolidin-2-yl-methanone<br><br>the compound is isolated as trifluoroacetic acid salt | H | Mass spectrum (ESI$^+$): m/z = 329 [M + H]$^+$ |
| 79 | [(2R,6S)-10-Hydroxy-6,11,11-trimethyl-1,2,5,6-tetrahydro-4H-2,6-methano-benzo[d]azocin-3-yl]-piperidin-2-yl-methanone<br><br>the compound is isolated as trifluoroacetic acid salt | H | Mass spectrum (ESI$^+$): m/z = 343 [M + H]$^+$ |
| 80 | [(2R,6S)-10-Hydroxy-6,11,11-trimethyl-1,2,5,6-tetrahydro-4H-2,6-methano-benzo[d]azocin-3-yl]-pyrrolidin-3-yl-methanone<br><br>isolated as trifluoroacetic acid salt | H | Mass spectrum (ESI$^+$): m/z = 329 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 81 | (2-Aza-bicyclo[2.1.1]hex-1-yl)-[(2R,6S)-10-hydroxy-6,11,11-trimethyl-1,2,5,6-tetrahydro-4H-2,6-methano-benzo[d]azocin-3-yl]-methanone<br><br>the compound is isolated as trifluoroacetic acid salt | H | Mass spectrum (ESI$^+$):<br>m/z = 341 [M + H]$^+$ |
| 82 | [(1S,5R)-2-Aza-bicyclo[3.1.0]hex-1-yl]-[(2R,6S)-10-hydroxy-6,11,11-trimethyl-1,2,5,6-tetrahydro-4H-2,6-benzo[d]azocin-3-yl]-methanone<br><br>the compound is isolated as trifluoroacetic acid salt | H | Mass spectrum (ESI$^+$):<br>m/z = 341 [M + H]$^+$ |
| 83 | [(2R,6S)-10-Hydroxy-6,11,11-trimethyl-1,2,5,6-tetrahydro-4H-2,6-methano-benzo[d]azocin-3-yl]-piperidin-3-yl-methanone<br><br>the compound is isolated as trifluoroacetic acid salt | H | Mass spectrum (ESI$^+$):<br>m/z = 343 [M + H]$^+$ |
| 84 | cis-4-[(2R,6S)-10-Hydroxy-6,11,11-trimethyl-1,2,5,6-tetrahydro-4H-2,6-methano-benzo[d]azocine-3-carbonyl]-cyclohexanecarboxylic acid amide<br><br>the compound is prepared from Example 52 and ammonia as described in Procedure B | B | Mass spectrum (ESI$^+$):<br>m/z = 385 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 85 | cis-4-[(2R,6S)-10-Hydroxy-6,11,11-trimethyl-1,2,5,6-tetrahydro-4H-2,6-methano-benzo[d]azocine-3-carbonyl]-cyclohexanecarboxylic acid methylamide<br>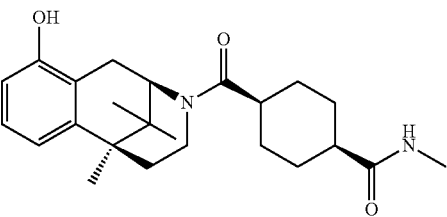<br>the compound is prepared from Example 52 and methylamine as described in Procedure B | B | Mass spectrum (ESI$^+$):<br>m/z = 399 [M + H]$^+$ |
| 86 | cis-4-[(2R,6S)-10-Hydroxy-6,11,11-trimethyl-1,2,5,6-tetrahydro-4H-2,6-methano-benzo[d]azocine-3-carbonyl]-cyclohexanecarboxylic acid dimethylamide<br>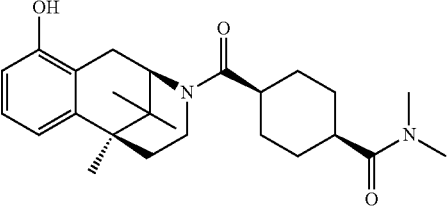<br>the compound is prepared from Example 52 and dimethylamine as described in Procedure B | B | Mass spectrum (ESI$^+$):<br>m/z = 413 [M + H]$^+$ |
| 87 | cis-4-[(2R,6S)-10-Hydroxy-6,11,11-trimethyl-1,2,5,6-tetrahydro-4H-2,6-methano-benzo[d]azocine-3-carbonyl]-cyclohexanecarboxylic acid propylamide<br>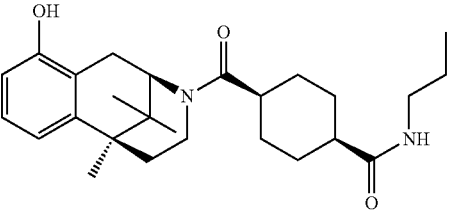<br>the compound is prepared from Example 52 and n-propylamine as described in Procedure B | B | Mass spectrum (ESI$^+$):<br>m/z = 427 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 88 | [(2R,6S)-10-Hydroxy-6,11,11-trimethyl-1,2,5,6-tetrahydro-4H-2,6-methano-benzo[d]azocin-3-yl]-[cis-4-(pyrrolidin-1-carbonyl)-cyclohexyl]-methanone<br><br>the compound is prepared from Example 52 and pyrrolidine as described in Procedure B | B | Mass spectrum (ESI$^+$):<br>m/z = 439 [M + H]$^+$ |
| 89 | cis-4-[(2R,6S)-10-Hydroxy-6,11,11-trimethyl-1,2,5,6-tetrahydro-4H-2,6-methano-benzo[d]azocine-3-carbonyl]-cyclohexanecarboxylic acid methyl-propyl-amide<br><br>the compound is prepared from Example 52 and methyl n-propylamine as described in Proc. B | B | Mass spectrum (ESI$^+$):<br>m/z = 441 [M + H]$^+$ |
| 90 | cis-4-[(2R,6S)-10-Hydroxy-6,11,11-trimethyl-1,2,5,6-tetrahydro-4H-2,6-methano-benzo[d]azocine-3-carbonyl]-cyclohexanecarboxylic acid phenylamide<br><br>the compound is prepared from Example 52 and aniline as described in Procedure B | B | Mass spectrum (ESI$^+$):<br>m/z = 461 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 91 | cis-4-[(2R,6S)-10-Hydroxy-6,11,11-trimethyl-1,2,5,6-tetrahydro-4H-2,6-methano-benzo[d]azocine-3-carbonyl]-cyclohexanecarboxylic acid benzylamide<br><br>the compound is prepared from Example 52 and benzylamine as described in Procedure B | B | Mass spectrum (ESI$^+$):<br>m/z = 475 [M + H]$^+$ |
| 92 | cis-4-[(2R,6S)-10-Hydroxy-6,11,11-trimethyl-1,2,5,6-tetrahydro-4H-2,6-methano-benzo[d]azocine-3-carbonyl]-cyclohexane-carboxylic acid isopropyl-methyl-amide<br><br>the compound is prepared from Example 52 and isopropyl-methyl-amine as described in Proc. B | B | Mass spectrum (ESI$^+$):<br>m/z = 441 [M + H]$^+$ |
| 93 | [(1R,3R)-3-Benzylamino-cyclopentyl]-[(2R,6S)-10-hydroxy-6,11,11-trimethyl-1,2,5,6-tetrahydro-4H-2,6-methano-benzo[d]azocin-3-yl]-methanone<br><br>the compound is isolated as trifluoroacetic acid salt | I | Mass spectrum (ESI$^+$):<br>m/z = 433 [M + H]$^+$ |
| 94 | [cis-4-(Azetidine-1-carbonyl)-cyclohexyl]-[(2R,6S)-10-hydroxy-6,11,11-trimethyl-1,2,5,6-tetrahydro-4H-2,6-methano-benzo[d]azocin-3-yl]-methanone<br><br>the compound is prepared from Example 52 and azetidine as described in Procedure B | B | Mass spectrum (ESI$^+$):<br>m/z = 425 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 95 | cis-4-[(2R,6S)-10-Hydroxy-6,11,11-trimethyl-1,2,5,6-tetrahydro-4H-2,6-methano-benzo[d]azocine-3-carbonyl]-cyclohexanecarboxylic acid ethyl-methyl-amide<br><br>the compound is prepared from Example 52 and ethyl-methyl-amine as described in Procedure B | B | Mass spectrum (ESI$^+$):<br>m/z = 427 [M + H]$^+$ |
| 96 | {cis-4-[(2R,6S)-10-Hydroxy-6,11,11-trimethyl-1,2,5,6-tetrahydro-4H-2,6-methano-benzo[d]azocine-3-carbonyl]-cyclohexyl}-carbamic acid tert-butyl ester | B | — |
| 97 | [(1R,3R)-3-Amino-cyclopentyl]-[(2R,6S)-10-hydroxy-6,11,11-trimethyl-1,2,5,6-tetrahydro-4H-2,6-methano-benzo[d]azocin-3-yl]-methanone<br><br>HCl in dioxane is used instead of trifluoroacetic acid; the hydrogen chloride salt is isolated | H | Mass spectrum (ESI$^+$):<br>m/z = 343 [M + H]$^+$ |
| 98 | N-{(1R,3R)-3-[(2R,6S)-10-Hydroxy-6,11,11-trimethyl-1,2,5,6-tetrahydro-4H-2,6-methano-benzo[d]azocine-3-carbonyl]-cyclopentyl}-acetamide<br><br>the compound is prepared from Example 97 and acetic acid as described in Procedure B | B | Mass spectrum (ESI$^+$):<br>m/z = 385 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 99 | N-{(1R,3R)-3-[(2R,6S)-10-Hydroxy-6,11,11-trimethyl-1,2,5,6-tetrahydro-4H-2,6-methano-benzo[d]azocine-3-carbonyl]-cyclopentyl}-butyramide<br><br>the compound is prepared from Example 97 and butyric acid as described in Procedure B | B | Mass spectrum (ESI$^+$):<br>m/z = 413 [M + H]$^+$ |
| 100 | N-{(1R,3R)-3-[(2R,6S)-10-Hydroxy-6,11,11-trimethyl-1,2,5,6-tetrahydro-4H-2,6-methano-benzo[d]azocine-3-carbonyl]-cyclopentyl}-2-phenyl-acetamide<br><br>the compound is prepared from Example 97 and phenylacetic acid as described in Procedure B | B | Mass spectrum (ESI$^+$):<br>m/z = 461 [M + H]$^+$ |
| 101 | N-{(1R,3R)-3-[(2R,6S)-10-Hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI$^+$):<br>m/z = 483 [M + H]$^+$ |
| 102 | N-{(1R,3R)-3-[(2R,6S)-10-Hydroxy-6,11,11-trimethyl-1,2,5,6-tetrahydro-4H-2,6-methano-benzo[d]azocine-3-carbonyl]-cyclopentyl}-methanesulfonamide | J | Mass spectrum (ESI$^+$):<br>m/z = 421 [M + H]$^+$ |

TABLE 3-continued

Compounds prepared in analogy to the examples described above

| Example No. | Chemical Name/Structure/Remarks | Prepared in analogy to Procedure | Characterization |
| --- | --- | --- | --- |
| 103 | N-{(1R,3R)-3-[(2R,6S)-10-Hydroxy-6,11,11-trimethyl-1,2,5,6-tetrahydro-4H-2,6-methano-benzo[d]azocine-3-carbonyl]-cyclopentyl}-2-propionacetamide<br><br>the compound is prepared from Example 97 and phenylacetic acid as described in Procedure B | B | Mass spectrum (ESI$^+$): m/z = 399 [M + H]$^+$ |
| 104 | 1-{(1R,3R)-3-[(2R,6S)-10-Hydroxy-6,11,11-trimethyl-1,2,5,6-tetrahydro-4H-2,6-methano-benzo[d]azocine-3-carbonyl]-cyclopentyl}-3-phenyl-urea | K | Mass spectrum (ESI$^+$): m/z = 462 [M + H]$^+$ |
| 105 | [(2R,6S)-10-Hydroxy-6,11,11-trimethyl-1,2,5,6-tetrahydro-4H-2,6-methano-benzo[d]azocin-3-yl]-[(1R,3R)-3-isopropylamino-cyclopentyl]-methanone<br><br>the compound is isolated as trifluoroacetic acid salt | L | Mass spectrum (ESI$^+$): m/z = 385 [M + H]$^+$ |
| 106 | 1-[2-((2R,6S)-10-Hydroxy-6,11,11-trimethyl-1,2,5,6-tetrahydro-4H-2,6-methano-benzo[d]azocine-3-carbonyl)-piperidin-1-yl]-ethanone<br><br>the compound is prepared from Example 79 and acetic acid as described in Procedure B | B | Mass spectrum (ESI$^+$): m/z = 385 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 107 | 1-[2-((2R,6S)-10-Hydroxy-6,11,11-trimethyl-1,2,5,6-tetrahydro-4H-2,6-methano-benzo[d]azocine-3-carbonyl)-piperidin-1-yl]-propan-1-one<br>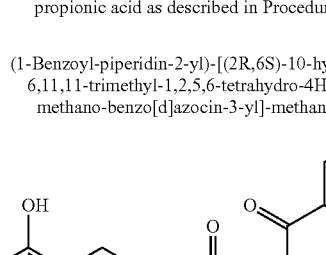<br>the compound is prepared from Example 79 and propionic acid as described in Procedure B | B | Mass spectrum (ESI$^+$):<br>m/z = 399 [M + H]$^+$ |
| 108 | (1-Benzoyl-piperidin-2-yl)-[(2R,6S)-10-hydroxy-6,11,11-trimethyl-1,2,5,6-tetrahydro-4H-2,6-methano-benzo[d]azocin-3-yl]-methanone<br>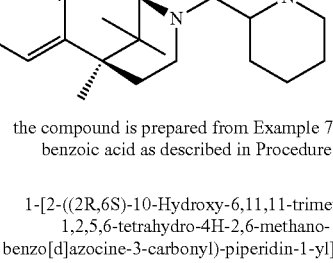<br>the compound is prepared from Example 79 and benzoic acid as described in Procedure B | B | Mass spectrum (ESI$^+$):<br>m/z = 447 [M + H]$^+$ |
| 109 | 1-[2-((2R,6S)-10-Hydroxy-6,11,11-trimethyl-1,2,5,6-tetrahydro-4H-2,6-methano-benzo[d]azocine-3-carbonyl)-piperidin-1-yl]-butan-1-one<br>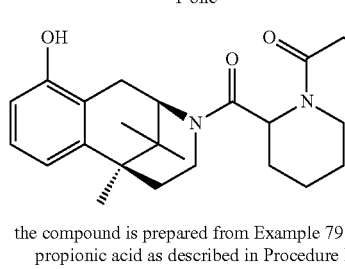<br>the compound is prepared from Example 79 and propionic acid as described in Procedure B | B | Mass spectrum (ESI$^+$):<br>m/z = 413 [M + H]$^+$ |
| 110 | 1-[2-((2R,6S)-10-Hydroxy-6,11,11-trimethyl-1,2,5,6-tetrahydro-4H-2,6-methano-benzo[d]azocine-3-carbonyl)-pyrrolidin-1-yl]-butan-1-one<br>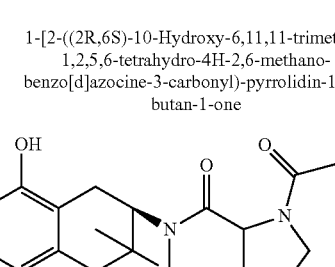<br>the compound is prepared from Example 78 and butyric acid as described in Procedure B | B | Mass spectrum (ESI$^+$):<br>m/z = 399 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 111 | 1-{2-[(2R,6S)-10-Hydroxy-6,11,11-trimethyl-1,2,5,6-tetrahydro-4H-2,6-methano-benzo[d]azocine-3-carbonyl]-pyrrolidin-1-yl}-propan-1-one<br><br>the compound is prepared from Example 78 and propionic acid as described in Procedure B | B | Mass spectrum (ESI$^+$):<br>m/z = 385 [M + H]$^+$ |
| 112 | [(2R,6S)-10-Hydroxy-6,11,11-trimethyl-1,2,5,6-tetrahydro-4H-2,6-methano-benzo[d]azocin-3-yl]-(1-methanesulfonyl-piperidin-2-yl)-methanone | J | Mass spectrum (ESI$^+$):<br>m/z = 421 [M + H]$^+$ |
| 113 | (1-Benzenesulfonyl-piperidin-2-yl)-[(2R,6S)-10-hydroxy-6,11,11-trimethyl-1,2,5,6-tetrahydro-4H-2,6-methano-benzo[d]azocin-3-yl]-methanone | J | Mass spectrum (ESI$^+$):<br>m/z = 483 [M + H]$^+$ |
| 114 | [(2R,6S)-10-Hydroxy-6,11,11-trimethyl-1,2,5,6-tetrahydro-4H-2,6-methano-benzo[d]azocin-3-yl]-(1-methanesulfonyl-pyrrolidin-2-yl)-methanone | J | Mass spectrum (ESI$^+$):<br>m/z = 407 [M + H]$^+$ |

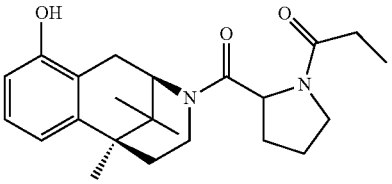

TABLE 3-continued

Compounds prepared in analogy to the examples described above

| Example No. | Chemical Name/Structure/Remarks | Prepared in analogy to Procedure | Characterization |
|---|---|---|---|
| 115 | (1-Benzenesulfonyl-pyrrolidin-2-yl)-[(2R,6S)-10-hydroxy-6,11,11-trimethyl-1,2,5,6-tetrahydro-4H-2,6-methano-benzo[d]azocin-3-yl]-methanone | J | Mass spectrum (ESI$^+$): m/z = 469 [M + H]$^+$ |
| 116 | (1S,4R)-1-[(2R,6S)-10-Hydroxy-6,11,11-trimethyl-1,2,5,6-tetrahydro-4H-2,6-methano-benzo[d]azocine-3-carbonyl]-4,7,7-trimethyl-2-oxa-bicyclo[2.2.1]heptan-3-one | D | Mass spectrum (ESI$^+$): m/z = 412 [M + H]$^+$ |
| 117 | 1-tert-Butyl-3-{(1R,3R)-3-[(2R,6S)-10-hydroxy-6,11,11-trimethyl-1,2,5,6-tetrahydro-4H-2,6-methano-benzo[d]azocine-3-carbonyl]-cyclopentyl}-urea | M | Mass spectrum (ESI$^+$): m/z = 442 [M + H]$^+$ |
| 118 | Chroman-2-yl-[(2R,6S)-10-hydroxy-6,11,11-trimethyl-1,2,5,6-tetrahydro-4H-2,6-methano-benzo[d]azocin-3-yl]-methanone | B | Mass spectrum (ESI$^+$): m/z = 392 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 119 | 2-[(2R,6S)-10-Hydroxy-6,11,11-trimethyl-1,2,5,6-tetrahydro-4H-2,6-methano-benzo[d]azocine-3-carbonyl]-piperidine-1-carboxylic acid phenylamide | M | Mass spectrum (ESI$^+$): m/z = 462 [M + H]$^+$ |
| 120 | 2-[(2R,6S)-10-Hydroxy-6,11,11-trimethyl-1,2,5,6-tetrahydro-4H-2,6-methano-benzo[d]azocine-3-carbonyl]-pyrrolidine-1-carboxylic acid ethylamide | M | Mass spectrum (ESI$^+$): m/z = 400 [M + H]$^+$ |
| 121 | 2-[(2R,6S)-10-Hydroxy-6,11,11-trimethyl-1,2,5,6-tetrahydro-4H-2,6-methano-benzo[d]azocine-3-carbonyl]-pyrrolidine-1-carboxylic acid phenylamide | M | Mass spectrum (ESI$^+$): m/z = 448 [M + H]$^+$ |
| 122 | 2-[(2R,6S)-10-Hydroxy-6,11,11-trimethyl-1,2,5,6-tetrahydro-4H-2,6-methano-benzo[d]azocine-3-carbonyl}-piperidine-1-carboxylic acid ethylamide | M | Mass spectrum (ESI$^+$): m/z = 414 [M + H]$^+$ |
| 123 | [(2R,6S)-10-Hydroxy-6,11,11-trimethyl-1,2,5,6-tetrahydro-4H-2,6-methano-benzo[d]azocin-3-yl]-(1-propyl-piperidin-2-yl)-methanone<br><br>the compound is isolated as trifluoroacetic acid salt | L | Mass spectrum (ESI$^+$): m/z = 385 [M + H]$^+$ |

TABLE 3-continued

Compounds prepared in analogy to the examples described above

| Example No. | Chemical Name/Structure/Remarks | Prepared in analogy to Procedure | Characterization |
| --- | --- | --- | --- |
| 124 | [(2R,6S)-10-Hydroxy-6,11,11-trimethyl-1,2,5,6-tetrahydro-4H-2,6-methano-benzo[d]azocin-3-yl]-[1-(3-methyl-butyl)-piperidin-2-yl]-methanone<br><br>the compound is isolated as trifluoroacetic acid salt | L | Mass spectrum (ESI$^+$):<br>m/z = 413 [M + H]$^+$ |
| 125 | [(2R,6S)-10-Hydroxy-6,11,11-trimethyl-1,2,5,6-tetrahydro-4H-2,6-methano-benzo[d]azocin-3-yl]-(1-benzyl-piperidin-2-yl)-methanone<br><br>the compound is isolated as trifluoroacetic acid salt | I | Mass spectrum (ESI$^+$):<br>m/z = 433 [M + H]$^+$ |
| 126 | [(2R,6S)-10-Hydroxy-6,11,11-trimethyl-1,2,5,6-tetrahydro-4H-2,6-methano-benzo[d]azocin-3-yl]-[1-(3-methyl-butyl)-pyrrolidin-2-yl]-methanone<br><br>the compound is isolated as trifluoroacetic acid salt | L | Mass spectrum (ESI$^+$):<br>m/z = 399 [M + H]$^+$ |
| 127 | [(2R,6S)-10-Hydroxy-6,11,11-trimethyl-1,2,5,6-tetrahydro-4H-2,6-methano-benzo[d]azocin-3-yl]-(1-propyl-pyrrolidin-2-yl)-methanone<br><br>the compound is isolated as trifluoroacetic acid salt | L | Mass spectrum (ESI$^+$):<br>m/z = 371 [M + H]$^+$ |

TABLE 3-continued

Compounds prepared in analogy to the examples described above

| Example No. | Chemical Name/Structure/Remarks | Prepared in analogy to Procedure | Characterization |
| --- | --- | --- | --- |
| 128 | 4-[(2R,6S)-10-Hydroxy-6,11,11-trimethyl-1,2,5,6-tetrahydro-4H-2,6-methano-benzo[d]azocine-3-carbonyl]-cyclohexane carboxylic acid ethyl ester | N | Mass spectrum (ESI$^+$): m/z = 414 [M + H]$^+$ |
| 129 | 1-[3-((2R,6S)-10-Hydroxy-6,11,11-trimethyl-1,2,5,6-tetrahydro-4H-2,6-methano-benzo[d]azocine-3-carbonyl)-pyrrolidin-1-yl]-ethanone | B | Mass spectrum (ESI$^+$): m/z = 371 [M + H]$^+$ |
| 130 | 1-[3-((2R,6S)-10-Hydroxy-6,11,11-trimethyl-1,2,5,6-tetrahydro-4H-2,6-methano-benzo[d]azocine-3-carbonyl)-pyrrolidin-1-yl]-butan-1-one | B | Mass spectrum (ESI$^+$): m/z = 399 [M + H]$^+$ |
| 131 | 1-{3-[(2R,6S)-10-Hydroxy-6,11,11-trimethyl-1,2,5,6-tetrahydro-4H-2,6-methano-benzo[d]azocine-3-carbonyl]-piperidin-1-yl}-propan-1-one | B | Mass spectrum (ESI$^+$): m/z = 399 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 132 | 1-{3-[(2R,6S)-10-Hydroxy-6,11,11-trimethyl-1,2,5,6-tetrahydro-4H-2,6-methano-benzo[d]azocine-3-carbonyl]-piperidin-1-yl}-butan-1-one | B | Mass spectrum (ESI$^+$): m/z = 413 [M + H]$^+$ |
| 133 | 4-[(2R,6S)-10-Hydroxy-6,11,11-trimethyl-1,2,5,6-tetrahydro-4H-2,6-methano-benzo[d]azocine-3-carbonyl]-cyclohexane carboxylic acid isopropyl ester | N | Mass spectrum (ESI$^+$): m/z = 418 [M + H]$^+$ |
| 134 | 1-{3-[(2R,6S)-10-Hydroxy-6,11,11-trimethyl-1,2,5,6-tetrahydro-4H-2,6-methano-benzo[d]azocine-3-carbonyl]-pyrrolidin-1-yl}-propan-1-one | B | Mass spectrum (ESI$^+$): m/z = 385 [M + H]$^+$ |
| 135 | 1-{3-[(2R,6S)-10-Hydroxy-6,11,11-trimethyl-1,2,5,6-tetrahydro-4H-2,6-methano-benzo[d]azocine-3-carbonyl]-piperidin-1-yl}-ethanone | B | Mass spectrum (ESI$^+$): m/z = 385 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 136 | 3-[(2R,6S)-10-Hydroxy-6,11,11-trimethyl-1,2,5,6-tetrahydro-4H-2,6-methano-benzo[d]azocine-3-carbonyl]-piperidine-1-carboxylic acid phenylamide | M | Mass spectrum (ESI+): m/z = 462 [M + H]+ |
| 137 | 3-[(2R,6S)-10-Hydroxy-6,11,11-trimethyl-1,2,5,6-tetrahydro-4H-2,6-methano-benzo[d]azocine-3-carbonyl)-pyrrolidine-1-carboxylic acid phenylamide | M | Mass spectrum (ESI+): m/z = 448 [M + H]+ |
| 138 | 3-[(2R,6S)-10-Hydroxy-6,11,11-trimethyl-1,2,5,6-tetrahydro-4H-2,6-methano-benzo[d]azocine-3-carbonyl]-piperidine-1-carboxylic acid ethylamide | M | Mass spectrum (ESI+): m/z = 414 [M + H]+ |
| 139 | 3-[(2R,6S)-10-Hydroxy-6,11,11-trimethyl-1,2,5,6-tetrahydro-4H-2,6-methano-benzo[d]azocine-3-carbonyl]-pyrrolidine-1-carboxylic acid ethylamide | M | Mass spectrum (ESI+): m/z = 400 [M + H]+ |
| 140 | (1-Benzenesulfonyl-piperidin-3-yl)-[(2R,6S)-10-hydroxy-6,11,11-trimethyl-1,2,5,6-tetrahydro-4H-2,6-methano-benzo[d]azocin-3-yl]-methanone | J | Mass spectrum (ESI+): m/z = 483 [M + H]+ |

TABLE 3-continued

Compounds prepared in analogy to the examples described above

| Example No. | Chemical Name/Structure/Remarks | Prepared in analogy to Procedure | Characterization |
|---|---|---|---|
| 141 | [(2R,6S)-10-Hydroxy-6,11,11-trimethyl-1,2,5,6-tetrahydro-4H-2,6-methano-benzo[d]azocin-3-yl]-(1-methanesulfonyl-piperidin-3-yl)-methanone | J | Mass spectrum (ESI+): m/z = 421 [M + H]+ |
| 142 | [(2R,6S)-10-Hydroxy-6,11,11-trimethyl-1,2,5,6-tetrahydro-4H-2,6-methano-benzo[d]azocin-3-yl]-(1-methanesulfonyl-pyrrolidin-3-yl)-methanone | J | Mass spectrum (ESI+): m/z = 407 [M + H]+ |
| 143 | (1R,3R)-3-Fluoro-N-{3-[(2R,6S)-10-hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI+): m/z = 501 [M + H]+ |
| 144 | (1R,3R)-3-Methyl-N-{3-[(2R,6S)-10-hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI+): m/z = 497 [M + H]+ |
| 145 | (1R,3R)-3-Methoxy-N-{3-[(2R,6S)-10-hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI+): m/z = 513 [M + H]+ |

TABLE 3-continued

Compounds prepared in analogy to the examples described above

| Example No. | Chemical Name/Structure/Remarks | Prepared in analogy to Procedure | Characterization |
|---|---|---|---|
| 146 | Cyclopropanesulfonic acid {(1R,3R)-3-[(2R,6S)-10-hydroxy-6,11,11-trimethyl-1,2,5,6-tetrahydro-4H-2,6-methano-benzo[d]azocine-3-carbonyl]-cyclopentyl}-amide | J | Mass spectrum (ESI$^+$): m/z = 447 [M + H]$^+$ |
| 147 | (1R,3R)-2,5-Dimethyl-N-{3-[(2R,6S)-10-hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI$^+$): m/z = 511 [M + H]$^+$ |
| 148 | (1R,3R)-3-Methoxy-N-{3-[(2R,6S)-10-hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI$^+$): m/z = 513 [M + H]$^+$ |
| 149 | (1R,3R)-2-Fluoro-N-{3-[(2R,6S)-10-hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI$^+$): m/z = 501 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 150 | (1R,3R)-5-Fluoro-2-methyl-N-{3-[(2R,6S)-10-hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI$^+$): m/z = 515 [M + H]$^+$ |
| 151 | (1R,3R)-2-Methyl-N-{3-[(2R,6S)-10-hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI$^+$): m/z = 497 [M + H]$^+$ |
| 152 | Furan-2-sulfonic acid {(1R,3R)-3-[(2R,6S)-10-hydroxy-6,11,11-trimethyl-1,2,5,6-tetrahydro-4H-2,6-methano-benzo[d]azocine-3-carbonyl]-cyclopentyl}-amide | J | Mass spectrum (ESI$^+$): m/z = 473 [M + H]$^+$ |
| 153 | Cyclohexanesulfonic acid {(1R,3R)-3-[(2R,6S)-10-hydroxy-6,11,11-trimethyl-1,2,5,6-tetrahydro-4H-2,6-methano-benzo[d]azocine-3-carbonyl]-cyclopentyl}-amide | J | Mass spectrum (ESI$^+$): m/z = 489 [M + H]$^+$ |

TABLE 3-continued

Compounds prepared in analogy to the examples described above

| Example No. | Chemical Name/Structure/Remarks | Prepared in analogy to Procedure | Characterization |
| --- | --- | --- | --- |
| 154 | (1R,3R)-2-Methoxy-N-{3-[(2R,6S)-10-hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI$^+$): m/z = 513 [M + H]$^+$ |
| 155 | 2,5-Dimethyl-furan-3-sulfonic acid {(1R,3R)-3-[(2R,6S)-10-hydroxy-6,11,11-trimethyl-1,2,5,6-tetrahydro-4H-2,6-methano-benzo[d]azocine-3-carbonyl]-cyclopentyl}-amide | J | Mass spectrum (ESI$^+$): m/z = 501 [M + H]$^+$ |
| 156 | Methyl-1H-pyrazole-4-sulfonic acid {(1R,3R)-3-[(2R,6S)-10-hydroxy-6,11,11-trimethyl-1,2,5,6-tetrahydro-4H-2,6-methano-benzo[d]azocine-3-carbonyl]-cyclopentyl}-amide | J | Mass spectrum (ESI$^+$): m/z = 487 [M + H]$^+$ |
| 157 | (1R,3R)-2-Fluoro-5-methyl-N-{3-[(2R,6S)-10-hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI$^+$): m/z = 515 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 158 | Pyridine-3-sulfonic acid {(1R,3R)-3-[(2R,6S)-10-hydroxy-6,11,11-trimethyl-1,2,5,6-tetrahydro-4H-2,6-methano-benzo[d]azocine-3-carbonyl]-cyclopentyl}-amide | J | Mass spectrum (ESI$^+$): m/z = 484 [M + H]$^+$ |
| 159 | Propane-2-sulfonic acid {(1R,3R)-3-[(2R,6S)-10-hydroxy-6,11,11-trimethyl-1,2,5,6-tetrahydro-4H-2,6-methano-benzo[d]azocine-3-carbonyl]-cyclopentyl}-amide | J | Mass spectrum (ESI$^+$): m/z = 449 [M + H]$^+$ |
| 160 | Propane-1-sulfonic acid {(1R,3R)-3-[(2R,6S)-10-hydroxy-6,11,11-trimethyl-1,2,5,6-tetrahydro-4H-2,6-methano-benzo[d]azocine-3-carbonyl]-cyclopentyl}-amide | J | Mass spectrum (ESI$^+$): m/z = 449 [M + H]$^+$ |
| 161 | (1R,3R)-4-Methyl-N-{3-[(2R,6S)-10-hydroxy-6,11,11-trimethyl-1,2,5,6-tetrahydro-4H-2,6-methano-benzo[d]azocine-3-carbonyl]-cyclopentyl}-benzenesulfonamide | J | Mass spectrum (ESI$^+$): m/z = 497 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 162 | Ethanesulfonic acid {(1R,3R)-3-[(2R,6S)-10-hydroxy-6,11,11-trimethyl-1,2,5,6-tetrahydro-4H-2,6-methano-benzo[d]azocine-3-carbonyl]-cyclopentyl}-amide | J | Mass spectrum (ESI+): m/z = 435 [M + H]+ |
| 163 | N-{(1R,3R)-3-[(2R,6S)-10-Hydroxy-6,11,11-trimethyl-1,2,5,6-tetrahydro-4H-2,6-methano-benzo[d]azocine-3-carbonyl]-cyclopentyl}-C-phenyl-methanesulfonamide | J | Mass spectrum (ESI+): m/z = 497 [M + H]+ |
| 164 | Thiophene-2-sulfonic acid {(1R,3R)-3-[(2R,6S)-10-hydroxy-6,11,11-trimethyl-1,2,5,6-tetrahydro-4H-2,6-methano-benzo[d]azocine-3-carbonyl]-cyclopentyl}-amide | J | Mass spectrum (ESI+): m/z = 489 [M + H]+ |
| 165 | (1-Benzenesulfonyl-pyrrolidin-3-yl)-[(2R,6S)-10-hydroxy-6,11,11-trimethyl-1,2,5,6-tetrahydro-4H-2,6-methano-benzo[d]azocin-3-yl]-methanone | J | Mass spectrum (ESI+): m/z = 469 [M + H]+ |

TABLE 3-continued

Compounds prepared in analogy to the examples described above

| Example No. | Chemical Name/Structure/Remarks | Prepared in analogy to Procedure | Characterization |
|---|---|---|---|
| 166 | {cis-4-[(2R,6S)-10-Hydroxy-6,11,11-trimethyl-1,2,5,6-tetrahydro-4H-2,6-methano-benzo[d]azocine-3-carbonyl]-cyclohexyl}-butyramide | B | Mass spectrum (ESI$^+$): m/z = 427 [M + H]$^+$ |
| 167 | {cis-4-[(2R,6S)-10-Hydroxy-6,11,11-trimethyl-1,2,5,6-tetrahydro-4H-2,6-methano-benzo[d]azocine-3-carbonyl]-cyclohexyl}-benzamide | B | Mass spectrum (ESI$^+$): m/z = 461 [M + H]$^+$ |
| 168 | {cis-4-[(2R,6S)-10-Hydroxy-6,11,11-trimethyl-1,2,5,6-tetrahydro-4H-2,6-methano-benzo[d]azocine-3-carbonyl]-cyclohexyl}-acetamide | B | Mass spectrum (ESI$^+$): m/z = 399 [M + H]$^+$ |
| 169 | {cis-4-[(2R,6S)-10-Hydroxy-6,11,11-trimethyl-1,2,5,6-tetrahydro-4H-2,6-methano-benzo[d]azocine-3-carbonyl]-cyclohexyl}-propionamide | B | Mass spectrum (ESI$^+$): m/z = 413 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 170 | {cis-4-[(2R,6S)-10-Hydroxy-6,11,11-trimethyl-1,2,5,6-tetrahydro-4H-2,6-methano-benzo[d]azocine-3-carbonyl]-cyclohexyl}-isobutyramide | B | Mass spectrum (ESI+): m/z = 427 [M + H]+ |
| 171 | {cis-4-[(2R,6S)-10-Hydroxy-6,11,11-trimethyl-1,2,5,6-tetrahydro-4H-2,6-methano-benzo[d]azocine-3-carbonyl]-cyclohexyl}-2-phenyl-acetamide | B | Mass spectrum (ESI+): m/z = 475 [M + H]+ |
| 172 | 1-[(2R,6S)-10-Hydroxy-6,11,11-trimethyl-1,2,5,6-tetrahydro-4H-2,6-methano-benzo[d]azocine-3-carbonyl]-2-aza-bicyclo[2.1.1]hexane-2-carboxylic acid tert-butyl ester | B | Mass spectrum (ESI+): m/z = 441 [M + H]+ |
| 173 | (1S,5R)-1-[(2R,6S)-10-Hydroxy-6,11,11-trimethyl-1,2,5,6-tetrahydro-4H-2,6-methano-benzo[d]azocine-3-carbonyl]-2-aza-bicyclo[3.1.0]hexane-2-carboxylic acid tert-butyl ester | B | Mass spectrum (ESI+): m/z = 441 [M + H]+ |

TABLE 3-continued

Compounds prepared in analogy to the examples described above

| Example No. | Chemical Name/Structure/Remarks | Prepared in analogy to Procedure | Characterization |
|---|---|---|---|
| 174 | Adamantan-2-yl-[(2R,6S)-10-hydroxy-6,11,11-trimethyl-1,2,5,6-tetrahydro-4H-2,6-methano-benzo[d]azocin-3-yl]-methanone | B | Mass spectrum (ESI⁺): m/z = 394 [M + H]⁺ |
| 175 | Bicyclo[2.2.2]oct-2-yl-[(2R,6S)-6,11,11-trimethyl-1,2,5,6-tetrahydro-4H-2,6-methano-benzo[d]azocin-3-yl]-methanone | B | Mass spectrum (ESI⁺): m/z = 352 [M + H]⁺ |
| 176 | Chroman-2-yl-[(2R,6S)-6,11,11-trimethyl-1,2,5,6-tetrahydro-4H-2,6-methano-benzo[d]azocin-3-yl]-methanone | B | Mass spectrum (ESI⁺): m/z = 376 [M + H]⁺ |
| 177 | (trans-4-Hydroxy-cyclohexyl)-[(2R,6S)-6,11,11-trimethyl-1,2,5,6-tetrahydro-4H-2,6-methano-benzo[d]azocin-3-yl]-methanone | B | Mass spectrum (ESI⁺): m/z = 342 [M + H]⁺ |
| 178 | (trans-4-Methoxy-cyclohexyl)-[(2R,6S)-6,11,11-trimethyl-1,2,5,6-tetrahydro-4H-2,6-methano-benzo[d]azocin-3-yl]-methanone obtained from the mixture with compound 179 after chromatographic separation | B | Mass spectrum (ESI⁺): m/z = 376 [M + H]⁺ |

TABLE 3-continued

Compounds prepared in analogy to the examples described above

| Example No. | Chemical Name/Structure/Remarks | Prepared in analogy to Procedure | Characterization |
|---|---|---|---|
| 179 | (cis-4-Methoxy-cyclohexyl)-[(2R,6S)-6,11,11-trimethyl-1,2,5,6-tetrahydro-4H-2,6-methano-benzo[d]azocin-3-yl]-methanone<br><br>obtained from the mixture with compound 178 after chromatographic separation | B | Mass spectrum (ESI+): m/z = 376 [M + H]+ |
| 180 | cis-4-[(2R,6S)-9-tert-Butyl-10-hydroxy-6,11,11-trimethyl-1,2,5,6-tetrahydro-4H-2,6-methano-benzo[d]azocine-3-carbonyl]-cyclohexanecarboxylic acid | O | Mass spectrum (ESI+): m/z = 442 [M + H]+ |
| 181 | cis-4-[(2R,6S)-9-tert-Butyl-10-hydroxy-6,11,11-trimethyl-1,2,5,6-tetrahydro-4H-2,6-methano-benzo[d]azocine-3-carbonyl]-cyclohexanecarboxylic acid amide | B | Mass spectrum (ESI+): m/z = 441 [M + H]+ |
| 182 | N-{cis-4-[(2R,6S)-10-Hydroxy-6,11,11-trimethyl-1,2,5,6-tetrahydro-4H-2,6-methano-benzo[d]azocine-3-carbonyl]-cyclohexyl}-N-methyl-2-phenyl-acetamide<br><br>the compound is obtained from compound Example 187 | B | Mass spectrum (ESI+): m/z = 489 [M + H]+ |

TABLE 3-continued

Compounds prepared in analogy to the examples described above

| Example No. | Chemical Name/Structure/Remarks | Prepared in analogy to Procedure | Characterization |
|---|---|---|---|
| 183 | cis-N-[(2R,6S)-6,11,11-Trimethyl-1,2,5,6-tetrahydro-4H-2,6-methano-benzo[d]azocine-3-carbonyl]-cyclohexanecarboxylic acid dimethylamide amide | B | Mass spectrum (ESI$^+$): m/z = 397 [M + H]$^+$ |
| 184 | Adamantan-2-yl-[(2R,6S)-6,11,11-trimethyl-1,2,5,6-tetrahydro-4H-2,6-methano-benzo[d]azocin-3-yl]-methanone | B | Mass spectrum (ESI$^+$): m/z = 378 [M + H]$^+$ |
| 185 | N-{(1R,3R)-3-[(2R,6S)-6,11,11-Trimethyl-1,2,5,6-tetrahydro-4H-2,6-methano-benzo[d]azocine-3-carbonyl]-cyclopentyl}-benzenesulfonamide | J | Mass spectrum (ESI$^+$): m/z = 467 [M + H]$^+$ |
| 186 | {4-[(2R,6S)-10-Hydroxy-6,11,11-trimethyl-1,2,5,6-tetrahydro-4H-2,6-methano-benzo[d]azocine-3-carbonyl]-cyclohexyl}-methyl-carbamic acid tert-butyl ester | B | — |
| 187 | [(2R,6S)-10-Hydroxy-6,11,11-trimethyl-1,2,5,6-tetrahydro-4H-2,6-methano-benzo[d]azocin-3-yl]-(4-methylamino-cyclohexyl)-methanone | H | Mass spectrum (ESI$^+$): m/z = 370 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 188 | N-{cis-4-[(2R,6S)-10-Hydroxy-6,11,11-trimethyl-1,2,5,6-tetrahydro-4H-2,6-methano-benzo[d]azocine-3-carbonyl]-cyclohexyl}-N-methyl-propionamide<br><br>the compound is obtained from compound Example 187 | B | Mass spectrum (ESI$^+$):<br>m/z = 427 [M + H]$^+$ |
| 189 | N-{cis-4-[(2R,6S)-10-Hydroxy-6,11,11-trimethyl-1,2,5,6-tetrahydro-4H-2,6-methano-benzo[d]azocine-3-carbonyl]-cyclohexyl}-N-methyl-benzamide<br><br>the compound is obtained from compound Example 187 | B | Mass spectrum (ESI$^+$):<br>m/z = 475 [M + H]$^+$ |
| 190 | (1-Benzoyl-piperidin-2-yl)-[(2R,6S)-6,11,11-trimethyl-1,2,5,6-tetrahydro-4H-2,6-methano-benzo[d]azocin-3-yl]-methanone | B | Mass spectrum (ESI$^+$):<br>m/z = 431 [M + H]$^+$ |
| 191 | (1-Benzenesulfonyl-pyrrolidin-2-yl)-[(2R,6S)-6,11,11-trimethyl-1,2,5,6-tetrahydro-4H-2,6-methano-benzo[d]azocin-3-yl]-methanone | B | Mass spectrum (ESI$^+$):<br>m/z = 453 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 192 | [1-(3-Chloro-2-methyl-benzenesulfonyl)-pyrrolidin-2-yl]-[(2R,6S)-10-hydroxy-6,11,11-trimethyl-1,2,5,6-tetrahydro-4H-2,6-methano-benzo[d]azocin-3-yl]-methanone | J | Mass spectrum (ESI$^+$): m/z = 517/519 (Cl) [M + H]$^+$ |
| 193 | cis-3-[(2R,6S)-6,11,11-Trimethyl-1,2,5,6-tetrahydro-4H-2,6-methano-benzo[d]azocine-3-carbonyl]-cyclohexanecarboxylic acid methyl ester<br><br>diastereomeric 1:1 mixture of the two cis-configured cyclohexane enantiomers | B | Mass spectrum (ESI$^+$): m/z = 384 [M + H]$^+$ |
| 194 | cis-4-[(2R,6S)-6,11,11-Trimethyl-1,2,5,6-tetrahydro-4H-2,6-methano-benzo[d]azocine-3-carbonyl]-cyclohexanecarboxylic acid methyl ester | B | Mass spectrum (ESI$^+$): m/z = 384 [M + H]$^+$ |
| 195 | [cis-3-(1-Hydroxy-1-methyl-ethyl)-cyclohexyl]-[(2R,6S)-6,11,11-trimethyl-1,2,5,6-tetrahydro-4H-2,6-methano-benzo[d]azocin-3-yl)-methanone<br><br>diastereomeric mixture derived from compound Example 193 | P | Mass spectrum (ESI$^+$): m/z = 384 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 196 | cis-4-[(2R,6S)-6,11,11-Trimethyl-1,2,5,6-tetrahydro-4H-2,6-methano-benzo[d]azocine-3-carbonyl]-cyclohexanecarboxylic acid methyl ester | P | Mass spectrum (ESI$^+$): m/z = 384 [M + H]$^+$ |
| 197 | (cis-4-Hydroxymethyl-cyclohexyl)-[(2R,6S)-6,11,11-trimethyl-1,2,5,6-tetrahydro-4H-2,6-methano-benzo[d]azocin-3-yl]-methanone | Q | Mass spectrum (ESI$^+$): m/z = 356 [M + H]$^+$ |
| 198 | trans-4-[(2R,6S)-6,11,11-Trimethyl-1,2,5,6-tetrahydro-4H-2,6-methano-benzo[d]azocine-3-carbonyl]-cyclohexanecarboxylic acid methyl ester | B | Mass spectrum (ESI$^+$): m/z = 384 [M + H]$^+$ |
| 199 | 4-[(2R,6S)-6,11,11-Trimethyl-1,2,5,6-tetrahydro-4H-2,6-methano-benzo[d]azocine-3-carbonyl]-cyclohexanone | B | Mass spectrum (ESI$^+$): m/z = 340 [M + H]$^+$ |
| 200 | (anti-5-Hydroxy-adamantan-2-yl)-[(2R,6S)-6,11,11-trimethyl-1,2,5,6-tetrahydro-4H-2,6-methano-benzo[d]azocin-3-yl]-methanone | B | Mass spectrum (ESI$^+$): m/z = 394 [M + H]$^+$ |

TABLE 3-continued

Compounds prepared in analogy to the examples described above

| Example No. | Chemical Name/Structure/Remarks | Prepared in analogy to Procedure | Characterization |
|---|---|---|---|
| 201 | (syn-5-Hydroxy-adamantan-2-yl)-[(2R,6S)-6,11,11-trimethyl-1,2,5,6-tetrahydro-4H-2,6-methano-benzo[d]azocin-3-yl]-methanone | B | Mass spectrum (ESI$^+$): m/z = 394 [M + H]$^+$ |
| 202 | trans-4-[(2R,6S)-6,11,11-Trimethyl-1,2,5,6-tetrahydro-4H-2,6-methano-benzo[d]azocine-3-carbonyl)-cyclohexanecarboxylic acid methyl ester | P | Mass spectrum (ESI$^+$): m/z = 384 [M + H]$^+$ |
| 203 | (4-Hydroxy-4-trifluoromethyl-cyclohexyl)-[(2R,6S)-6,11,11-trimethyl-1,2,5,6-tetrahydro-4H-2,6-methano-benzo[d]azocin-3-yl]-methanone<br><br>diastereomeric mixture derived from the two cyclohexane diastereomers | R | Mass spectrum (ESI$^+$): m/z = 410 [M + H]$^+$ |
| 204 | (cis-3-Hydroxymethyl-cyclohexyl)-[(2R,6S)-6,11,11-trimethyl-1,2,5,6-tetrahydro-4H-2,6-methano-benzo[d]azocin-3-yl]-methanone<br><br>diastereomeric mixture derived from compound Example 193 | Q | Mass spectrum (ESI$^+$): m/z = 356 [M + H]$^+$ |

TABLE 3-continued

Compounds prepared in analogy to the examples described above

| Example No. | Chemical Name/Structure/Remarks | Prepared in analogy to Procedure | Characterization |
| --- | --- | --- | --- |
| 205 | (trans-4-Hydroxymethyl-cyclohexyl)-[(2R,6S)-6,11,11-trimethyl-1,2,5,6-tetrahydro-4H-2,6-methano-benzo[d]azocin-3-yl]-methanone | Q | Mass spectrum (ESI$^+$): m/z = 356 [M + H]$^+$ |
| 206 | (trans-4-Hydroxy-4-methyl-cyclohexyl)-[(2R,6S)-6,11,11-trimethyl-1,2,5,6-tetrahydro-4H-2,6-methano-benzo[d]azocin-3-yl]-methanone<br><br>obtained from compound Example 199 | P | Mass spectrum (ESI$^+$): m/z = 356 [M + H]$^+$ |
| 207 | (cis-4-Hydroxy-4-methyl-cyclohexyl)-[(2R,6S)-6,11,11-trimethyl-1,2,5,6-tetrahydro-4H-2,6-methano-benzo[d]azocin-3-yl]-methanone<br><br>obtained from compound Example 199 | P | Mass spectrum (ESI$^+$): m/z = 356 [M + H]$^+$ |
| 208 | (4-Hydroxy-bicyclo[2.2.2]oct-1-yl)-[(2R,6S)-6,11,11-trimethyl-1,2,5,6-tetrahydro-4H-2,6-methano-benzo[d]azocin-3-yl]-methanone | B | Mass spectrum (ESI$^+$): m/z = 368 [M + H]$^+$ |

The following compounds are also prepared analogously to the above-mentioned Examples and other methods known from the literature:

| Example No. | Chemical Name/Structure/Remarks | In analogy to Procedure |
|---|---|---|
| 209 | 1-[(2S,6R)-6,11,11-Trimethyl-3-(piperidine-1-carbonyl)-1,2,3,4,5,6-hexahydro-2,6-methano-benzo[d]azocin-9-yl]-ethanone 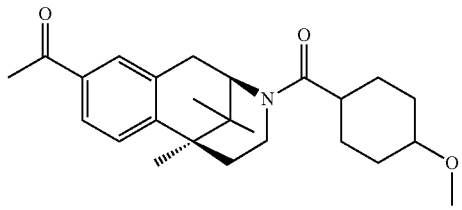 | B |
| 210 | [(6R,10S)-5,6,7,8,9,10-hexahydro-10,12,12-trimethyl-6,10-methano-1H-imidazo[5,4-i][3]benzazocin-7-yl]-(4-methoxy-cyclohexyl)-methanone 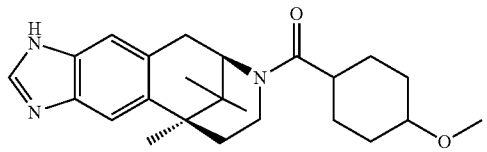 | B |
| 211 | (4-Methoxy-cyclohexyl)-(1-methyl-11-aza-tricyclo[8.3.1.0*2,7*]tetradeca-2,4,6-trien-11-yl)-methanone 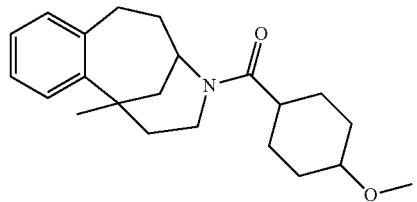 | B |
| 212 | (6-Hydroxy-11,11-dimethyl-1,2,5,6-tetrahydro-4H-2,6-methano-benzo[d]azocin-3-yl)-(4-methoxy-cyclohexyl)-methanone 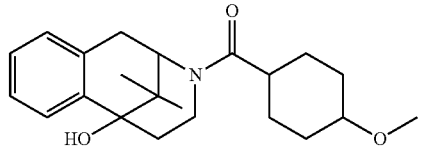 | B |
| 213 | 8-Hydroxy-3-(4-methoxy-cyclohexanecarbonyl)-2,3,4,5-tetrahydro-1H-2,6-methano-benzo[d]azocine-6-carboxylic acid methyl ester 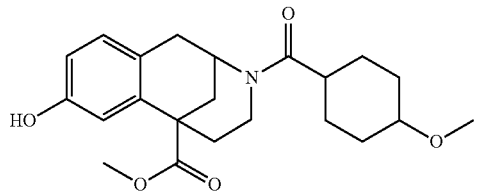 | B |

-continued

| Example No. | Chemical Name/Structure/Remarks | In analogy to Procedure |
|---|---|---|
| 214 | (4-Methoxy-9-aza-tricyclo[6.3.1.0*2,7*]dodeca-2,4,6-trien-9-yl)-(4-methoxy-cyclohexyl)-methanone | B |
| 215 | (4-Hydroxy-9-aza-tricyclo[6.3.1.0*2,7*]dodeca-2,4,6-trien-9-yl)-(4-methoxy-cyclohexyl)-methanone | B |
| 216 | (9-Hydroxy-6,11,11-trimethyl-1,2,5,6-tetrahydro-4H-2,6-methano-benzo[d]azocin-3-yl)-(4-methoxy-cyclohexyl)-methanone | B |
| 217 | 3-(4-Methoxy-cyclohexanecarbonyl)-6,11,11-trimethyl-1,2,3,4,5,6-hexahydro-2,6-methano-benzo[d]azocine-9-carboxylic acid ethyl ester | B |
| 218 | (2R,6R,11S)-3-(4-Methoxy-cyclohexanecarbonyl)-6,11-dimethyl-1,2,3,4,5,6-hexahydro-2,6-methano-benzo[d]azocine-8-carboxylic acid ethyl ester | B |
| 219 | (2R,6S)-3-(4-Methoxy-cyclohexanecarbonyl)-6,11,11-trimethyl-1,2,3,4,5,6-hexahydro-2,6-methano-benzo[d]azocine-10-carboxylic acid ethyl ester | B |

-continued

| Example No. | Chemical Name/Structure/Remarks | In analogy to Procedure |
|---|---|---|
| 220 | (2R,6S)-3-(4-Methoxy-cyclohexanecarbonyl)-6,11,11-trimethyl-1,2,3,4,5,6-hexahydro-2,6-methano-benzo[d]azocine-10-carbonitrile | B |
| 221 | (4-Methoxy-cyclohexyl)-(6,11,11-trimethyl-9-phenyl-1,2,5,6-tetrahydro-4H-2,6-methano-benzo[d]azocin-3-yl)-methanone | B |
| 222 | (2S,6R)-[9-(1-Hydroxy-ethyl)-6,11,11-trimethyl-1,2,5,6-tetrahydro-4H-2,6-methano-benzo[d]azocin-3-yl]-(4-methoxy-cyclohexyl)-methanone | Procedure B followed by reduction with NaBH$_4$ in EtOH at room temperature |
| 223 | 3-(4-Methoxy-cyclohexanecarbonyl)-6,11,11-trimethyl-1,2,3,4,5,6-hexahydro-2,6-methano-benzo[d]azocine-9-carbonitrile | B |
| 224 | (2R,6S)-(10-Amino-6,11,11-trimethyl-1,2,5,6-tetrahydro-4H-2,6-methano-benzo[d]azocin-3-yl)-(4-methoxy-cyclohexyl)-methanone | B |
| 225 | (9-Amino-6,11,11-trimethyl-1,2,5,6-tetrahydro-4H-2,6-methano-benzo[d]azocin-3-yl)-(4-methoxy-cyclohexyl)-methanone | B |

-continued

| Example No. | Chemical Name/Structure/Remarks | In analogy to Procedure |
| --- | --- | --- |
| 226 | (4-Methoxy-cyclohexyl)-[(2S,6R)-8-methoxy-6,9,11,11-tetramethyl-1,2,5,6-tetrhydro-4H-2,6-methano-benzo[d]azocin-3-yl]-methanone | B |
| 227 | (4-Methoxy-cyclohexyl)-[(2R,6S)-8-methoxy-6,9,11,11-tetramethyl-1,2,5,6-tetrahydro-4H-2,6-methano-benzo[d]azocin-3-yl]-methanone | B |
| 228 | (4-Methoxy-cyclohexyl)-[(2S,6R)-9-methoxy-6,8,11,11-tetramethyl-1,2,5,6-tetrahydro-4H-2,6-methano-benzo[d]azocin-3-yl]-methanone | B |
| 229 | (4-Methoxy-cyclohexyl)-[(2R,6S)-9-methoxy-6,8,11,11-tetramethyl-1,2,5,6-tetrahydro-4H-2,6-methano-benzo[d]azocin-3-yl]-methanone | B |
| 230 | (8,9-Dimethoxy-6,11,11-trimethyl-1,2,5,6-tetrahydro-4H-2,6-methano-benzo[d]azocin-3-yl)-(4-methoxy-cyclohexyl)-methanone | B |
| 231 | (9-Hydroxy-8-methoxy-6,11,11-trimethyl-1,2,5,6-tetrahydro-4H-2,6-methano-benzo[d]azocin-3-yl)-(4-methoxy-cyclohexyl)-methanone | B |

-continued

| Example No. | Chemical Name/Structure/Remarks | In analogy to Procedure |
| --- | --- | --- |
| 232 | (8-Hydroxy-9-methoxy-6,11,11-trimethyl-1,2,5,6-tetrahydro-4H-2,6-methano-benzo[d]azocin-3-yl)-(4-methoxy-cyclohexyl)-methanone | B |
| 233 | (2R,6S)-3-(4-Methoxy-cyclohexanecarbonyl)-6,11,11-trimethyl-1,2,3,4,5,6-hexahydro-2,6-methano-benzo[d]azocine-9-carbonitrile | B |
| 234 | [(2R,6S)-10-Fluoro-6,11,11-trimethyl-1,2,5,6-tetrahydro-4H-2,6-methano-benzo[d]azocin-3-yl]-(4-methoxy-cyclohexyl)-methanone | B |
| 235 | (8-Fluoro-6,11,11-trimethyl-1,2,5,6-tetrahydro-4H-2,6-methano-benzo[d]azocin-3-yl)-(4-methoxy-cyclohexyl)-methanone | B |
| 236 | (9-Fluoro-6,11,11-trimethyl-1,2,5,6-tetrahydro-4H-2,6-methano-benzo[d]azocin-3-yl)-(4-methoxy-cyclohexyl)-methanone | B |
| 237 | (8,9-Methylenedioxy-6,11,11-trimethyl-1,2,5,6-tetrahydro-4H-2,6-methano-benzo[d]azocin-3-yl)-(4-methoxy-cyclohexyl)-methanone | B |

| Example No. | Chemical Name/Structure/Remarks | In analogy to Procedure |
|---|---|---|
| 238 | (4-Methoxy-cyclohexyl)-(10-methoxy-11,11-dimethyl-1,2,5,6-tetrahydro-4H-2,6-methano-benzo[d]azocin-3-yl)-methanone | B |
| 239 | (4-Methoxy-cyclohexyl)-[(2S,6R)-9-methoxy-6,11,11-trimethyl-1,2,5,6-tetrahydro-4H-2,6-methano-benzo[d]azocin-3-yl]-methanone | B |
| 240 | [(2S,6R)-8-(1-Hydroxy-ethyl)-6,11,11-trimethyl-1,2,5,6-tetrahydro-4H-2,6-methano-benzo[d]azocin-3-yl]-(4-methoxy-cyclohexyl)-methanone | Procedure B followed by reduction with NaBH$_4$ in EtOH at room temperature |
| 241 | [(5R,9S)-4,5,6,7,8,9-hexahydro-2,10,12,12-trimethyl-5,9-methano-1H-imidazo[5,4-j][3]benzazocin-6-yl]-(4-methoxy-cyclohexyl)-methanone | B |
| 242 | (2S,6R)-3-(4-Methoxy-cyclohexanecarbonyl)-6,11,11-trimethyl-1,2,3,4,5,6-hexahydro-2,6-methano-benzo[d]azocine-8-sulfonic acid dimethylamide | B |
| 243 | (2S,6R)-3-(4-Methoxy-cyclohexanecarbonyl)-6,11,11-trimethyl-1,2,3,4,5,6-hexahydro-2,6-methano-benzo[d]azocine-8-sulfonic acid methylamide | B |

-continued

| Example No. | Chemical Name/Structure/Remarks | In analogy to Procedure |
|---|---|---|
| 244 | (2S,6R)-3-(4-Methoxy-cyclohexanecarbonyl)-6,11,11-trimethyl-1,2,3,4,5,6-hexahydro-2,6-methano-benzo[d]azocine-8-sulfonic acid amide<br>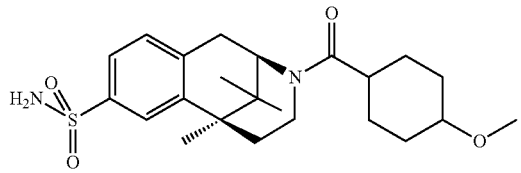 | B |
| 245 | (2S,6R)-1-[3-(4-Methoxy-cyclohexanecarbonyl)-6,11,11-trimethyl-1,2,3,4,5,6-hexahydro-2,6-methano-benzo[d]azocin-8-yl]-ethanone<br>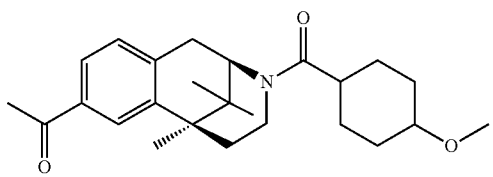 | B |
| 246 | 8-Hydroxy-3-(4-methoxy-cyclohexanecarbonyl)-2,3,4,5-tetrahydro-1H-2,6-methano-benzo[d]azocine-6-carboxylic acid<br>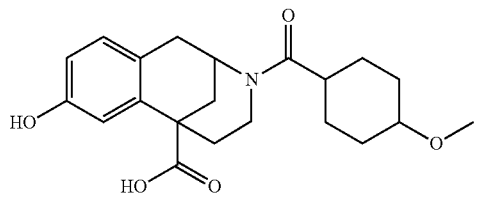 | G |
| 247 | 8-Hydroxy-3-(4-methoxy-cyclohexanecarbonyl)-2,3,4,5-tetrahydro-1H-2,6-methano-benzo[d]azocine-6-carboxylic acid dimethylamide<br>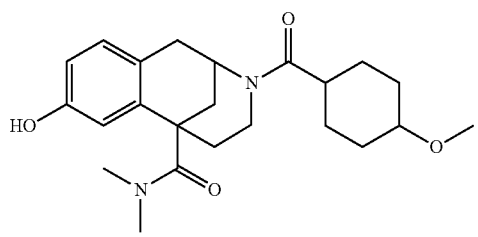<br>compound may be prepared from Example 246 and dimethylamine | B |
| 248 | 8-Hydroxy-3-(4-methoxy-cyclohexanecarbonyl)-2,3,4,5-tetrahydro-1H-2,6-methano-benzo[d]azocine-6-carboxylic acid methylamide<br>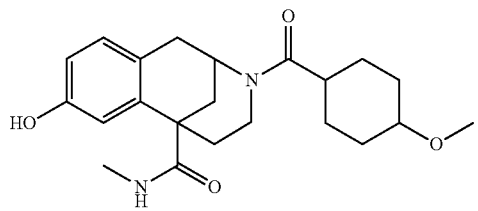<br>may be prepared from Example 246 and methylamine | B |

-continued

| Example No. | Chemical Name/Structure/Remarks | In analogy to Procedure |
|---|---|---|
| 249 | 8-Hydroxy-3-(4-methoxy-cyclohexanecarbonyl)-2,3,4,5-tetrahydro-1H-2,6-methano-benzo[d]azocine-6-carboxylic acid amide<br><br>may be prepared from Example 246 and NH$_3$ | B |
| 250 | 8-Hydroxy-3-(4-methoxy-cyclohexanecarbonyl)-2,3,4,5-tetrahydro-1H-2,6-methano-benzo[d]azocine-6-carbonitrile | from Example 249 with (F$_3$CO)$_2$O, iPr$_2$NEt in CH$_2$Cl$_2$ at room temperature and subsequent treatment with NaOH in MeOH |
| 251 | (4-Methoxy-cyclohexyl)-(6-methoxy-11,11-dimethyl-1,2,5,6-tetrahydro-4H-2,6-methano-benzo[d]azocin-3-yl)-methanone | from compound Example 212 employing the conditions described in Example LVI |
| 252 | [(2S,6R)-8-Methanesulfonyl-6,11,11-trimethyl-1,2,5,6-tetrahydro-4H-2,6-methano-benzo[d]azocin-3-yl]-(4-methoxy-cyclohexyl)-methanone | B |
| 253 | [(2S,6R)-10-Methanesulfonyl-6,11,11-trimethyl-1,2,5,6-tetrahydro-4H-2,6-methano-benzo[d]azocin-3-yl]-(4-methoxy-cyclohexyl)-methanone | B |

-continued

| Example No. | Chemical Name/Structure/Remarks | In analogy to Procedure |
|---|---|---|
| 254 | [(6R,10S)-5,6,7,8,9,10-Hexahydro-2,10,12,12-tetramethyl-6,10-methano-imidazo[4,5-i][3]benzazocin-7-yl]-(4-methoxy-cyclohexyl)-methanone | B |
| 255 | [(6R,10S)-5,6,7,8,9,10-Hexahydro-10,12,12-trimethyl-6,10-methano-imidazo[4,5-i][3]benzazocin-7-yl]-(4-methoxy-cyclohexyl)-methanone | B |
| 256 | [(2R,6R,11S)-9-Cyano-6,11,11-trimethyl-1,2,5,6-tetrahydro-4H-2,6-methano-benzo[d]azocin-3-yl]-(4-methoxy-cyclohexyl)-methanone | B |
| 257 | [(2R,6R,11R)-9-Cyano-6,11,11-trimethyl-1,2,5,6-tetrahydro-4H-2,6-methano-benzo[d]azocin-3-yl]-(4-methoxy-cyclohexyl)-methanone | B |
| 258 | [(7R,11S)-6,7,8,9,10,11-Hexahydro-11,13,13-trimethyl-6,10-methano-pyrazino[2,3-i][3]benzazocin-8-yl]-(4-methoxy-cyclohexyl)-methanone | B |
| 259 | [(7R,11S)-6,7,8,9,10,11-Hexahydro-2,3,11,13,13-pentamethyl-7,11-methano-pyrazino[2,3-i][3]benzazocin-8-yl]-(4-methoxy-cyclohexyl)-methanone | B |

-continued

| Example No. | Chemical Name/Structure/Remarks | In analogy to Procedure |
|---|---|---|
| 260 | [(6R,10S)-5,6,7,8,9,10-Hexahydro-3,10,12,12-tetramethyl-6,10-methano-imidazo[4,5-i][3]benzazocin-7-yl]-(4-methoxy-cyclohexyl)-methanone 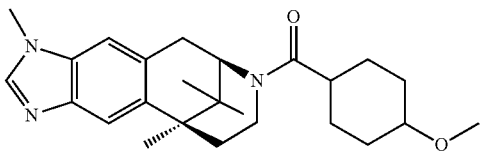 | B |
| 261 | [(6R,10S)-5,6,7,8,9,10-hexahydro-1,10,12,12-tetramethyl-6,10-methano-imidazo[5,4-i][3]benzazocin-7-yl]-(4-methoxy-cyclohexyl)-methanone 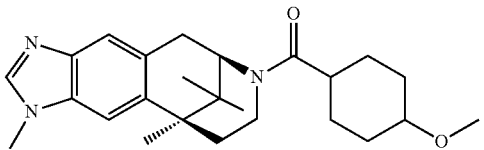 | B |
| 262 | [(6R,10S)-5,6,7,8,9,10-hexahydro-2,3,10,12,12-pentamethyl-6,10-methano-imidazo[4,5-i][3]benzazocin-7-yl]-(4-methoxy-cyclohexyl)-methanone 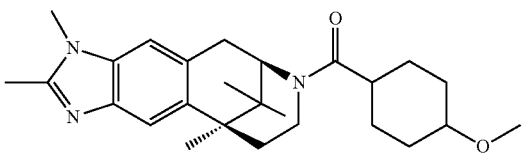 | B |
| 263 | [(6R,10S)-5,6,7,8,9,10-hexahydro-1,2,10,12,12-pentamethyl-6,10-methano-imidazo[5,4-i][3]benzazocin-7-yl]-(4-methoxy-cyclohexyl)-methanone 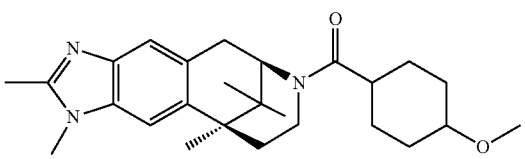 | B |
| 264 | (2,3,4,5,6,7-Hexahydro-2,6-methano-azocino[5,4-b]indol-3-yl)-(4-Methoxy-cyclohexyl)-methanone 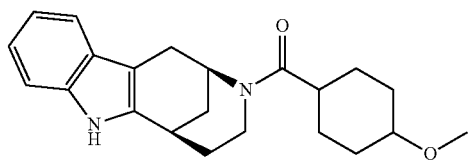 | B |

Some examples of formulations will now be described in which the term "active substance" denotes one or more compounds according to the invention, including the salts thereof. In the case of one of the combinations with one or additional active substances as described previously, the term "active substance" also includes the additional active substances.

EXAMPLE A

Tablets Containing 100 mg of Active Substance
Composition:

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE B

Tablets Containing 150 mg of Active Substance
Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE C

Hard Gelatine Capsules Containing 150 mg of Active Substance
Composition:

| 1 capsule contains: | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE D

Suppositories Containing 150 mg of Active Substance
Composition:

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation

After the suppository mass has been melted the active substance is homogeneously distributed therein and the melt is poured into chilled moulds.

EXAMPLE E

Ampoules Containing 10 mg Active Substance
Composition:

| active substance | 10.0 mg |
|---|---|
| 0.01N hydrochloric acid | q.s. |
| double-distilled water | ad 2.0 mL |

Preparation:

The active substance is dissolved in the necessary amount of 0.01 N HCl, made isotonic with common salt, filtered sterile and transferred into 2 mL ampoules.

EXAMPLE F

Ampoules Containing 50 mg of Active Substance
Composition:

| active substance | 50.0 mg |
|---|---|
| 0.01N hydrochloric acid | q.s. |
| double-distilled water | ad 10.0 mL |

Preparation:

The active substance is dissolved in the necessary amount of 0.01 N HCl, made isotonic with common salt, filtered sterile and transferred into 10 mL ampoules.

The invention claimed is:
1. A compound of formula I

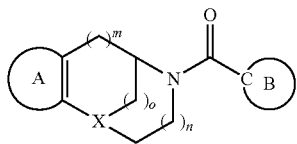

wherein
X denotes CH,
m, n, o independently of each other denote 1,
wherein the bicyclic azacycloalkene core structure of formula I annelated with ring A and attached to the carbonyl group is optionally substituted with 3 to 5 substituents independently of each other selected from the group consisting of $R^{11}$ and $R^{12}$,
A denotes a benzo ring, which is optionally substituted with one to four substituents independently of each other selected from $R^1$ or wherein 2 adjacent C-atoms are optionally substituted with $R^2$ and $R^3$ and one or two carbon atoms are optionally substituted independently with substituents selected from $R^1$;
and
B denotes a cyclohexyl group, and
wherein said cyclohexyl B group is substituted with one or more substituents independently of each other selected from $L^1$, and wherein said cyclohexyl B group optionally is substituted with 1 or 2 substituents independently of each other selected from $L^2$, and
wherein 2 adjacent C-atoms of said cyclohexyl B group optionally are substituted with $L^3$ and $L^4$, and
wherein 2 adjacent C-atoms of said cyclohexyl B group optionally are substituted with $L^5$ and $L^6$, with the proviso that two of $L^3$ to $L^6$ are not attached to the same carbon atom;
$R^N$ independently of each other denotes hydrogen, $C_{1-6}$-alkyl, $C_{3-6}$-alkenyl, $C_{3-6}$-alkynyl, $C_{3-6}$-cycloalkyl, (het) aryl, $C_{1-4}$-alkylcarbonyl, $C_{1-4}$-alkyloxycarbonyl, $C_{1-4}$-alkylaminocarbonyl, di-($C_{1-3}$-alkyl)aminocarbonyl, $C_{1-4}$-alkylsulfonyl, (het)arylcarbonyl, (het)arylaminocarbonyl, or (het)arylsulfonyl,
wherein each alkyl, alkenyl, and alkynyl group optionally is mono- or polysubstituted with fluorine, and optionally is monosubstitued with hydroxy, $C_{1-4}$-alkoxy, $C_{1-4}$-alkylsulfanyl, $C_{1-4}$-alkylsulfinyl, $C_{1-4}$-alkylsulfonyl, amino, $C_{1-4}$-alkylamino, di-($C_{1-4}$-alkyl)amino, $C_{1-4}$-alkylcarbonylamino, cyano, carboxy, $C_{1-4}$-alkoxycarbonyl, aminocarbonyl, $C_{1-4}$-alkylaminocarbonyl, di-($C_{1-4}$-alkyl)aminocarbonyl, or (het)aryl,
$R^1$ denotes fluorine, chlorine, bromine, iodine, cyano, nitro, $C_{1-4}$-alkyl, hydroxy, $C_{1-4}$-alkyloxy, $C_{3-6}$-alkenyloxy, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, $C_{1-3}$-alkyl-carbonyl, (het) aryl-carbonyl,
amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl,
$C_{1-3}$-alkyl-carbonylamino, (het)aryl-carbonylamino, (het)aryl-$C_{1-3}$-alkyl-carbonyl-amino, $C_{1-3}$-alkyloxy-carbonylamino, aminocarbonylamino, $C_{1-3}$-alkyl-amino-carbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, $C_{1-3}$-alkyl-sul-fonylamino, aminosulfonylamino, $C_{1-3}$-alkylamino-sulfonylamino, di-($C_{1-3}$-alkyl)-aminosulfonylamino, pyrrolidin-1-yl-sulfonylamino, piperidin-1-yl-sulfonylamino, morpholin-4-yl-sulfonylamino, piperazin-1-yl-sulfonylamino, 4-($C_{1-3}$-alkyl)-piperazin-1-yl-sulfonylamino, ($C_{1-3}$-alkyloxycarbonylamino)carbonylamino, (het)arylsulfonylamino, (het)aryl-$C_{1-3}$-alkyl-sulfonylamino,
N—($C_{1-3}$-alkyl)-$C_{1-3}$-alkyl-carbonylamino, N—($C_{1-3}$-alkyl)-(het) arylcarbonylamino, N—($C_{1-3}$-alkyl)-(het)aryl-$C_{1-3}$-alkyl-carbonylamino, N—($C_{1-3}$-alkyl)-$C_{1-3}$-alkyloxy-carbonylamino, N-(aminocarbonyl)-$C_{1-3}$-alkylamino, N—($C_{1-3}$-alkyl-aminocarbonyl)-$C_{1-3}$-alkylamino, N—[di-($C_{1-3}$-alkyl) aminocarbonyl]-$C_{1-3}$-alkylamino,
N—($C_{1-3}$-alkyl)-$C_{1-3}$-alkyl-sulfonylamino, N—($C_{1-3}$-alkyl)-(het)arylsulfonylamino, N—($C_{1-3}$-alkyl)-(het) aryl-$C_{1-3}$-alkyl-sulfonylamino,
oxo-imidazolidin-1-yl, 2,4-dioxo-imidazolidin-1-yl, 2,5-dioxo-imidazolidin-1-yl, 2-oxo-hexahydropyrimidin-1-yl, wherein the nitrogen atom in position 3 of the aforementioned groups is optionally substituted with methyl or ethyl,
(hydroxyimino)aminomethyl, ($C_{1-3}$-alkyloxyimino) aminomethyl, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl,
carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl)-piperazin-1-yl-carbonyl-$C_{1-3}$-alkyl,
carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl- $C_{1-3}$-alkyl-oxy, piperazin-1-yl-carbonyl-$C_{1-3}$-alkyloxy, 4-($C_{1-3}$-alkyl)-piperazin-1-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, $C_{1-4}$-alkylcarbonyl-amino-$C_{1-3}$-alkyl, N—($C_{1-3}$-alkyl)-$C_{1-4}$-alkylcarbonyl-amino-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, 3-oxo-morpholin-4-yl-$C_{1-3}$-alkyl, piperazin-1-yl-$C_{1-3}$-alkyl, 2-oxo-piperazin-1-y1-$C_{1-3}$-alkyl, 3-oxo-piperazin-1-yl -$C_{1-3}$-alkyl, 4-($C_{1-3}$-alkyl)-piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)-piperazin-1-yl-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl -$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)-piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkysulfinyl, $C_{1-3}$-alkylsulfonyl, $C_{1-3}$-alkylsulfonyloxy, (het)arylsulfonyl, (het)arylsulfonyloxy, trifluoromethylsulfanyl, trifluoromethyl-sulfinyl, trifluoromethylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, or 4-($C_{1-3}$-alkyl)-piperazin-1-yl-sulfonyl, wherein the above-mentioned saturated heterocycles and cycloalkyl-rings are optionally substituted with one or two groups selected independently from fluorine, $C_{1-3}$-alkyl, $C_{1-3}$-alkoxy, $C_{1-3}$-alkoxy-$C_{1-3}$-alkyl, and hydroxy, $R^2$ and $R^3$ are linked to each other to form a methylenedioxy, ethylenedioxy or $C_{3-5}$-alkylene bridging group, which optionally is mono- or disubstituted with methyl, and which optionally and independently is mono- or polyfluorinated; or $R^2$ and $R^3$ together, and combined with the carbon atoms to which they are attached, form a benzo, pyrido, pyrazino, pyridazino, pyrimido, pyrrolo, furano, thieno, pyrazolo, imidazo, triazolo, oxazolo, thiazolo, isoxazolo, or isothiazolo ring, wherein each of said rings optionally is substituted with one to three substituents, independently of each other selected from halogen, $C_{1-3}$-alkyl, trifluoromethyl, amino, $C_{1-3}$-alkylamino, di-($C_{1-3}$-alkyl)amino, $C_{1-3}$-alkylcarbonylamino, $C_{1-3}$-alkylsulfonylamino, hydroxy, cyano, carboxy, $C_{1-3}$-alkyloxycarbonyl and $C_{1-3}$-alkyloxy, $R^{10}$ denotes halogen, $C_{1-3}$-alkyl, difluoromethyl, trifluoromethyl, cyano, nitro, amino, $C_{1-3}$-alkylamino, di-($C_{1-3}$-alkyl)amino, acetylamino, $C_{1-3}$-alkylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, hydroxy, $C_{1-3}$-alkyloxy, difluoromethoxy, trifluoromethoxy, or phenyl optionally substituted with 1 or 2 substituents independently of each other selected from fluorine, methyl, methoxy, cyano, and hydroxy, $R^{11}$ denotes fluorine, $C_{1-4}$-alkyl, (het)aryl, hydroxy, $C_{1-4}$-alkyloxy, cyano, carboxy, $C_{1-4}$-alkyloxycarbonyl, aminocarbonyl, $C_{1-4}$-alkylamino-carbonyl, di-($C_{1-4}$-alkyl)-aminocarbonyl, hydroxy-$C_{1-4}$-alkyl or $C_{1-3}$-alkyloxy-$C_{1-4}$-alkyl, $R^{12}$ denotes fluorine or $C_{1-4}$-alkyl, and $L^1$ denotes halogen, $C_{1-4}$-alkyl, trifluoromethyl, hydroxy, $C_{1-4}$-alkyloxy, or cyano;

$L^2$ denotes fluorine, chlorine, bromine, iodine, nitro, cyano, hydroxy, $C_{3-6}$-cycloalkyl, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl, (het)aryloxy, $C_{1-6}$-alkyl, $C_{2-6}$-alkenyl, $C_{2-6}$-alkynyl, $C_{1-6}$-alkyloxy, $C_{1-6}$-alkylamino, wherein in each group one $CH_2$ group optionally is replaced by carbonyl or sulfonyl, and wherein each group optionally is mono or polyfluorinated, and wherein each group optionally is additionally substituted with hydroxy, chlorine, $C_{1-3}$-alkyl, $C_{3-6}$-cycloalkyl, $C_{1-3}$-alkyloxy, amino, $C_{1-3}$-alkyl-amino, di-($C_{1-3}$-alkyl)-amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin--yl, 2-oxo-piperazin-1-yl, 3-oxo-piperazin-1-yl, 4-($C_{1-3}$-alkyl)-piperazin-1-yl, 2-oxo-4-($C_{1-3}$-alkyl)-piperazin-1-yl, 3-oxo-4-($C_{1-3}$-alkyl)-piperazin-1-yl, carboxy, $C_{1-3}$-alkyloxy-carbonyl, cyano, aminocarbonyl, $C_{1-3}$-alkylamino-carbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, $C_{1-3}$-alkylcarbonylamino, arylcarbonylamino, $C_{1-3}$-alkylsulfanyl, $C_{1-3}$-alkylsulfinyl, $C_{1-3}$-alkylsulfonyl, $C_{3-6}$-cycloalkyl, (het)aryl, or (het)aryloxy;

or $L^2$ denotes amino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$- alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, (het)aryl-carbonylamino, $C_{1-4}$-alkyloxy-carbonylamino, aminocarbonylamino, $C_{1-4}$-alkyl-aminocarbonylamino, (het)aryl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, aminosulfonylamino, $C_{1-3}$-alkylamino -sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, piperazin-1-yl -sulfonylamino, 4-($C_{1-3}$-alkyl)-piperazin-1-yl-sulfonylamino, ($C_{1-3}$-alkyloxy-carbonylamino) carbonylamino, (het)arylsulfonylamino, N—($C_{1-3}$-alkyl)-$C_{1-3}$-alkyl-carbonylamino, N—($C_{1-3}$-alkyl)-(het)arylcarbonylamino, N—($C_{1-3}$-alkyl)-(het)aryl-$C_{1-3}$-alkyl-carbonylamino, N—($C_{1-3}$- alkyl)-$C_{1-3}$-alkyloxy-carbonylamino,
N—(aminocarbonyl)-$C_{1-3}$-alkylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino,
N—($C_{1-3}$-alkyl)-$C_{1-3}$-alkyl-sulfonylamino, N—($C_{1-3}$-alkyl)-(het)arylsulfonylamino, N—($C_{1-3}$-alkyl)-(het)aryl-$C_{1-3}$-alkyl-sulfonylamino, carboxy, $C_{1-3}$-alkyloxy-carbonyl, aminocarbonyl, $C_{1-3}$-alkyl-aminocarbonyl, di-($C_{1-3}$-alkyl)-aminocarbonyl, azetidin-1-yl-carbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, (het)arylaminocarbonyl, N—($C_{1-3}$-alkyl)-(het)aryl-aminocarbonyl, (het)aryl-$C_{1-3}$-alkylaminocarbonyl, N—($C_{1-3}$-alkyl)-(het)aryl-$C_{1-3}$-alkylaminocarbonyl, $C_{1-3}$-alkylsulfanyl, $C_{1-3}$-alkysulfinyl, (het)arylsulfonyl, trifluoromethylsulfanyl, trifluoromethylsulfinyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)-piperazin-1-yl-sulfonyl, wherein the saturated heterocycles and cycloalkyl-rings mentioned in the definition of $L^2$ as a single unit or a sub-moiety within another group are optionally substituted with one or two groups selected from fluorine, $C_{1-3}$-alkyl, $C_{1-3}$-alkoxy, $C_{1-3}$-alkoxy-$C_{1-3}$-alkyl, and hydroxy, and wherein $L^3$ and $L^4$ are linked to each other and wherein $L^5$ and $L^6$ are linked to each other, such that independently of each other and in each case together with the 2 adjacent C-atoms to which either $L^3$ and $L^4$ or $L^5$ and $L^6$ are attached an aryl- or heteroaryl-group is formed which is fused to the cyclic group B and which is optionally substituted with 1, 2, or 3 identical or different groups selected from $R^{10}$, while by aryl is meant phenyl or naphthyl and by heteroaryl is meant pyrrolyl, furanyl, thienyl, pyridyl, indolyl, benzofuranyl, benzothio-phenyl, quinolinyl, isoquinolinyl, or pyrrolyl, furanyl, thienyl, and pyridyl wherein in each 1 or 2 CH groups are replaced by N, or indolyl, benzofuranyl, benzothiophenyl, quinolinyl, and isoquinolinyl wherein in each 1 to 3 CH groups are replaced by N, and where in each >N—H containing heteroaryl all the >N—H groups present are optionally replaced by other groups independently selected from >N—$R^N$, while the (het)aryl mentioned hereinbefore as a single unit or a sub-moiety within another group is an aryl group as defined hereinbefore, or a heteroaryl group as defined hereinbefore, or a ring selected from the group consisting of 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-di-hydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzol[1,4]dioxinyl and 3,4-dihydro-3-oxo-2H-benzol[1,4]oxazinyl, wherein each of said rings is optionally substituted with 1, 2 or 3 substituents independently of each other selected from $R^{10}$, and wherein each >N—H containing (het)aryl all the >N—H groups present are optionally replaced by other groups independently selected from >N—$R^N$, whilst each of the above-mentioned alkyl or alkylene moieties may be branched or unbranched, a tautomer, stereoisomer thereof, mixture thereof, or salt thereof, while the compounds comprised by the formula II

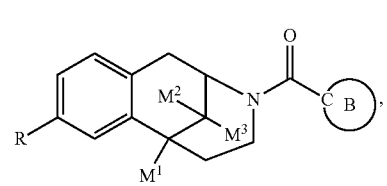

II wherein

R is hydrogen or R' O, while R' is any substituent, $M^1$ is methyl, ethyl, propyl, or phenyl, $M^2$ and $M^3$ independently of each other are hydrogen, methyl, ethyl, or hydroxy, and ring B is cyclohexyl which is optionally substituted with one or more $C_{1-5}$-alkyl groups resulting in B having ≤10 carbon atoms in total, or 1-($C_{1-3}$-alkoxy)-cyclohex-1-yl, 3-hydroxycyclohexyl, 4-hydroxycyclohexyl, 3-acetoxy-cyclohexyl, 4-acetoxy-cyclohexyl, cyclohexanon-4-yl, are excluded.

2. A compound according to claim 1, represented by formula I.1

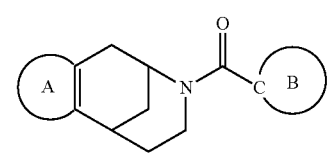

I.1 wherein the bicyclic azacycloalkene core structure of formula I.1 condensed with ring A and attached to the carbonyl group is substituted with 3 to 5 substituents independently of each other selected from the group consisting of $R^{11}$ and $R^{12}$, and wherein the rings A and B are defined as in claim 1, $R^{11}$ denotes a fluorine atom, $C_{1-3}$-alkyl, phenyl, hydroxy, $C_{1-3}$-alkyloxy, cyano, carboxy, $C_{1-4}$-alkyloxycarbonyl, aminocarbonyl, $C_{1-4}$-alkylamino-carbonyl, di-($C_{1-4}$-alkyl)-aminocarbonyl, hydroxy-$C_{1-4}$-alkyl, or $C_{1-3}$-alkyloxy-$C_{1-4}$-alkyl, $R^{12}$ denotes a fluorine atom or $C_{1-3}$-alkyl, a tautomer, stereoisomer, mixture thereof, or salt thereof.

3. A compound of formulae I.1-RR or I.1-SS as substructures of formula I.1 according to claim 2,

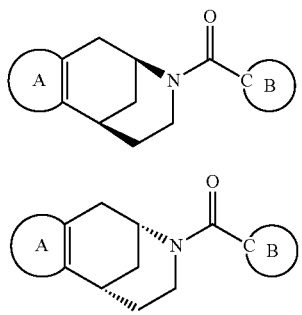

I.1-RR

I.1-SS wherein the 2,6-methano-azocin core structure with the stereochemical configuration as depicted is substituted with 3, 4, or 5 substituents, independently of each other selected from the group consisting of $R^{11}$ and $R^{12}$, and wherein the rings A, B and $R^{11}$, $R^{12}$ are defined as in claim 3, a tautomer, stereoisomer, mixture thereof, or salt thereof.

4. The compound according to claim 2, wherein the bicyclic azacycloalkene core structure of formulae I condensed with ring A and attached to the carbonyl group is mono-substituted with $R^{11}$ and substituted with 2 substituents independently of each other selected from $R^{12}$, while $R^{11}$ and $R^{12}$ are defined as in claim 3, a tautomer, stereoisomer, mixture thereof, or salt thereof.

5. A physiologically acceptable salt of the compound according to claim 1 with an inorganic or organic acid or base.

6. A pharmaceutical composition containing a compound according to claim 1 or a physiologically acceptable salt with an inorganic or organic acid or base optionally together with one or more inert carriers and/or diluents.

7. Process for preparing a compound of formula I according to claim 1 or a physiologically acceptable salt with an inorganic or organic acid or base, wherein
an amine of the formula III

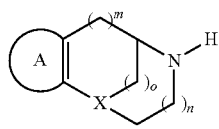

III wherein
the groups A, X, m, n, and o are defined as in claim 1, is reacted with a compound of the formula IV

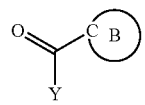

IV wherein B is defined as in claim 1, and wherein Y is a leaving group, and, if necessary any protective group used in the reactions described above is cleaved concurrently or subsequently;

and optionally the compound of formula I thus obtained is converted into a physiologically acceptable salt thereof.

\* \* \* \* \*